US012534716B2

(12) United States Patent
Doig et al.

(10) Patent No.: US 12,534,716 B2
(45) Date of Patent: Jan. 27, 2026

(54) COMPOSITIONS AND METHODS FOR ENHANCED PROTEIN PRODUCTION IN BACILLUS LICHENIFORMIS

(71) Applicant: DANISCO US INC., Palo Alto, CA (US)

(72) Inventors: Steven D. Doig, Wilmington, DE (US); Ryan L Frisch, Newark, DE (US); Hongxian He, Wilmington, DE (US); Chris Leeflang, Oegstgeest (NL); Zhen Ma, Garnet Valley, PA (US); Brian James Paul, Wilmington, DE (US)

(73) Assignee: DANISCO US INC., Palo Alto, CA (US)

( * ) Notice: Subject to any disclaimer, the term of this patent is extended or adjusted under 35 U.S.C. 154(b) by 579 days.

(21) Appl. No.: 17/791,502

(22) PCT Filed: Jan. 14, 2021

(86) PCT No.: PCT/US2021/013420

§ 371 (c)(1),
(2) Date: Jul. 7, 2022

(87) PCT Pub. No.: WO2021/146411

PCT Pub. Date: Jul. 22, 2021

(65) Prior Publication Data

US 2023/0340442 A1 Oct. 26, 2023

Related U.S. Application Data

(60) Provisional application No. 62/961,234, filed on Jan. 15, 2020.

(51) Int. Cl.

| | |
|---|---|
| ***C12N 9/28*** | (2006.01) |
| ***C07K 14/32*** | (2006.01) |
| ***C12N 15/75*** | (2006.01) |
| ***C12R 1/10*** | (2006.01) |

(52) U.S. Cl.

CPC ............ *C12N 9/2417* (2013.01); *C07K 14/32* (2013.01); *C12N 15/75* (2013.01); *C12Y 302/01001* (2013.01); *C12R 2001/10* (2021.05)

(58) Field of Classification Search

CPC .... C12N 9/2417; C12N 15/75; C12N 9/1235; C12N 9/93; C12N 9/90; C12N 15/67; C12N 9/2411; C12N 9/50; C07K 14/32; C12Y 302/01001; C12Y 502/01008; C12R 2001/10; C12P 21/02

See application file for complete search history.

(56) References Cited

U.S. PATENT DOCUMENTS

| | | | | |
|---|---|---|---|---|
| 2008/0050774 | A1 * | 2/2008 | Berka | C07K 14/32 435/270 |
| 2010/0255534 | A1 | 10/2010 | Endo et al. | |

OTHER PUBLICATIONS

Kontinen et al, "The PrsA lipoprotein is essential for protein secretion in Bacillus subtilis and sets a limit for high-level secretion", Molecular Microbiology, Wiley-Blackwell Publishing Ltd, GB, vol. 8, No. 4, May 1, 1993 (May 1, 1993), p. 727-737.

Lindholm et al, "Heterologous protein secretion in Lactococcus lactis is enhanced by the Bacillus subtilis chaperone-like protein PrsA", Applied Microbiology and Biotechnology, Springer, Berlin, DE, vol. 73, No. 4, Aug. 30, 2006 (Aug. 30, 2006), p. 904-914.

Quesada-Ganuza Ane et al, "Identification andoptimization of PrsA inBacillus subtilis for improved yield of amylase", Microb Cell Fact, vol. 18, Jan. 1, 2019 (Jan. 1, 2019), p. 158.

International Search Report and Written Opinion from PCT App. No. PCT/US2021/013420 dated Apr. 26, 2021, 15 pages.

* cited by examiner

*Primary Examiner* — Robert B Mondesi
*Assistant Examiner* — Naghmeh Nina Moazzami

(57) ABSTRACT

The present disclosure is generally related to compositions and methods for constructing and/or obtaining *B. licheniformis* cells (e.g., protein production hosts) comprising enhanced protein production capabilities. Thus, certain embodiments are related to genetically modified *Bacillus licheniformis* strains derived from parental *B. licheniformis* strains producing increased amounts of one or more proteins of interest.

14 Claims, No Drawings

Specification includes a Sequence Listing.

SEQUENCE LISTING

<160> NUMBER OF SEQ ID NOS: 158

<210> SEQ ID NO 1
<211> LENGTH: 1368
<212> TYPE: PRT
<213> ORGANISM: Streptococcus pyogenes

<400> SEQUENCE: 1

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

Ser Thr Asp Lys Ala Asp Leu Arg Leu Ile Tyr Leu Ala Leu Ala His
145 150 155 160

Met Ile Lys Phe Arg Gly His Phe Leu Ile Glu Gly Asp Leu Asn Pro
165 170 175

Asp Asn Ser Asp Val Asp Lys Leu Phe Ile Gln Leu Val Gln Thr Tyr
180 185 190

Asn Gln Leu Phe Glu Glu Asn Pro Ile Asn Ala Ser Gly Val Asp Ala
195 200 205

Lys Ala Ile Leu Ser Ala Arg Leu Ser Lys Ser Arg Arg Leu Glu Asn
210 215 220

Leu Ile Ala Gln Leu Pro Gly Glu Lys Lys Asn Gly Leu Phe Gly Asn
225 230 235 240

Leu Ile Ala Leu Ser Leu Gly Leu Thr Pro Asn Phe Lys Ser Asn Phe
245 250 255

```
Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560

Val Lys Gln Leu Lys Glu Asp Tyr Phe Lys Lys Ile Glu Cys Phe Asp
                565                 570                 575

Ser Val Glu Ile Ser Gly Val Glu Asp Arg Phe Asn Ala Ser Leu Gly
            580                 585                 590

Thr Tyr His Asp Leu Leu Lys Ile Ile Lys Asp Lys Asp Phe Leu Asp
        595                 600                 605

Asn Glu Glu Asn Glu Asp Ile Leu Glu Asp Ile Val Leu Thr Leu Thr
    610                 615                 620

Leu Phe Glu Asp Arg Glu Met Ile Glu Glu Arg Leu Lys Thr Tyr Ala
625                 630                 635                 640

His Leu Phe Asp Asp Lys Val Met Lys Gln Leu Lys Arg Arg Arg Tyr
                645                 650                 655

Thr Gly Trp Gly Arg Leu Ser Arg Lys Leu Ile Asn Gly Ile Arg Asp
            660                 665                 670
```

```
Lys Gln Ser Gly Lys Thr Ile Leu Asp Phe Leu Lys Ser Asp Gly Phe
        675                 680                 685

Ala Asn Arg Asn Phe Met Gln Leu Ile His Asp Asp Ser Leu Thr Phe
    690                 695                 700

Lys Glu Asp Ile Gln Lys Ala Gln Val Ser Gly Gln Gly Asp Ser Leu
705                 710                 715                 720

His Glu His Ile Ala Asn Leu Ala Gly Ser Pro Ala Ile Lys Lys Gly
                725                 730                 735

Ile Leu Gln Thr Val Lys Val Val Asp Glu Leu Val Lys Val Met Gly
            740                 745                 750

Arg His Lys Pro Glu Asn Ile Val Ile Glu Met Ala Arg Glu Asn Gln
        755                 760                 765

Thr Thr Gln Lys Gly Gln Lys Asn Ser Arg Glu Arg Met Lys Arg Ile
    770                 775                 780

Glu Glu Gly Ile Lys Glu Leu Gly Ser Gln Ile Leu Lys Glu His Pro
785                 790                 795                 800

Val Glu Asn Thr Gln Leu Gln Asn Glu Lys Leu Tyr Leu Tyr Tyr Leu
                805                 810                 815

Gln Asn Gly Arg Asp Met Tyr Val Asp Gln Glu Leu Asp Ile Asn Arg
            820                 825                 830

Leu Ser Asp Tyr Asp Val Asp His Ile Val Pro Gln Ser Phe Leu Lys
        835                 840                 845

Asp Asp Ser Ile Asp Asn Lys Val Leu Thr Arg Ser Asp Lys Asn Arg
    850                 855                 860

Gly Lys Ser Asp Asn Val Pro Ser Glu Glu Val Val Lys Lys Met Lys
865                 870                 875                 880

Asn Tyr Trp Arg Gln Leu Leu Asn Ala Lys Leu Ile Thr Gln Arg Lys
                885                 890                 895

Phe Asp Asn Leu Thr Lys Ala Glu Arg Gly Gly Leu Ser Glu Leu Asp
            900                 905                 910

Lys Ala Gly Phe Ile Lys Arg Gln Leu Val Glu Thr Arg Gln Ile Thr
        915                 920                 925

Lys His Val Ala Gln Ile Leu Asp Ser Arg Met Asn Thr Lys Tyr Asp
    930                 935                 940

Glu Asn Asp Lys Leu Ile Arg Glu Val Lys Val Ile Thr Leu Lys Ser
945                 950                 955                 960

Lys Leu Val Ser Asp Phe Arg Lys Asp Phe Gln Phe Tyr Lys Val Arg
                965                 970                 975

Glu Ile Asn Asn Tyr His His Ala His Asp Ala Tyr Leu Asn Ala Val
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                1015                1020

Lys Ser  Glu Gln Glu Ile Gly  Lys Ala Thr Ala Lys  Tyr Phe Phe
    1025                1030                1035

Tyr Ser  Asn Ile Met Asn Phe  Phe Lys Thr Glu Ile  Thr Leu Ala
    1040                1045                1050

Asn Gly  Glu Ile Arg Lys Arg  Pro Leu Ile Glu Thr  Asn Gly Glu
    1055                1060                1065

Thr Gly  Glu Ile Val Trp Asp  Lys Gly Arg Asp Phe  Ala Thr Val
    1070                1075                1080

Arg Lys  Val Leu Ser Met Pro  Gln Val Asn Ile Val  Lys Lys Thr
```

```
    1085                1090                1095

Glu Val  Gln Thr Gly Gly Phe  Ser Lys Glu Ser Ile  Leu Pro Lys
    1100                1105                1110

Arg Asn  Ser Asp Lys Leu Ile  Ala Arg Lys Lys Asp  Trp Asp Pro
    1115                1120                1125

Lys Lys  Tyr Gly Gly Phe Asp  Ser Pro Thr Val Ala  Tyr Ser Val
    1130                1135                1140

Leu Val  Val Ala Lys Val Glu  Lys Gly Lys Ser Lys  Lys Leu Lys
    1145                1150                1155

Ser Val  Lys Glu Leu Leu Gly  Ile Thr Ile Met Glu  Arg Ser Ser
    1160                1165                1170

Phe Glu  Lys Asn Pro Ile Asp  Phe Leu Glu Ala Lys  Gly Tyr Lys
    1175                1180                1185

Glu Val  Lys Lys Asp Leu Ile  Ile Lys Leu Pro Lys  Tyr Ser Leu
    1190                1195                1200

Phe Glu  Leu Glu Asn Gly Arg  Lys Arg Met Leu Ala  Ser Ala Gly
    1205                1210                1215

Glu Leu  Gln Lys Gly Asn Glu  Leu Ala Leu Pro Ser  Lys Tyr Val
    1220                1225                1230

Asn Phe  Leu Tyr Leu Ala Ser  His Tyr Glu Lys Leu  Lys Gly Ser
    1235                1240                1245

Pro Glu  Asp Asn Glu Gln Lys  Gln Leu Phe Val Glu  Gln His Lys
    1250                1255                1260

His Tyr  Leu Asp Glu Ile Ile  Glu Gln Ile Ser Glu  Phe Ser Lys
    1265                1270                1275

Arg Val  Ile Leu Ala Asp Ala  Asn Leu Asp Lys Val  Leu Ser Ala
    1280                1285                1290

Tyr Asn  Lys His Arg Asp Lys  Pro Ile Arg Glu Gln  Ala Glu Asn
    1295                1300                1305

Ile Ile  His Leu Phe Thr Leu  Thr Asn Leu Gly Ala  Pro Ala Ala
    1310                1315                1320

Phe Lys  Tyr Phe Asp Thr Thr  Ile Asp Arg Lys Arg  Tyr Thr Ser
    1325                1330                1335

Thr Lys  Glu Val Leu Asp Ala  Thr Leu Ile His Gln  Ser Ile Thr
    1340                1345                1350

Gly Leu  Tyr Glu Thr Arg Ile  Asp Leu Ser Gln Leu  Gly Gly Asp
    1355                1360                1365
```

<210> SEQ ID NO 2
<211> LENGTH: 4188
<212> TYPE: DNA
<213> ORGANISM: Artificial Sequence
<220> FEATURE:
<223> OTHER INFORMATION: synthetic

<400> SEQUENCE: 2

```
gtggccccaa aaaagaaacg caaggttatg gataaaaaat acagcattgg tctggatatc     60

ggaaccaaca gcgttgggtg ggcagtaata acagatgaat acaaagtgcc gtcaaaaaaa    120

tttaaggttc tggggaatac agatcgccac agcataaaaa agaatctgat tggggcattg    180

ctgtttgatt cgggtgagac agctgaggcc acgcgtctga aacgtacagc aagaagacgt    240

tacacacgtc gtaaaaatcg tatttgctac ttacaggaaa tttttctaa cgaaatggcc     300

aaggtagatg atagtttctt ccatcgtctc gaagaatctt ttctggttga ggaagataaa    360

aaacacgaac gtcaccctat ctttggcaat atcgtggatg aagtggccta tcatgaaaaa    420
```

```
taccctacga tttatcatct tcgcaagaag ttggttgata gtacggacaa agcggatctg    480
cgtttaatct atcttgcgtt agcgcacatg atcaaatttc gtggtcattt cttaattgaa    540
ggtgatctga atcctgataa ctctgatgtg gacaaattgt ttatacaatt agtgcaaacc    600
tataatcagc tgttcgagga aaaccccatt aatgcctctg gagttgatgc caaagcgatt    660
ttaagcgcga gactttctaa gtcccggcgt ctggagaatc tgatcgccca gttaccaggg    720
gaaaagaaaa atggtctgtt tggtaatctg attgccctca gtctggggct taccccgaac    780
ttcaaatcca attttgacct ggctgaggac gcaaagctgc agctgagcaa agatacttat    840
gatgatgacc tcgacaatct gctcgcccag attggtgacc aatatgcgga tctgtttctg    900
gcagcgaaga atctttcgga tgctatcttg ctgtcggata ttctgcgtgt taataccgaa    960
atcaccaaag cgcctctgtc tgcaagtatg atcaagagat acgacgagca ccaccaggac   1020
ctgactcttc ttaaggcact ggtacgccaa cagcttccgg agaaatacaa agaaatattc   1080
ttcgaccagt ccaagaatgg ttacgcgggc tacatcgatg gtggtgcatc acaggaagag   1140
ttctataaat ttattaaacc aatccttgag aaaatggatg gcacggaaga gttacttgtt   1200
aaacttaacc gcgaagactt gcttagaaag caacgtacat tcgacaacgg ctccatccca   1260
caccagattc atttaggtga acttcacgcc atcttgcgca gacaagaaga tttctatccc   1320
ttcttaaaag acaatcggga gaaaatcgag aagatcctga cgttccgcat tccctattat   1380
gtcggtcccc tggcacgtgg taattctcgg tttgcctgga tgacgcgcaa aagtgaggaa   1440
accatcaccc cttggaactt tgaagaagtc gtggataaag gtgctagcgc gcagtctttt   1500
atagaaagaa tgacgaactt cgataaaaac ttgcccaacg aaaaagtcct gcccaagcac   1560
tctcttttat atgagtactt tactgtgtac aacgaactga ctaaagtgaa atacgttacg   1620
gaaggtatgc gcaaacctgc ctttcttagt ggcgagcaga aaaaagcaat tgtcgatctt   1680
ctctttaaaa cgaatcgcaa ggtaactgta aaacagctga aggaagatta tttcaaaaag   1740
atcgaatgct ttgattctgt cgagatctcg ggtgtcgaag atcgtttcaa cgcttcctta   1800
gggacctatc atgatttgct gaagataata aaagacaaag actttctcga caatgaagaa   1860
aatgaagata ttctggagga tattgttttg accttgacct tattcgaaga tagagagatg   1920
atcgaggagc gcttaaaaac ctatgcccac ctgtttgatg acaaagtcat gaagcaatta   1980
aagcgccgca gatatacggg gtggggccgc ttgagccgca agttgattaa cggtattaga   2040
gacaagcaga gcggaaaaac tatcctggat ttcctcaaat ctgacggatt tgcgaaccgc   2100
aattttatgc agcttataca tgatgattcg cttacattca aagaggatat tcagaaggct   2160
caggtgtctg ggcaaggtga ttcactccac gaacatatag caaatttggc cggctctcct   2220
gcgattaaga aggggatcct gcaaacagtt aaagttgtgg atgaacttgt aaaagtaatg   2280
ggccgccaca agccggagaa tatcgtgata gaaatggcgc gcgagaatca aacgacacaa   2340
aaaggtcaaa agaactcaag agagagaatg aagcgcattg aggaggggat aaaggaactt   2400
ggatctcaaa ttctgaaaga acatccagtt gaaaacactc agctgcaaaa tgaaaaattg   2460
tacctgtact acctgcagaa tggaagagac atgtacgtgg atcaggaatt ggatatcaat   2520
agactctcgg actatgacgt agatcacatt gtccctcaga gcttcctcaa ggatgattct   2580
atagataata aagtacttac gagatcggac aaaaatcgcg gtaaatcgga taacgtccca   2640
tcggaggaag tcgttaaaaa gatgaaaaac tattggcgtc aactgctgaa cgccaagctg   2700
atcacacagc gtaagtttga taatctgact aaagccgaac gcggtggtct tagtgaactc   2760
```

```
gataaagcag gatttataaa acggcagtta gtagaaacgc gccaaattac gaaacacgtg   2820

gctcagatcc tcgattctag aatgaataca aagtacgatg aaaacgataa actgatccgt   2880

gaagtaaaag tcattacctt aaaatctaaa cttgtgtccg atttccgcaa agattttcag   2940

ttttacaagg tccgggaaat caataactat caccatgcac atgatgcata tttaaatgcg   3000

gttgtaggca cggcccttat taagaaatac cctaaactcg aaagtgagtt tgtttatggg   3060

gattataaag tgtatgacgt tcgcaaaatg atcgcgaaat cagaacagga aatcggtaag   3120

gctaccgcta aatacttttt ttattccaac attatgaatt tttttaagac cgaaataact   3180

ctcgcgaatg gtgaaatccg taaacggcct cttatagaaa ccaatggtga aacgggagaa   3240

atcgtttggg ataaaggtcg tgactttgcc accgttcgta aagtcctctc aatgccgcaa   3300

gttaacattg tcaagaagac ggaagttcaa acagggggat tctccaaaga atctatcctg   3360

ccgaagcgta acagtgataa acttattgcc agaaaaaaag attgggatcc aaaaaaatac   3420

ggaggctttg attcccctac cgtcgcgtat agtgtgctgg tggttgctaa agtcgagaaa   3480

gggaaaagca agaaattgaa atcagttaaa gaactgctgg gtattacaat tatggaaaga   3540

tcgtcctttg agaaaaatcc gatcgacttt ttagaggcca aggggtataa ggaagtgaaa   3600

aaagatctca tcatcaaatt accgaagtat agtctttttg agctggaaaa cggcagaaaa   3660

agaatgctgg cctccgcggg cgagttacag aagggaaatg agctggcgct gccttccaaa   3720

tatgttaatt ttctgtacct tgccagtcat tatgagaaac tgaagggcag ccccgaagat   3780

aacgaacaga aacaattatt cgtggaacag cataagcact atttagatga aattatagag   3840

caaattagtg aatttttctaa gcgcgttatc ctcgcggatg ctaatttaga caaagtactg   3900

tcagcttata ataaacatcg ggataagccg attagagaac aggccgaaaa tatcattcat   3960

ttgtttacct taaccaacct tggagcacca gctgccttca aatatttcga taccacaatt   4020

gatcgtaaac ggtatacaag tacaaaagaa gtcttggacg caaccctcat tcatcaatct   4080

attactggat tatatgagac acgcattgat ctttcacagc tgggcggaga caagaagaaa   4140

aaactgaaac tgcaccatca tcaccatcat catcaccatc attgataa                 4188
```

<210> SEQ ID NO 3
<211> LENGTH: 8
<212> TYPE: PRT
<213> ORGANISM: Artificial Sequence
<220> FEATURE:
<223> OTHER INFORMATION: synthetic

<400> SEQUENCE: 3

```
Ala Pro Lys Lys Lys Arg Lys Val
1               5
```

<210> SEQ ID NO 4
<211> LENGTH: 6
<212> TYPE: PRT
<213> ORGANISM: Artificial Sequence
<220> FEATURE:
<223> OTHER INFORMATION: synthetic

<400> SEQUENCE: 4

```
Lys Lys Lys Lys Leu Lys
1               5
```

<210> SEQ ID NO 5
<211> LENGTH: 10
<212> TYPE: PRT
<213> ORGANISM: Artificial Sequence
<220> FEATURE:
<223> OTHER INFORMATION: synthetic

<400> SEQUENCE: 5

His His His His His His His His His His
1 5 10

<210> SEQ ID NO 6
<211> LENGTH: 607
<212> TYPE: DNA
<213> ORGANISM: Bacillus subtilis

<400> SEQUENCE: 6
attcctccat tttcttctgc tatcaaaata acagactcgt gattttccaa acgagctttc 60
aaaaaagcct ctgccccttg caaatcggat gcctgtctat aaaattcccg atattggtta 120
aacagcggcg caatggcggc cgcatctgat gtctttgctt ggcgaatgtt catcttattt 180
cttcctccct ctcaataatt ttttcattct atccctttc tgtaaagttt atttttcaga 240
atacttttat catcatgctt tgaaaaaata tcacgataat atccattgtt ctcacggaag 300
cacacgcagg tcatttgaac gaattttttc gacaggaatt tgccgggact caggagcatt 360
taacctaaaa aagcatgaca tttcagcata atgaacattt actcatgtct attttcgttc 420
ttttctgtat gaaaatagtt atttcgagtc tctacggaaa tagcgagaga tgatatacct 480
aaatagagat aaaatcatct caaaaaaatg ggtctactaa aatattattc catctattac 540
aataaattca cagaatagtc ttttaagtaa gtctactctg aatttttta aaaggagagg 600 gtaacta 607

<210> SEQ ID NO 7
<211> LENGTH: 247
<212> TYPE: DNA
<213> ORGANISM: Artificial Sequence
<220> FEATURE:
<223> OTHER INFORMATION: synthetic

<400> SEQUENCE: 7
acataaaaaa ccggccttgg ccccgccggt tttttattat ttttcttcct ccgcatgttc 60
aatccgctcc ataatcgacg gatggctccc tctgaaaatt ttaacgagaa acggcgggtt 120
gacccggctc agtcccgtaa cggccaagtc ctgaaacgtc tcaatcgccg cttcccggtt 180
tccggtcagc tcaatgccgt aacggtcggc ggcgttttcc tgataccggg agacggcatt 240
cgtaatc 247

<210> SEQ ID NO 8
<211> LENGTH: 50
<212> TYPE: DNA
<213> ORGANISM: Artificial Sequence
<220> FEATURE:
<223> OTHER INFORMATION: synthetic

<400> SEQUENCE: 8
atatatgagt aaacttggtc tgacagaatt cctccatttt cttctgctat 50

<210> SEQ ID NO 9
<211> LENGTH: 35
<212> TYPE: DNA
<213> ORGANISM: Artificial Sequence
<220> FEATURE:
<223> OTHER INFORMATION: synthetic

<400> SEQUENCE: 9
tgcggccgcg aattcgatta cgaatgccgt ctccc 35

<210> SEQ ID NO 10
<211> LENGTH: 3290
<212> TYPE: DNA
<213> ORGANISM: Artificial Sequence
<220> FEATURE:
<223> OTHER INFORMATION: synthetic

<400> SEQUENCE: 10
gaattcgcgg ccgcacgcgt ccatggggat ccccgcgggt cgacctcgag agttacgcta 60
gggataacag ggtaatatag gagctccagt cggcttaaac cagttttcgc tggtgcgaaa 120
aaagagtgtc ttgtgacacc taaattcaaa atctatcggt cagatttata ccgatttgat 180
tttatatatt cttgaataac atacgccgag ttatcacata aaagcgggaa ccaatcataa 240
aatttaaact tcattgcata atccattaaa ctcttaaatt ctacgattcc ttgttcatca 300
ataaactcaa tcatttcttt aattaattta tatctatctg ttgttgtttt ctttaataat 360
tcattaacat ctacaccgcc ataaactatc atatcttctt tttgatattt aaatttatta 420
ggatcgtcca tgtgaagcat atatctcaca agacctttca cacttcctgc aatctgcgga 480
atagtcgcat tcaattcttc tgttaattat ttttatctgt tcataagatt tattaccctc 540
atacatcact agaatatgat aatgctcttt tttcatccta ccttctgtat cagtatccct 600
atcatgtaat ggagacacta caaattgaat gtgtaactct tttaaatact ctaaccactc 660
ggcttttgct gattctggat ataaaacaaa tgtccaatta cgtcctcttg aatttttctt 720
gttttcagtt tcttttatta cattttcgct catgatataa taacggtgct aatacactta 780
acaaaattta gtcatagata ggcagcatgc cagtgctgtc tatctttttt tgtttaaaat 840
gcaccgtatt cctcctttgc atattttttt attagaatac cggttgcatc tgatttgcta 900
atattatatt tttctttgat tctatttaat atctcatttt cttctgttgt aagtcttaaa 960
gtaacagcaa ctttttctc ttcttttcta tctacaacta tcactgtacc tcccaacatc 1020 tgttttttc actttaacat aaaaaacaac cttttaacat taaaaaccca atatttattt 1080
atttgtttgg acaatggaca ctggacacct agggggagg tcgtagtacc cccctatgtt 1140
ttctccccta aataacccca aaaatctaag aaaaaaagac ctcaaaaagg tctttaatta 1200
acatctcaaa tttcgcattt attccaattt cctttttgcg tgtgatgcga gctcatcggc 1260
tccgtcgata ctatgttata cgccaacttt caaaacaact ttgaaaaagc tgttttctgg 1320
tatttaaggt tttagaatgc aaggaacagt gaattggagt tcgtcttgtt ataattagct 1380
tcttggggta tctttaaata ctgtagaaaa gaggaaggaa ataataaatg gctaaaatga 1440
gaatatcacc ggaattgaaa aaactgatcg aaaaataccg ctgcgtaaaa gatacggaag 1500
gaatgtctcc tgctaaggta tataagctgg tgggagaaaa tgaaaaccta tatttaaaaa 1560
tgacggacag ccggtataaa gggaccacct atgatgtgga acgggaaaag gacatgatgc 1620
tatggctgga aggaaagctg cctgttccaa aggtcctgca ctttgaacgg catgatggct 1680
ggagcaatct gctcatgagt gaggccgatg gcgtcctttg ctcggaagag tatgaagatg 1740
aacaaagccc tgaaaagatt atcgagctgt atgcggagtg catcaggctc tttcactcca 1800
tcgacatatc ggattgtccc tatacgaata gcttagacag ccgcttagcc gaattggatt 1860
acttactgaa taacgatctg gccgatgtgg attgcgaaaa ctgggaagaa gacactccat 1920
ttaaagatcc gcgcgagctg tatgattttt taaagacgga aaagcccgaa gaggaacttg 1980

```
tcttttccca cggcgacctg ggagacagca acatctttgt gaaagatggc aaagtaagtg   2040

gctttattga tcttgggaga agcggcaggg cggacaagtg gtatgacatt gccttctgcg   2100

tccggtcgat cagggaggat atcggggaag aacagtatgt cgagctattt tttgacttac   2160

tggggatcaa gcctgattgg gagaaaataa aatattatat tttactggat gaattgtttt   2220

agtgactgca gtgagatctg gtaatgactc tctagcttga ggcatcaaat aaaacgaaag   2280

gctcagtcga aagactgggc ctttcgtttt atctgttgtt tgtcggtgaa cgctctcctg   2340

agtaggacaa atccgccgct ctagctaagc agaaggccat cctgacggat ggcctttttg   2400

cgtttctaca aactcttgtt aactctagag ctgcctgccg cgtttcggtg atgaagatct   2460

tcccgatgat taattaattc agaacgctcg gttgccgccg ggcgtttttt atgaagcttc   2520

gttgctggcg tttttccata ggctccgccc ccctgacgag catcacaaaa atcgacgctc   2580

aagtcagagg tggcgaaacc cgacaggact ataaagatac caggcgtttc cccctggaag   2640

ctccctcgtg cgctctcctg ttccgaccct gccgcttacc ggatacctgt ccgcctttct   2700

cccttcggga agcgtggcgc tttctcatag ctcacgctgt aggtatctca gttcggtgta   2760

ggtcgttcgc tccaagctgg gctgtgtgca cgaacccccc gttcagcccg accgctgcgc   2820

cttatccggt aactatcgtc ttgagtccaa cccggtaaga cacgacttat cgccactggc   2880

agcagccact ggtaacagga ttagcagagc gaggtatgta ggcggtgcta cagagttctt   2940

gaagtggtgg cctaactacg gctacactag aaggacagta tttggtatct gcgctctgct   3000

gaagccagtt accttcggaa aaagagttgg tagctcttga tccggcaaac aaaccaccgc   3060

tggtagcggt ggtttttttg tttgcaagca gcagattacg cgcagaaaaa aaggatctca   3120

agaagatcct ttgatctttt ctacggggtc tgacgctcag tggaacgaaa actcacgtta   3180

agggattttg gtcatgagat tatcaaaaag gatcttcacc tagatccttt taaattaaaa   3240

atgaagtttt aaatcaatct aaagtatata tgagtaaact tggtctgaca              3290
```

<210> SEQ ID NO 11
<211> LENGTH: 4204
<212> TYPE: DNA
<213> ORGANISM: Artificial Sequence
<220> FEATURE:
<223> OTHER INFORMATION: synthetic

<400> SEQUENCE: 11

```
gcggccgcac gcgtccatgg ggatccccgc gggtcgacct cgagagttac gctagggata     60

acagggtaat ataggagctc cagtcggctt aaaccagttt tcgctggtgc gaaaaaagag    120

tgtcttgtga cacctaaatt caaaatctat cggtcagatt tataccgatt tgattttata    180

tattcttgaa taacatacgc cgagttatca cataaaagcg ggaaccaatc ataaaattta    240

aacttcattg cataatccat taaactctta aattctacga ttccttgttc atcaataaac    300

tcaatcattt ctttaattaa tttatatcta tctgttgttg ttttctttaa taattcatta    360

acatctacac cgccataaac tatcatatct tctttttgat atttaaattt attaggatcg    420

tccatgtgaa gcatatatct cacaagacct ttcacacttc ctgcaatctg cggaatagtc    480

gcattcaatt cttctgttaa ttatttttat ctgttcataa gatttattac cctcatacat    540

cactagaata tgataatgct ctttttttcat cctaccttct gtatcagtat ccctatcatg    600

taatggagac actacaaatt gaatgtgtaa ctcttttaaa tactctaacc actcggcttt    660

tgctgattct ggatataaaa caaatgtcca attacgtcct cttgaatttt tcttgttttc    720

agtttctttt attacatttt cgctcatgat ataataacgg tgctaataca cttaacaaaa    780
```

```
tttagtcata gataggcagc atgccagtgc tgtctatctt tttttgttta aaatgcaccg    840
tattcctcct ttgcatattt ttttattaga ataccggttg catctgattt gctaatatta    900
tatttttctt tgattctatt taatatctca ttttcttctg ttgtaagtct taaagtaaca    960
gcaacttttt tctcttcttt tctatctaca actatcactg tacctcccaa catctgtttt   1020
tttcacttta acataaaaaa caacctttta acattaaaaa cccaatattt atttatttgt   1080
ttggacaatg gacactggac acctaggggg gaggtcgtag taccccccta tgttttctcc   1140
cctaaataac cccaaaaatc taagaaaaaa agacctcaaa aaggtcttta attaacatct   1200
caaatttcgc atttattcca atttcctttt tgcgtgtgat gcgagctcat cggctccgtc   1260
gatactatgt tatacgccaa ctttcaaaac aactttgaaa aagctgtttt ctggtattta   1320
aggttttaga atgcaaggaa cagtgaattg gagttcgtct tgttataatt agcttcttgg   1380
ggtatcttta aatactgtag aaaagaggaa ggaaataata aatggctaaa atgagaatat   1440
caccggaatt gaaaaaactg atcgaaaaat accgctgcgt aaaagatacg gaaggaatgt   1500
ctcctgctaa ggtatataag ctggtgggag aaaatgaaaa cctatattta aaaatgacgg   1560
acagccggta taaagggacc acctatgatg tggaacggga aaaggacatg atgctatggc   1620
tggaaggaaa gctgcctgtt ccaaaggtcc tgcactttga acggcatgat ggctggagca   1680
atctgctcat gagtgaggcc gatggcgtcc tttgctcgga agagtatgaa gatgaacaaa   1740
gccctgaaaa gattatcgag ctgtatgcgg agtgcatcag gctctttcac tccatcgaca   1800
tatcggattg tccctatacg aatagcttag acagccgctt agccgaattg gattacttac   1860
tgaataacga tctggccgat gtggattgcg aaaactggga agaagacact ccatttaaag   1920
atccgcgcga gctgtatgat tttttaaaga cggaaaagcc cgaagaggaa cttgtctttt   1980
cccacggcga cctgggagac agcaacatct ttgtgaaaga tggcaaagta agtggcttta   2040
ttgatcttgg gagaagcggc agggcggaca agtggtatga cattgccttc tgcgtccggt   2100
cgatcaggga ggatatcggg gaagaacagt atgtcgagct atttttgac ttactgggga   2160
tcaagcctga ttgggagaaa ataaaatatt atattttact ggatgaattg ttttagtgac   2220
tgcagtgaga tctggtaatg actctctagc ttgaggcatc aaataaaacg aaaggctcag   2280
tcgaaagact gggcctttcg ttttatctgt tgtttgtcgg tgaacgctct cctgagtagg   2340
acaaatccgc cgctctagct aagcagaagg ccatcctgac ggatggcctt tttgcgtttc   2400
tacaaactct tgttaactct agagctgcct gccgcgtttc ggtgatgaag atcttcccga   2460
tgattaatta attcagaacg ctcggttgcc gccgggcgtt ttttatgaag cttcgttgct   2520
ggcgtttttc cataggctcc gcccccctga cgagcatcac aaaaatcgac gctcaagtca   2580
gaggtggcga aacccgacag gactataaag ataccaggcg tttccccctg gaagctccct   2640
cgtgcgctct cctgttccga ccctgccgct taccggatac ctgtccgcct ttctcccttc   2700
gggaagcgtg gcgctttctc atagctcacg ctgtaggtat ctcagttcgg tgtaggtcgt   2760
tcgctccaag ctgggctgtg tgcacgaacc ccccgttcag cccgaccgct gcgccttatc   2820
cggtaactat cgtcttgagt ccaacccggt aagacacgac ttatcgccac tggcagcagc   2880
cactggtaac aggattagca gagcgaggta tgtaggcggt gctacagagt tcttgaagtg   2940
gtggcctaac tacggctaca ctagaaggac agtatttggt atctgcgctc tgctgaagcc   3000
agttaccttc ggaaaaagag ttggtagctc ttgatccggc aaacaaacca ccgctggtag   3060
cggtggtttt tttgtttgca agcagcagat tacgcgcaga aaaaaaggat ctcaagaaga   3120
```

tcctttgatc ttttctacgg ggtctgacgc tcagtggaac gaaaactcac gttaagggat 3180
tttggtcatg agattatcaa aaaggatctt cacctagatc cttttaaatt aaaaatgaag 3240
ttttaaatca atctaaagta tatatgagta aacttggtct gacagttacc aatgcttaat 3300
cagtgaggca cctatctcag cgatctgtct atttcgttca tccatagttg cctgactccc 3360
cgtcgtgtag ataactacga tacgggaggg cttaccatct ggccccagtg ctgcaatgat 3420
accgcgagac ccacgctcac cggctccaga tttatcagca ataaaccagc cagccggaag 3480
ggccgagcgc agaagtggtc ctgcaacttt atccgcctcc atccagtcta ttaattgttg 3540
ccgggaagct agagtaagta gttcgccagt taatagtttg cgcaacgttg ttgccattgc 3600
tacaggcatc gtggtgtcac gctcgtcgtt tggtatggct tcattcagct ccggttccca 3660
acgatcaagg cgagttacat gatcccccat gttgtgcaaa aaagcggtta gctccttcgg 3720
tcctccgatc gttgtcagaa gtaagttggc cgcagtgtta tcactcatgg ttatggcagc 3780
actgcataat tctcttactg tcatgccatc cgtaagatgc ttttctgtga ctggtgagta 3840
ctcaaccaag tcattctgag aatagtgtat gcggcgaccg agttgctctt gcccggcgtc 3900
aatacgggat aataccgcgc cacatagcag aactttaaaa gtgctcatca ttggaaaacg 3960
ttcttcgggg cgaaaactct caaggatctt accgctgttg agatccagtt cgatgtaacc 4020
cactcgtgca cccaactgat cttcagcatc ttttactttc accagcgttt ctgggtgagc 4080
aaaaacagga aggcaaaatg ccgcaaaaaa gggaataagg gcgacacgga aatgttgaat 4140
actcatactc ttcctttttc aatattattg aagcatttat cagggttatt gtctcatgga 4200
attc 4204

<210> SEQ ID NO 12
<211> LENGTH: 35
<212> TYPE: DNA
<213> ORGANISM: Artificial Sequence
<220> FEATURE:
<223> OTHER INFORMATION: synthetic

<400> SEQUENCE: 12
gggagacggc attcgtaatc gaattcgcgg ccgca 35

<210> SEQ ID NO 13
<211> LENGTH: 50
<212> TYPE: DNA
<213> ORGANISM: Artificial Sequence
<220> FEATURE:
<223> OTHER INFORMATION: synthetic

<400> SEQUENCE: 13
atagcagaag aaaatggagg aattctgtca gaccaagttt actcatatat 50

<210> SEQ ID NO 14
<211> LENGTH: 23
<212> TYPE: DNA
<213> ORGANISM: Artificial Sequence
<220> FEATURE:
<223> OTHER INFORMATION: synthetic

<400> SEQUENCE: 14
ccgactggag ctcctatatt acc 23

<210> SEQ ID NO 15
<211> LENGTH: 20
<212> TYPE: DNA
<213> ORGANISM: Artificial Sequence
<220> FEATURE:
<223> OTHER INFORMATION: synthetic

<400> SEQUENCE: 15
gctgtggcga tctgtattcc 20

<210> SEQ ID NO 16
<211> LENGTH: 22
<212> TYPE: DNA
<213> ORGANISM: Artificial Sequence
<220> FEATURE:
<223> OTHER INFORMATION: synthetic

<400> SEQUENCE: 16
gtcttttaag taagtctact ct 22

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
ccaaagcgat tttaagcgcg 20

<210> SEQ ID NO 18
<211> LENGTH: 20
<212> TYPE: DNA
<213> ORGANISM: Artificial Sequence
<220> FEATURE:
<223> OTHER INFORMATION: synthetic

<400> SEQUENCE: 18
cctggcacgt ggtaattctc 20

<210> SEQ ID NO 19
<211> LENGTH: 20
<212> TYPE: DNA
<213> ORGANISM: Artificial Sequence
<220> FEATURE:
<223> OTHER INFORMATION: synthetic

<400> SEQUENCE: 19
ggatttcctc aaatctgacg 20

<210> SEQ ID NO 20
<211> LENGTH: 21
<212> TYPE: DNA
<213> ORGANISM: Artificial Sequence
<220> FEATURE:
<223> OTHER INFORMATION: synthetic

<400> SEQUENCE: 20
gtagaaacgc gccaaattac g 21

<210> SEQ ID NO 21
<211> LENGTH: 20
<212> TYPE: DNA
<213> ORGANISM: Artificial Sequence
<220> FEATURE:
<223> OTHER INFORMATION: synthetic

<400> SEQUENCE: 21
gctggtggtt gctaaagtcg 20

<210> SEQ ID NO 22
<211> LENGTH: 20
<212> TYPE: DNA
<213> ORGANISM: Artificial Sequence
<220> FEATURE:
<223> OTHER INFORMATION: synthetic

<400> SEQUENCE: 22
ggacgcaacc ctcattcatc 20

<210> SEQ ID NO 23
<211> LENGTH: 20
<212> TYPE: DNA
<213> ORGANISM: Artificial Sequence
<220> FEATURE:
<223> OTHER INFORMATION: synthetic

<400> SEQUENCE: 23
caggcatccg atttgcaagg 20

<210> SEQ ID NO 24
<211> LENGTH: 19
<212> TYPE: DNA
<213> ORGANISM: Artificial Sequence
<220> FEATURE:
<223> OTHER INFORMATION: synthetic

<400> SEQUENCE: 24
gcaagcagca gattacgcg 19

<210> SEQ ID NO 25
<211> LENGTH: 8347
<212> TYPE: DNA
<213> ORGANISM: Artificial Sequence
<220> FEATURE:
<223> OTHER INFORMATION: synthetic

<400> SEQUENCE: 25
gaattcctcc attttcttct gctatcaaaa taacagactc gtgattttcc aaacgagctt 60
tcaaaaaagc ctctgcccct tgcaaatcgg atgcctgtct ataaaattcc cgatattggt 120
taaacagcgg cgcaatggcg gccgcatctg atgtctttgc ttggcgaatg ttcatcttat 180
ttcttcctcc ctctcaataa ttttttcatt ctatcccttt tctgtaaagt ttatttttca 240
gaatactttt atcatcatgc tttgaaaaaa tatcacgata atatccattg ttctcacgga 300
agcacacgca ggtcatttga acgaattttt tcgacaggaa tttgccggga ctcaggagca 360
tttaacctaa aaaagcatga catttcagca taatgaacat ttactcatgt ctattttcgt 420
tcttttctgt atgaaaatag ttatttcgag tctctacgga aatagcgaga gatgatatac 480
ctaaatagag ataaaatcat ctcaaaaaaa tgggtctact aaaatattat tccatctatt 540
acaataaatt cacagaatag tcttttaagt aagtctactc tgaatttttt taaaaggaga 600
gggtaactag tggccccaaa aaagaaacgc aaggttatgg ataaaaaata cagcattggt 660
ctggatatcg gaaccaacag cgttgggtgg gcagtaataa cagatgaata caaagtgccg 720
tcaaaaaaat ttaaggttct ggggaataca gatcgccaca gcataaaaaa gaatctgatt 780
ggggcattgc tgtttgattc gggtgagaca gctgaggcca cgcgtctgaa acgtacagca 840
agaagacgtt acacacgtcg taaaaatcgt atttgctact tacaggaaat tttttctaac 900
gaaatggcca aggtagatga tagtttcttc catcgtctcg aagaatcttt tctggttgag 960
gaagataaaa aacacgaacg tcaccctatc tttggcaata tcgtggatga agtggcctat 1020

```
catgaaaaat accctacgat ttatcatctt cgcaagaagt tggttgatag tacggacaaa   1080
gcggatctgc gtttaatcta tcttgcgtta gcgcacatga tcaaatttcg tggtcatttc   1140
ttaattgaag gtgatctgaa tcctgataac tctgatgtgg acaaattgtt tatacaatta   1200
gtgcaaacct ataatcagct gttcgaggaa aaccccatta atgcctctgg agttgatgcc   1260
aaagcgattt taagcgcgag actttctaag tcccggcgtc tggagaatct gatcgcccag   1320
ttaccagggg aaaagaaaaa tggtctgttt ggtaatctga ttgccctcag tctggggctt   1380
accccgaact tcaaatccaa ttttgacctg gctgaggacg caaagctgca gctgagcaaa   1440
gatacttatg atgatgacct cgacaatctg ctcgcccaga ttggtgacca atatgcggat   1500
ctgtttctgg cagcgaagaa tctttcggat gctatcttgc tgtcggatat tctgcgtgtt   1560
aataccgaaa tcaccaaagc gcctctgtct gcaagtatga tcaagagata cgacgagcac   1620
caccaggacc tgactcttct taaggcactg gtacgccaac agcttccgga gaaatacaaa   1680
gaaatattct tcgaccagtc caagaatggt tacgcgggct acatcgatgg tggtgcatca   1740
caggaagagt tctataaatt tattaaacca atccttgaga aaatggatgg cacggaagag   1800
ttacttgtta aacttaaccg cgaagacttg cttagaaagc aacgtacatt cgacaacggc   1860
tccatcccac accagattca tttaggtgaa cttcacgcca tcttgcgcag acaagaagat   1920
ttctatccct tcttaaaaga caatcgggag aaaatcgaga agatcctgac gttccgcatt   1980
ccctattatg tcggtcccct ggcacgtggt aattctcggt ttgcctggat gacgcgcaaa   2040
agtgaggaaa ccatcacccc ttggaacttt gaagaagtcg tggataaagg tgctagcgcg   2100
cagtctttta tagaaagaat gacgaacttc gataaaaact tgcccaacga aaaagtcctg   2160
cccaagcact ctcttttata tgagtacttt actgtgtaca acgaactgac taaagtgaaa   2220
tacgttacgg aaggtatgcg caaacctgcc tttcttagtg gcgagcagaa aaaagcaatt   2280
gtcgatcttc tctttaaaac gaatcgcaag gtaactgtaa aacagctgaa ggaagattat   2340
ttcaaaaaga tcgaatgctt tgattctgtc gagatctcgg gtgtcgaaga tcgtttcaac   2400
gcttccttag ggacctatca tgatttgctg aagataataa aagacaaaga ctttctcgac   2460
aatgaagaaa atgaagatat tctggaggat attgttttga ccttgacctt attcgaagat   2520
agagagatga tcgaggagcg cttaaaaacc tatgcccacc tgtttgatga caaagtcatg   2580
aagcaattaa agcgccgcag atatacgggg tggggccgct tgagccgcaa gttgattaac   2640
ggtattagag acaagcagag cggaaaaact atcctggatt tcctcaaatc tgacggattt   2700
gcgaaccgca attttatgca gcttatacat gatgattcgc ttacattcaa agaggatatt   2760
cagaaggctc aggtgtctgg gcaaggtgat tcactccacg aacatatagc aaatttggcc   2820
ggctctcctg cgattaagaa ggggatcctg caaacagtta aagttgtgga tgaacttgta   2880
aaagtaatgg gccgccacaa gccggagaat atcgtgatag aaatggcgcg cgagaatcaa   2940
acgacacaaa aaggtcaaaa gaactcaaga gagagaatga agcgcattga ggaggggata   3000
aaggaacttg gatctcaaat tctgaaagaa catccagttg aaaacactca gctgcaaaat   3060
gaaaaattgt acctgtacta cctgcagaat ggaagagaca tgtacgtgga tcaggaattg   3120
gatatcaata gactctcgga ctatgacgta gatcacattg tccctcagag cttcctcaag   3180
gatgattcta tagataataa agtacttacg agatcggaca aaaatcgcgg taaatcggat   3240
aacgtcccat cggaggaagt cgttaaaaag atgaaaaact attggcgtca actgctgaac   3300
gccaagctga tcacacagcg taagtttgat aatctgacta aagccgaacg cggtggtctt   3360
```

```
agtgaactcg ataaagcagg atttataaaa cggcagttag tagaaacgcg ccaaattacg   3420
aaacacgtgg ctcagatcct cgattctaga atgaatacaa agtacgatga aaacgataaa   3480
ctgatccgtg aagtaaaagt cattacctta aaatctaaac ttgtgtccga tttccgcaaa   3540
gattttcagt tttacaaggt ccgggaaatc aataactatc accatgcaca tgatgcatat   3600
ttaaatgcgg ttgtaggcac ggcccttatt aagaaatacc ctaaactcga aagtgagttt   3660
gtttatgggg attataaagt gtatgacgtt cgcaaaatga tcgcgaaatc agaacaggaa   3720
atcggtaagg ctaccgctaa atactttttt tattccaaca ttatgaattt ttttaagacc   3780
gaaataactc tcgcgaatgg tgaaatccgt aaacggcctc ttatagaaac caatggtgaa   3840
acgggagaaa tcgtttggga taaaggtcgt gactttgcca ccgttcgtaa agtcctctca   3900
atgccgcaag ttaacattgt caagaagacg gaagttcaaa cagggggatt ctccaaagaa   3960
tctatcctgc cgaagcgtaa cagtgataaa cttattgcca gaaaaaaaga ttgggatcca   4020
aaaaaatacg gaggctttga ttcccctacc gtcgcgtata gtgtgctggt ggttgctaaa   4080
gtcgagaaag ggaaaagcaa gaaattgaaa tcagttaaag aactgctggg tattacaatt   4140
atggaaagat cgtcctttga gaaaaatccg atcgactttt tagaggccaa ggggtataag   4200
gaagtgaaaa aagatctcat catcaaatta ccgaagtata gtctttttga gctggaaaac   4260
ggcagaaaaa gaatgctggc ctccgcgggc gagttacaga agggaaatga gctggcgctg   4320
ccttccaaat atgttaattt tctgtacctt gccagtcatt atgagaaact gaagggcagc   4380
cccgaagata acgaacagaa acaattattc gtggaacagc ataagcacta tttagatgaa   4440
attatagagc aaattagtga attttctaag cgcgttatcc tcgcggatgc taatttagac   4500
aaagtactgt cagcttataa taaacatcgg gataagccga ttagagaaca ggccgaaaat   4560
atcattcatt tgtttacctt aaccaacctt ggagcaccag ctgccttcaa atatttcgat   4620
accacaattg atcgtaaacg gtatacaagt acaaaagaag tcttggacgc aaccctcatt   4680
catcaatcta ttactggatt atatgagaca cgcattgatc tttcacagct gggcggagac   4740
aagaagaaaa aactgaaact gcaccatcat caccatcatc atcaccatca ttgataactc   4800
gagaaagctt acataaaaaa ccggccttgg ccccgccggt tttttattat tttcttcct    4860
ccgcatgttc aatccgctcc ataatcgacg gatggctccc tctgaaaatt ttaacgagaa   4920
acggcgggtt gacccggctc agtcccgtaa cggccaagtc ctgaaacgtc tcaatcgccg   4980
cttcccggtt tccggtcagc tcaatgccgt aacggtcggc ggcgttttcc tgataccggg   5040
agacggcatt cgtaatcgaa ttcgcggccg cacgcgtcca tggggatccc cgcgggtcga   5100
cctcgagagt tacgctaggg ataacagggt aatataggag ctccagtcgg cttaaaccag   5160
ttttcgctgg tgcgaaaaaa gagtgtcttg tgacacctaa attcaaaatc tatcggtcag   5220
atttataccg atttgatttt atatattctt gaataacata cgccgagtta tcacataaaa   5280
gcgggaacca atcataaaat ttaaacttca ttgcataatc cattaaactc ttaaattcta   5340
cgattccttg ttcatcaata aactcaatca tttctttaat taatttatat ctatctgttg   5400
ttgttttctt taataattca ttaacatcta caccgccata aactatcata tcttcttttt   5460
gatatttaaa tttattagga tcgtccatgt gaagcatata tctcacaaga cctttcacac   5520
ttcctgcaat ctgcggaata gtcgcattca attcttctgt taattatttt tatctgttca   5580
taagatttat taccctcata catcactaga atatgataat gctctttttt catcctacct   5640
tctgtatcag tatccctatc atgtaatgga gacactacaa attgaatgtg taactctttt   5700
aaatactcta accactcggc ttttgctgat tctggatata aaacaaatgt ccaattacgt   5760
```

cctcttgaat ttttcttgtt ttcagtttct tttattacat tttcgctcat gatataataa 5820
cggtgctaat acacttaaca aaatttagtc atagataggc agcatgccag tgctgtctat 5880
cttttttgt ttaaaatgca ccgtattcct cctttgcata tttttttatt agaataccgg 5940
ttgcatctga tttgctaata ttatattttt ctttgattct atttaatatc tcattttctt 6000
ctgttgtaag tcttaaagta acagcaactt ttttctcttc ttttctatct acaactatca 6060
ctgtacctcc caacatctgt ttttttcact ttaacataaa aaacaacctt ttaacattaa 6120
aaacccaata tttatttatt tgtttggaca atggacactg gacacctagg ggggaggtcg 6180
tagtaccccc ctatgttttc tcccctaaat aaccccaaaa atctaagaaa aaaagacctc 6240
aaaaaggtct ttaattaaca tctcaaattt cgcatttatt ccaatttcct ttttgcgtgt 6300
gatgcgagct catcggctcc gtcgatacta tgttatacgc caactttcaa aacaactttg 6360
aaaaagctgt tttctggtat ttaaggtttt agaatgcaag gaacagtgaa ttggagttcg 6420
tcttgttata attagcttct tggggtatct ttaaatactg tagaaaagag gaaggaaata 6480
ataaatggct aaaatgagaa tatcaccgga attgaaaaaa ctgatcgaaa aataccgctg 6540
cgtaaaagat acggaaggaa tgtctcctgc taaggtatat aagctggtgg gagaaaatga 6600
aaacctatat ttaaaaatga cggacagccg gtataaaggg accacctatg atgtggaacg 6660
ggaaaaggac atgatgctat ggctggaagg aaagctgcct gttccaaagg tcctgcactt 6720
tgaacggcat gatggctgga gcaatctgct catgagtgag gccgatggcg tcctttgctc 6780
ggaagagtat gaagatgaac aaagccctga aaagattatc gagctgtatg cggagtgcat 6840
caggctcttt cactccatcg acatatcgga ttgtccctat acgaatagct tagacagccg 6900
cttagccgaa ttggattact tactgaataa cgatctggcc gatgtggatt gcgaaaactg 6960
ggaagaagac actccattta aagatccgcg cgagctgtat gattttttaa agacggaaaa 7020
gcccgaagag gaacttgtct ttcccacgg cgacctggga gacagcaaca tctttgtgaa 7080
agatggcaaa gtaagtggct ttattgatct tgggagaagc ggcagggcgg acaagtggta 7140
tgacattgcc ttctgcgtcc ggtcgatcag ggaggatatc ggggaagaac agtatgtcga 7200
gctatttttt gacttactgg ggatcaagcc tgattgggag aaaataaaat attatatttt 7260
actggatgaa ttgttttagt gactgcagtg agatctggta atgactctct agcttgaggc 7320
atcaaataaa acgaaaggct cagtcgaaag actgggcctt tcgttttatc tgttgtttgt 7380
cggtgaacgc tctcctgagt aggacaaatc cgccgctcta gctaagcaga aggccatcct 7440
gacggatggc ctttttgcgt ttctacaaac tcttgttaac tctagagctg cctgccgcgt 7500
ttcggtgatg aagatcttcc cgatgattaa ttaattcaga acgctcggtt gccgccgggc 7560
gtttttatg aagcttcgtt gctggcgttt ttccataggc tccgcccccc tgacgagcat 7620
cacaaaaatc gacgctcaag tcagaggtgg cgaaacccga caggactata aagataccag 7680
gcgtttcccc ctggaagctc cctcgtgcgc tctcctgttc cgaccctgcc gcttaccgga 7740
tacctgtccg cctttctccc ttcgggaagc gtggcgcttt ctcatagctc acgctgtagg 7800
tatctcagtt cggtgtaggt cgttcgctcc aagctgggct gtgtgcacga accccccgtt 7860
cagcccgacc gctgcgcctt atccggtaac tatcgtcttg agtccaaccc ggtaagacac 7920
gacttatcgc cactggcagc agccactggt aacaggatta gcagagcgag gtatgtaggc 7980
ggtgctacag agttcttgaa gtggtggcct aactacggct acactagaag gacagtattt 8040
ggtatctgcg ctctgctgaa gccagttacc ttcggaaaaa gagttggtag ctcttgatcc 8100
ggcaaacaaa ccaccgctgg tagcggtggt ttttttgttt gcaagcagca gattacgcgc 8160
agaaaaaaag gatctcaaga agatcctttg atcttttcta cggggtctga cgctcagtgg 8220
aacgaaaact cacgttaagg gattttggtc atgagattat caaaaaggat cttcacctag 8280
atccttttaa attaaaaatg aagttttaaa tcaatctaaa gtatatatga gtaaacttgg 8340
tctgaca 8347

<210> SEQ ID NO 26
<211> LENGTH: 9724
<212> TYPE: DNA
<213> ORGANISM: Artificial Sequence
<220> FEATURE:
<223> OTHER INFORMATION: synthetic

<400> SEQUENCE: 26
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180
aaaagttgtt gactttatct acaaggtgtg gcataatgtg tggactcgac ttcgaataca 240
tccagtttta gagctagaaa tagcaagtta aaataaggct agtccgttat caacttgaaa 300
aagtggcacc gagtcggtgc gactcctgtt gatagatcca gtaatgacct cagaactcca 360
tctggatttg ttcagaacgc tcggttgccg ccgggcgttt tttattggtg agaatgtcga 420
cctcgagagt tacgctaggg ataacagggt aatataggag ctccagtcgg cttaaaccag 480
ttttcgctgg tgcgaaaaaa gagtgtcttg tgacacctaa attcaaaatc tatcggtcag 540
atttataccg atttgatttt atatattctt gaataacata cgccgagtta tcacataaaa 600
gcgggaacca atcataaaat ttaaacttca ttgcataatc cattaaactc ttaaattcta 660
cgattccttg ttcatcaata aactcaatca tttctttaat taatttatat ctatctgttg 720
ttgttttctt taataattca ttaacatcta caccgccata aactatcata tcttcttttt 780
gatatttaaa tttattagga tcgtccatgt gaagcatata tctcacaaga cctttcacac 840
ttcctgcaat ctgcggaata gtcgcattca attcttctgt taattatttt tatctgttca 900
taagatttat taccctcata catcactaga atatgataat gctctttttt catcctacct 960
tctgtatcag tatccctatc atgtaatgga gacactacaa attgaatgtg taactctttt 1020
aaatactcta accactcggc ttttgctgat tctggatata aaacaaatgt ccaattacgt 1080
cctcttgaat ttttcttgtt ttcagtttct tttattacat tttcgctcat gatataataa 1140
cggtgctaat acacttaaca aaatttagtc atagataggc agcatgccag tgctgtctat 1200 cttttttttgt ttaaaatgca ccgtattcct cctttgcata tttttttatt agaataccgg 1260
ttgcatctga tttgctaata ttatattttt ctttgattct atttaatatc tcattttctt 1320
ctgttgtaag tcttaaagta acagcaactt ttttctcttc ttttctatct acaactatca 1380
ctgtacctcc caacatctgt ttttttcact ttaacataaa aaacaacctt ttaacattaa 1440
aaacccaata tttatttatt tgtttggaca atggacactg gacacctagg ggggaggtcg 1500
tagtaccccc ctatgttttc tcccctaaat aaccccaaaa atctaagaaa aaaagacctc 1560
aaaaaggtct ttaattaaca tctcaaattt cgcatttatt ccaatttcct ttttgcgtgt 1620
gatgcgagct catcggctcc gtcgatacta tgttatacgc caactttcaa aacaactttg 1680
aaaaagctgt tttctggtat ttaaggtttt agaatgcaag gaacagtgaa ttggagttcg 1740
tcttgttata attagcttct tggggtatct ttaaatactg tagaaaagag gaaggaaata 1800
ataaatggct aaaatgagaa tatcaccgga attgaaaaaa ctgatcgaaa aataccgctg 1860
cgtaaaagat acggaaggaa tgtctcctgc taaggtatat aagctggtgg gagaaaatga 1920
aaacctatat ttaaaaatga cggacagccg gtataaaggg accacctatg atgtggaacg 1980
ggaaaaggac atgatgctat ggctggaagg aaagctgcct gttccaaagg tcctgcactt 2040
tgaacggcat gatggctgga gcaatctgct catgagtgag gccgatggcg tcctttgctc 2100
ggaagagtat gaagatgaac aaagccctga aaagattatc gagctgtatg cggagtgcat 2160
caggctcttt cactccatcg acatatcgga ttgtccctat acgaatagct tagacagccg 2220
cttagccgaa ttggattact tactgaataa cgatctggcc gatgtggatt gcgaaaactg 2280
ggaagaagac actccattta aagatccgcg cgagctgtat gatttttaa agacggaaaa 2340
gcccgaagag gaacttgtct tttcccacgg cgacctggga gacagcaaca tctttgtgaa 2400
agatggcaaa gtaagtggct ttattgatct tgggagaagc ggcagggcgg acaagtggta 2460
tgacattgcc ttctgcgtcc ggtcgatcag ggaggatatc ggggaagaac agtatgtcga 2520
gctatttttt gacttactgg ggatcaagcc tgattgggag aaaataaaat attatatttt 2580
actggatgaa ttgttttagt gactgcagtg agatctggta atgactctct agcttgaggc 2640
atcaaataaa acgaaaggct cagtcgaaag actgggcctt tcgttttatc tgttgtttgt 2700
cggtgaacgc tctcctgagt aggacaaatc cgccgctcta gctaagcaga aggccatcct 2760
gacggatggc ctttttgcgt ttctacaaac tcttgttaac tctagagctg cctgccgcgt 2820
ttcggtgatg aagatcttcc cgatgattaa ttaattcaga acgctcggtt gccgccgggc 2880
gtttttatg aagcttcgtt gctggcgttt ttccataggc tccgcccccc tgacgagcat 2940
cacaaaaatc gacgctcaag tcagaggtgg cgaaacccga caggactata aagataccag 3000
gcgtttcccc ctggaagctc cctcgtgcgc tctcctgttc cgaccctgcc gcttaccgga 3060
tacctgtccg cctttctccc ttcgggaagc gtggcgcttt ctcatagctc acgctgtagg 3120
tatctcagtt cggtgtaggt cgttcgctcc aagctgggct gtgtgcacga accccccgtt 3180
cagcccgacc gctgcgcctt atccggtaac tatcgtcttg agtccaaccc ggtaagacac 3240
gacttatcgc cactggcagc agccactggt aacaggatta gcagagcgag gtatgtaggc 3300
ggtgctacag agttcttgaa gtggtggcct aactacggct acactagaag gacagtattt 3360
ggtatctgcg ctctgctgaa gccagttacc ttcggaaaaa gagttggtag ctcttgatcc 3420
ggcaaacaaa ccaccgctgg tagcggtggt ttttttgttt gcaagcagca gattacgcgc 3480
agaaaaaaag gatctcaaga agatcctttg atcttttcta cggggtctga cgctcagtgg 3540
aacgaaaact cacgttaagg gattttggtc atgagattat caaaaaggat cttcacctag 3600
atccttttaa attaaaaatg aagttttaaa tcaatctaaa gtatatatga gtaaacttgg 3660
tctgacaaat ggttctttcc cctgtcctaa acaaaaaacc cgctttattg aaaaagcggg 3720
gctgttttac agacaggtca aataaacgtt tgaaaatgtt catttcaaaa cgcgcggaac 3780
ctccatcttc tcccatccag actatactgt cggcttcgga atcgcaccga atcctgccca 3840
taaaaaggct cgcgggctta gagcgcttgc tcatcaccgc cggtagggaa tttcaccctg 3900
ccccgaagat tgatcttatt tatttttaat actgatatta ttataaatta attgtgaaaa 3960
aatgtacagg tgcaaagctt attgcgctgt tttgggacat cctgcacgat atttcggtaa 4020
actcactttt tccgcatact aaaaaccgca cattcacagt tatttcattt ttaattttcg 4080
tctttccgcg tgaaactcat tgacactctt tatggaatat ggtaaattat cagatattta 4140

```
tgacgcttat ttaggaggaa atcttacaca gaagctgcgg aacctgaaaa gaattccttt   4200

caggttccgt ttttttagg aattctccct gatctcaagc atctggcggg gataaatccg   4260

ctctcctttc aaatcgttcc attctttgag gcgctgtaca gttacgccca tttttcggc    4320

gatatgatga agcgtatccc ctttccgcac tacatatgta ccggtcttcg attcatcgtc   4380

atgaaggcgg agtgtttggc cggccttgag atttgaatgt ttcaacccgt ttattctcat   4440

gatctcctcg atggatatac cgctatcctt gctgattctc cagagcgtgt cccctttttg   4500

aacggtcacc gcaccgctca ttgtcccggc gttttgataa acgtggatag aattttgccg   4560

gaacgcctcc tcacgaagca ccgtcagcgg attgattgca tatcttttat cttcagtcca   4620

tgaaccgtga tgcatttcaa aatgcaggtg ggttccggtc gatattcgaa ttcctccatt   4680

ttcttctgct atcaaaataa cagactcgtg attttccaaa cgagctttca aaaaagcctc   4740

tgccccttgc aaatcggatg cctgtctata aaattcccga tattggttaa acagcggcgc   4800

aatggcggcc gcatctgatg tctttgcttg gcgaatgttc atcttatttc ttcctccctc   4860

tcaataattt tttcattcta tccctttct gtaaagttta tttttcagaa tacttttatc    4920

atcatgcttt gaaaaaatat cacgataata tccattgttc tcacggaagc acacgcaggt   4980

catttgaacg aatttttcg acaggaattt gccgggactc aggagcattt aacctaaaaa    5040

agcatgacat ttcagcataa tgaacattta ctcatgtcta ttttcgttct tttctgtatg   5100

aaaatagtta tttcgagtct ctacggaaat agcgagagat gatatacta aatagagata    5160

aaatcatctc aaaaaaatgg gtctactaaa atattattcc atctattaca ataaattcac   5220

agaatagtct tttaagtaag tctactctga attttttaa aaggagaggg taactagtgg    5280

ccccaaaaaa gaaacgcaag gttatggata aaaaatacag cattggtctg gatatcggaa   5340

ccaacagcgt tgggtgggca gtaataacag atgaatacaa agtgccgtca aaaaaattta   5400

aggttctggg gaatacagat cgccacagca taaaaaagaa tctgattggg gcattgctgt   5460

ttgattcggg tgagacagct gaggccacgc gtctgaaacg tacagcaaga agacgttaca   5520

cacgtcgtaa aaatcgtatt tgctacttac aggaaatttt ttctaacgaa atggccaagg   5580

tagatgatag tttcttccat cgtctcgaag aatcttttct ggttgaggaa gataaaaaac   5640

acgaacgtca ccctatcttt ggcaatatcg tggatgaagt ggcctatcat gaaaaatacc   5700

ctacgattta tcatcttcgc aagaagttgg ttgatagtac ggacaaagcg gatctgcgtt   5760

taatctatct tgcgttagcg cacatgatca aatttcgtgg tcatttctta attgaaggtg   5820

atctgaatcc tgataactct gatgtggaca aattgtttat acaattagtg caaacctata   5880

atcagctgtt cgaggaaaac cccattaatg cctctggagt tgatgccaaa gcgattttaa   5940

gcgcgagact ttctaagtcc cggcgtctgg agaatctgat cgcccagtta ccaggggaaa   6000

agaaaaatgg tctgtttggt aatctgattg ccctcagtct ggggcttacc ccgaacttca   6060

aatccaattt tgacctggct gaggacgcaa agctgcagct gagcaaagat acttatgatg   6120

atgacctcga caatctgctc gcccagattg gtgaccaata tgcggatctg tttctggcag   6180

cgaagaatct ttcggatgct atcttgctgt cggatattct gcgtgttaat accgaaatca   6240

ccaaagcgcc tctgtctgca agtatgatca agagatacga cgagcaccac caggacctga   6300

ctcttcttaa ggcactggta cgccaacagc ttccggagaa atacaaagaa atattcttcg   6360

accagtccaa gaatggttac gcgggctaca tcgatggtgg tgcatcacag gaagagttct   6420

ataaatttat taaaccaatc cttgagaaaa tggatggcac ggaagagtta cttgttaaac   6480

ttaaccgcga agacttgctt agaaagcaac gtacattcga caacggctcc atcccacacc   6540
```

agattcattt aggtgaactt cacgccatct tgcgcagaca agaagatttc tatcccttct 6600
taaaagacaa tcgggagaaa atcgagaaga tcctgacgtt ccgcattccc tattatgtcg 6660
gtcccctggc acgtggtaat tctcggtttg cctggatgac gcgcaaaagt gaggaaacca 6720
tcacccccttg gaactttgaa gaagtcgtgg ataaaggtgc tagcgcgcag tcttttatag 6780
aaagaatgac gaacttcgat aaaaacttgc ccaacgaaaa agtcctgccc aagcactctc 6840
ttttatatga gtactttact gtgtacaacg aactgactaa agtgaaatac gttacggaag 6900
gtatgcgcaa acctgccttt cttagtggcg agcagaaaaa agcaattgtc gatcttctct 6960
ttaaaacgaa tcgcaaggta actgtaaaac agctgaagga agattatttc aaaaagatcg 7020
aatgctttga ttctgtcgag atctcgggtg tcgaagatcg tttcaacgct tccttaggga 7080
cctatcatga tttgctgaag ataataaaag acaaagactt tctcgacaat gaagaaaatg 7140
aagatattct ggaggatatt gttttgacct tgaccttatt cgaagataga gagatgatcg 7200
aggagcgctt aaaaacctat gcccacctgt ttgatgacaa agtcatgaag caattaaagc 7260
gccgcagata tacggggtgg ggccgcttga gccgcaagtt gattaacggt attagagaca 7320
agcagagcgg aaaaactatc ctggatttcc tcaaatctga cggatttgcg aaccgcaatt 7380
ttatgcagct tatacatgat gattcgctta cattcaaaga ggatattcag aaggctcagg 7440
tgtctgggca aggtgattca ctccacgaac atatagcaaa tttggccggc tctcctgcga 7500
ttaagaaggg gatcctgcaa acagttaaag ttgtggatga acttgtaaaa gtaatgggcc 7560
gccacaagcc ggagaatatc gtgatagaaa tggcgcgcga gaatcaaacg acacaaaaag 7620
gtcaaaagaa ctcaagagag agaatgaagc gcattgagga ggggataaag gaacttggat 7680
ctcaaattct gaaagaacat ccagttgaaa acactcagct gcaaaatgaa aaattgtacc 7740
tgtactacct gcagaatgga agagacatgt acgtggatca ggaattggat atcaatagac 7800
tctcggacta tgacgtagat cacattgtcc ctcagagctt cctcaaggat gattctatag 7860
ataataaagt acttacgaga tcggacaaaa atcgcggtaa atcggataac gtcccatcgg 7920
aggaagtcgt taaaaagatg aaaaactatt ggcgtcaact gctgaacgcc aagctgatca 7980
cacagcgtaa gtttgataat ctgactaaag ccgaacgcgg tggtcttagt gaactcgata 8040
aagcaggatt tataaaacgg cagttagtag aaacgcgcca aattacgaaa cacgtggctc 8100
agatcctcga ttctagaatg aatacaaagt acgatgaaaa cgataaactg atccgtgaag 8160
taaaagtcat taccttaaaa tctaaacttg tgtccgattt ccgcaaagat tttcagtttt 8220
acaaggtccg ggaaatcaat aactatcacc atgcacatga tgcatattta aatgcggttg 8280
taggcacggc ccttattaag aaataccta aactcgaaag tgagtttgtt tatggggatt 8340
ataaagtgta tgacgttcgc aaaatgatcg cgaaatcaga acaggaaatc ggtaaggcta 8400
ccgctaaata ctttttttat tccaacatta tgaatttttt taagaccgaa ataactctcg 8460
cgaatggtga aatccgtaaa cggcctctta tagaaaccaa tggtgaaacg ggagaaatcg 8520
tttgggataa aggtcgtgac tttgccaccg ttcgtaaagt cctctcaatg ccgcaagtta 8580
acattgtcaa gaagacggaa gttcaaacag ggggattctc caaagaatct atcctgccga 8640
agcgtaacag tgataaactt attgccagaa aaaaagattg ggatccaaaa aaatacggag 8700
gctttgattc ccctaccgtc gcgtatagtg tgctggtggt tgctaaagtc gagaaaggga 8760
aaagcaagaa attgaaatca gttaaagaac tgctgggtat tacaattatg gaaagatcgt 8820
cctttgagaa aaatccgatc gactttttag aggccaaggg gtataaggaa gtgaaaaaag 8880

```
atctcatcat caaattaccg aagtatagtc tttttgagct ggaaaacggc agaaaaagaa   8940
tgctggcctc cgcgggcgag ttacagaagg gaaatgagct ggcgctgcct tccaaatatg   9000
ttaattttct gtaccttgcc agtcattatg agaaactgaa gggcagcccc gaagataacg   9060
aacagaaaca attattcgtg gaacagcata agcactattt agatgaaatt atagagcaaa   9120
ttagtgaatt ttctaagcgc gttatcctcg cggatgctaa tttagacaaa gtactgtcag   9180
cttataataa acatcgggat aagccgatta gagaacaggc cgaaaatatc attcatttgt   9240
ttaccttaac caaccttgga gcaccagctg ccttcaaata tttcgatacc acaattgatc   9300
gtaaacggta tacaagtaca aaagaagtct tggacgcaac cctcattcat caatctatta   9360
ctggattata tgagacacgc attgatcttt cacagctggg cggagacaag aagaaaaaac   9420
tgaaactgca ccatcatcac catcatcatc accatcattg ataactcgag aaagcttaca   9480
taaaaaaccg gccttggccc cgccggtttt ttattatttt tcttcctccg catgttcaat   9540
ccgctccata atcgacggat ggctccctct gaaaatttta acgagaaacg gcgggttgac   9600
ccggctcagt cccgtaacgg ccaagtcctg aaacgtctca atcgccgctt cccggtttcc   9660
ggtcagctca atgccgtaac ggtcggcggc gttttcctga taccgggaga cggcattcgt   9720
aatc                                                                9724
```

<210> SEQ ID NO 27
<211> LENGTH: 9724
<212> TYPE: DNA
<213> ORGANISM: Artificial Sequence
<220> FEATURE:
<223> OTHER INFORMATION: synthetic

<400> SEQUENCE: 27

```
gggtgaagtg gtcaagacct cactaggcac cttaaaaata gcgcaccctg aagaagattt     60
atttgaggta gcccttgcct acctagcttc caagaaagat atcctaacag cacaagagcg    120
gaaagatgtt ttgttctaca tccagaacaa cctctgctaa aattcctgaa aaattttgca    180
aaaagttgtt gactttatct acaaggtgtg gcataatgtg tggagatgcc atcagttcct    240
catagtttta gagctagaaa tagcaagtta aaataaggct agtccgttat caacttgaaa    300
aagtggcacc gagtcggtgc gactcctgtt gatagatcca gtaatgacct cagaactcca    360
tctggatttg ttcagaacgc tcggttgccg ccgggcgttt tttattggtg agaatgtcga    420
cctcgagagt tacgctaggg ataacagggt aatataggag ctccagtcgg cttaaaccag    480
ttttcgctgg tgcgaaaaaa gagtgtcttg tgacacctaa attcaaaatc tatcggtcag    540
atttataccg atttgatttt atatattctt gaataacata cgccgagtta tcacataaaa    600
gcgggaacca atcataaaat ttaaacttca ttgcataatc cattaaactc ttaaattcta    660
cgattccttg ttcatcaata aactcaatca tttctttaat taatttatat ctatctgttg    720
ttgttttctt taataattca ttaacatcta caccgccata aactatcata tcttcttttt    780
gatatttaaa tttattagga tcgtccatgt gaagcatata tctcacaaga cctttcacac    840
ttcctgcaat ctgcggaata gtcgcattca attcttctgt taattatttt tatctgttca    900
taagatttat taccctcata catcactaga atatgataat gctctttttt catcctacct    960
tctgtatcag tatccctatc atgtaatgga gacactacaa attgaatgtg taactctttt   1020
aaatactcta accactcggc ttttgctgat tctggatata aaacaaatgt ccaattacgt   1080
cctcttgaat ttttcttgtt ttcagtttct tttattacat tttcgctcat gatataataa   1140
cggtgctaat acacttaaca aaatttagtc atagataggc agcatgccag tgctgtctat   1200
```

```
ctttttttgt ttaaaatgca ccgtattcct cctttgcata ttttttttatt agaataccgg   1260
ttgcatctga tttgctaata ttatattttt ctttgattct atttaatatc tcattttctt   1320
ctgttgtaag tcttaaagta acagcaactt ttttctcttc ttttctatct acaactatca   1380
ctgtacctcc caacatctgt ttttttcact ttaacataaa aaacaacctt ttaacattaa   1440
aaacccaata tttatttatt tgtttggaca atggacactg gacacctagg ggggaggtcg   1500
tagtaccccc ctatgttttc tcccctaaat aaccccaaaa atctaagaaa aaaagacctc   1560
aaaaaggtct ttaattaaca tctcaaattt cgcatttatt ccaatttcct ttttgcgtgt   1620
gatgcgagct catcggctcc gtcgatacta tgttatacgc caactttcaa aacaactttg   1680
aaaaagctgt tttctggtat ttaaggtttt agaatgcaag gaacagtgaa ttggagttcg   1740
tcttgttata attagcttct tggggtatct ttaaatactg tagaaaagag gaaggaaata   1800
ataaatggct aaaatgagaa tatcaccgga attgaaaaaa ctgatcgaaa aataccgctg   1860
cgtaaaagat acggaaggaa tgtctcctgc taaggtatat aagctggtgg gagaaaatga   1920
aaacctatat ttaaaaatga cggacagccg gtataaaggg accacctatg atgtggaacg   1980
ggaaaaggac atgatgctat ggctggaagg aaagctgcct gttccaaagg tcctgcactt   2040
tgaacggcat gatggctgga gcaatctgct catgagtgag gccgatggcg tcctttgctc   2100
ggaagagtat gaagatgaac aaagccctga aaagattatc gagctgtatg cggagtgcat   2160
caggctcttt cactccatcg acatatcgga ttgtccctat acgaatagct tagacagccg   2220
cttagccgaa ttggattact tactgaataa cgatctggcc gatgtggatt gcgaaaactg   2280
ggaagaagac actccattta aagatccgcg cgagctgtat gatttttaa agacggaaaa   2340
gcccgaagag gaacttgtct ttcccacgg cgacctggga gacagcaaca tctttgtgaa   2400
agatggcaaa gtaagtggct ttattgatct tgggagaagc ggcagggcgg acaagtggta   2460
tgacattgcc ttctgcgtcc ggtcgatcag ggaggatatc ggggaagaac agtatgtcga   2520
gctatttttt gacttactgg ggatcaagcc tgattgggag aaaataaaat attatatttt   2580
actggatgaa ttgttttagt gactgcagtg agatctggta atgactctct agcttgaggc   2640
atcaaataaa acgaaaggct cagtcgaaag actgggcctt tcgttttatc tgttgtttgt   2700
cggtgaacgc tctcctgagt aggacaaatc cgccgctcta gctaagcaga aggccatcct   2760
gacggatggc ctttttgcgt ttctacaaac tcttgttaac tctagagctg cctgccgcgt   2820
ttcggtgatg aagatcttcc cgatgattaa ttaattcaga acgctcggtt gccgccgggc   2880
gtttttatg aagcttcgtt gctggcgttt ttccataggc tccgcccccc tgacgagcat   2940
cacaaaaatc gacgctcaag tcagaggtgg cgaaacccga caggactata aagataccag   3000
gcgtttcccc ctggaagctc cctcgtgcgc tctcctgttc cgaccctgcc gcttaccgga   3060
tacctgtccg cctttctccc ttcgggaagc gtggcgcttt ctcatagctc acgctgtagg   3120
tatctcagtt cggtgtaggt cgttcgctcc aagctgggct gtgtgcacga accccccgtt   3180
cagcccgacc gctgcgcctt atccggtaac tatcgtcttg agtccaaccc ggtaagacac   3240
gacttatcgc cactggcagc agccactggt aacaggatta gcagagcgag gtatgtaggc   3300
ggtgctacag agttcttgaa gtggtggcct aactacggct acactagaag gacagtattt   3360
ggtatctgcg ctctgctgaa gccagttacc ttcggaaaaa gagttggtag ctcttgatcc   3420
ggcaaacaaa ccaccgctgg tagcggtggt ttttttgttt gcaagcagca gattacgcgc   3480
agaaaaaaag gatctcaaga agatcctttg atcttttcta cggggtctga cgctcagtgg   3540
```

```
aacgaaaact cacgttaagg gattttggtc atgagattat caaaaaggat cttcacctag   3600
atccttttaa attaaaaatg aagttttaaa tcaatctaaa gtatatatga gtaaacttgg   3660
tctgacattg atattcagca ccctgcgcat ttcgaccggg agaacgactc tgccgagctc   3720
atcgattctc cggacaatcc cggtattttt cacgtttgaa aagcctcctt ttctcctttc   3780
tttattgact tttgtcaaca tctttataat aaaagagatc ttcaaatttt ttgttgaaat   3840
actgaatcat ctttccgatc acaagttgtc cgggcctcct ttcgccattt aaaactctgc   3900
tgagtgtcgc cggggatacg ccgatttcaa tggcaagctg atttaaggag agattgtgtt   3960
caatcatgta ctggagaaca aaatctcttt tgatatgaat cttttttacc atgattactc   4020
ccctttctaa tctcttatgt ttctttttat ctacattgaa catatacgat ttgttaactt   4080
ttgtcaatac ttttaccatc catatgtttc ctataggcaa tattcgtact aaaatatttt   4140
ataataagag attgcgaggt tttggccata cttctccgcg gcacactctc ctctctatca   4200
ttttcgtctg tttacgatcc tgctgttatt ttatccctta tgttaacttt tgtcaatatt   4260
tttcctgtct aagtatttcc tatagtcaac atttgtatta aaatgttcat atcatgaatt   4320
tgcggggggg atggcgatga caaggttcgg cgagcggctc aaagagctga gggaacaaag   4380
aagcctgtcg gttaatcagc ttgccatgta tgccggtgtg agcgccgcag ccatttccag   4440
agccgcagcc atttccagaa tcgaaaacgg ccaccgcggc gttcccaagc ccgcgacgat   4500
cagaaaattg gccgaggctc tgaaaatgcc gtacgagcag ctcatggata ttgccggtta   4560
tatgagagct gacgagattc gcgaacagcc gcgcggctat gtcacgatgc aggagatcgc   4620
ggccaagcac ggcgtcgaag acctgtggct gtttaaaccc gagaaatgaa ttcctccatt   4680
ttcttctgct atcaaaataa cagactcgtg attttccaaa cgagctttca aaaaagcctc   4740
tgccccttgc aaatcggatg cctgtctata aaattcccga tattggttaa acagcggcgc   4800
aatggcggcc gcatctgatg tctttgcttg gcgaatgttc atcttatttc ttcctccctc   4860
tcaataattt tttcattcta tccctttct gtaaagttta tttttcagaa tacttttatc   4920
atcatgcttt gaaaaaatat cacgataata tccattgttc tcacggaagc acacgcaggt   4980
catttgaacg aatttttcg acaggaattt gccgggactc aggagcattt aacctaaaaa   5040
agcatgacat ttcagcataa tgaacattta ctcatgtcta ttttcgttct tttctgtatg   5100
aaaatagtta tttcgagtct ctacggaaat agcgagagat gatataccta aatagagata   5160
aaatcatctc aaaaaaatgg gtctactaaa atattattcc atctattaca ataaattcac   5220
agaatagtct tttaagtaag tctactctga atttttttaa aaggagaggg taactagtgg   5280
ccccaaaaaa gaaacgcaag gttatggata aaaaatacag cattggtctg gatatcggaa   5340
ccaacagcgt tgggtgggca gtaataacag atgaatacaa agtgccgtca aaaaaattta   5400
aggttctggg gaatacagat cgccacagca taaaaaagaa tctgattggg gcattgctgt   5460
ttgattcggg tgagacagct gaggccacgc gtctgaaacg tacagcaaga agacgttaca   5520
cacgtcgtaa aaatcgtatt tgctacttac aggaaatttt ttctaacgaa atggccaagg   5580
tagatgatag tttcttccat cgtctcgaag aatcttttct ggttgaggaa gataaaaaac   5640
acgaacgtca ccctatcttt ggcaatatcg tggatgaagt ggcctatcat gaaaaatacc   5700
ctacgattta tcatcttcgc aagaagttgg ttgatagtac ggacaaagcg gatctgcgtt   5760
taatctatct tgcgttagcg cacatgatca aatttcgtgg tcatttctta attgaaggtg   5820
atctgaatcc tgataactct gatgtggaca aattgtttat acaattagtg caaacctata   5880
atcagctgtt cgaggaaaac cccattaatg cctctggagt tgatgccaaa gcgattttaa   5940
```

```
gcgcgagact ttctaagtcc cggcgtctgg agaatctgat cgcccagtta ccaggggaaa   6000
agaaaaatgg tctgtttggt aatctgattg ccctcagtct ggggcttacc ccgaacttca   6060
aatccaattt tgacctggct gaggacgcaa agctgcagct gagcaaagat acttatgatg   6120
atgacctcga caatctgctc gcccagattg gtgaccaata tgcggatctg tttctggcag   6180
cgaagaatct ttcggatgct atcttgctgt cggatattct gcgtgttaat accgaaatca   6240
ccaaagcgcc tctgtctgca agtatgatca agagatacga cgagcaccac caggacctga   6300
ctcttcttaa ggcactggta cgccaacagc ttccggagaa atacaaagaa atattcttcg   6360
accagtccaa gaatggttac gcgggctaca tcgatggtgg tgcatcacag gaagagttct   6420
ataaatttat taaaccaatc cttgagaaaa tggatggcac ggaagagtta cttgttaaac   6480
ttaaccgcga agacttgctt agaaagcaac gtacattcga caacggctcc atcccacacc   6540
agattcattt aggtgaactt cacgccatct tgcgcagaca agaagatttc tatcccttct   6600
taaaagacaa tcgggagaaa atcgagaaga tcctgacgtt ccgcattccc tattatgtcg   6660
gtcccctggc acgtggtaat tctcggtttg cctggatgac gcgcaaaagt gaggaaacca   6720
tcaccccttg gaactttgaa gaagtcgtgg ataaaggtgc tagcgcgcag tcttttatag   6780
aaagaatgac gaacttcgat aaaaacttgc ccaacgaaaa agtcctgccc aagcactctc   6840
ttttatatga gtactttact gtgtacaacg aactgactaa agtgaaatac gttacggaag   6900
gtatgcgcaa acctgccttt cttagtggcg agcagaaaaa agcaattgtc gatcttctct   6960
ttaaaacgaa tcgcaaggta actgtaaaac agctgaagga agattatttc aaaaagatcg   7020
aatgctttga ttctgtcgag atctcgggtg tcgaagatcg tttcaacgct tccttaggga   7080
cctatcatga tttgctgaag ataataaaag acaaagactt tctcgacaat gaagaaaatg   7140
aagatattct ggaggatatt gttttgacct tgaccttatt cgaagataga gagatgatcg   7200
aggagcgctt aaaaacctat gcccacctgt ttgatgacaa agtcatgaag caattaaagc   7260
gccgcagata tacggggtgg ggccgcttga gccgcaagtt gattaacggt attagagaca   7320
agcagagcgg aaaaactatc ctggatttcc tcaaatctga cggatttgcg aaccgcaatt   7380
ttatgcagct tatacatgat gattcgctta cattcaaaga ggatattcag aaggctcagg   7440
tgtctgggca aggtgattca ctccacgaac atatagcaaa tttggccggc tctcctgcga   7500
ttaagaaggg gatcctgcaa acagttaaag ttgtggatga acttgtaaaa gtaatgggcc   7560
gccacaagcc ggagaatatc gtgatagaaa tggcgcgcga gaatcaaacg acacaaaaag   7620
gtcaaaagaa ctcaagagag agaatgaagc gcattgagga ggggataaag gaacttggat   7680
ctcaaattct gaaagaacat ccagttgaaa acactcagct gcaaaatgaa aaattgtacc   7740
tgtactacct gcagaatgga agagacatgt acgtggatca ggaattggat atcaatagac   7800
tctcggacta tgacgtagat cacattgtcc ctcagagctt cctcaaggat gattctatag   7860
ataataaagt acttacgaga tcggacaaaa atcgcggtaa atcggataac gtcccatcgg   7920
aggaagtcgt taaaaagatg aaaaactatt ggcgtcaact gctgaacgcc aagctgatca   7980
cacagcgtaa gtttgataat ctgactaaag ccgaacgcgg tggtcttagt gaactcgata   8040
aagcaggatt tataaaacgg cagttagtag aaacgcgcca aattacgaaa cacgtggctc   8100
agatcctcga ttctagaatg aatacaaagt acgatgaaaa cgataaactg atccgtgaag   8160
taaaagtcat taccttaaaa tctaaacttg tgtccgattt ccgcaaagat tttcagtttt   8220
acaaggtccg ggaaatcaat aactatcacc atgcacatga tgcatattta aatgcggttg   8280
```

```
taggcacggc ccttattaag aaataccccta aactcgaaag tgagtttgtt tatggggatt   8340

ataaagtgta tgacgttcgc aaaatgatcg cgaaatcaga acaggaaatc ggtaaggcta   8400

ccgctaaata cttttttat tccaacatta tgaatttttt taagaccgaa ataactctcg   8460

cgaatggtga aatccgtaaa cggcctctta tagaaaccaa tggtgaaacg ggagaaatcg   8520

tttgggataa aggtcgtgac tttgccaccg ttcgtaaagt cctctcaatg ccgcaagtta   8580

acattgtcaa gaagacggaa gttcaaacag gggattctc caaagaatct atcctgccga   8640

agcgtaacag tgataaactt attgccagaa aaaaagattg ggatccaaaa aaatacggag   8700

gctttgattc ccctaccgtc gcgtatagtg tgctggtggt tgctaaagtc gagaaaggga   8760

aaagcaagaa attgaaatca gttaaagaac tgctgggtat tacaattatg gaaagatcgt   8820

cctttgagaa aaatccgatc gactttttag aggccaaggg gtataaggaa gtgaaaaaag   8880

atctcatcat caaattaccg aagtatagtc tttttgagct ggaaaacggc agaaaaagaa   8940

tgctggcctc cgcgggcgag ttacagaagg gaaatgagct ggcgctgcct tccaaatatg   9000

ttaattttct gtaccttgcc agtcattatg agaaactgaa gggcagcccc gaagataacg   9060

aacagaaaca attattcgtg gaacagcata agcactattt agatgaaatt atagagcaaa   9120

ttagtgaatt ttctaagcgc gttatcctcg cggatgctaa tttagacaaa gtactgtcag   9180

cttataataa acatcgggat aagccgatta gagaacaggc cgaaaatatc attcatttgt   9240

ttaccttaac caaccttgga gcaccagctg ccttcaaata tttcgatacc acaattgatc   9300

gtaaacggta tacaagtaca aaagaagtct tggacgcaac cctcattcat caatctatta   9360

ctggattata tgagacacgc attgatcttt cacagctggg cggagacaag aagaaaaaac   9420

tgaaactgca ccatcatcac catcatcatc accatcattg ataactcgag aaagcttaca   9480

taaaaaaccg gccttggccc cgccggtttt ttattatttt tcttcctccg catgttcaat   9540

ccgctccata atcgacggat ggctccctct gaaaatttta acgagaaacg gcgggttgac   9600

ccggctcagt cccgtaacgg ccaagtcctg aaacgtctca atcgccgctt cccggtttcc   9660

ggtcagctca atgccgtaac ggtcggcggc gttttcctga taccgggaga cggcattcgt   9720

aatc                                                                9724
```

<210> SEQ ID NO 28
<211> LENGTH: 20
<212> TYPE: DNA
<213> ORGANISM: Bacillus licheniformis

<400> SEQUENCE: 28

```
ctcgacttcg aatacatcca                                                 20
```

<210> SEQ ID NO 29
<211> LENGTH: 20
<212> TYPE: DNA
<213> ORGANISM: Bacillus licheniformis

<400> SEQUENCE: 29

```
gatgccatca gttcctcata                                                 20
```

<210> SEQ ID NO 30
<211> LENGTH: 1578
<212> TYPE: DNA
<213> ORGANISM: Bacillus licheniformis

<400> SEQUENCE: 30

```
atgtttcgag tattggtctc agataaaatg tccagcgacg gcctcaaacc attaatggaa     60
```

gcagatttta ttgaaattgt agaaaagaat gttgcggaag cggaagacga gcttcatacg 120
tttgacgcgc tcttggtgcg gagcgccacg aaggtaaccg aagagctgtt taaaaagatg 180
acttcgctga aaatcgtcgc cagagcaggt gtcggcgtcg acaatatcga tattgacgag 240
gcgacaaaac acggtgttat cgtcgtaaac gcgccaaacg ggaatacaat ttcaaccgct 300
gaacatacct ttgcaatgtt ttcagcgtta atgagacata ttccgcaggc aaacatctcc 360
gtgaaatcaa gggagtggaa tcgttcggct tacgtcggtt cagagcttta cggaaaaacg 420
ctcggcatca tcggaatggg ccgcatcgga agcgaaatcg cgagccgcgc aaaagcattc 480
ggtatgaccg ttcatgtatt tgacccgttc ctgacccaag aaagggcaag caagctcggc 540
gttaacgcga acagctttga agaagttctg gcatgcgccg acatcattac ggttcatacc 600
ccgctcacga aagaaacgaa gggacttttg aacaaagaaa ccatcgcaaa aacgaaaaaa 660
ggcgttcgtc tcgttaactg tgcaagaggc ggcatcatcg atgaagcagc gcttttggaa 720
gctctggaaa gcggacatgt cgctggcgct gccttggatg tattcgaagt cgagcctccg 780
gtcgattcaa aactgatcga tcatccgctt gtagtcgcga ctcctcactt gggcgcctca 840
acaaaagaag cccagctgaa tgtcgctgca caagtgtccg aagaagtcct tcagtatgcg 900
caaggaaacc ctgtgatgtc cgcgatcaac cttccggcca tgacaaagga ttcattcgaa 960
aaaatccagc cttatcatca gtttgccaat acgatcggaa accttgtgtc tcagtgcatg 1020
aatgagcctg ttcaagatgt agccatccaa tatgaaggct ccatcgccaa acttgaaacg 1080
tcatttatta cgaaaagcct tttggccgga tttctgaagc cgagggtcgc ggctaccgtt 1140
aacgaagtga atgccggcac cgttgcgaaa gagcgcggca tcagcttcag cgaaaaaatt 1200
tcttccaatg agtcaggcta tgaaaactgc atctctgtga ctgtcacggg agatgtaaca 1260
acattctctt taagagcgac gtacattccg cacttcggcg gacgcatcgt tgccttaaac 1320
ggctttgata ttgattttta tccggctgga caccttgtct acattcacca ccaggataaa 1380
ccaggggcta tcggccatgt cggacgaatt ttaggagacc atgacatcaa tatcgccact 1440
atgcaggtag gccgaaaaga aaaaggcgga gaagcgatca tgatgctttc ctttgaccgc 1500
caccttgagg acgatatttt agctgagctg aaaaacatcc cggatatcgt gtctgttaaa 1560
gccatcgacc ttccttaa 1578

<210> SEQ ID NO 31
<211> LENGTH: 3
<212> TYPE: DNA
<213> ORGANISM: Bacillus licheniformis

<400> SEQUENCE: 31 agg 3

<210> SEQ ID NO 32
<211> LENGTH: 20
<212> TYPE: DNA
<213> ORGANISM: Bacillus licheniformis

<400> SEQUENCE: 32
ctcgacttcg aatacatcca 20

<210> SEQ ID NO 33
<211> LENGTH: 76
<212> TYPE: DNA
<213> ORGANISM: Artificial Sequence
<220> FEATURE:

<223> OTHER INFORMATION: synthetic

<400> SEQUENCE: 33
gttttagagc tagaaatagc aagttaaaat aaggctagtc cgttatcaac ttgaaaaagt 60
ggcaccgagt cggtgc 76

<210> SEQ ID NO 34
<211> LENGTH: 96
<212> TYPE: RNA
<213> ORGANISM: Artificial Sequence
<220> FEATURE:
<223> OTHER INFORMATION: synthetic

<400> SEQUENCE: 34
cucgacuucg aauacaucca guuuuagagc uagaaauagc aaguuaaaau aaggcuaguc 60
cguuaucaac uugaaaaagu ggcaccgagu cggugc 96

<210> SEQ ID NO 35
<211> LENGTH: 224
<212> TYPE: DNA
<213> ORGANISM: Artificial Sequence
<220> FEATURE:
<223> OTHER INFORMATION: synthetic

<400> SEQUENCE: 35
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180
aaaagttgtt gactttatct acaaggtgtg gcataatgtg tgga 224

<210> SEQ ID NO 36
<211> LENGTH: 95
<212> TYPE: DNA
<213> ORGANISM: Artificial Sequence
<220> FEATURE:
<223> OTHER INFORMATION: synthetic

<400> SEQUENCE: 36
gactcctgtt gatagatcca gtaatgacct cagaactcca tctggatttg ttcagaacgc 60
tcggttgccg ccgggcgttt tttattggtg agaat 95

<210> SEQ ID NO 37
<211> LENGTH: 500
<212> TYPE: DNA
<213> ORGANISM: Bacillus licheniformis

<400> SEQUENCE: 37
aatggttctt tcccctgtcc taaacaaaaa acccgcttta ttgaaaaagc ggggctgttt 60
tacagacagg tcaaataaac gtttgaaaat gttcatttca aaacgcgcgg aacctccatc 120
ttctcccatc cagactatac tgtcggcttc ggaatcgcac cgaatcctgc ccataaaaag 180
gctcgcgggc ttagagcgct tgctcatcac cgccggtagg gaatttcacc ctgccccgaa 240
gattgatctt atttattttt aatactgata ttattataaa ttaattgtga aaaaatgtac 300
aggtgcaaag cttattgcgc tgttttggga catcctgcac gatatttcgg taaactcact 360
ttttccgcat actaaaaacc gcacattcac agttatttca tttttaattt tcgtctttcc 420
gcgtgaaact cattgacact ctttatggaa tatggtaaat tatcagatat ttatgacgct 480
tatttaggag gaaatcttac 500

<210> SEQ ID NO 38
<211> LENGTH: 40
<212> TYPE: DNA
<213> ORGANISM: Artificial Sequence
<220> FEATURE:
<223> OTHER INFORMATION: synthetic

<400> SEQUENCE: 38
tgagtaaact tggtctgaca aatggttctt tcccctgtcc 40

<210> SEQ ID NO 39
<211> LENGTH: 46
<212> TYPE: DNA
<213> ORGANISM: Artificial Sequence
<220> FEATURE:
<223> OTHER INFORMATION: synthetic

<400> SEQUENCE: 39
aggttccgca gcttctgtgt aagatttcct cctaaataag cgtcat 46

<210> SEQ ID NO 40
<211> LENGTH: 500
<212> TYPE: DNA
<213> ORGANISM: Bacillus licheniformis

<400> SEQUENCE: 40
acagaagctg cggaacctga aaagaattcc tttcaggttc cgttttttt aggaattctc 60 cctgatctca agcatctggc ggggataaat ccgctctcct ttcaaatcgt tccattcttt 120
gaggcgctgt acagttacgc ccatttttc ggcgatatga tgaagcgtat cccctttccg 180
cactacatat gtaccggtct tcgattcatc gtcatgaagg cggagtgttt ggccggcctt 240
gagatttgaa tgtttcaacc cgtttattct catgatctcc tcgatggata taccgctatc 300
cttgctgatt ctccagagcg tgtccccttt ttgaacggtc accgcaccgc tcattgtccc 360
ggcgttttga taaacgtgga tagaattttg ccggaacgcc tcctcacgaa gcaccgtcag 420
cggattgatt gcatatcttt tatcttcagt ccatgaaccg tgatgcattt caaaatgcag 480
gtgggttccg gtcgatattc 500

<210> SEQ ID NO 41
<211> LENGTH: 46
<212> TYPE: DNA
<213> ORGANISM: Artificial Sequence
<220> FEATURE:
<223> OTHER INFORMATION: synthetic

<400> SEQUENCE: 41
atgacgctta tttaggagga aatcttacac agaagctgcg gaacct 46

<210> SEQ ID NO 42
<211> LENGTH: 41
<212> TYPE: DNA
<213> ORGANISM: Artificial Sequence
<220> FEATURE:
<223> OTHER INFORMATION: synthetic

<400> SEQUENCE: 42
cagaagaaaa tggaggaatt cgaatatcga ccggaaccca c 41

<210> SEQ ID NO 43
<211> LENGTH: 415
<212> TYPE: DNA

<213> ORGANISM: Artificial Sequence
<220> FEATURE:
<223> OTHER INFORMATION: synthetic

<400> SEQUENCE: 43

```
gggtgaagtg gtcaagacct cactaggcac cttaaaaata gcgcaccctg aagaagattt      60

atttgaggta gcccttgcct acctagcttc caagaaagat atcctaacag cacaagagcg     120

gaaagatgtt ttgttctaca tccagaacaa cctctgctaa aattcctgaa aaattttgca     180

aaaagttgtt gactttatct acaaggtgtg gcataatgtg tggactcgac ttcgaataca     240

tccagtttta gagctagaaa tagcaagtta aaataaggct agtccgttat caacttgaaa     300

aagtggcacc gagtcggtgc gactcctgtt gatagatcca gtaatgacct cagaactcca     360

tctggatttg ttcagaacgc tcggttgccg ccgggcgttt tttattggtg agaat          415
```

<210> SEQ ID NO 44
<211> LENGTH: 1000
<212> TYPE: DNA
<213> ORGANISM: Artificial Sequence
<220> FEATURE:
<223> OTHER INFORMATION: synthetic

<400> SEQUENCE: 44

```
aatggttctt tcccctgtcc taaacaaaaa acccgcttta ttgaaaaagc ggggctgttt      60

tacagacagg tcaaataaac gtttgaaaat gttcatttca aaacgcgcgg aacctccatc     120

ttctcccatc cagactatac tgtcggcttc ggaatcgcac cgaatcctgc ccataaaaag     180

gctcgcgggc ttagagcgct tgctcatcac cgccggtagg gaatttcacc ctgccccgaa     240

gattgatctt atttattttt aatactgata ttattataaa ttaattgtga aaaaatgtac     300

aggtgcaaag cttattgcgc tgttttggga catcctgcac gatatttcgg taaactcact     360

ttttccgcat actaaaaacc gcacattcac agttatttca tttttaattt tcgtctttcc     420

gcgtgaaact cattgacact ctttatggaa tatggtaaat tatcagatat ttatgacgct     480

tatttaggag gaaatcttac acagaagctg cggaacctga aaagaattcc tttcaggttc     540

cgtttttttt aggaattctc cctgatctca agcatctggc ggggataaat ccgctctcct     600

ttcaaatcgt tccattcttt gaggcgctgt acagttacgc ccattttttc ggcgatatga     660

tgaagcgtat ccccttttccg cactacatat gtaccggtct tcgattcatc gtcatgaagg     720

cggagtgttt ggccggcctt gagatttgaa tgtttcaacc cgtttattct catgatctcc     780

tcgatggata taccgctatc cttgctgatt ctccagagcg tgtccccttt ttgaacggtc     840

accgcaccgc tcattgtccc ggcgttttga taaacgtgga tagaattttg ccggaacgcc     900

tcctcacgaa gcaccgtcag cggattgatt gcatatcttt tatcttcagt ccatgaaccg     960

tgatgcattt caaaatgcag gtgggttccg gtcgatattc                         1000
```

<210> SEQ ID NO 45
<211> LENGTH: 402
<212> TYPE: DNA
<213> ORGANISM: Bacillus licheniformis

<400> SEQUENCE: 45

```
atgacgaact ttggacacca tttacgacaa ttaagggaac ggaaaaaact gaccgtcaat      60

caactggcga tgtattccgg cgtcagttcg gcaggcattt cgcgaatcga aaacggaaag     120

cgcggcgtgc cgaagccggc gacgatcaga aaactggcgg acgctttgaa agtcccgtat     180

gaggaactga tggcatctgc aggctatatc agcgcgtcta cagtccagga agcaagaagc     240
```

agctatgatt ccatttacga catcgtgtca cagtacgatt tagaggacct ttctctgttt 300
gacagcgaaa agtggaaggt gctttcaaaa aaagacatcg aaaacctgga caaatatttc 360
gactttctcg tgcaggaagc aagcagccga aacaaaaact ga 402

<210> SEQ ID NO 46
<211> LENGTH: 3
<212> TYPE: DNA
<213> ORGANISM: Artificial Sequence
<220> FEATURE:
<223> OTHER INFORMATION: synthetic

<400> SEQUENCE: 46 cgg 3

<210> SEQ ID NO 47
<211> LENGTH: 96
<212> TYPE: RNA
<213> ORGANISM: Artificial Sequence
<220> FEATURE:
<223> OTHER INFORMATION: synthetic

<400> SEQUENCE: 47
gaugccauca guuccucaua guuuuagagc uagaaauagc aaguuaaaau aaggcuaguc 60
cguuaucaac uugaaaaagu ggcaccgagu cggugc 96

<210> SEQ ID NO 48
<211> LENGTH: 500
<212> TYPE: DNA
<213> ORGANISM: Bacillus licheniformis

<400> SEQUENCE: 48
ttgatattca gcaccctgcg catttcgacc gggagaacga ctctgccgag ctcatcgatt 60
ctccggacaa tcccggtatt tttcacgttt gaaaagcctc cttttctcct ttctttattg 120
acttttgtca acatctttat aataaaagag atcttcaaat tttttgttga aatactgaat 180
catctttccg atcacaagtt gtccgggcct cctttcgcca tttaaaactc tgctgagtgt 240
cgccggggat acgccgattt caatggcaag ctgatttaag gagagattgt gttcaatcat 300
gtactggaga acaaaatctc ttttgatatg aatctttttt accatgatta ctcccctttc 360
taatctctta tgtttctttt tatctacatt gaacatatac gatttgttaa cttttgtcaa 420
tacttttacc atccatatgt ttcctatagg caatattcgt actaaaatat tttataataa 480
gagattgcga ggttttggcc 500

<210> SEQ ID NO 49
<211> LENGTH: 40
<212> TYPE: DNA
<213> ORGANISM: Artificial Sequence
<220> FEATURE:
<223> OTHER INFORMATION: synthetic

<400> SEQUENCE: 49
tgagtaaact tggtctgaca ttgatattca gcaccctgcg 40

<210> SEQ ID NO 50
<211> LENGTH: 38
<212> TYPE: DNA
<213> ORGANISM: Artificial Sequence
<220> FEATURE:
<223> OTHER INFORMATION: synthetic

<400> SEQUENCE: 50
tgtgccgcgg agaagtatgg ccaaaacctc gcaatctc 38

<210> SEQ ID NO 51
<211> LENGTH: 500
<212> TYPE: DNA
<213> ORGANISM: Bacillus licheniformis

<400> SEQUENCE: 51
atacttctcc gcggcacact ctcctctcta tcattttcgt ctgtttacga tcctgctgtt 60
attttatccc ttatgttaac ttttgtcaat atttttcctg tctaagtatt tcctatagtc 120
aacatttgta ttaaaatgtt catatcatga atttgcgggg gggatggcga tgacaaggtt 180
cggcgagcgg ctcaaagagc tgagggaaca aagaagcctg tcggttaatc agcttgccat 240
gtatgccggt gtgagcgccg cagccatttc cagagccgca gccatttcca gaatcgaaaa 300
cggccaccgc ggcgttccca agcccgcgac gatcagaaaa ttggccgagg ctctgaaaat 360
gccgtacgag cagctcatgg atattgccgg ttatatgaga gctgacgaga ttcgcgaaca 420
gccgcgcggc tatgtcacga tgcaggagat cgcggccaag cacggcgtcg aagacctgtg 480
gctgtttaaa cccgagaaat 500

<210> SEQ ID NO 52
<211> LENGTH: 38
<212> TYPE: DNA
<213> ORGANISM: Artificial Sequence
<220> FEATURE:
<223> OTHER INFORMATION: synthetic

<400> SEQUENCE: 52
gagattgcga ggttttggcc atacttctcc gcggcaca 38

<210> SEQ ID NO 53
<211> LENGTH: 44
<212> TYPE: DNA
<213> ORGANISM: Artificial Sequence
<220> FEATURE:
<223> OTHER INFORMATION: synthetic

<400> SEQUENCE: 53
cagaagaaaa tggaggaatt catttctcgg gtttaaacag ccac 44

<210> SEQ ID NO 54
<211> LENGTH: 415
<212> TYPE: DNA
<213> ORGANISM: Artificial Sequence
<220> FEATURE:
<223> OTHER INFORMATION: synthetic

<400> SEQUENCE: 54
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180
aaaagttgtt gactttatct acaaggtgtg gcataatgtg tggagatgcc atcagttcct 240
catagtttta gagctagaaa tagcaagtta aaataaggct agtccgttat caacttgaaa 300
aagtggcacc gagtcggtgc gactcctgtt gatagatcca gtaatgacct cagaactcca 360
tctggatttg ttcagaacgc tcggttgccg ccgggcgttt tttattggtg agaat 415

<210> SEQ ID NO 55
<211> LENGTH: 1000
<212> TYPE: DNA
<213> ORGANISM: Artificial Sequence
<220> FEATURE:
<223> OTHER INFORMATION: synthetic

<400> SEQUENCE: 55
ttgatattca gcaccctgcg catttcgacc gggagaacga ctctgccgag ctcatcgatt 60
ctccggacaa tcccggtatt tttcacgttt gaaaagcctc cttttctcct ttctttattg 120
acttttgtca acatctttat aataaaagag atcttcaaat tttttgttga aatactgaat 180
catctttccg atcacaagtt gtccgggcct cctttcgcca tttaaaactc tgctgagtgt 240
cgccggggat acgccgattt caatggcaag ctgatttaag gagagattgt gttcaatcat 300
gtactggaga acaaaatctc ttttgatatg aatctttttt accatgatta ctcccctttc 360
taatctctta tgtttctttt tatctacatt gaacatatac gatttgttaa cttttgtcaa 420
tacttttacc atccatatgt ttcctatagg caatattcgt actaaaatat tttataataa 480
gagattgcga ggttttggcc atacttctcc gcggcacact ctcctctcta tcattttcgt 540
ctgtttacga tcctgctgtt attttatccc ttatgttaac ttttgtcaat atttttcctg 600
tctaagtatt tcctatagtc aacatttgta ttaaaatgtt catatcatga atttgcgggg 660
gggatggcga tgacaaggtt cggcgagcgg ctcaaagagc tgagggaaca aagaagcctg 720
tcggttaatc agcttgccat gtatgccggt gtgagcgccg cagccatttc cagagccgca 780
gccatttcca gaatcgaaaa cggccaccgc ggcgttccca agcccgcgac gatcagaaaa 840
ttggccgagg ctctgaaaat gccgtacgag cagctcatgg atattgccgg ttatatgaga 900
gctgacgaga ttcgcgaaca gccgcgcggc tatgtcacga tgcaggagat cgcggccaag 960
cacggcgtcg aagacctgtg gctgtttaaa cccgagaaat 1000

<210> SEQ ID NO 56
<211> LENGTH: 1368
<212> TYPE: PRT
<213> ORGANISM: Artificial Sequence
<220> FEATURE:
<223> OTHER INFORMATION: synthetic

<400> SEQUENCE: 56

Met Asp Lys Lys Tyr Ser Ile Gly Leu Asp Ile Gly Thr Asn Ser Val
1 5 10 15

Gly Trp Ala Val Ile Thr Asp Glu Tyr Lys Val Pro Ser Lys Lys Phe
20 25 30

Lys Val Leu Gly Asn Thr Asp Arg His Ser Ile Lys Lys Asn Leu Ile
35 40 45

Gly Ala Leu Leu Phe Asp Ser Gly Glu Thr Ala Glu Ala Thr Arg Leu
50 55 60

Lys Arg Thr Ala Arg Arg Arg Tyr Thr Arg Arg Lys Asn Arg Ile Cys
65 70 75 80

Tyr Leu Gln Glu Ile Phe Ser Asn Glu Met Ala Lys Val Asp Asp Ser
85 90 95

Phe Phe His Arg Leu Glu Glu Ser Phe Leu Val Glu Glu Asp Lys Lys
100 105 110

His Glu Arg His Pro Ile Phe Gly Asn Ile Val Asp Glu Val Ala Tyr
115 120 125

His Glu Lys Tyr Pro Thr Ile Tyr His Leu Arg Lys Lys Leu Val Asp
130 135 140

```
Ser Thr Asp Lys Ala Asp Leu Arg Leu Ile His Leu Ala Leu Ala His
145                 150                 155                 160

Met Ile Lys Phe Arg Gly His Phe Leu Ile Glu Gly Asp Leu Asn Pro
                165                 170                 175

Asp Asn Ser Asp Val Asp Lys Leu Phe Ile Gln Leu Val Gln Thr Tyr
            180                 185                 190

Asn Gln Leu Phe Glu Glu Asn Pro Ile Asn Ala Ser Gly Val Asp Ala
        195                 200                 205

Lys Ala Ile Leu Ser Ala Arg Leu Ser Lys Ser Arg Arg Leu Glu Asn
    210                 215                 220

Leu Ile Ala Gln Leu Pro Gly Glu Lys Lys Asn Gly Leu Phe Gly Asn
225                 230                 235                 240

Leu Ile Ala Leu Ser Leu Gly Leu Thr Pro Asn Phe Lys Ser Asn Phe
                245                 250                 255

Asp Leu Ala Glu Asp Ala Lys Leu Gln Leu Ser Lys Asp Thr Tyr Asp
            260                 265                 270

Asp Asp Leu Asp Asn Leu Leu Ala Gln Ile Gly Asp Gln Tyr Ala Asp
        275                 280                 285

Leu Phe Leu Ala Ala Lys Asn Leu Ser Asp Ala Ile Leu Leu Ser Asp
    290                 295                 300

Ile Leu Arg Val Asn Thr Glu Ile Thr Lys Ala Pro Leu Ser Ala Ser
305                 310                 315                 320

Met Ile Lys Arg Tyr Asp Glu His His Gln Asp Leu Thr Leu Leu Lys
                325                 330                 335

Ala Leu Val Arg Gln Gln Leu Pro Glu Lys Tyr Lys Glu Ile Phe Phe
            340                 345                 350

Asp Gln Ser Lys Asn Gly Tyr Ala Gly Tyr Ile Asp Gly Gly Ala Ser
        355                 360                 365

Gln Glu Glu Phe Tyr Lys Phe Ile Lys Pro Ile Leu Glu Lys Met Asp
    370                 375                 380

Gly Thr Glu Glu Leu Leu Val Lys Leu Asn Arg Glu Asp Leu Leu Arg
385                 390                 395                 400

Lys Gln Arg Thr Phe Asp Asn Gly Ser Ile Pro His Gln Ile His Leu
                405                 410                 415

Gly Glu Leu His Ala Ile Leu Arg Arg Gln Glu Asp Phe Tyr Pro Phe
            420                 425                 430

Leu Lys Asp Asn Arg Glu Lys Ile Glu Lys Ile Leu Thr Phe Arg Ile
        435                 440                 445

Pro Tyr Tyr Val Gly Pro Leu Ala Arg Gly Asn Ser Arg Phe Ala Trp
    450                 455                 460

Met Thr Arg Lys Ser Glu Glu Thr Ile Thr Pro Trp Asn Phe Glu Glu
465                 470                 475                 480

Val Val Asp Lys Gly Ala Ser Ala Gln Ser Phe Ile Glu Arg Met Thr
                485                 490                 495

Asn Phe Asp Lys Asn Leu Pro Asn Glu Lys Val Leu Pro Lys His Ser
            500                 505                 510

Leu Leu Tyr Glu Tyr Phe Thr Val Tyr Asn Glu Leu Thr Lys Val Lys
        515                 520                 525

Tyr Val Thr Glu Gly Met Arg Lys Pro Ala Phe Leu Ser Gly Glu Gln
    530                 535                 540

Lys Lys Ala Ile Val Asp Leu Leu Phe Lys Thr Asn Arg Lys Val Thr
545                 550                 555                 560
```

Val Lys Gln Leu Lys Glu Asp Tyr Phe Lys Lys Ile Glu Cys Phe Asp
565 570 575

Ser Val Glu Ile Ser Gly Val Glu Asp Arg Phe Asn Ala Ser Leu Gly
580 585 590

Thr Tyr His Asp Leu Leu Lys Ile Ile Lys Asp Lys Asp Phe Leu Asp
595 600 605

Asn Glu Glu Asn Glu Asp Ile Leu Glu Asp Ile Val Leu Thr Leu Thr
610 615 620

Leu Phe Glu Asp Arg Glu Met Ile Glu Glu Arg Leu Lys Thr Tyr Ala
625 630 635 640

His Leu Phe Asp Asp Lys Val Met Lys Gln Leu Lys Arg Arg Arg Tyr
645 650 655

Thr Gly Trp Gly Arg Leu Ser Arg Lys Leu Ile Asn Gly Ile Arg Asp
660 665 670

Lys Gln Ser Gly Lys Thr Ile Leu Asp Phe Leu Lys Ser Asp Gly Phe
675 680 685

Ala Asn Arg Asn Phe Met Gln Leu Ile His Asp Asp Ser Leu Thr Phe
690 695 700

Lys Glu Asp Ile Gln Lys Ala Gln Val Ser Gly Gln Gly Asp Ser Leu
705 710 715 720

His Glu His Ile Ala Asn Leu Ala Gly Ser Pro Ala Ile Lys Lys Gly
725 730 735

Ile Leu Gln Thr Val Lys Val Val Asp Glu Leu Val Lys Val Met Gly
740 745 750

Arg His Lys Pro Glu Asn Ile Val Ile Glu Met Ala Arg Glu Asn Gln
755 760 765

Thr Thr Gln Lys Gly Gln Lys Asn Ser Arg Glu Arg Met Lys Arg Ile
770 775 780

Glu Glu Gly Ile Lys Glu Leu Gly Ser Gln Ile Leu Lys Glu His Pro
785 790 795 800

Val Glu Asn Thr Gln Leu Gln Asn Glu Lys Leu Tyr Leu Tyr Tyr Leu
805 810 815

Gln Asn Gly Arg Asp Met Tyr Val Asp Gln Glu Leu Asp Ile Asn Arg
820 825 830

Leu Ser Asp Tyr Asp Val Asp His Ile Val Pro Gln Ser Phe Leu Lys
835 840 845

Asp Asp Ser Ile Asp Asn Lys Val Leu Thr Arg Ser Asp Lys Asn Arg
850 855 860

Gly Lys Ser Asp Asn Val Pro Ser Glu Glu Val Val Lys Lys Met Lys
865 870 875 880

Asn Tyr Trp Arg Gln Leu Leu Asn Ala Lys Leu Ile Thr Gln Arg Lys
885 890 895

Phe Asp Asn Leu Thr Lys Ala Glu Arg Gly Gly Leu Ser Glu Leu Asp
900 905 910

Lys Ala Gly Phe Ile Lys Arg Gln Leu Val Glu Thr Arg Gln Ile Thr
915 920 925

Lys His Val Ala Gln Ile Leu Asp Ser Arg Met Asn Thr Lys Tyr Asp
930 935 940

Glu Asn Asp Lys Leu Ile Arg Glu Val Lys Val Ile Thr Leu Lys Ser
945 950 955 960

Lys Leu Val Ser Asp Phe Arg Lys Asp Phe Gln Phe Tyr Lys Val Arg
965 970 975

Glu Ile Asn Asn Tyr His His Ala His Asp Ala Tyr Leu Asn Ala Val

-continued

```
            980                 985                 990

Val Gly Thr Ala Leu Ile Lys Lys  Tyr Pro Lys Leu Glu  Ser Glu Phe
        995                 1000                1005

Val Tyr  Gly Asp Tyr Lys Val  Tyr Asp Val Arg Lys  Met Ile Ala
    1010                 1015                 1020

Lys Ser  Glu Gln Glu Ile Gly  Lys Ala Thr Ala Lys  Tyr Phe Phe
    1025                 1030                 1035

Tyr Ser  Asn Ile Met Asn Phe  Phe Lys Thr Glu Ile  Thr Leu Ala
    1040                 1045                 1050

Asn Gly  Glu Ile Arg Lys Arg  Pro Leu Ile Glu Thr  Asn Gly Glu
    1055                 1060                 1065

Thr Gly  Glu Ile Val Trp Asp  Lys Gly Arg Asp Phe  Ala Thr Val
    1070                 1075                 1080

Arg Lys  Val Leu Ser Met Pro  Gln Val Asn Ile Val  Lys Lys Thr
    1085                 1090                 1095

Glu Val  Gln Thr Gly Gly Phe  Ser Lys Glu Ser Ile  Leu Pro Lys
    1100                 1105                 1110

Arg Asn  Ser Asp Lys Leu Ile  Ala Arg Lys Lys Asp  Trp Asp Pro
    1115                 1120                 1125

Lys Lys  Tyr Gly Gly Phe Asp  Ser Pro Thr Val Ala  Tyr Ser Val
    1130                 1135                 1140

Leu Val  Val Ala Lys Val Glu  Lys Gly Lys Ser Lys  Lys Leu Lys
    1145                 1150                 1155

Ser Val  Lys Glu Leu Leu Gly  Ile Thr Ile Met Glu  Arg Ser Ser
    1160                 1165                 1170

Phe Glu  Lys Asn Pro Ile Asp  Phe Leu Glu Ala Lys  Gly Tyr Lys
    1175                 1180                 1185

Glu Val  Lys Lys Asp Leu Ile  Ile Lys Leu Pro Lys  Tyr Ser Leu
    1190                 1195                 1200

Phe Glu  Leu Glu Asn Gly Arg  Lys Arg Met Leu Ala  Ser Ala Gly
    1205                 1210                 1215

Glu Leu  Gln Lys Gly Asn Glu  Leu Ala Leu Pro Ser  Lys Tyr Val
    1220                 1225                 1230

Asn Phe  Leu Tyr Leu Ala Ser  His Tyr Glu Lys Leu  Lys Gly Ser
    1235                 1240                 1245

Pro Glu  Asp Asn Glu Gln Lys  Gln Leu Phe Val Glu  Gln His Lys
    1250                 1255                 1260

His Tyr  Leu Asp Glu Ile Ile  Glu Gln Ile Ser Glu  Phe Ser Lys
    1265                 1270                 1275

Arg Val  Ile Leu Ala Asp Ala  Asn Leu Asp Lys Val  Leu Ser Ala
    1280                 1285                 1290

Tyr Asn  Lys His Arg Asp Lys  Pro Ile Arg Glu Gln  Ala Glu Asn
    1295                 1300                 1305

Ile Ile  His Leu Phe Thr Leu  Thr Asn Leu Gly Ala  Pro Ala Ala
    1310                 1315                 1320

Phe Lys  Tyr Phe Asp Thr Thr  Ile Asp Arg Lys Arg  Tyr Thr Ser
    1325                 1330                 1335

Thr Lys  Glu Val Leu Asp Ala  Thr Leu Ile His Gln  Ser Ile Thr
    1340                 1345                 1350

Gly Leu  Tyr Glu Thr Arg Ile  Asp Leu Ser Gln Leu  Gly Gly Asp
    1355                 1360                 1365
```

<210> SEQ ID NO 57

<211> LENGTH: 33
<212> TYPE: DNA
<213> ORGANISM: Artificial Sequence
<220> FEATURE:
<223> OTHER INFORMATION: synthetic

<400> SEQUENCE: 57
gatctgcgtt taatccatct tgcgttagcg cac 33

<210> SEQ ID NO 58
<211> LENGTH: 33
<212> TYPE: DNA
<213> ORGANISM: Artificial Sequence
<220> FEATURE:
<223> OTHER INFORMATION: synthetic

<400> SEQUENCE: 58
gtgcgctaac gcaagatgga ttaaacgcag atc 33

<210> SEQ ID NO 59
<211> LENGTH: 9724
<212> TYPE: DNA
<213> ORGANISM: Artificial Sequence
<220> FEATURE:
<223> OTHER INFORMATION: synthetic

<400> SEQUENCE: 59
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180
aaaagttgtt gactttatct acaaggtgtg gcataatgtg tggactcgac ttcgaataca 240
tccagtttta gagctagaaa tagcaagtta aaataaggct agtccgttat caacttgaaa 300
aagtggcacc gagtcggtgc gactcctgtt gatagatcca gtaatgacct cagaactcca 360
tctggatttg ttcagaacgc tcggttgccg ccgggcgttt tttattggtg agaatgtcga 420
cctcgagagt tacgctaggg ataacagggt aatataggag ctccagtcgg cttaaaccag 480
ttttcgctgg tgcgaaaaaa gagtgtcttg tgacacctaa attcaaaatc tatcggtcag 540
atttataccg atttgatttt atatattctt gaataacata cgccgagtta tcacataaaa 600
gcgggaacca atcataaaat ttaaacttca ttgcataatc cattaaactc ttaaattcta 660
cgattccttg ttcatcaata aactcaatca tttctttaat taatttatat ctatctgttg 720
ttgttttctt taataattca ttaacatcta caccgccata aactatcata tcttcttttt 780
gatatttaaa tttattagga tcgtccatgt gaagcatata tctcacaaga cctttcacac 840
ttcctgcaat ctgcggaata gtcgcattca attcttctgt taattatttt tatctgttca 900
taagatttat taccctcata catcactaga atatgataat gctctttttt catcctacct 960
tctgtatcag tatccctatc atgtaatgga gacactacaa attgaatgtg taactctttt 1020
aaatactcta accactcggc ttttgctgat tctggatata aaacaaatgt ccaattacgt 1080
cctcttgaat tttcttgttt ttcagtttct tttattacat tttcgctcat gatataataa 1140
cggtgctaat acacttaaca aaatttagtc atagataggc agcatgccag tgctgtctat 1200
ctttttttgt ttaaaatgca ccgtattcct cctttgcata ttttttttatt agaataccgg 1260 ttgcatctga tttgctaata ttatattttt ctttgattct atttaatatc tcattttctt 1320
ctgttgtaag tcttaaagta acagcaactt ttttctcttc ttttctatct acaactatca 1380
ctgtacctcc caacatctgt ttttttcact ttaacataaa aaacaacctt ttaacattaa 1440
aaacccaata tttatttatt tgtttggaca atggacactg gacacctagg ggggaggtcg 1500
tagtaccccc ctatgttttc tcccctaaat aaccccaaaa atctaagaaa aaaagacctc 1560
aaaaaggtct ttaattaaca tctcaaattt cgcatttatt ccaatttcct ttttgcgtgt 1620
gatgcgagct catcggctcc gtcgatacta tgttatacgc caactttcaa aacaactttg 1680
aaaaagctgt tttctggtat ttaaggtttt agaatgcaag gaacagtgaa ttggagttcg 1740
tcttgttata attagcttct tggggtatct ttaaatactg tagaaaagag gaaggaaata 1800
ataaatggct aaaatgagaa tatcaccgga attgaaaaaa ctgatcgaaa aataccgctg 1860
cgtaaaagat acggaaggaa tgtctcctgc taaggtatat aagctggtgg gagaaaatga 1920
aaacctatat ttaaaaatga cggacagccg gtataaaggg accacctatg atgtggaacg 1980
ggaaaaggac atgatgctat ggctggaagg aaagctgcct gttccaaagg tcctgcactt 2040
tgaacggcat gatggctgga gcaatctgct catgagtgag gccgatggcg tcctttgctc 2100
ggaagagtat gaagatgaac aaagccctga aaagattatc gagctgtatg cggagtgcat 2160
caggctcttt cactccatcg acatatcgga ttgtccctat acgaatagct tagacagccg 2220
cttagccgaa ttggattact tactgaataa cgatctggcc gatgtggatt gcgaaaactg 2280
ggaagaagac actccattta aagatccgcg cgagctgtat gattttttaa agacggaaaa 2340
gcccgaagag gaacttgtct ttcccacggc cgacctggga gacagcaaca tctttgtgaa 2400
agatggcaaa gtaagtggct ttattgatct tgggagaagc ggcagggcgg acaagtggta 2460
tgacattgcc ttctgcgtcc ggtcgatcag ggaggatatc ggggaagaac agtatgtcga 2520
gctatttttt gacttactgg ggatcaagcc tgattgggag aaaataaaat attatatttt 2580
actggatgaa ttgttttagt gactgcagtg agatctggta atgactctct agcttgaggc 2640
atcaaataaa acgaaaggct cagtcgaaag actgggcctt tcgttttatc tgttgtttgt 2700
cggtgaacgc tctcctgagt aggacaaatc cgccgctcta gctaagcaga aggccatcct 2760
gacggatggc ctttttgcgt ttctacaaac tcttgttaac tctagagctg cctgccgcgt 2820
ttcggtgatg aagatcttcc cgatgattaa ttaattcaga acgctcggtt gccgccgggc 2880
gtttttttatg aagcttcgtt gctggcgttt ttccataggc tccgcccccc tgacgagcat 2940
cacaaaaatc gacgctcaag tcagaggtgg cgaaacccga caggactata aagataccag 3000
gcgtttcccc ctggaagctc cctcgtgcgc tctcctgttc cgaccctgcc gcttaccgga 3060
tacctgtccg cctttctccc ttcgggaagc gtggcgcttt ctcatagctc acgctgtagg 3120
tatctcagtt cggtgtaggt cgttcgctcc aagctgggct gtgtgcacga accccccgtt 3180
cagcccgacc gctgcgcctt atccggtaac tatcgtcttg agtccaaccc ggtaagacac 3240
gacttatcgc cactggcagc agccactggt aacaggatta gcagagcgag gtatgtaggc 3300
ggtgctacag agttcttgaa gtggtggcct aactacggct acactagaag gacagtattt 3360
ggtatctgcg ctctgctgaa gccagttacc ttcggaaaaa gagttggtag ctcttgatcc 3420
ggcaaacaaa ccaccgctgg tagcggtggt ttttttgttt gcaagcagca gattacgcgc 3480
agaaaaaaag gatctcaaga agatcctttg atcttttcta cggggtctga cgctcagtgg 3540
aacgaaaact cacgttaagg gattttggtc atgagattat caaaaaggat cttcacctag 3600
atccttttaa attaaaaatg aagttttaaa tcaatctaaa gtatatatga gtaaacttgg 3660
tctgacaaat ggttctttcc cctgtcctaa acaaaaaacc cgctttattg aaaaagcggg 3720
gctgttttac agacaggtca aataaacgtt tgaaaatgtt catttcaaaa cgcgcggaac 3780

```
ctccatcttc tcccatccag actatactgt cggcttcgga atcgcaccga atcctgccca   3840
taaaaaggct cgcgggctta gagcgcttgc tcatcaccgc cggtagggaa tttcaccctg   3900
ccccgaagat tgatcttatt tatttttaat actgatatta ttataaatta attgtgaaaa   3960
aatgtacagg tgcaaagctt attgcgctgt tttgggacat cctgcacgat atttcggtaa   4020
actcactttt tccgcatact aaaaaccgca cattcacagt tatttcattt ttaattttcg   4080
tctttccgcg tgaaactcat tgacactctt tatggaatat ggtaaattat cagatattta   4140
tgacgcttat ttaggaggaa atcttacaca gaagctgcgg aacctgaaaa gaattccttt   4200
caggttccgt ttttttagg aattctccct gatctcaagc atctggcggg gataaatccg   4260
ctctcctttc aaatcgttcc attctttgag gcgctgtaca gttacgccca tttttcggc   4320
gatatgatga agcgtatccc ctttccgcac tacatatgta ccggtcttcg attcatcgtc   4380
atgaaggcgg agtgtttggc cggccttgag atttgaatgt ttcaacccgt ttattctcat   4440
gatctcctcg atggatatac cgctatcctt gctgattctc cagagcgtgt cccctttttg   4500
aacggtcacc gcaccgctca ttgtcccggc gttttgataa acgtggatag aatttgccg    4560
gaacgcctcc tcacgaagca ccgtcagcgg attgattgca tatcttttat cttcagtcca   4620
tgaaccgtga tgcatttcaa aatgcaggtg ggttccggtc gatattcgaa ttcctccatt   4680
ttcttctgct atcaaaataa cagactcgtg attttccaaa cgagctttca aaaaagcctc   4740
tgccccttgc aaatcggatg cctgtctata aaattcccga tattggttaa acagcggcgc   4800
aatggcggcc gcatctgatg tctttgcttg gcgaatgttc atcttatttc ttcctccctc   4860
tcaataattt tttcattcta tccctttct gtaaagttta tttttcagaa tacttttatc    4920
atcatgcttt gaaaaaatat cacgataata tccattgttc tcacggaagc acacgcaggt   4980
catttgaacg aatttttcg acaggaattt gccgggactc aggagcattt aacctaaaaa    5040
agcatgacat ttcagcataa tgaacattta ctcatgtcta ttttcgttct tttctgtatg   5100
aaaatagtta tttcgagtct ctacggaaat agcgagagat gatataccta aatagagata   5160
aaatcatctc aaaaaaatgg gtctactaaa atattattcc atctattaca ataaattcac   5220
agaatagtct tttaagtaag tctactctga attttttaa aaggagaggg taactagtgg    5280
ccccaaaaaa gaaacgcaag gttatggata aaaaatacag cattggtctg gatatcggaa   5340
ccaacagcgt tgggtgggca gtaataacag atgaatacaa agtgccgtca aaaaaattta   5400
aggttctggg gaatacagat cgccacagca taaaaaagaa tctgattggg gcattgctgt   5460
ttgattcggg tgagacagct gaggccacgc gtctgaaacg tacagcaaga agacgttaca   5520
cacgtcgtaa aaatcgtatt tgctacttac aggaaatttt ttctaacgaa atggccaagg   5580
tagatgatag tttcttccat cgtctcgaag aatcttttct ggttgaggaa gataaaaaac   5640
acgaacgtca ccctatcttt ggcaatatcg tggatgaagt ggcctatcat gaaaaatacc   5700
ctacgattta tcatcttcgc aagaagttgg ttgatagtac ggacaaagcg gatctgcgtt   5760
taatccatct tgcgttagcg cacatgatca aatttcgtgg tcatttctta attgaaggtg   5820
atctgaatcc tgataactct gatgtggaca aattgtttat acaattagtg caaacctata   5880
atcagctgtt cgaggaaaac cccattaatg cctctggagt tgatgccaaa gcgattttaa   5940
gcgcgagact ttctaagtcc cggcgtctgg agaatctgat cgcccagtta ccaggggaaa   6000
agaaaaatgg tctgtttggt aatctgattg ccctcagtct ggggcttacc ccgaacttca   6060
aatccaattt tgacctggct gaggacgcaa agctgcagct gagcaaagat acttatgatg   6120
atgacctcga caatctgctc gcccagattg gtgaccaata tgcggatctg tttctggcag   6180
```

```
cgaagaatct ttcggatgct atcttgctgt cggatattct gcgtgttaat accgaaatca   6240
ccaaagcgcc tctgtctgca agtatgatca agagatacga cgagcaccac caggacctga   6300
ctcttcttaa ggcactggta cgccaacagc ttccggagaa atacaaagaa atattcttcg   6360
accagtccaa gaatggttac gcgggctaca tcgatggtgg tgcatcacag gaagagttct   6420
ataaatttat taaaccaatc cttgagaaaa tggatggcac ggaagagtta cttgttaaac   6480
ttaaccgcga agacttgctt agaaagcaac gtacattcga caacggctcc atcccacacc   6540
agattcattt aggtgaactt cacgccatct tgcgcagaca agaagatttc tatcccttct   6600
taaaagacaa tcgggagaaa atcgagaaga tcctgacgtt ccgcattccc tattatgtcg   6660
gtcccctggc acgtggtaat tctcggtttg cctggatgac gcgcaaaagt gaggaaacca   6720
tcacccccttg gaactttgaa gaagtcgtgg ataaaggtgc tagcgcgcag tcttttatag   6780
aaagaatgac gaacttcgat aaaaacttgc ccaacgaaaa agtcctgccc aagcactctc   6840
ttttatatga gtactttact gtgtacaacg aactgactaa agtgaaatac gttacggaag   6900
gtatgcgcaa acctgccttt cttagtggcg agcagaaaaa agcaattgtc gatcttctct   6960
ttaaaacgaa tcgcaaggta actgtaaaac agctgaagga agattatttc aaaaagatcg   7020
aatgctttga ttctgtcgag atctcgggtg tcgaagatcg tttcaacgct tccttaggga   7080
cctatcatga tttgctgaag ataataaaag acaaagactt tctcgacaat gaagaaaatg   7140
aagatattct ggaggatatt gttttgacct tgaccttatt cgaagataga gagatgatcg   7200
aggagcgctt aaaaacctat gcccacctgt ttgatgacaa agtcatgaag caattaaagc   7260
gccgcagata tacggggtgg ggccgcttga gccgcaagtt gattaacggt attagagaca   7320
agcagagcgg aaaaactatc ctggatttcc tcaaatctga cggatttgcg aaccgcaatt   7380
ttatgcagct tatacatgat gattcgctta cattcaaaga ggatattcag aaggctcagg   7440
tgtctgggca aggtgattca ctccacgaac atatagcaaa tttggccggc tctcctgcga   7500
ttaagaaggg gatcctgcaa acagttaaag ttgtggatga acttgtaaaa gtaatgggcc   7560
gccacaagcc ggagaatatc gtgatagaaa tggcgcgcga gaatcaaacg acacaaaaag   7620
gtcaaaagaa ctcaagagag agaatgaagc gcattgagga ggggataaag gaacttggat   7680
ctcaaattct gaaagaacat ccagttgaaa acactcagct gcaaaatgaa aaattgtacc   7740
tgtactacct gcagaatgga agagacatgt acgtggatca ggaattggat atcaatagac   7800
tctcggacta tgacgtagat cacattgtcc ctcagagctt cctcaaggat gattctatag   7860
ataataaagt acttacgaga tcggacaaaa atcgcggtaa atcggataac gtcccatcgg   7920
aggaagtcgt taaaaagatg aaaaactatt ggcgtcaact gctgaacgcc aagctgatca   7980
cacagcgtaa gtttgataat ctgactaaag ccgaacgcgg tggtcttagt gaactcgata   8040
aagcaggatt tataaaacgg cagttagtag aaacgcgcca aattacgaaa cacgtggctc   8100
agatcctcga ttctagaatg aatacaaagt acgatgaaaa cgataaactg atccgtgaag   8160
taaaagtcat taccttaaaa tctaaacttg tgtccgattt ccgcaaagat tttcagtttt   8220
acaaggtccg ggaaatcaat aactatcacc atgcacatga tgcatattta aatgcggttg   8280
taggcacggc ccttattaag aaataccta aactcgaaag tgagtttgtt tatggggatt   8340
ataaagtgta tgacgttcgc aaaatgatcg cgaaatcaga acaggaaatc ggtaaggcta   8400
ccgctaaata ctttttttat tccaacatta tgaatttttt taagaccgaa ataactctcg   8460
cgaatggtga aatccgtaaa cggcctctta tagaaaccaa tggtgaaacg ggagaaatcg   8520
```

tttgggataa aggtcgtgac tttgccaccg ttcgtaaagt cctctcaatg ccgcaagtta 8580
acattgtcaa gaagacggaa gttcaaacag ggggattctc caaagaatct atcctgccga 8640
agcgtaacag tgataaactt attgccagaa aaaaagattg ggatccaaaa aaatacggag 8700
gctttgattc ccctaccgtc gcgtatagtg tgctggtggt tgctaaagtc gagaaaggga 8760
aaagcaagaa attgaaatca gttaaagaac tgctgggtat tacaattatg gaaagatcgt 8820
cctttgagaa aaatccgatc gactttttag aggccaaggg gtataaggaa gtgaaaaaag 8880
atctcatcat caaattaccg aagtatagtc tttttgagct ggaaaacggc agaaaaagaa 8940
tgctggcctc cgcgggcgag ttacagaagg gaaatgagct ggcgctgcct tccaaatatg 9000
ttaattttct gtaccttgcc agtcattatg agaaactgaa gggcagcccc gaagataacg 9060
aacagaaaca attattcgtg gaacagcata agcactattt agatgaaatt atagagcaaa 9120
ttagtgaatt ttctaagcgc gttatcctcg cggatgctaa tttagacaaa gtactgtcag 9180
cttataataa acatcgggat aagccgatta gagaacaggc cgaaaatatc attcatttgt 9240
ttaccttaac caaccttgga gcaccagctg ccttcaaata tttcgatacc acaattgatc 9300
gtaaacggta tacaagtaca aaagaagtct tggacgcaac cctcattcat caatctatta 9360
ctggattata tgagacacgc attgatcttt cacagctggg cggagacaag aagaaaaaac 9420
tgaaactgca ccatcatcac catcatcatc accatcattg ataactcgag aaagcttaca 9480
taaaaaaccg gccttggccc cgccggtttt ttattatttt tcttcctccg catgttcaat 9540
ccgctccata atcgacggat ggctccctct gaaaatttta acgagaaacg gcgggttgac 9600
ccggctcagt cccgtaacgg ccaagtcctg aaacgtctca atcgccgctt cccggtttcc 9660
ggtcagctca atgccgtaac ggtcggcggc gttttcctga taccgggaga cggcattcgt 9720
aatc 9724

<210> SEQ ID NO 60
<211> LENGTH: 5055
<212> TYPE: DNA
<213> ORGANISM: Artificial Sequence
<220> FEATURE:
<223> OTHER INFORMATION: synthetic

<400> SEQUENCE: 60
attcctccat tttcttctgc tatcaaaata acagactcgt gattttccaa acgagctttc 60
aaaaaagcct ctgccccttg caaatcggat gcctgtctat aaaattcccg atattggtta 120
aacagcggcg caatggcggc cgcatctgat gtctttgctt ggcgaatgtt catcttattt 180
cttcctccct ctcaataatt ttttcattct atcccttttc tgtaaagttt atttttcaga 240
atacttttat catcatgctt tgaaaaaata tcacgataat atccattgtt ctcacggaag 300
cacacgcagg tcatttgaac gaattttttc gacaggaatt tgccgggact caggagcatt 360
taacctaaaa aagcatgaca tttcagcata atgaacattt actcatgtct attttcgttc 420
ttttctgtat gaaaatagtt atttcgagtc tctacggaaa tagcgagaga tgatatacct 480
aaatagagat aaaatcatct caaaaaaatg ggtctactaa aatattattc catctattac 540
aataaattca cagaatagtc ttttaagtaa gtctactctg aattttttta aaaggagagg 600
gtaactagtg gccccaaaaa agaaacgcaa ggttatggat aaaaaataca gcattggtct 660
ggatatcgga accaacagcg ttgggtgggc agtaataaca gatgaataca aagtgccgtc 720
aaaaaaattt aaggttctgg ggaatacaga tcgccacagc ataaaaaaga atctgattgg 780
ggcattgctg tttgattcgg gtgagacagc tgaggccacg cgtctgaaac gtacagcaag 840

```
aagacgttac acacgtcgta aaaatcgtat ttgctactta caggaaattt tttctaacga    900
aatggccaag gtagatgata gtttcttcca tcgtctcgaa gaatcttttc tggttgagga    960
agataaaaaa cacgaacgtc accctatctt tggcaatatc gtggatgaag tggcctatca   1020
tgaaaaatac cctacgattt atcatcttcg caagaagttg gttgatagta cggacaaagc   1080
ggatctgcgt ttaatccatc ttgcgttagc gcacatgatc aaatttcgtg gtcatttctt   1140
aattgaaggt gatctgaatc ctgataactc tgatgtggac aaattgttta tacaattagt   1200
gcaaacctat aatcagctgt tcgaggaaaa ccccattaat gcctctggag ttgatgccaa   1260
agcgatttta agcgcgagac tttctaagtc ccggcgtctg gagaatctga tcgcccagtt   1320
accaggggaa aagaaaaatg gtctgtttgg taatctgatt gccctcagtc tggggcttac   1380
cccgaacttc aaatccaatt ttgacctggc tgaggacgca aagctgcagc tgagcaaaga   1440
tacttatgat gatgacctcg acaatctgct cgcccagatt ggtgaccaat atgcggatct   1500
gtttctggca gcgaagaatc tttcggatgc tatcttgctg tcggatattc tgcgtgttaa   1560
taccgaaatc accaaagcgc ctctgtctgc aagtatgatc aagagatacg acgagcacca   1620
ccaggacctg actcttctta aggcactggt acgccaacag cttccggaga aatacaaaga   1680
aatattcttc gaccagtcca agaatggtta cgcgggctac atcgatggtg gtgcatcaca   1740
ggaagagttc tataaattta ttaaaccaat ccttgagaaa atggatggca cggaagagtt   1800
acttgttaaa cttaaccgcg aagacttgct tagaaagcaa cgtacattcg acaacggctc   1860
catcccacac cagattcatt taggtgaact tcacgccatc ttgcgcagac aagaagattt   1920
ctatcccttc ttaaaagaca atcgggagaa aatcgagaag atcctgacgt tccgcattcc   1980
ctattatgtc ggtcccctgg cacgtggtaa ttctcggttt gcctggatga cgcgcaaaag   2040
tgaggaaacc atcacccctt ggaactttga agaagtcgtg gataaaggtg ctagcgcgca   2100
gtcttttata gaaagaatga cgaacttcga taaaaacttg cccaacgaaa aagtcctgcc   2160
caagcactct cttttatatg agtactttac tgtgtacaac gaactgacta aagtgaaata   2220
cgttacggaa ggtatgcgca aacctgcctt tcttagtggc gagcagaaaa aagcaattgt   2280
cgatcttctc tttaaaacga atcgcaaggt aactgtaaaa cagctgaagg aagattattt   2340
caaaaagatc gaatgctttg attctgtcga gatctcgggt gtcgaagatc gtttcaacgc   2400
ttccttaggg acctatcatg atttgctgaa gataataaaa gacaaagact ttctcgacaa   2460
tgaagaaaat gaagatattc tggaggatat tgttttgacc ttgaccttat tcgaagatag   2520
agagatgatc gaggagcgct taaaaaccta tgcccacctg tttgatgaca aagtcatgaa   2580
gcaattaaag cgccgcagat atacggggtg gggccgcttg agccgcaagt tgattaacgg   2640
tattagagac aagcagagcg gaaaaactat cctggatttc ctcaaatctg acggatttgc   2700
gaaccgcaat tttatgcagc ttatacatga tgattcgctt acattcaaag aggatattca   2760
gaaggctcag gtgtctgggc aaggtgattc actccacgaa catatagcaa atttggccgg   2820
ctctcctgcg attaagaagg ggatcctgca aacagttaaa gttgtggatg aacttgtaaa   2880
agtaatgggc cgccacaagc cggagaatat cgtgatagaa atggcgcgcg agaatcaaac   2940
gacacaaaaa ggtcaaaaga actcaagaga gagaatgaag cgcattgagg aggggataaa   3000
ggaacttgga tctcaaattc tgaaagaaca tccagttgaa aacactcagc tgcaaaatga   3060
aaaattgtac ctgtactacc tgcagaatgg aagagacatg tacgtggatc aggaattgga   3120
tatcaataga ctctcggact atgacgtaga tcacattgtc cctcagagct tcctcaagga   3180
```

tgattctata gataataaag tacttacgag atcggacaaa aatcgcggta aatcggataa 3240
cgtcccatcg gaggaagtcg ttaaaaagat gaaaaactat tggcgtcaac tgctgaacgc 3300
caagctgatc acacagcgta agtttgataa tctgactaaa gccgaacgcg gtggtcttag 3360
tgaactcgat aaagcaggat ttataaaacg gcagttagta gaaacgcgcc aaattacgaa 3420
acacgtggct cagatcctcg attctagaat gaatacaaag tacgatgaaa acgataaact 3480
gatccgtgaa gtaaaagtca ttaccttaaa atctaaactt gtgtccgatt tccgcaaaga 3540
ttttcagttt tacaaggtcc gggaaatcaa taactatcac catgcacatg atgcatattt 3600
aaatgcggtt gtaggcacgg cccttattaa gaaataccct aaactcgaaa gtgagtttgt 3660
ttatggggat tataaagtgt atgacgttcg caaaatgatc gcgaaatcag aacaggaaat 3720
cggtaaggct accgctaaat acttttttta ttccaacatt atgaattttt ttaagaccga 3780
aataactctc gcgaatggtg aaatccgtaa acggcctctt atagaaacca atggtgaaac 3840
gggagaaatc gtttgggata aaggtcgtga ctttgccacc gttcgtaaag tcctctcaat 3900
gccgcaagtt aacattgtca agaagacgga agttcaaaca gggggattct ccaaagaatc 3960
tatcctgccg aagcgtaaca gtgataaact tattgccaga aaaaaagatt gggatccaaa 4020
aaaatacgga ggctttgatt cccctaccgt cgcgtatagt gtgctggtgg ttgctaaagt 4080
cgagaaaggg aaaagcaaga aattgaaatc agttaaagaa ctgctgggta ttacaattat 4140
ggaaagatcg tcctttgaga aaaatccgat cgacttttta gaggccaagg ggtataagga 4200
agtgaaaaaa gatctcatca tcaaattacc gaagtatagt ctttttgagc tggaaaacgg 4260
cagaaaaaga atgctggcct ccgcgggcga gttacagaag ggaaatgagc tggcgctgcc 4320
ttccaaatat gttaattttc tgtaccttgc cagtcattat gagaaactga agggcagccc 4380
cgaagataac gaacagaaac aattattcgt ggaacagcat aagcactatt tagatgaaat 4440
tatagagcaa attagtgaat tttctaagcg cgttatcctc gcggatgcta atttagacaa 4500
agtactgtca gcttataata aacatcggga taagccgatt agagaacagg ccgaaaatat 4560
cattcatttg tttaccttaa ccaaccttgg agcaccagct gccttcaaat atttcgatac 4620
cacaattgat cgtaaacggt atacaagtac aaaagaagtc ttggacgcaa ccctcattca 4680
tcaatctatt actggattat atgagacacg cattgatctt tcacagctgg gcggagacaa 4740
gaagaaaaaa ctgaaactgc accatcatca ccatcatcat caccatcatt gataactcga 4800
gaaagcttac ataaaaaacc ggccttggcc ccgccggttt tttattattt ttcttcctcc 4860
gcatgttcaa tccgctccat aatcgacgga tggctccctc tgaaaatttt aacgagaaac 4920
ggcgggttga cccggctcag tcccgtaacg gccaagtcct gaaacgtctc aatcgccgct 4980
tcccggtttc cggtcagctc aatgccgtaa cggtcggcgg cgttttcctg ataccgggag 5040
acggcattcg taatc 5055

<210> SEQ ID NO 61
<211> LENGTH: 9724
<212> TYPE: DNA
<213> ORGANISM: Artificial Sequence
<220> FEATURE:
<223> OTHER INFORMATION: synthetic

<400> SEQUENCE: 61
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180

```
aaaagttgtt gactttatct acaaggtgtg gcataatgtg tggagatgcc atcagttcct    240
catagtttta gagctagaaa tagcaagtta aaataaggct agtccgttat caacttgaaa    300
aagtggcacc gagtcggtgc gactcctgtt gatagatcca gtaatgacct cagaactcca    360
tctggatttg ttcagaacgc tcggttgccg ccgggcgttt tttattggtg agaatgtcga    420
cctcgagagt tacgctaggg ataacagggt aatataggag ctccagtcgg cttaaaccag    480
ttttcgctgg tgcgaaaaaa gagtgtcttg tgacacctaa attcaaaatc tatcggtcag    540
atttataccg atttgatttt atatattctt gaataacata cgccgagtta tcacataaaa    600
gcgggaacca atcataaaat ttaaacttca ttgcataatc cattaaactc ttaaattcta    660
cgattccttg ttcatcaata aactcaatca tttctttaat taatttatat ctatctgttg    720
ttgttttctt taataattca ttaacatcta caccgccata aactatcata tcttcttttt    780
gatatttaaa tttattagga tcgtccatgt gaagcatata tctcacaaga cctttcacac    840
ttcctgcaat ctgcggaata gtcgcattca attcttctgt taattatttt tatctgttca    900
taagatttat taccctcata catcactaga atatgataat gctctttttt catcctacct    960
tctgtatcag tatccctatc atgtaatgga gacactacaa attgaatgtg taactctttt   1020
aaatactcta accactcggc ttttgctgat tctggatata aaacaaatgt ccaattacgt   1080
cctcttgaat tttcttgtt  ttcagtttct tttattacat tttcgctcat gatataataa   1140
cggtgctaat acacttaaca aaatttagtc atagataggc agcatgccag tgctgtctat   1200
ctttttttgt ttaaaatgca ccgtattcct cctttgcata tttttttatt agaataccgg   1260
ttgcatctga tttgctaata ttatattttt ctttgattct atttaatatc tcattttctt   1320
ctgttgtaag tcttaaagta acagcaactt ttttctcttc ttttctatct acaactatca   1380
ctgtacctcc caacatctgt tttttcact  ttaacataaa aaacaacctt ttaacattaa   1440
aaacccaata tttatttatt tgtttggaca atggacactg gacacctagg ggggaggtcg   1500
tagtaccccc ctatgttttc tcccctaaat aaccccaaaa atctaagaaa aaaagacctc   1560
aaaaaggtct ttaattaaca tctcaaattt cgcatttatt ccaatttcct ttttgcgtgt   1620
gatgcgagct catcggctcc gtcgatacta tgttatacgc caactttcaa aacaactttg   1680
aaaaagctgt tttctggtat ttaaggtttt agaatgcaag gaacagtgaa ttggagttcg   1740
tcttgttata attagcttct tggggtatct ttaaatactg tagaaaagag gaaggaaata   1800
ataaatggct aaaatgagaa tatcaccgga attgaaaaaa ctgatcgaaa aataccgctg   1860
cgtaaaagat acggaaggaa tgtctcctgc taaggtatat aagctggtgg gagaaaatga   1920
aaacctatat ttaaaaatga cggacagccg gtataaaggg accacctatg atgtggaacg   1980
ggaaaaggac atgatgctat ggctggaagg aaagctgcct gttccaaagg tcctgcactt   2040
tgaacggcat gatggctgga gcaatctgct catgagtgag gccgatggcg tcctttgctc   2100
ggaagagtat gaagatgaac aaagccctga aaagattatc gagctgtatg cggagtgcat   2160
caggctcttt cactccatcg acatatcgga ttgtccctat acgaatagct tagacagccg   2220
cttagccgaa ttggattact tactgaataa cgatctggcc gatgtggatt gcgaaaactg   2280
ggaagaagac actccattta aagatccgcg cgagctgtat gattttttaa agacggaaaa   2340
gcccgaagag gaacttgtct tttcccacgg cgacctggga gacagcaaca tctttgtgaa   2400
agatggcaaa gtaagtggct ttattgatct tgggagaagc ggcagggcgg acaagtggta   2460
tgacattgcc ttctgcgtcc ggtcgatcag ggaggatatc ggggaagaac agtatgtcga   2520
```

-continued

```
gctatttttt gacttactgg ggatcaagcc tgattgggag aaaataaaat attatatttt   2580
actggatgaa ttgttttagt gactgcagtg agatctggta atgactctct agcttgaggc   2640
atcaaataaa acgaaaggct cagtcgaaag actgggcctt tcgttttatc tgttgtttgt   2700
cggtgaacgc tctcctgagt aggacaaatc cgccgctcta gctaagcaga aggccatcct   2760
gacggatggc ctttttgcgt ttctacaaac tcttgttaac tctagagctg cctgccgcgt   2820
ttcggtgatg aagatcttcc cgatgattaa ttaattcaga acgctcggtt gccgccgggc   2880
gtttttatg aagcttcgtt gctggcgttt ttccataggc tccgcccccc tgacgagcat   2940
cacaaaaatc gacgctcaag tcagaggtgg cgaaacccga caggactata aagataccag   3000
gcgtttcccc ctggaagctc cctcgtgcgc tctcctgttc cgaccctgcc gcttaccgga   3060
tacctgtccg cctttctccc ttcgggaagc gtggcgcttt ctcatagctc acgctgtagg   3120
tatctcagtt cggtgtaggt cgttcgctcc aagctgggct gtgtgcacga accccccgtt   3180
cagcccgacc gctgcgcctt atccggtaac tatcgtcttg agtccaaccc ggtaagacac   3240
gacttatcgc cactggcagc agccactggt aacaggatta gcagagcgag gtatgtaggc   3300
ggtgctacag agttcttgaa gtggtggcct aactacggct acactagaag gacagtattt   3360
ggtatctgcg ctctgctgaa gccagttacc ttcggaaaaa gagttggtag ctcttgatcc   3420
ggcaaacaaa ccaccgctgg tagcggtggt ttttttgttt gcaagcagca gattacgcgc   3480
agaaaaaaag gatctcaaga agatcctttg atcttttcta cggggtctga cgctcagtgg   3540
aacgaaaact cacgttaagg gattttggtc atgagattat caaaaaggat cttcacctag   3600
atccttttaa attaaaaatg aagttttaaa tcaatctaaa gtatatatga gtaaacttgg   3660
tctgacattg atattcagca ccctgcgcat ttcgaccggg agaacgactc tgccgagctc   3720
atcgattctc cggacaatcc cggtattttt cacgtttgaa aagcctcctt ttctcctttc   3780
tttattgact tttgtcaaca tctttataat aaaagagatc ttcaaatttt ttgttgaaat   3840
actgaatcat ctttccgatc acaagttgtc cgggcctcct ttcgccattt aaaactctgc   3900
tgagtgtcgc cggggatacg ccgatttcaa tggcaagctg atttaaggag agattgtgtt   3960
caatcatgta ctggagaaca aaatctcttt tgatatgaat cttttttacc atgattactc   4020
ccctttctaa tctcttatgt ttctttttat ctacattgaa catatacgat ttgttaactt   4080
ttgtcaatac ttttaccatc catatgtttc ctataggcaa tattcgtact aaaatatttt   4140
ataataagag attgcgaggt tttggccata cttctccgcg gcacactctc ctctctatca   4200
ttttcgtctg tttacgatcc tgctgttatt ttatccctta tgttaacttt tgtcaatatt   4260
tttcctgtct aagtatttcc tatagtcaac atttgtatta aaatgttcat atcatgaatt   4320
tgcggggggg atggcgatga caaggttcgg cgagcggctc aaagagctga gggaacaaag   4380
aagcctgtcg gttaatcagc ttgccatgta tgccggtgtg agcgccgcag ccatttccag   4440
agccgcagcc atttccagaa tcgaaaacgg ccaccgcggc gttcccaagc ccgcgacgat   4500
cagaaaattg gccgaggctc tgaaaatgcc gtacgagcag ctcatggata ttgccggtta   4560
tatgagagct gacgagattc gcgaacagcc gcgcggctat gtcacgatgc aggagatcgc   4620
ggccaagcac ggcgtcgaag acctgtggct gtttaaaccc gagaaatgaa ttcctccatt   4680
ttcttctgct atcaaaataa cagactcgtg attttccaaa cgagctttca aaaaagcctc   4740
tgccccttgc aaatcggatg cctgtctata aaattcccga tattggttaa acagcggcgc   4800
aatggcggcc gcatctgatg tctttgcttg gcgaatgttc atcttatttc ttcctccctc   4860
tcaataattt tttcattcta tccctttttct gtaaagttta tttttcagaa tacttttatc   4920
```

```
atcatgcttt gaaaaaatat cacgataata tccattgttc tcacggaagc acacgcaggt   4980

catttgaacg aatttttcg acaggaattt gccgggactc aggagcattt aacctaaaaa   5040

agcatgacat ttcagcataa tgaacattta ctcatgtcta ttttcgttct tttctgtatg   5100

aaaatagtta tttcgagtct ctacggaaat agcgagagat gatataccta aatagagata   5160

aaatcatctc aaaaaaatgg gtctactaaa atattattcc atctattaca ataaattcac   5220

agaatagtct tttaagtaag tctactctga attttttaa aaggagaggg taactagtgg   5280

ccccaaaaaa gaaacgcaag gttatggata aaaaatacag cattggtctg gatatcggaa   5340

ccaacagcgt tgggtgggca gtaataacag atgaatacaa agtgccgtca aaaaaattta   5400

aggttctggg gaatacagat cgccacagca taaaaaagaa tctgattggg gcattgctgt   5460

ttgattcggg tgagacagct gaggccacgc gtctgaaacg tacagcaaga agacgttaca   5520

cacgtcgtaa aaatcgtatt tgctacttac aggaaatttt ttctaacgaa atggccaagg   5580

tagatgatag tttcttccat cgtctcgaag aatcttttct ggttgaggaa gataaaaaac   5640

acgaacgtca ccctatcttt ggcaatatcg tggatgaagt ggcctatcat gaaaaatacc   5700

ctacgattta tcatcttcgc aagaagttgg ttgatagtac ggacaaagcg gatctgcgtt   5760

taatccatct tgcgttagcg cacatgatca aatttcgtgg tcatttctta attgaaggtg   5820

atctgaatcc tgataactct gatgtggaca aattgtttat acaattagtg caaacctata   5880

atcagctgtt cgaggaaaac cccattaatg cctctggagt tgatgccaaa gcgattttaa   5940

gcgcgagact ttctaagtcc cggcgtctgg agaatctgat cgcccagtta ccaggggaaa   6000

agaaaaatgg tctgtttggt aatctgattg ccctcagtct ggggcttacc ccgaacttca   6060

aatccaattt tgacctggct gaggacgcaa agctgcagct gagcaaagat acttatgatg   6120

atgacctcga caatctgctc gcccagattg gtgaccaata tgcggatctg tttctggcag   6180

cgaagaatct ttcggatgct atcttgctgt cggatattct gcgtgttaat accgaaatca   6240

ccaaagcgcc tctgtctgca agtatgatca agagatacga cgagcaccac caggacctga   6300

ctcttcttaa ggcactggta cgccaacagc ttccggagaa atacaaagaa atattcttcg   6360

accagtccaa gaatggttac gcgggctaca tcgatggtgg tgcatcacag gaagagttct   6420

ataaatttat taaaccaatc cttgagaaaa tggatggcac ggaagagtta cttgttaaac   6480

ttaaccgcga agacttgctt agaaagcaac gtacattcga caacggctcc atcccacacc   6540

agattcattt aggtgaactt cacgccatct tgcgcagaca agaagatttc tatcccttct   6600

taaaagacaa tcgggagaaa atcgagaaga tcctgacgtt ccgcattccc tattatgtcg   6660

gtcccctggc acgtggtaat tctcggtttg cctggatgac gcgcaaaagt gaggaaacca   6720

tcacccttg gaactttgaa gaagtcgtgg ataaaggtgc tagcgcgcag tcttttatag   6780

aaagaatgac gaacttcgat aaaaacttgc ccaacgaaaa agtcctgccc aagcactctc   6840

ttttatatga gtactttact gtgtacaacg aactgactaa agtgaaatac gttacggaag   6900

gtatgcgcaa acctgccttt cttagtggcg agcagaaaaa agcaattgtc gatcttctct   6960

ttaaaacgaa tcgcaaggta actgtaaaac agctgaagga agattatttc aaaaagatcg   7020

aatgctttga ttctgtcgag atctcgggtg tcgaagatcg tttcaacgct tccttaggga   7080

cctatcatga tttgctgaag ataataaaag acaaagactt tctcgacaat gaagaaaatg   7140

aagatattct ggaggatatt gttttgacct tgaccttatt cgaagataga gagatgatcg   7200

aggagcgctt aaaaacctat gcccacctgt ttgatgacaa agtcatgaag caattaaagc   7260
```

-continued gccgcagata tacggggtgg ggccgcttga gccgcaagtt gattaacggt attagagaca 7320
agcagagcgg aaaaactatc ctggatttcc tcaaatctga cggatttgcg aaccgcaatt 7380
ttatgcagct tatacatgat gattcgctta cattcaaaga ggatattcag aaggctcagg 7440
tgtctgggca aggtgattca ctccacgaac atatagcaaa tttggccggc tctcctgcga 7500
ttaagaaggg gatcctgcaa acagttaaag ttgtggatga acttgtaaaa gtaatgggcc 7560
gccacaagcc ggagaatatc gtgatagaaa tggcgcgcga gaatcaaacg acacaaaaag 7620
gtcaaaagaa ctcaagagag agaatgaagc gcattgagga ggggataaag gaacttggat 7680
ctcaaattct gaaagaacat ccagttgaaa acactcagct gcaaaatgaa aaattgtacc 7740
tgtactacct gcagaatgga agagacatgt acgtggatca ggaattggat atcaatagac 7800
tctcggacta tgacgtagat cacattgtcc ctcagagctt cctcaaggat gattctatag 7860
ataataaagt acttacgaga tcggacaaaa atcgcggtaa atcggataac gtcccatcgg 7920
aggaagtcgt taaaaagatg aaaaactatt ggcgtcaact gctgaacgcc aagctgatca 7980
cacagcgtaa gtttgataat ctgactaaag ccgaacgcgg tggtcttagt gaactcgata 8040
aagcaggatt tataaaacgg cagttagtag aaacgcgcca aattacgaaa cacgtggctc 8100
agatcctcga ttctagaatg aatacaaagt acgatgaaaa cgataaactg atccgtgaag 8160
taaaagtcat taccttaaaa tctaaacttg tgtccgattt ccgcaaagat tttcagtttt 8220
acaaggtccg ggaaatcaat aactatcacc atgcacatga tgcatattta aatgcggttg 8280
taggcacggc ccttattaag aaatacccta aactcgaaag tgagtttgtt tatgggggatt 8340 ataaagtgta tgacgttcgc aaaatgatcg cgaaatcaga acaggaaatc ggtaaggcta 8400
ccgctaaata ctttttttat tccaacatta tgaatttttt taagaccgaa ataactctcg 8460
cgaatggtga aatccgtaaa cggcctctta tagaaaccaa tggtgaaacg ggagaaatcg 8520
tttgggataa aggtcgtgac tttgccaccg ttcgtaaagt cctctcaatg ccgcaagtta 8580
acattgtcaa gaagacggaa gttcaaacag gggggattctc caaagaatct atcctgccga 8640
agcgtaacag tgataaactt attgccagaa aaaaagattg ggatccaaaa aaatacggag 8700
gctttgattc ccctaccgtc gcgtatagtg tgctggtggt tgctaaagtc gagaaaggga 8760
aaagcaagaa attgaaatca gttaaagaac tgctgggtat tacaattatg gaaagatcgt 8820
cctttgagaa aaatccgatc gactttttag aggccaaggg gtataaggaa gtgaaaaaag 8880
atctcatcat caaattaccg aagtatagtc tttttgagct ggaaaacggc agaaaaagaa 8940
tgctggcctc cgcgggcgag ttacagaagg gaaatgagct ggcgctgcct tccaaatatg 9000
ttaattttct gtaccttgcc agtcattatg agaaactgaa gggcagcccc gaagataacg 9060
aacagaaaca attattcgtg gaacagcata agcactattt agatgaaatt atagagcaaa 9120
ttagtgaatt ttctaagcgc gttatcctcg cggatgctaa tttagacaaa gtactgtcag 9180
cttataataa acatcgggat aagccgatta gagaacaggc cgaaaatatc attcatttgt 9240
ttaccttaac caaccttgga gcaccagctg ccttcaaata tttcgatacc acaattgatc 9300
gtaaacggta tacaagtaca aaagaagtct tggacgcaac cctcattcat caatctatta 9360
ctggattata tgagacacgc attgatcttt cacagctggg cggagacaag aagaaaaaac 9420
tgaaactgca ccatcatcac catcatcatc accatcattg ataactcgag aaagcttaca 9480
taaaaaaccg gccttggccc cgccggtttt ttattatttt tcttcctccg catgttcaat 9540
ccgctccata atcgacggat ggctccctct gaaaatttta acgagaaacg gcgggttgac 9600
ccggctcagt cccgtaacgg ccaagtcctg aaacgtctca atcgccgctt cccggtttcc 9660
ggtcagctca atgccgtaac ggtcggcggc gttttcctga taccgggaga cggcattcgt 9720
aatc 9724

<210> SEQ ID NO 62
<211> LENGTH: 8352
<212> TYPE: DNA
<213> ORGANISM: Artificial Sequence
<220> FEATURE:
<223> OTHER INFORMATION: synthetic

<400> SEQUENCE: 62
gaattcctcc attttcttct gctatcaaaa taacagactc gtgattttcc aaacgagctt 60
tcaaaaaagc ctctgcccct tgcaaatcgg atgcctgtct ataaaattcc cgatattggt 120
taaacagcgg cgcaatggcg gccgcatctg atgtctttgc ttggcgaatg ttcatcttat 180
ttcttcctcc ctctcaataa tttttcatt ctatcccttt tctgtaaagt ttatttttca 240
gaatactttt atcatcatgc tttgaaaaaa tatcacgata atatccattg ttctcacgga 300
agcacacgca ggtcatttga acgaattttt tcgacaggaa tttgccggga ctcaggagca 360
tttaacctaa aaaagcatga catttcagca taatgaacat ttactcatgt ctattttcgt 420
tcttttctgt atgaaaatag ttatttcgag tctctacgga aatagcgaga gatgatatac 480
ctaaatagag ataaaatcat ctcaaaaaaa tgggtctact aaaatattat tccatctatt 540
acaataaatt cacagaatag tcttttaagt aagtctactc tgaatttttt taaaaggaga 600
gggtaactag tggccccaaa aaagaaacgc aaggttatgg ataaaaaata cagcattggt 660
ctggatatcg gaaccaacag cgttgggtgg gcagtaataa cagatgaata caaagtgccg 720
tcaaaaaaat ttaaggttct ggggaataca gatcgccaca gcataaaaaa gaatctgatt 780
ggggcattgc tgtttgattc gggtgagaca gctgaggcca cgcgtctgaa acgtacagca 840
agaagacgtt acacacgtcg taaaaatcgt atttgctact tacaggaaat tttttctaac 900
gaaatggcca aggtagatga tagtttcttc catcgtctcg aagaatcttt tctggttgag 960
gaagataaaa aacacgaacg tcaccctatc tttggcaata tcgtggatga agtggcctat 1020
catgaaaaat accctacgat ttatcatctt cgcaagaagt tggttgatag tacggacaaa 1080
gcggatctgc gtttaatcca tcttgcgtta gcgcacatga tcaaatttcg tggtcatttc 1140
ttaattgaag gtgatctgaa tcctgataac tctgatgtgg acaaattgtt tatacaatta 1200
gtgcaaacct ataatcagct gttcgaggaa aaccccatta atgcctctgg agttgatgcc 1260
aaagcgattt taagcgcgag actttctaag tcccggcgtc tggagaatct gatcgcccag 1320
ttaccagggg aaaagaaaaa tggtctgttt ggtaatctga ttgccctcag tctggggctt 1380
accccgaact tcaaatccaa ttttgacctg gctgaggacg caaagctgca gctgagcaaa 1440
gatacttatg atgatgacct cgacaatctg ctcgcccaga ttggtgacca atatgcggat 1500
ctgtttctgg cagcgaagaa tctttcggat gctatcttgc tgtcggatat tctgcgtgtt 1560
aataccgaaa tcaccaaagc gcctctgtct gcaagtatga tcaagagata cgacgagcac 1620
caccaggacc tgactcttct taaggcactg gtacgccaac agcttccgga gaaatacaaa 1680
gaaatattct tcgaccagtc caagaatggt tacgcgggct acatcgatgg tggtgcatca 1740
caggaagagt tctataaatt tattaaacca atccttgaga aaatggatgg cacggaagag 1800
ttacttgtta aacttaaccg cgaagacttg cttagaaagc aacgtacatt cgacaacggc 1860
tccatcccac accagattca tttaggtgaa cttcacgcca tcttgcgcag acaagaagat 1920

-continued

```
ttctatccct tcttaaaaga caatcgggag aaaatcgaga agatcctgac gttccgcatt   1980
ccctattatg tcggtcccct ggcacgtggt aattctcggt ttgcctggat gacgcgcaaa   2040
agtgaggaaa ccatcacccc ttggaacttt gaagaagtcg tggataaagg tgctagcgcg   2100
cagtctttta tagaaagaat gacgaacttc gataaaaact tgcccaacga aaaagtcctg   2160
cccaagcact ctcttttata tgagtacttt actgtgtaca acgaactgac taaagtgaaa   2220
tacgttacgg aaggtatgcg caaacctgcc tttcttagtg gcgagcagaa aaaagcaatt   2280
gtcgatcttc tctttaaaac gaatcgcaag gtaactgtaa aacagctgaa ggaagattat   2340
ttcaaaaaga tcgaatgctt tgattctgtc gagatctcgg gtgtcgaaga tcgtttcaac   2400
gcttccttag ggacctatca tgatttgctg aagataataa aagacaaaga ctttctcgac   2460
aatgaagaaa atgaagatat tctggaggat attgttttga ccttgacctt attcgaagat   2520
agagagatga tcgaggagcg cttaaaaacc tatgcccacc tgtttgatga caaagtcatg   2580
aagcaattaa agcgccgcag atatacgggg tggggccgct tgagccgcaa gttgattaac   2640
ggtattagag acaagcagag cggaaaaact atcctggatt tcctcaaatc tgacggattt   2700
gcgaaccgca attttatgca gcttatacat gatgattcgc ttacattcaa agaggatatt   2760
cagaaggctc aggtgtctgg gcaaggtgat tcactccacg aacatatagc aaatttggcc   2820
ggctctcctg cgattaagaa ggggatcctg caaacagtta aagttgtgga tgaacttgta   2880
aaagtaatgg gccgccacaa gccggagaat atcgtgatag aaatggcgcg cgagaatcaa   2940
acgacacaaa aaggtcaaaa gaactcaaga gagagaatga agcgcattga ggaggggata   3000
aaggaacttg gatctcaaat tctgaaagaa catccagttg aaaacactca gctgcaaaat   3060
gaaaaattgt acctgtacta cctgcagaat ggaagagaca tgtacgtgga tcaggaattg   3120
gatatcaata gactctcgga ctatgacgta gatcacattg tccctcagag cttcctcaag   3180
gatgattcta tagataataa agtacttacg agatcggaca aaaatcgcgg taaatcggat   3240
aacgtcccat cggaggaagt cgttaaaaag atgaaaaact attggcgtca actgctgaac   3300
gccaagctga tcacacagcg taagtttgat aatctgacta aagccgaacg cggtggtctt   3360
agtgaactcg ataaagcagg atttataaaa cggcagttag tagaaacgcg ccaaattacg   3420
aaacacgtgg ctcagatcct cgattctaga atgaatacaa agtacgatga aaacgataaa   3480
ctgatccgtg aagtaaaagt cattacctta aaatctaaac ttgtgtccga tttccgcaaa   3540
gattttcagt tttacaaggt ccgggaaatc aataactatc accatgcaca tgatgcatat   3600
ttaaatgcgg ttgtaggcac ggcccttatt aagaaatacc ctaaactcga aagtgagttt   3660
gtttatgggg attataaagt gtatgacgtt cgcaaaatga tcgcgaaatc agaacaggaa   3720
atcggtaagg ctaccgctaa atactttttt tattccaaca ttatgaattt ttttaagacc   3780
gaaataactc tcgcgaatgg tgaaatccgt aaacggcctc ttatagaaac caatggtgaa   3840
acgggagaaa tcgtttggga taaaggtcgt gactttgcca ccgttcgtaa agtcctctca   3900
atgccgcaag ttaacattgt caagaagacg gaagttcaaa caggggggatt ctccaaagaa   3960
tctatcctgc cgaagcgtaa cagtgataaa cttattgcca gaaaaaaaga ttgggatcca   4020
aaaaaatacg gaggctttga ttcccctacc gtcgcgtata gtgtgctggt ggttgctaaa   4080
gtcgagaaag ggaaaagcaa gaaattgaaa tcagttaaag aactgctggg tattacaatt   4140
atggaaagat cgtcctttga gaaaaatccg atcgactttt tagaggccaa ggggtataag   4200
gaagtgaaaa aagatctcat catcaaatta ccgaagtata gtctttttga gctggaaaac   4260
ggcagaaaaa gaatgctggc ctccgcgggc gagttacaga agggaaatga gctggcgctg   4320
```

ccttccaaat atgttaattt tctgtacctt gccagtcatt atgagaaact gaagggcagc 4380
cccgaagata acgaacagaa acaattattc gtggaacagc ataagcacta tttagatgaa 4440
attatagagc aaattagtga attttctaag cgcgttatcc tcgcggatgc taatttagac 4500
aaagtactgt cagcttataa taaacatcgg gataagccga ttagagaaca ggccgaaaat 4560
atcattcatt tgtttacctt aaccaacctt ggagcaccag ctgccttcaa atatttcgat 4620
accacaattg atcgtaaacg gtatacaagt acaaaagaag tcttggacgc aaccctcatt 4680
catcaatcta ttactggatt atatgagaca cgcattgatc tttcacagct gggcggagac 4740
aagaagaaaa aactgaaact gcaccatcat caccatcatc atcaccatca ttgataactc 4800
gagaaagctt acataaaaaa ccggccttgg ccccgccggt tttttattat ttttcttcct 4860
ccgcatgttc aatccgctcc ataatcgacg gatggctccc tctgaaaatt ttaacgagaa 4920
acggcgggtt gacccggctc agtcccgtaa cggccaagtc ctgaaacgtc tcaatcgccg 4980
cttcccggtt tccggtcagc tcaatgccgt aacggtcggc ggcgttttcc tgataccggg 5040
agacggcatt cgtaatcgaa ttcgcggccg cacgcgtcca tggggatccc cgcgggtcga 5100
cctcgagagt tacgctaggg ataacagggt aatataggag ctccagtcgg cttaaaccag 5160
ttttcgctgg tgcgaaaaaa gagtgtcttg tgacactctt aaattcaaaa tctatcggtc 5220
agatttatac cgatttgatt ttatatattc ttgaataaca tacgccgagt tatcacataa 5280
aagcgggaac caatcataaa atttaaactt cattgcataa tccattaaac tcttaaattc 5340
tacgattcct tgttcatcaa taaactcaat catttcttta attaatttat atctatctgt 5400
tgttgttttc tttaataatt cattaacatc tacaccgcca taaactatca tatcttcttt 5460
ttgatattta aatttattag gatcgtccat gtgaagcata tatctcacaa gacctttcac 5520
acttcctgca atctgcggaa tagtcgcatt caattcttct gtaattattt ttatctgttc 5580
ataagattta ttaccctcat acatcactag aatatgataa tgctcttttt tcatcctacc 5640
ttctgtatca gtatccctat catgtaatgg agacactaca aattgaatgt gtaactcttt 5700
taaatactct aaccactcgg cttttgctga ttctggatat aaaacaaatg tccaattacg 5760
tcctcttgaa tttttcttgt tttcagtttc ttttattaca ttttcgctca tgatataata 5820
acggtgctaa tacacttaac aaaatttagt catagatagg cagcatgcca gtgctgtcta 5880
tctttttttg tttaaaatgc accgtattcc tcctttgcat attttttat tagaataccg 5940
gttgcatctg atttgctaat attatatttt tctttgattc tatttaatat ctcattttct 6000
tctgttgtaa gtcttaaagt aacagcaact tttttctctt cttttctatc tacaactatc 6060
actgtacctc ccaacatctg tttttttcac tttaacataa aaaacaacct tttaacatta 6120
aaaacccaat atttatttat ttgtttggac aatggacact ggacacctag gggggaggtc 6180
gtagtacccc cctatgtttt ctcccctaaa taaccccaaa aatctaagaa aaaaagacct 6240
caaaaaggtc tttaattaac atctcaaatt tcgcatttat tccaatttcc tttttgcgtg 6300
tgatgcgagc tcatcggctc cgtcgatact atgttatacg ccaactttga aaacaacttt 6360
gaaaaagctg ttttctggta tttaaggttt tagaatgcaa ggaacagtga attggagttc 6420
gtcttgttat aattagcttc ttggggtatc tttaaatact gtagaaaaga ggaaggaaat 6480
aataaatggc taaaatgaga atatcaccgg aattgaaaaa actgatcgaa aaataccgct 6540
gcgtaaaaga tacggaagga atgtctcctg ctaaggtata taagctggtg ggagaaaatg 6600
aaaacctata tttaaaaatg acggacagcc ggtataaagg gaccacctat gatgtggaac 6660
gggaaaagga catgatgcta tggctggaag gaaagctgcc tgttccaaag gtcctgcact 6720
ttgaacggca tgatggctgg agcaatctgc tcatgagtga ggccgatggc gtcctttgct 6780
cggaagagta tgaagatgaa caaagccctg aaaagattat cgagctgtat gcggagtgca 6840
tcaggctctt tcactccatc gacatatcgg attgtcccta tacgaatagc ttagacagcc 6900
gcttagccga attggattac ttactgaata acgatctggc cgatgtggat tgcgaaaact 6960
gggaagaaga cactccattt aaagatccgc gcgagctgta tgattttta aagacggaaa 7020 agcccgaaga ggaacttgtc ttttcccacg gcgacctggg agacagcaac atctttgtga 7080
aagatggcaa agtaagtggc tttattgatc ttgggagaag cggcagggcg gacaagtggt 7140
atgacattgc cttctgcgtc cggtcgatca gggaggatat cggggaagaa cagtatgtcg 7200
agctattttt tgacttactg gggatcaagc ctgattggga gaaaataaaa tattatattt 7260
tactggatga attgttttag tgactgcagt cgggaagatc tggtaatgac tctctagctt 7320
gaggcatcaa ataaaacgaa aggctcagtc gaaagactgg gcctttcgtt ttatctgttg 7380
tttgtcggtg aacgctctcc tgagtaggac aaatccgccg ctctagctaa gcagaaggcc 7440
atcctgacgg atggcctttt tgcgtttcta caaactcttg ttaactctag agctgcctgc 7500
cgcgtttcgg tgatgaagat cttcccgatg attaattaat tcagaacgct cggttgccgc 7560
cgggcgtttt ttatgaagct tcgttgctgg cgtttttcca taggctccgc ccccctgacg 7620
agcatcacaa aaatcgacgc tcaagtcaga ggtggcgaaa cccgacagga ctataaagat 7680
accaggcgtt tccccctgga agctccctcg tgcgctctcc tgttccgacc ctgccgctta 7740
ccggatacct gtccgccttt ctcccttcgg gaagcgtggc gctttctcat agctcacgct 7800
gtaggtatct cagttcggtg taggtcgttc gctccaagct gggctgtgtg cacgaacccc 7860
ccgttcagcc cgaccgctgc gccttatccg gtaactatcg tcttgagtcc aacccggtaa 7920
gacacgactt atcgccactg gcagcagcca ctggtaacag gattagcaga gcgaggtatg 7980
taggcggtgc tacagagttc ttgaagtggt ggcctaacta cggctacact agaagaacag 8040
tatttggtat ctgcgctctg ctgaagccag ttaccttcgg aaaaagagtt ggtagctctt 8100
gatccggcaa acaaaccacc gctggtagcg gtggtttttt tgtttgcaag cagcagatta 8160
cgcgcagaaa aaaaggatct caagaagatc ctttgatctt ttctacgggg tctgacgctc 8220
agtggaacga aaactcacgt taagggattt tggtcatgag attatcaaaa aggatcttca 8280
cctagatcct tttaaattaa aaatgaagtt ttaaatcaat ctaaagtata tatgagtaaa 8340
cttggtctga ca 8352

<210> SEQ ID NO 63
<211> LENGTH: 498
<212> TYPE: DNA
<213> ORGANISM: Artificial Sequence
<220> FEATURE:
<223> OTHER INFORMATION: synthetic

<400> SEQUENCE: 63
cacgtcgtaa aaatcgtatt tgctacttac aggaaatttt ttctaacgaa atggccaagg 60
tagatgatag tttcttccat cgtctcgaag aatcttttct ggttgaggaa gataaaaaac 120
acgaacgtca ccctatcttt ggcaatatcg tggatgaagt ggcctatcat gaaaaatacc 180
ctacgattta tcatcttcgc aagaagttgg ttgatagtac ggacaaagcg gatctgcgtt 240
taatccatct tgcgttagcg cacatgatca aatttcgtgg tcatttctta attgaaggtg 300
atctgaatcc tgataactct gatgtggaca aattgtttat acaattagtg caaacctata 360
atcagctgtt cgaggaaaac cccattaatg cctctggagt tgatgccaaa gcgattttaa 420
gcgcgagact ttctaagtcc cggcgtctgg agaatctgat cgcccagtta ccaggggaaa 480
agaaaaatgg tctgtttg 498

<210> SEQ ID NO 64
<211> LENGTH: 20
<212> TYPE: DNA
<213> ORGANISM: Artificial Sequence
<220> FEATURE:
<223> OTHER INFORMATION: synthetic

<400> SEQUENCE: 64
cacgtcgtaa aaatcgtatt 20

<210> SEQ ID NO 65
<211> LENGTH: 20
<212> TYPE: DNA
<213> ORGANISM: Artificial Sequence
<220> FEATURE:
<223> OTHER INFORMATION: synthetic

<400> SEQUENCE: 65
caaacagacc atttttcttt 20

<210> SEQ ID NO 66
<211> LENGTH: 7888
<212> TYPE: DNA
<213> ORGANISM: Artificial Sequence
<220> FEATURE:
<223> OTHER INFORMATION: synthetic

<400> SEQUENCE: 66
aaagaaaaat ggtctgtttg gtaatctgat tgccctcagt ctggggctta ccccgaactt 60
caaatccaat tttgacctgg ctgaggacgc aaagctgcag ctgagcaaag atacttatga 120
tgatgacctc gacaatctgc tcgcccagat tggtgaccaa tatgcggatc tgtttctggc 180
agcgaagaat ctttcggatg ctatcttgct gtcggatatt ctgcgtgtta ataccgaaat 240
caccaaagcg cctctgtctg caagtatgat caagagatac gacgagcacc accaggacct 300
gactcttctt aaggcactgg tacgccaaca gcttccggag aaatacaaag aaatattctt 360
cgaccagtcc aagaatggtt acgcgggcta catcgatggt ggtgcatcac aggaagagtt 420
ctataaattt attaaaccaa tccttgagaa aatggatggc acggaagagt tacttgttaa 480
acttaaccgc gaagacttgc ttagaaagca acgtacattc gacaacggct ccatcccaca 540
ccagattcat ttaggtgaac ttcacgccat cttgcgcaga caagaagatt tctatccctt 600
cttaaaagac aatcgggaga aaatcgagaa gatcctgacg ttccgcattc cctattatgt 660
cggtcccctg gcacgtggta attctcggtt tgcctggatg acgcgcaaaa gtgaggaaac 720
catcacccct tggaactttg aagaagtcgt ggataaaggt gctagcgcgc agtcttttat 780
agaaagaatg acgaacttcg ataaaaactt gcccaacgaa aaagtcctgc ccaagcactc 840
tcttttatat gagtacttta ctgtgtacaa cgaactgact aaagtgaaat acgttacgga 900
aggtatgcgc aaacctgcct ttcttagtgg cgagcagaaa aaagcaattg tcgatcttct 960
ctttaaaacg aatcgcaagg taactgtaaa acagctgaag gaagattatt tcaaaaagat 1020
cgaatgcttt gattctgtcg agatctcggg tgtcgaagat cgtttcaacg cttccttagg 1080
gacctatcat gatttgctga agataataaa agacaaagac tttctcgaca atgaagaaaa 1140

```
tgaagatatt ctggaggata ttgttttgac cttgacctta ttcgaagata gagagatgat   1200
cgaggagcgc ttaaaaacct atgcccacct gtttgatgac aaagtcatga agcaattaaa   1260
gcgccgcaga tatacggggt ggggccgctt gagccgcaag ttgattaacg gtattagaga   1320
caagcagagc ggaaaaacta tcctggattt cctcaaatct gacggatttg cgaaccgcaa   1380
ttttatgcag cttatacatg atgattcgct tacattcaaa gaggatattc agaaggctca   1440
ggtgtctggg caaggtgatt cactccacga acatatagca aatttggccg gctctcctgc   1500
gattaagaag gggatcctgc aaacagttaa agttgtggat gaacttgtaa aagtaatggg   1560
ccgccacaag ccggagaata tcgtgataga aatggcgcgc gagaatcaaa cgacacaaaa   1620
aggtcaaaag aactcaagag agagaatgaa gcgcattgag gaggggataa aggaacttgg   1680
atctcaaatt ctgaaagaac atccagttga aaacactcag ctgcaaaatg aaaaattgta   1740
cctgtactac ctgcagaatg gaagagacat gtacgtggat caggaattgg atatcaatag   1800
actctcggac tatgacgtag atcacattgt ccctcagagc ttcctcaagg atgattctat   1860
agataataaa gtacttacga gatcggacaa aaatcgcggt aaatcggata acgtcccatc   1920
ggaggaagtc gttaaaaaga tgaaaaacta ttggcgtcaa ctgctgaacg ccaagctgat   1980
cacacagcgt aagtttgata atctgactaa agccgaacgc ggtggtctta gtgaactcga   2040
taaagcagga tttataaaac ggcagttagt agaaacgcgc caaattacga aacacgtggc   2100
tcagatcctc gattctagaa tgaatacaaa gtacgatgaa aacgataaac tgatccgtga   2160
agtaaaagtc attaccttaa aatctaaact tgtgtccgat ttccgcaaag attttcagtt   2220
ttacaaggtc cgggaaatca ataactatca ccatgcacat gatgcatatt taaatgcggt   2280
tgtaggcacg gcccttatta agaaataccc taaactcgaa agtgagtttg tttatgggga   2340
ttataaagtg tatgacgttc gcaaaatgat cgcgaaatca gaacaggaaa tcggtaaggc   2400
taccgctaaa tacttttttt attccaacat tatgaatttt tttaagaccg aaataactct   2460
cgcgaatggt gaaatccgta aacggcctct tatagaaacc aatggtgaaa cgggagaaat   2520
cgtttgggat aaaggtcgtg actttgccac cgttcgtaaa gtcctctcaa tgccgcaagt   2580
taacattgtc aagaagacgg aagttcaaac agggggattc tccaaagaat ctatcctgcc   2640
gaagcgtaac agtgataaac ttattgccag aaaaaaagat tgggatccaa aaaaatacgg   2700
aggctttgat tcccctaccg tcgcgtatag tgtgctggtg gttgctaaag tcgagaaagg   2760
gaaaagcaag aaattgaaat cagttaaaga actgctgggt attacaatta tggaaagatc   2820
gtcctttgag aaaaatccga tcgacttttt agaggccaag gggtataagg aagtgaaaaa   2880
agatctcatc atcaaattac cgaagtatag tctttttgag ctggaaaacg gcagaaaaag   2940
aatgctggcc tccgcgggcg agttacagaa gggaaatgag ctggcgctgc cttccaaata   3000
tgttaatttt ctgtaccttg ccagtcatta tgagaaactg aagggcagcc ccgaagataa   3060
cgaacagaaa caattattcg tggaacagca taagcactat ttagatgaaa ttatagagca   3120
aattagtgaa ttttctaagc gcgttatcct cgcggatgct aatttagaca aagtactgtc   3180
agcttataat aaacatcggg ataagccgat tagagaacag gccgaaaata tcattcattt   3240
gtttacctta accaaccttg gagcaccagc tgccttcaaa tatttcgata ccacaattga   3300
tcgtaaacgg tatacaagta caaaagaagt cttggacgca accctcattc atcaatctat   3360
tactggatta tatgagacac gcattgatct ttcacagctg ggcggagaca agaagaaaaa   3420
actgaaactg caccatcatc accatcatca tcaccatcat tgataactcg agaaagctta   3480
cataaaaaac cggccttggc cccgccggtt ttttattatt tttcttcctc cgcatgttca   3540
```

atccgctcca taatcgacgg atggctccct ctgaaaattt taacgagaaa cggcgggttg 3600
acccggctca gtcccgtaac ggccaagtcc tgaaacgtct caatcgccgc ttcccggttt 3660
ccggtcagct caatgccgta acggtcggcg gcgttttcct gataccggga gacggcattc 3720
gtaatcgaat tcgcggccgc acgcgtccat ggggatcccc gcgggtcgac ctcgagagtt 3780
acgctaggga taacagggta atataggagc tccagtcggc ttaaaccagt tttcgctggt 3840
gcgaaaaaag agtgtcttgt gacacctaaa ttcaaaatct atcggtcaga tttataccga 3900
tttgatttta tatattcttg aataacatac gccgagttat cacataaaag cgggaaccaa 3960
tcataaaatt taaacttcat tgcataatcc attaaactct taaattctac gattccttgt 4020
tcatcaataa actcaatcat ttctttaatt aatttatatc tatctgttgt tgtttctttt 4080
aataattcat taacatctac accgccataa actatcatat cttcttttttg atatttaaat 4140 ttattaggat cgtccatgtg aagcatatat ctcacaagac ctttcacact tcctgcaatc 4200
tgcggaatag tcgcattcaa ttcttctgtt aattattttt atctgttcat aagatttatt 4260
accctcatac atcactagaa tatgataatg ctctttttttc atcctacctt ctgtatcagt 4320
atccctatca tgtaatggag acactacaaa ttgaatgtgt aactctttta aatactctaa 4380
ccactcggct tttgctgatt ctggatataa aacaaatgtc caattacgtc ctcttgaatt 4440
tttcttgttt tcagtttctt ttattacatt ttcgctcatg atataataac ggtgctaata 4500
cacttaacaa aatttagtca tagataggca gcatgccagt gctgtctatc ttttttttgtt 4560 taaaatgcac cgtattcctc ctttgcatat tttttttatta gaataccggt tgcatctgat 4620
ttgctaatat tatattttttc tttgattcta tttaatatct cattttcttc tgttgtaagt 4680
cttaaagtaa cagcaacttt tttctcttct tttctatcta caactatcac tgtacctccc 4740
aacatctgtt tttttcactt taacataaaa aacaaccttt taacattaaa aacccaatat 4800
ttatttattt gtttggacaa tggacactgg acacctaggg gggaggtcgt agtacccccc 4860
tatgttttct cccctaaata accccaaaaa tctaagaaaa aaagacctca aaaaggtctt 4920
taattaacat ctcaaatttc gcatttattc caatttcctt tttgcgtgtg atgcgagctc 4980
atcggctccg tcgatactat gttatacgcc aactttcaaa acaactttga aaaagctgtt 5040
ttctggtatt taaggtttta gaatgcaagg aacagtgaat tggagttcgt cttgttataa 5100
ttagcttctt ggggtatctt taaatactgt agaaaagagg aaggaaataa taaatggcta 5160
aaatgagaat atcaccggaa ttgaaaaaac tgatcgaaaa ataccgctgc gtaaaagata 5220
cggaaggaat gtctcctgct aaggtatata agctggtggg agaaaatgaa aacctatatt 5280
taaaaatgac ggacagccgg tataaaggga ccacctatga tgtggaacgg gaaaaggaca 5340
tgatgctatg gctggaagga aagctgcctg ttccaaaggt cctgcacttt gaacggcatg 5400
atggctggag caatctgctc atgagtgagg ccgatggcgt cctttgctcg gaagagtatg 5460
aagatgaaca aagccctgaa aagattatcg agctgtatgc ggagtgcatc aggctctttc 5520
actccatcga catatcggat tgtccctata cgaatagctt agacagccgc ttagccgaat 5580
tggattactt actgaataac gatctggccg atgtggattg cgaaaactgg gaagaagaca 5640
ctccatttaa agatccgcgc gagctgtatg attttttaaa gacggaaaag cccgaagagg 5700
aacttgtctt ttcccacggc gacctgggag acagcaacat ctttgtgaaa gatggcaaag 5760
taagtggctt tattgatctt gggagaagcg gcagggcgga caagtggtat gacattgcct 5820
tctgcgtccg gtcgatcagg gaggatatcg ggaagaaca gtatgtcgag ctatttttttg 5880 acttactggg gatcaagcct gattgggaga aaataaaata ttatatttta ctggatgaat 5940
tgttttagtg actgcagtga gatctggtaa tgactctcta gcttgaggca tcaaataaaa 6000
cgaaaggctc agtcgaaaga ctgggccttt cgttttatct gttgtttgtc ggtgaacgct 6060
ctcctgagta ggacaaatcc gccgctctag ctaagcagaa ggccatcctg acggatggcc 6120
tttttgcgtt tctacaaact cttgttaact ctagagctgc ctgccgcgtt tcggtgatga 6180
agatcttccc gatgattaat taattcagaa cgctcggttg ccgccgggcg tttttttatga 6240 agcttcgttg ctggcgtttt tccataggct ccgcccccct gacgagcatc acaaaaatcg 6300
acgctcaagt cagaggtggc gaaacccgac aggactataa agataccagg cgtttccccc 6360
tggaagctcc ctcgtgcgct ctcctgttcc gaccctgccg cttaccggat acctgtccgc 6420
ctttctccct tcgggaagcg tggcgctttc tcatagctca cgctgtaggt atctcagttc 6480
ggtgtaggtc gttcgctcca agctgggctg tgtgcacgaa ccccccgttc agcccgaccg 6540
ctgcgcctta tccggtaact atcgtcttga gtccaacccg gtaagacacg acttatcgcc 6600
actggcagca gccactggta acaggattag cagagcgagg tatgtaggcg gtgctacaga 6660
gttcttgaag tggtggccta actacggcta cactagaagg acagtatttg gtatctgcgc 6720
tctgctgaag ccagttacct tcggaaaaag agttggtagc tcttgatccg gcaaacaaac 6780
caccgctggt agcggtggtt tttttgtttg caagcagcag attacgcgca gaaaaaaagg 6840
atctcaagaa gatcctttga tcttttctac ggggtctgac gctcagtgga acgaaaactc 6900
acgttaaggg attttggtca tgagattatc aaaaaggatc ttcacctaga tccttttaaa 6960
ttaaaaatga agttttaaat caatctaaag tatatatgag taaacttggt ctgacagaat 7020
tcctccattt tcttctgcta tcaaaataac agactcgtga ttttccaaac gagctttcaa 7080
aaaagcctct gccccttgca aatcggatgc ctgtctataa aattcccgat attggttaaa 7140
cagcggcgca atggcggccg catctgatgt ctttgcttgg cgaatgttca tcttatttct 7200
tcctccctct caataatttt ttcattctat cccttttctg taaagtttat ttttcagaat 7260
acttttatca tcatgctttg aaaaaatatc acgataatat ccattgttct cacggaagca 7320
cacgcaggtc atttgaacga attttttcga caggaatttg ccgggactca ggagcattta 7380
acctaaaaaa gcatgacatt tcagcataat gaacatttac tcatgtctat tttcgttctt 7440
ttctgtatga aaatagttat ttcgagtctc tacggaaata gcgagagatg atatacctaa 7500
atagagataa aatcatctca aaaaaatggg tctactaaaa tattattcca tctattacaa 7560
taaattcaca gaatagtctt ttaagtaagt ctactctgaa tttttttaaa aggagagggt 7620
aactagtggc cccaaaaaag aaacgcaagg ttatggataa aaaatacagc attggtctgg 7680
atatcggaac caacagcgtt gggtgggcag taataacaga tgaatacaaa gtgccgtcaa 7740
aaaaatttaa ggttctgggg aatacagatc gccacagcat aaaaaagaat ctgattgggg 7800
cattgctgtt tgattcgggt gagacagctg aggccacgcg tctgaaacgt acagcaagaa 7860
gacgttacac acgtcgtaaa aatcgtat 7888

<210> SEQ ID NO 67
<211> LENGTH: 20
<212> TYPE: DNA
<213> ORGANISM: Artificial Sequence
<220> FEATURE:
<223> OTHER INFORMATION: synthetic

<400> SEQUENCE: 67
aaagaaaaat ggtctgtttg 20

<210> SEQ ID NO 68
<211> LENGTH: 20
<212> TYPE: DNA
<213> ORGANISM: Artificial Sequence
<220> FEATURE:
<223> OTHER INFORMATION: synthetic

<400> SEQUENCE: 68
aatacgattt ttacgacgtg 20

<210> SEQ ID NO 69
<211> LENGTH: 9790
<212> TYPE: DNA
<213> ORGANISM: Artificial Sequence
<220> FEATURE:
<223> OTHER INFORMATION: synthetic

<400> SEQUENCE: 69
gaattcctcc attttcttct gctatcaaaa taacagactc gtgattttcc aaacgagctt 60
tcaaaaaagc ctctgcccct tgcaaatcgg atgcctgtct ataaaattcc cgatattggt 120
taaacagcgg cgcaatggcg gccgcatctg atgtctttgc ttggcgaatg ttcatcttat 180
ttcttcctcc ctctcaataa ttttttcatt ctatcccttt tctgtaaagt ttatttttca 240
gaatactttt atcatcatgc tttgaaaaaa tatcacgata atatccattg ttctcacgga 300
agcacacgca ggtcatttga acgaattttt tcgacaggaa tttgccggga ctcaggagca 360
tttaacctaa aaaagcatga catttcagca taatgaacat ttactcatgt ctattttcgt 420
tcttttctgt atgaaaatag ttatttcgag tctctacgga aatagcgaga gatgatatac 480
ctaaatagag ataaaatcat ctcaaaaaaa tgggtctact aaaatattat tccatctatt 540
acaataaatt cacagaatag tcttttaagt aagtctactc tgaatttttt taaaaggaga 600
gggtaactag tggccccaaa aaagaaacgc aaggttatgg ataaaaaata cagcattggt 660
ctggatatcg gaaccaacag cgttgggtgg gcagtaataa cagatgaata caaagtgccg 720
tcaaaaaaat ttaaggttct ggggaataca gatcgccaca gcataaaaaa gaatctgatt 780
ggggcattgc tgtttgattc gggtgagaca gctgaggcca cgcgtctgaa acgtacagca 840
agaagacgtt acacacgtcg taaaaatcgt atttgctact tacaggaaat tttttctaac 900
gaaatggcca aggtagatga tagtttcttc catcgtctcg aagaatcttt tctggttgag 960
gaagataaaa aacacgaacg tcaccctatc tttggcaata tcgtggatga agtggcctat 1020
catgaaaaat accctacgat ttatcatctt cgcaagaagt tggttgatag tacggacaaa 1080
gcggatctgc gtttaatcca tcttgcgtta gcgcacatga tcaaatttcg tggtcatttc 1140
ttaattgaag gtgatctgaa tcctgataac tctgatgtgg acaaattgtt tatacaatta 1200
gtgcaaacct ataatcagct gttcgaggaa aaccccatta atgcctctgg agttgatgcc 1260
aaagcgattt taagcgcgag actttctaag tcccggcgtc tggagaatct gatcgcccag 1320
ttaccagggg aaaagaaaaa tggtctgttt ggtaatctga ttgccctcag tctggggctt 1380
accccgaact tcaaatccaa ttttgacctg gctgaggacg caaagctgca gctgagcaaa 1440
gatacttatg atgatgacct cgacaatctg ctcgcccaga ttggtgacca atatgcggat 1500
ctgtttctgg cagcgaagaa tctttcggat gctatcttgc tgtcggatat tctgcgtgtt 1560
aataccgaaa tcaccaaagc gcctctgtct gcaagtatga tcaagagata cgacgagcac 1620
caccaggacc tgactcttct taaggcactg gtacgccaac agcttccgga gaaatacaaa 1680

-continued

```
gaaatattct tcgaccagtc caagaatggt tacgcgggct acatcgatgg tggtgcatca   1740
caggaagagt tctataaatt tattaaacca atccttgaga aaatggatgg cacggaagag   1800
ttacttgtta aacttaaccg cgaagacttg cttagaaagc aacgtacatt cgacaacggc   1860
tccatcccac accagattca tttaggtgaa cttcacgcca tcttgcgcag acaagaagat   1920
ttctatccct tcttaaaaga caatcgggag aaaatcgaga agatcctgac gttccgcatt   1980
ccctattatg tcggtcccct ggcacgtggt aattctcggt ttgcctggat gacgcgcaaa   2040
agtgaggaaa ccatcacccc ttggaacttt gaagaagtcg tggataaagg tgctagcgcg   2100
cagtctttta tagaaagaat gacgaacttc gataaaaact tgcccaacga aaaagtcctg   2160
cccaagcact ctcttttata tgagtacttt actgtgtaca acgaactgac taaagtgaaa   2220
tacgttacgg aaggtatgcg caaacctgcc tttcttagtg gcgagcagaa aaaagcaatt   2280
gtcgatcttc tctttaaaac gaatcgcaag gtaactgtaa aacagctgaa ggaagattat   2340
ttcaaaaaga tcgaatgctt tgattctgtc gagatctcgg gtgtcgaaga tcgtttcaac   2400
gcttccttag ggacctatca tgatttgctg aagataataa aagacaaaga ctttctcgac   2460
aatgaagaaa atgaagatat tctggaggat attgttttga ccttgacctt attcgaagat   2520
agagagatga tcgaggagcg cttaaaaacc tatgcccacc tgtttgatga caaagtcatg   2580
aagcaattaa agcgccgcag atatacgggg tggggccgct tgagccgcaa gttgattaac   2640
ggtattagag acaagcagag cggaaaaact atcctggatt tcctcaaatc tgacggattt   2700
gcgaaccgca attttatgca gcttatacat gatgattcgc ttacattcaa agaggatatt   2760
cagaaggctc aggtgtctgg gcaaggtgat tcactccacg aacatatagc aaatttggcc   2820
ggctctcctg cgattaagaa ggggatcctg caaacagtta aagttgtgga tgaacttgta   2880
aaagtaatgg gccgccacaa gccggagaat atcgtgatag aaatggcgcg cgagaatcaa   2940
acgacacaaa aaggtcaaaa gaactcaaga gagagaatga agcgcattga ggaggggata   3000
aaggaacttg gatctcaaat tctgaaagaa catccagttg aaaacactca gctgcaaaat   3060
gaaaaattgt acctgtacta cctgcagaat ggaagagaca tgtacgtgga tcaggaattg   3120
gatatcaata gactctcgga ctatgacgta gatcacattg tccctcagag cttcctcaag   3180
gatgattcta tagataataa agtacttacg agatcggaca aaaatcgcgg taaatcggat   3240
aacgtcccat cggaggaagt cgttaaaaag atgaaaaact attggcgtca actgctgaac   3300
gccaagctga tcacacagcg taagtttgat aatctgacta aagccgaacg cggtggtctt   3360
agtgaactcg ataaagcagg atttataaaa cggcagttag tagaaacgcg ccaaattacg   3420
aaacacgtgg ctcagatcct cgattctaga atgaatacaa agtacgatga aaacgataaa   3480
ctgatccgtg aagtaaaagt cattacctta aaatctaaac ttgtgtccga tttccgcaaa   3540
gattttcagt tttacaaggt ccgggaaatc aataactatc accatgcaca tgatgcatat   3600
ttaaatgcgg ttgtaggcac ggcccttatt aagaaatacc ctaaactcga aagtgagttt   3660
gtttatgggg attataaagt gtatgacgtt cgcaaaatga tcgcgaaatc agaacaggaa   3720
atcggtaagg ctaccgctaa atactttttt tattccaaca ttatgaattt ttttaagacc   3780
gaaataactc tcgcgaatgg tgaaatccgt aaacggcctc ttatagaaac caatggtgaa   3840
acgggagaaa tcgtttggga taaaggtcgt gactttgcca ccgttcgtaa agtcctctca   3900
atgccgcaag ttaacattgt caagaagacg gaagttcaaa caggggggatt ctccaaagaa   3960
tctatcctgc cgaagcgtaa cagtgataaa cttattgcca gaaaaaaaga ttgggatcca   4020
aaaaaatacg gaggctttga ttcccctacc gtcgcgtata gtgtgctggt ggttgctaaa   4080
```

```
gtcgagaaag ggaaaagcaa gaaattgaaa tcagttaaag aactgctggg tattacaatt   4140
atggaaagat cgtcctttga gaaaaatccg atcgactttt tagaggccaa ggggtataag   4200
gaagtgaaaa aagatctcat catcaaatta ccgaagtata gtctttttga gctggaaaac   4260
ggcagaaaaa gaatgctggc ctccgcgggc gagttacaga agggaaatga gctggcgctg   4320
ccttccaaat atgttaattt tctgtacctt gccagtcatt atgagaaact gaagggcagc   4380
cccgaagata acgaacagaa acaattattc gtggaacagc ataagcacta tttagatgaa   4440
attatagagc aaattagtga attttctaag cgcgttatcc tcgcggatgc taatttagac   4500
aaagtactgt cagcttataa taaacatcgg gataagccga ttagagaaca ggccgaaaat   4560
atcattcatt tgtttacctt aaccaacctt ggagcaccag ctgccttcaa atatttcgat   4620
accacaattg atcgtaaacg gtatacaagt acaaaagaag tcttggacgc aaccctcatt   4680
catcaatcta ttactggatt atatgagaca cgcattgatc tttcacagct gggcggagac   4740
aagaagaaaa aactgaaact gcaccatcat caccatcatc atcaccatca ttgataactc   4800
gagaaagctt acataaaaaa ccggccttgg ccccgccggt tttttattat tttcttcct    4860
ccgcatgttc aatccgctcc ataatcgacg gatggctccc tctgaaaatt ttaacgagaa   4920
acggcgggtt gacccggctc agtcccgtaa cggccaagtc ctgaaacgtc tcaatcgccg   4980
cttcccggtt tccggtcagc tcaatgccgt aacggtcggc ggcgttttcc tgataccggg   5040
agacggcatt cgtaatcggg tgaagtggtc aagacctcac taggcacctt aaaaatagcg   5100
caccctgaag aagatttatt tgaggtagcc cttgcctacc tagcttccaa gaaagatatc   5160
ctaacagcac aagagcggaa agatgttttg ttctacatcc agaacaacct ctgctaaaat   5220
tcctgaaaaa ttttgcaaaa agttgttgac tttatctaca aggtgtggca taatgtgtgg   5280
aagaatcgaa aacggccacc ggttttagag ctagaaatag caagttaaaa taaggctagt   5340
ccgttatcaa cttgaaaaag tggcaccgag tcggtgcgac tcctgttgat agatccagta   5400
atgacctcag aactccatct ggatttgttc agaacgctcg gttgccgccg ggcgtttttt   5460
attggtgaga atcgcgtcta cagtccagga agcaagaagc agctatgatt ccatttacga   5520
catcgtgtca cagtacgatt tagaggacct ttctctgttt gacagcgaaa agtggaaggt   5580
gctttcaaaa aaagacatcg aaaacctgga caaatatttc gactttctcg tgcaggaagc   5640
aagcagccga aacaaaaact gaatacttct ccgcggcaca ctctcctctc tatcattttc   5700
gtctgtttac gatcctgctg ttattttatc ccttatgtta acttttgtca atatttttcc   5760
tgtctaagta tttcctatag tcaacatttg tattaaaatg ttcatatcat gaatttgcgg   5820
gggggatggc gatgacaagg ttcggcgagc ggctcaaaga gctgagggaa caaagaagcc   5880
tgtcggttaa tcagcttgcc atgtatgccg gtgtgagcgc cgcagccatt tccagaatcg   5940
aaaacggcca ccgctaagtt cccaagcccg cgacgatcag aaaattggcc tgataactga   6000
aaatgccgta cgagcagctc atggatattg ccggttatat gagagctgac gagattcgcg   6060
aacagccgcg cggctatgtc acgatgcagg agatcgcggc caagcacggc gtcgaagacc   6120
tgtggctgtt taaacccgag aaatgggact gtttgtcccg cgaagacctg ctcaacctcg   6180
aacagtattt tcattttttg gttaatgaag cgaagaagcg ccaatcataa aaagccgaat   6240
ttccctttta ggagaagttc ggcttttttc ggctgcctta agcggcatcc ggattcggcg   6300
tcttgccttt atgatgctta acggggctca gcgcacgctc gagccatccc atgaacagat   6360
cggcgatgat cgccatcagc gccgtcggga tcgcgcctgc tagaatgatc gctgttccgt   6420
```

-continued

```
tggtcgcgtt tgatcccctg acaatgatat ccccgaggcc gcctgcgccg acaaacgtgc   6480
cgatggccgt aatgcgaatt cgcggccgca cgcgtccatg gggatccccg cgggtcgacc   6540
tcgagagtta cgctagggat aacagggtaa tataggagct ccagtcggct taaaccagtt   6600
ttcgctggtg cgaaaaaaga gtgtcttgtg acactcttaa attcaaaatc tatcggtcag   6660
atttataccg atttgatttt atatattctt gaataacata cgccgagtta tcacataaaa   6720
gcgggaacca atcataaaat ttaaacttca ttgcataatc cattaaactc ttaaattcta   6780
cgattccttg ttcatcaata aactcaatca tttctttaat taatttatat ctatctgttg   6840
ttgttttctt taataattca ttaacatcta caccgccata aactatcata tcttcttttt   6900
gatatttaaa tttattagga tcgtccatgt gaagcatata tctcacaaga cctttcacac   6960
ttcctgcaat ctgcggaata gtcgcattca attcttctgt aattattttt atctgttcat   7020
aagatttatt accctcatac atcactagaa tatgataatg ctctttttc atcctacctt   7080
ctgtatcagt atccctatca tgtaatggag acactacaaa ttgaatgtgt aactctttta   7140
aatactctaa ccactcggct tttgctgatt ctggatataa aacaaatgtc caattacgtc   7200
ctcttgaatt tttcttgttt tcagtttctt ttattacatt ttcgctcatg atataataac   7260
ggtgctaata cacttaacaa aatttagtca tagataggca gcatgccagt gctgtctatc   7320
tttttttgtt taaaatgcac cgtattcctc ctttgcatat tttttatta gaataccggt   7380
tgcatctgat ttgctaatat tatattttc tttgattcta tttaatatct cattttcttc   7440
tgttgtaagt cttaaagtaa cagcaacttt ttctcttct tttctatcta caactatcac   7500
tgtacctccc aacatctgtt tttttcactt taacataaaa aacaaccttt taacattaaa   7560
aacccaatat ttatttattt gtttggacaa tggacactgg acacctaggg gggaggtcgt   7620
agtacccccc tatgttttct cccctaaata accccaaaaa tctaagaaaa aaagacctca   7680
aaaaggtctt taattaacat ctcaaatttc gcatttattc caatttcctt tttgcgtgtg   7740
atgcgagctc atcggctccg tcgatactat gttatacgcc aactttgaaa acaactttga   7800
aaaagctgtt ttctggtatt taaggtttta gaatgcaagg aacagtgaat tggagttcgt   7860
cttgttataa ttagcttctt ggggtatctt taaatactgt agaaaagagg aaggaaataa   7920
taaatggcta aaatgagaat atcaccggaa ttgaaaaaac tgatcgaaaa ataccgctgc   7980
gtaaaagata cggaaggaat gtctcctgct aaggtatata agctggtggg agaaaatgaa   8040
aacctatatt taaaaatgac ggacagccgg tataaaggga ccacctatga tgtggaacgg   8100
gaaaaggaca tgatgctatg gctggaagga aagctgcctg ttccaaaggt cctgcacttt   8160
gaacggcatg atggctggag caatctgctc atgagtgagg ccgatggcgt cctttgctcg   8220
gaagagtatg aagatgaaca aagccctgaa aagattatcg agctgtatgc ggagtgcatc   8280
aggctctttc actccatcga catatcggat tgtccctata cgaatagctt agacagccgc   8340
ttagccgaat tggattactt actgaataac gatctggccg atgtggattg cgaaaactgg   8400
gaagaagaca ctccatttaa agatccgcgc gagctgtatg attttttaaa gacggaaaag   8460
cccgaagagg aacttgtctt ttcccacggc gacctgggag acagcaacat ctttgtgaaa   8520
gatggcaaag taagtggctt tattgatctt gggagaagcg gcagggcgga caagtggtat   8580
gacattgcct tctgcgtccg gtcgatcagg gaggatatcg gggaagaaca gtatgtcgag   8640
ctattttttg acttactggg gatcaagcct gattgggaga aaataaaata ttatatttta   8700
ctggatgaat tgttttagtg actgcagtcg ggaagatctg gtaatgactc tctagcttga   8760
ggcatcaaat aaaacgaaag gctcagtcga aagactgggc ctttcgtttt atctgttgtt   8820
```

tgtcggtgaa cgctctcctg agtaggacaa atccgccgct ctagctaagc agaaggccat 8880
cctgacggat ggcctttttg cgtttctaca aactcttgtt aactctagag ctgcctgccg 8940
cgtttcggtg atgaagatct tcccgatgat taattaattc agaacgctcg gttgccgccg 9000
ggcgtttttt atgaagcttc gttgctggcg tttttccata ggctccgccc ccctgacgag 9060
catcacaaaa atcgacgctc aagtcagagg tggcgaaacc cgacaggact ataaagatac 9120
caggcgtttc cccctggaag ctccctcgtg cgctctcctg ttccgaccct gccgcttacc 9180
ggatacctgt ccgcctttct cccttcggga agcgtggcgc tttctcatag ctcacgctgt 9240
aggtatctca gttcggtgta ggtcgttcgc tccaagctgg gctgtgtgca cgaccccccc 9300
gttcagcccg accgctgcgc cttatccggt aactatcgtc ttgagtccaa cccggtaaga 9360
cacgacttat cgccactggc agcagccact ggtaacagga ttagcagagc gaggtatgta 9420
ggcggtgcta cagagttctt gaagtggtgg cctaactacg gctacactag aagaacagta 9480
tttggtatct gcgctctgct gaagccagtt accttcggaa aaagagttgg tagctcttga 9540
tccggcaaac aaaccaccgc tggtagcggt ggtttttttg tttgcaagca gcagattacg 9600
cgcagaaaaa aaggatctca agaagatcct ttgatctttt ctacggggtc tgacgctcag 9660
tggaacgaaa actcacgtta agggattttg gtcatgagat tatcaaaaag gatcttcacc 9720
tagatccttt taaattaaaa atgaagtttt aaatcaatct aaagtatata tgagtaaact 9780
tggtctgaca 9790

<210> SEQ ID NO 70
<211> LENGTH: 399
<212> TYPE: DNA
<213> ORGANISM: Bacillus licheniformis

<400> SEQUENCE: 70
atgacaaggt tcggcgagcg gctcaaagag ctgagggaac aaagaagcct gtcggttaat 60
cagcttgcca tgtatgccgg tgtgagcgcc gcagccattt ccagaatcga aaacggccac 120
cgcggcgttc ccaagcccgc gacgatcaga aaattggccg aggctctgaa aatgccgtac 180
gagcagctca tggatattgc cggttatatg agagctgacg agattcgcga acagccgcgc 240
ggctatgtca cgatgcagga gatcgcggcc aagcacggcg tcgaagacct gtggctgttt 300
aaacccgaga aatgggactg tttgtcccgc gaagacctgc tcaacctcga acagtatttt 360
cattttttgg ttaatgaagc gaagaagcgc caatcataa 399

<210> SEQ ID NO 71
<211> LENGTH: 1438
<212> TYPE: DNA
<213> ORGANISM: Artificial Sequence
<220> FEATURE:
<223> OTHER INFORMATION: synthetic

<400> SEQUENCE: 71
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180
aaaagttgtt gactttatct acaaggtgtg gcataatgtg tggaagaatc gaaaacggcc 240
accggtttta gagctagaaa tagcaagtta aaataaggct agtccgttat caacttgaaa 300
aagtggcacc gagtcggtgc gactcctgtt gatagatcca gtaatgacct cagaactcca 360

```
tctggatttg ttcagaacgc tcggttgccg ccgggcgttt tttattggtg agaatcgcgt    420
ctacagtcca ggaagcaaga agcagctatg attccattta cgacatcgtg tcacagtacg    480
atttagagga cctttctctg tttgacagcg aaaagtggaa ggtgctttca aaaaaagaca    540
tcgaaaacct ggacaaatat ttcgactttc tcgtgcagga agcaagcagc cgaaacaaaa    600
actgaatact tctccgcggc acactctcct ctctatcatt ttcgtctgtt tacgatcctg    660
ctgttatttt atcccttatg ttaacttttg tcaatatttt tcctgtctaa gtatttccta    720
tagtcaacat ttgtattaaa atgttcatat catgaatttg cggggggat ggcgatgaca    780
aggttcggcg agcggctcaa agagctgagg gaacaaagaa gcctgtcggt taatcagctt    840
gccatgtatg ccggtgtgag cgccgcagcc atttccagaa tcgaaaacgg ccaccgctaa    900
gttcccaagc ccgcgacgat cagaaaattg gcctgataac tgaaaatgcc gtacgagcag    960
ctcatggata ttgccggtta tatgagagct gacgagattc gcgaacagcc gcgcggctat   1020
gtcacgatgc aggagatcgc ggccaagcac ggcgtcgaag acctgtggct gtttaaaccc   1080
gagaaatggg actgtttgtc ccgcgaagac ctgctcaacc tcgaacagta ttttcatttt   1140
ttggttaatg aagcgaagaa gcgccaatca taaaaagccg aatttccctt ttaggagaag   1200
ttcggctttt ttcggctgcc ttaagcggca tccggattcg gcgtcttgcc tttatgatgc   1260
ttaacggggc tcagcgcacg ctcgagccat cccatgaaca gatcggcgat gatcgccatc   1320
agcgccgtcg ggatcgcgcc tgctagaatg atcgctgttc cgttggtcgc gtttgatccc   1380
ctgacaatga tatccccgag gccgcctgcg ccgacaaacg tgccgatggc cgtaatgc     1438
```

<210> SEQ ID NO 72
<211> LENGTH: 1023
<212> TYPE: DNA
<213> ORGANISM: Artificial Sequence
<220> FEATURE:
<223> OTHER INFORMATION: synthetic

<400> SEQUENCE: 72

```
cgcgtctaca gtccaggaag caagaagcag ctatgattcc atttacgaca tcgtgtcaca     60
gtacgattta gaggaccttt ctctgtttga cagcgaaaag tggaaggtgc tttcaaaaaa    120
agacatcgaa aacctggaca aatatttcga ctttctcgtg caggaagcaa gcagccgaaa    180
caaaaactga atacttctcc gcggcacact ctcctctcta tcattttcgt ctgtttacga    240
tcctgctgtt attttatccc ttatgttaac ttttgtcaat atttttcctg tctaagtatt    300
tcctatagtc aacatttgta ttaaaatgtt catatcatga atttgcgggg gggatggcga    360
tgacaaggtt cggcgagcgg ctcaaagagc tgagggaaca aagaagcctg tcggttaatc    420
agcttgccat gtatgccggt gtgagcgccg cagccatttc cagaatcgaa aacggccacc    480
gctaagttcc caagcccgcg acgatcagaa aattggcctg ataactgaaa atgccgtacg    540
agcagctcat ggatattgcc ggttatatga gagctgacga gattcgcgaa cagccgcgcg    600
gctatgtcac gatgcaggag atcgcggcca agcacggcgt cgaagacctg tggctgttta    660
aacccgagaa atgggactgt ttgtcccgcg aagacctgct caacctcgaa cagtattttc    720
atttttggt taatgaagcg aagaagcgcc aatcataaaa agccgaattt cccttttagg    780
agaagttcgg cttttttcgg ctgccttaag cggcatccgg attcggcgtc ttgcctttat    840
gatgcttaac ggggctcagc gcacgctcga gccatcccat gaacagatcg gcgatgatcg    900
ccatcagcgc cgtcgggatc gcgcctgcta gaatgatcgc tgttccgttg gtcgcgtttg    960
atcccctgac aatgatatcc ccgaggccgc ctgcgccgac aaacgtgccg atggccgtaa   1020
```

tgc 1023

<210> SEQ ID NO 73
<211> LENGTH: 415
<212> TYPE: DNA
<213> ORGANISM: Artificial Sequence
<220> FEATURE:
<223> OTHER INFORMATION: synthetic

<400> SEQUENCE: 73
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180
aaaagttgtt gactttatct acaaggtgtg gcataatgtg tggaagaatc gaaaacggcc 240
accggtttta gagctagaaa tagcaagtta aaataaggct agtccgttat caacttgaaa 300
aagtggcacc gagtcggtgc gactcctgtt gatagatcca gtaatgacct cagaactcca 360
tctggatttg ttcagaacgc tcggttgccg ccgggcgttt tttattggtg agaat 415

<210> SEQ ID NO 74
<211> LENGTH: 17
<212> TYPE: DNA
<213> ORGANISM: Artificial Sequence
<220> FEATURE:
<223> OTHER INFORMATION: synthetic

<400> SEQUENCE: 74
cgtgcggccg cgaattc 17

<210> SEQ ID NO 75
<211> LENGTH: 29
<212> TYPE: DNA
<213> ORGANISM: Artificial Sequence
<220> FEATURE:
<223> OTHER INFORMATION: synthetic

<400> SEQUENCE: 75
cctgataccg ggagacggca ttcgtaatc 29

<210> SEQ ID NO 76
<211> LENGTH: 17
<212> TYPE: DNA
<213> ORGANISM: Artificial Sequence
<220> FEATURE:
<223> OTHER INFORMATION: synthetic

<400> SEQUENCE: 76
gaattcgcgg ccgcacg 17

<210> SEQ ID NO 77
<211> LENGTH: 29
<212> TYPE: DNA
<213> ORGANISM: Artificial Sequence
<220> FEATURE:
<223> OTHER INFORMATION: synthetic

<400> SEQUENCE: 77
gattacgaat gccgtctccc ggtatcagg 29

<210> SEQ ID NO 78
<211> LENGTH: 9738
<212> TYPE: DNA

<213> ORGANISM: Artificial Sequence
<220> FEATURE:
<223> OTHER INFORMATION: synthetic

<400> SEQUENCE: 78
gggtgaagtg gtcaagacct cactaggcac cttaaaaata gcgcaccctg aagaagattt 60
atttgaggta gcccttgcct acctagcttc caagaaagat atcctaacag cacaagagcg 120
gaaagatgtt ttgttctaca tccagaacaa cctctgctaa aattcctgaa aaattttgca 180
aaaagttgtt gactttatct acaaggtgtg gcataatgtg tggagcgagc ggctcaaaga 240
gctggtttta gagctagaaa tagcaagtta aaataaggct agtccgttat caacttgaaa 300
aagtggcacc gagtcggtgc gactcctgtt gatagatcca gtaatgacct cagaactcca 360
tctggatttg ttcagaacgc tcggttgccg ccgggcgttt tttattggtg agaatgtcga 420
cctcgagagt tacgctaggg ataacagggt aatataggag ctccagtcgg cttaaaccag 480
ttttcgctgg tgcgaaaaaa gagtgtcttg tgacacctaa attcaaaatc tatcggtcag 540
atttataccg atttgatttt atatattctt gaataacata cgccgagtta tcacataaaa 600
gcgggaacca atcataaaat ttaaacttca ttgcataatc cattaaactc ttaaattcta 660
cgattccttg ttcatcaata aactcaatca tttctttaat taatttatat ctatctgttg 720
ttgttttctt taataattca ttaacatcta caccgccata aactatcata tcttcttttt 780
gatatttaaa tttattagga tcgtccatgt gaagcatata tctcacaaga cctttcacac 840
ttcctgcaat ctgcggaata gtcgcattca attcttctgt taattatttt tatctgttca 900
taagatttat taccctcata catcactaga atatgataat gctctttttt catcctacct 960
tctgtatcag tatccctatc atgtaatgga gacactacaa attgaatgtg taactctttt 1020
aaatactcta accactcggc ttttgctgat tctggatata aaacaaatgt ccaattacgt 1080
cctcttgaat tttcttgtt ttcagtttct tttattacat tttcgctcat gatataataa 1140
cggtgctaat acacttaaca aaatttagtc atagataggc agcatgccag tgctgtctat 1200 cttttttgt ttaaaatgca ccgtattcct cctttgcata tttttttatt agaataccgg 1260
ttgcatctga tttgctaata ttatattttt ctttgattct atttaatatc tcattttctt 1320
ctgttgtaag tcttaaagta acagcaactt ttttctcttc ttttctatct acaactatca 1380
ctgtacctcc caacatctgt tttttcact ttaacataaa aaacaacctt ttaacattaa 1440
aaacccaata tttatttatt tgtttggaca atggacactg gacacctagg ggggaggtcg 1500
tagtaccccc ctatgtttc tcccctaaat aaccccaaaa atctaagaaa aaaagacctc 1560
aaaaaggtct ttaattaaca tctcaaattt cgcatttatt ccaatttcct ttttgcgtgt 1620
gatgcgagct catcggctcc gtcgatacta tgttatacgc caactttcaa aacaactttg 1680
aaaaagctgt tttctggtat ttaaggtttt agaatgcaag gaacagtgaa ttggagttcg 1740
tcttgttata attagcttct tggggtatct ttaaatactg tagaaaagag gaaggaaata 1800
ataaatggct aaaatgagaa tatcaccgga attgaaaaaa ctgatcgaaa aataccgctg 1860
cgtaaaagat acggaaggaa tgtctcctgc taaggtatat aagctggtgg gagaaaatga 1920
aaacctatat ttaaaaatga cggacagccg gtataaaggg accacctatg atgtggaacg 1980
ggaaaaggac atgatgctat ggctggaagg aaagctgcct gttccaaagg tcctgcactt 2040
tgaacggcat gatggctgga gcaatctgct catgagtgag gccgatggcg tcctttgctc 2100
ggaagagtat gaagatgaac aaagccctga aaagattatc gagctgtatg cggagtgcat 2160
caggctcttt cactccatcg acatatcgga ttgtccctat acgaatagct tagacagccg 2220

```
cttagccgaa ttggattact tactgaataa cgatctggcc gatgtggatt gcgaaaactg   2280
ggaagaagac actccattta aagatccgcg cgagctgtat gattttttaa agacggaaaa   2340
gcccgaagag gaacttgtct tttcccacgg cgacctggga gacagcaaca tctttgtgaa   2400
agatggcaaa gtaagtggct ttattgatct tgggagaagc ggcagggcgg acaagtggta   2460
tgacattgcc ttctgcgtcc ggtcgatcag ggaggatatc ggggaagaac agtatgtcga   2520
gctatttttt gacttactgg ggatcaagcc tgattgggag aaaataaaat attatatttt   2580
actggatgaa ttgttttagt gactgcagtg agatctggta atgactctct agcttgaggc   2640
atcaaataaa acgaaaggct cagtcgaaag actgggcctt tcgttttatc tgttgtttgt   2700
cggtgaacgc tctcctgagt aggacaaatc cgccgctcta gctaagcaga aggccatcct   2760
gacggatggc ctttttgcgt ttctacaaac tcttgttaac tctagagctg cctgccgcgt   2820
ttcggtgatg aagatcttcc cgatgattaa ttaattcaga acgctcggtt gccgccgggc   2880
gtttttttatg aagcttcgtt gctggcgttt ttccataggc tccgcccccc tgacgagcat   2940
cacaaaaatc gacgctcaag tcagaggtgg cgaaacccga caggactata aagataccag   3000
gcgtttcccc ctggaagctc cctcgtgcgc tctcctgttc cgaccctgcc gcttaccgga   3060
tacctgtccg cctttctccc ttcgggaagc gtggcgcttt ctcatagctc acgctgtagg   3120
tatctcagtt cggtgtaggt cgttcgctcc aagctgggct gtgtgcacga accccccgtt   3180
cagcccgacc gctgcgcctt atccggtaac tatcgtcttg agtccaaccc ggtaagacac   3240
gacttatcgc cactggcagc agccactggt aacaggatta gcagagcgag gtatgtaggc   3300
ggtgctacag agttcttgaa gtggtggcct aactacggct acactagaag gacagtattt   3360
ggtatctgcg ctctgctgaa gccagttacc ttcggaaaaa gagttggtag ctcttgatcc   3420
ggcaaacaaa ccaccgctgg tagcggtggt ttttttgttt gcaagcagca gattacgcgc   3480
agaaaaaaag gatctcaaga agatcctttg atcttttcta cggggtctga cgctcagtgg   3540
aacgaaaact cacgttaagg gattttggtc atgagattat caaaaaggat cttcacctag   3600
atccttttaa attaaaaatg aagttttaaa tcaatctaaa gtatatatga gtaaacttgg   3660
tctgacacgt cagttcggca ggcatttcgc gaatcgaaaa cggaaagcgc ggcgtgccga   3720
agccggcgac gatcagaaaa ctggcggacg ctttgaaagt cccgtatgag gaactgatgg   3780
catctgcagg ctatatcagc gcgtctacag tccaggaagc aagaagcagc tatgattcca   3840
tttacgacat cgtgtcacag tacgatttag aggacctttc tctgtttgac agcgaaaagt   3900
ggaaggtgct ttcaaaaaaa gacatcgaaa acctggacaa atatttcgac tttctcgtgc   3960
aggaagcaag cagccgaaac aaaaactgaa tacttctccg cggcacactc tcctctctat   4020
cattttcgtc tgtttacgat cctgctgtta ttttatccct tatgttaact tttgtcaata   4080
tttttcctgt ctaagtattt cctatagtca acatttgtat taaaatgttc atatcatgaa   4140
tttgcggggg ggatggcgat gacaaggcaa tcataaaaag ccgaatttcc cttttaggag   4200
aagttcggct tttttcggct gccttaagcg gcatccggat tcggcgtctt gcctttatga   4260
tgcttaacgg ggctcagcgc acgctcgagc catcccatga acagatcggc gatgatcgcc   4320
atcagcgccg tcgggatcgc gcctgctaga atgatcgctg ttccgttggt cgcgtttgat   4380
cccctgacaa tgatatcccc gaggccgcct gcgccgacaa acgtgccgat ggccgtaatg   4440
ccgatcgcga tgacgagcgc ggttctgagc cccgccataa tgaccgacaa ggcgaggggga   4500
agctccacca tccggagcac ttgaaatttc gtcatgccca tcgccttccc tgattcaaga   4560
```

-continued

```
taggcatgct cgatgctggc gattcccgta tatgtgtttc gaatgatcgg caacagcgaa   4620
tacaaaaaca atgaaagaat caccgtgttt gcgccgagcc ccatgacaag catcaagacg   4680
ggaattcctc cattttcttc tgctatcaaa ataacagact cgtgattttc caaacgagct   4740
ttcaaaaaag cctctgcccc ttgcaaatcg gatgcctgtc tataaaattc ccgatattgg   4800
ttaaacagcg gcgcaatggc ggccgcatct gatgtctttg cttggcgaat gttcatctta   4860
tttcttcctc cctctcaata attttttcat tctatccctt ttctgtaaag tttatttttc   4920
agaatacttt tatcatcatg ctttgaaaaa atatcacgat aatatccatt gttctcacgg   4980
aagcacacgc aggtcatttg aacgaatttt ttcgacagga atttgccggg actcaggagc   5040
atttaaccta aaaaagcatg acatttcagc ataatgaaca tttactcatg tctattttcg   5100
ttcttttctg tatgaaaata gttatttcga gtctctacgg aaatagcgag agatgatata   5160
cctaaataga gataaaatca tctcaaaaaa atgggtctac taaaatatta ttccatctat   5220
tacaataaat tcacagaata gtcttttaag taagtctact ctgaattttt ttaaaaggag   5280
agggtaacta gtggccccaa aaaagaaacg caaggttatg gataaaaaat acagcattgg   5340
tctggatatc ggaaccaaca gcgttgggtg ggcagtaata acagatgaat acaaagtgcc   5400
gtcaaaaaaa tttaaggttc tggggaatac agatcgccac agcataaaaa agaatctgat   5460
tggggcattg ctgtttgatt cgggtgagac agctgaggcc acgcgtctga aacgtacagc   5520
aagaagacgt tacacacgtc gtaaaaatcg tatttgctac ttacaggaaa tttttttctaa   5580
cgaaatggcc aaggtagatg atagtttctt ccatcgtctc gaagaatctt ttctggttga   5640
ggaagataaa aaacacgaac gtcaccctat ctttggcaat atcgtggatg aagtggccta   5700
tcatgaaaaa taccctacga tttatcatct tcgcaagaag ttggttgata gtacggacaa   5760
agcggatctg cgtttaatcc atcttgcgtt agcgcacatg atcaaatttc gtggtcattt   5820
cttaattgaa ggtgatctga atcctgataa ctctgatgtg gacaaattgt ttatacaatt   5880
agtgcaaacc tataatcagc tgttcgagga aaaccccatt aatgcctctg gagttgatgc   5940
caaagcgatt ttaagcgcga gactttctaa gtcccggcgt ctggagaatc tgatcgccca   6000
gttaccaggg gaaaagaaaa atggtctgtt tggtaatctg attgccctca gtctggggct   6060
taccccgaac ttcaaatcca attttgacct ggctgaggac gcaaagctgc agctgagcaa   6120
agatacttat gatgatgacc tcgacaatct gctcgcccag attggtgacc aatatgcgga   6180
tctgtttctg gcagcgaaga atctttcgga tgctatcttg ctgtcggata ttctgcgtgt   6240
taataccgaa atcaccaaag cgcctctgtc tgcaagtatg atcaagagat acgacgagca   6300
ccaccaggac ctgactcttc ttaaggcact ggtacgccaa cagcttccgg agaaatacaa   6360
agaaatattc ttcgaccagt ccaagaatgg ttacgcgggc tacatcgatg gtggtgcatc   6420
acaggaagag ttctataaat ttattaaacc aatccttgag aaaatggatg gcacggaaga   6480
gttacttgtt aaacttaacc gcgaagactt gcttagaaag caacgtacat tcgacaacgg   6540
ctccatccca caccagattc atttaggtga acttcacgcc atcttgcgca gacaagaaga   6600
tttctatccc ttcttaaaag acaatcggga gaaaatcgag aagatcctga cgttccgcat   6660
tccctattat gtcggtcccc tggcacgtgg taattctcgg tttgcctgga tgacgcgcaa   6720
aagtgaggaa accatcaccc cttggaactt tgaagaagtc gtggataaag gtgctagcgc   6780
gcagtctttt atagaaagaa tgacgaactt cgataaaaac ttgcccaacg aaaaagtcct   6840
gcccaagcac tctcttttat atgagtactt tactgtgtac aacgaactga ctaaagtgaa   6900
atacgttacg gaaggtatgc gcaaacctgc ctttcttagt ggcgagcaga aaaaagcaat   6960
```

```
tgtcgatctt ctctttaaaa cgaatcgcaa ggtaactgta aaacagctga aggaagatta   7020
tttcaaaaag atcgaatgct ttgattctgt cgagatctcg ggtgtcgaag atcgtttcaa   7080
cgcttcctta gggacctatc atgatttgct gaagataata aaagacaaag actttctcga   7140
caatgaagaa aatgaagata ttctggagga tattgttttg accttgacct tattcgaaga   7200
tagagagatg atcgaggagc gcttaaaaac ctatgcccac ctgtttgatg acaaagtcat   7260
gaagcaatta aagcgccgca gatatacggg gtggggccgc ttgagccgca agttgattaa   7320
cggtattaga gacaagcaga gcggaaaaac tatcctggat ttcctcaaat ctgacggatt   7380
tgcgaaccgc aattttatgc agcttataca tgatgattcg cttacattca aagaggatat   7440
tcagaaggct caggtgtctg ggcaaggtga ttcactccac gaacatatag caaatttggc   7500
cggctctcct gcgattaaga aggggatcct gcaaacagtt aaagttgtgg atgaacttgt   7560
aaaagtaatg ggccgccaca agccggagaa tatcgtgata gaaatggcgc gcgagaatca   7620
aacgacacaa aaaggtcaaa agaactcaag agagagaatg aagcgcattg aggaggggat   7680
aaaggaactt ggatctcaaa ttctgaaaga acatccagtt gaaaacactc agctgcaaaa   7740
tgaaaaattg tacctgtact acctgcagaa tggaagagac atgtacgtgg atcaggaatt   7800
ggatatcaat agactctcgg actatgacgt agatcacatt gtccctcaga gcttcctcaa   7860
ggatgattct atagataata aagtacttac gagatcggac aaaaatcgcg gtaaatcgga   7920
taacgtccca tcggaggaag tcgttaaaaa gatgaaaaac tattggcgtc aactgctgaa   7980
cgccaagctg atcacacagc gtaagtttga taatctgact aaagccgaac gcggtggtct   8040
tagtgaactc gataaagcag gatttataaa acggcagtta gtagaaacgc gccaaattac   8100
gaaacacgtg gctcagatcc tcgattctag aatgaataca aagtacgatg aaaacgataa   8160
actgatccgt gaagtaaaag tcattacctt aaaatctaaa cttgtgtccg atttccgcaa   8220
agattttcag ttttacaagg tccgggaaat caataactat caccatgcac atgatgcata   8280
tttaaatgcg gttgtaggca cggcccttat taagaaatac cctaaactcg aaagtgagtt   8340
tgtttatggg gattataaag tgtatgacgt tcgcaaaatg atcgcgaaat cagaacagga   8400
aatcggtaag gctaccgcta aatacttttt ttattccaac attatgaatt tttttaagac   8460
cgaaataact ctcgcgaatg gtgaaatccg taaacggcct cttatagaaa ccaatggtga   8520
aacgggagaa atcgtttggg ataaaggtcg tgactttgcc accgttcgta aagtcctctc   8580
aatgccgcaa gttaacattg tcaagaagac ggaagttcaa acagggggat tctccaaaga   8640
atctatcctg ccgaagcgta acagtgataa acttattgcc agaaaaaaag attgggatcc   8700
aaaaaaatac ggaggctttg attcccctac cgtcgcgtat agtgtgctgg tggttgctaa   8760
agtcgagaaa gggaaaagca agaaattgaa atcagttaaa gaactgctgg gtattacaat   8820
tatggaaaga tcgtcctttg agaaaaatcc gatcgacttt ttagaggcca aggggtataa   8880
ggaagtgaaa aaagatctca tcatcaaatt accgaagtat agtctttttg agctggaaaa   8940
cggcagaaaa agaatgctgg cctccgcggg cgagttacag aagggaaatg agctggcgct   9000
gccttccaaa tatgttaatt ttctgtacct tgccagtcat tatgagaaac tgaagggcag   9060
ccccgaagat aacgaacaga aacaattatt cgtggaacag cataagcact atttagatga   9120
aattatagag caaattagtg aattttctaa gcgcgttatc ctcgcggatg ctaatttaga   9180
caaagtactg tcagcttata ataaacatcg ggataagccg attagagaac aggccgaaaa   9240
tatcattcat ttgtttacct taaccaacct tggagcacca gctgccttca aatatttcga   9300
```

taccacaatt gatcgtaaac ggtatacaag tacaaaagaa gtcttggacg caaccctcat 9360
tcatcaatct attactggat tatatgagac acgcattgat ctttcacagc tgggcggaga 9420
caagaagaaa aaactgaaac tgcaccatca tcaccatcat catcaccatc attgataact 9480
cgagaaagct tacataaaaa accggccttg gccccgccgg tttttatta tttttcttcc 9540 tccgcatgtt caatccgctc cataatcgac ggatggctcc ctctgaaaat tttaacgaga 9600
aacggcgggt tgacccggct cagtcccgta acggccaagt cctgaaacgt ctcaatcgcc 9660
gcttcccggt ttccggtcag ctcaatgccg taacggtcgg cggcgttttc ctgataccgg 9720
gagacggcat tcgtaatc 9738

<210> SEQ ID NO 79
<211> LENGTH: 23
<212> TYPE: DNA
<213> ORGANISM: Bacillus licheniformis

<400> SEQUENCE: 79
gcgagcggct caaagagctg agg 23

<210> SEQ ID NO 80
<211> LENGTH: 1014
<212> TYPE: DNA
<213> ORGANISM: Artificial Sequence
<220> FEATURE:
<223> OTHER INFORMATION: synthetic

<400> SEQUENCE: 80
cgtcagttcg gcaggcattt cgcgaatcga aaacggaaag cgcggcgtgc cgaagccggc 60
gacgatcaga aaactggcgg acgctttgaa agtcccgtat gaggaactga tggcatctgc 120
aggctatatc agcgcgtcta cagtccagga agcaagaagc agctatgatt ccatttacga 180
catcgtgtca cagtacgatt tagaggacct ttctctgttt gacagcgaaa agtggaaggt 240
gctttcaaaa aaagacatcg aaaacctgga caaatatttc gactttctcg tgcaggaagc 300
aagcagccga aacaaaaact gaatacttct ccgcggcaca ctctcctctc tatcattttc 360
gtctgtttac gatcctgctg ttattttatc ccttatgtta acttttgtca atatttttcc 420
tgtctaagta tttcctatag tcaacatttg tattaaaatg ttcatatcat gaatttgcgg 480
gggggatggc gatgacaagg caatcataaa aagccgaatt tccctttag gagaagttcg 540 gcttttttcg gctgccttaa gcggcatccg gattcggcgt cttgccttta tgatgcttaa 600
cggggctcag cgcacgctcg agccatccca tgaacagatc ggcgatgatc gccatcagcg 660
ccgtcgggat cgcgcctgct agaatgatcg ctgttccgtt ggtcgcgttt gatcccctga 720
caatgatatc cccgaggccg cctgcgccga caaacgtgcc gatggccgta atgccgatcg 780
cgatgacgag cgcggttctg agccccgcca taatgaccga caaggcgagg ggaagctcca 840
ccatccggag cacttgaaat ttcgtcatgc ccatcgcctt ccctgattca agataggcat 900
gctcgatgct ggcgattccc gtatatgtgt ttcgaatgat cggcaacagc gaatacaaaa 960
acaatgaaag aatcaccgtg tttgcgccga gccccatgac aagcatcaag acgg 1014

<210> SEQ ID NO 81
<211> LENGTH: 9724
<212> TYPE: DNA
<213> ORGANISM: Artificial Sequence
<220> FEATURE:
<223> OTHER INFORMATION: synthetic

<400> SEQUENCE: 81

```
gggtgaagtg gtcaagacct cactaggcac cttaaaaata gcgcaccctg aagaagattt     60
atttgaggta gcccttgcct acctagcttc caagaaagat atcctaacag cacaagagcg    120
gaaagatgtt ttgttctaca tccagaacaa cctctgctaa aattcctgaa aaattttgca    180
aaaagttgtt gactttatct acaaggtgtg gcataatgtg tggagagctt ctttttcttg    240
agcagtttta gagctagaaa tagcaagtta aaataaggct agtccgttat caacttgaaa    300
aagtggcacc gagtcggtgc gactcctgtt gatagatcca gtaatgacct cagaactcca    360
tctggatttg ttcagaacgc tcggttgccg ccgggcgttt tttattggtg agaatgtcga    420
cctcgagagt tacgctaggg ataacagggt aatataggag ctccagtcgg cttaaaccag    480
ttttcgctgg tgcgaaaaaa gagtgtcttg tgacacctaa attcaaaatc tatcggtcag    540
atttataccg atttgatttt atatattctt gaataacata cgccgagtta tcacataaaa    600
gcgggaacca atcataaaat ttaaacttca ttgcataatc cattaaactc ttaaattcta    660
cgattccttg ttcatcaata aactcaatca tttctttaat taatttatat ctatctgttg    720
ttgttttctt taataattca ttaacatcta caccgccata aactatcata tcttcttttt    780
gatatttaaa tttattagga tcgtccatgt gaagcatata tctcacaaga cctttcacac    840
ttcctgcaat ctgcggaata gtcgcattca attcttctgt taattatttt tatctgttca    900
taagatttat taccctcata catcactaga atatgataat gctctttttt catcctacct    960
tctgtatcag tatccctatc atgtaatgga gacactacaa attgaatgtg taactctttt   1020
aaatactcta accactcggc ttttgctgat tctggatata aaacaaatgt ccaattacgt   1080
cctcttgaat tttcttgttt ttcagtttct tttattacat tttcgctcat gatataataa   1140
cggtgctaat acacttaaca aaatttagtc atagataggc agcatgccag tgctgtctat   1200
cttttttgt ttaaaatgca ccgtattcct cctttgcata ttttttatt agaataccgg    1260
ttgcatctga tttgctaata ttatattttt ctttgattct atttaatatc tcattttctt   1320
ctgttgtaag tcttaaagta acagcaactt ttttctcttc ttttctatct acaactatca   1380
ctgtacctcc caacatctgt ttttttcact ttaacataaa aaacaacctt ttaacattaa   1440
aaacccaata tttatttatt tgtttggaca atggacactg gacacctagg ggggaggtcg   1500
tagtaccccc ctatgttttc tcccctaaat aaccccaaaa atctaagaaa aaaagacctc   1560
aaaaaggtct ttaattaaca tctcaaattt cgcatttatt ccaatttcct ttttgcgtgt   1620
gatgcgagct catcggctcc gtcgatacta tgttatacgc caactttcaa aacaactttg   1680
aaaaagctgt tttctggtat ttaaggtttt agaatgcaag gaacagtgaa ttggagttcg   1740
tcttgttata attagcttct tggggtatct ttaaatactg tagaaaagag gaaggaaata   1800
ataaatggct aaaatgagaa tatcaccgga attgaaaaaa ctgatcgaaa aataccgctg   1860
cgtaaaagat acggaaggaa tgtctcctgc taaggtatat aagctggtgg gagaaaatga   1920
aaacctatat ttaaaaatga cggacagccg gtataaaggg accacctatg atgtggaacg   1980
ggaaaaggac atgatgctat ggctggaagg aaagctgcct gttccaaagg tcctgcactt   2040
tgaacggcat gatggctgga gcaatctgct catgagtgag gccgatggcg tcctttgctc   2100
ggaagagtat gaagatgaac aaagccctga aaagattatc gagctgtatg cggagtgcat   2160
caggctcttt cactccatcg acatatcgga ttgtccctat acgaatagct tagacagccg   2220
cttagccgaa ttggattact tactgaataa cgatctggcc gatgtggatt gcgaaaactg   2280
ggaagaagac actccattta aagatccgcg cgagctgtat gattttttaa agacggaaaa   2340
```

```
gcccgaagag gaacttgtct tttcccacgg cgacctggga gacagcaaca tctttgtgaa   2400
agatggcaaa gtaagtggct ttattgatct tgggagaagc ggcagggcgg acaagtggta   2460
tgacattgcc ttctgcgtcc ggtcgatcag ggaggatatc ggggaagaac agtatgtcga   2520
gctatttttt gacttactgg ggatcaagcc tgattgggag aaaataaaat attatatttt   2580
actggatgaa ttgttttagt gactgcagtg agatctggta atgactctct agcttgaggc   2640
atcaaataaa acgaaaggct cagtcgaaag actgggcctt tcgttttatc tgttgtttgt   2700
cggtgaacgc tctcctgagt aggacaaatc cgccgctcta gctaagcaga aggccatcct   2760
gacggatggc ctttttgcgt ttctacaaac tcttgttaac tctagagctg cctgccgcgt   2820
ttcggtgatg aagatcttcc cgatgattaa ttaattcaga acgctcggtt gccgccgggc   2880
gtttttttatg aagcttcgtt gctggcgttt ttccataggc tccgcccccc tgacgagcat   2940
cacaaaaatc gacgctcaag tcagaggtgg cgaaacccga caggactata aagataccag   3000
gcgtttcccc ctggaagctc cctcgtgcgc tctcctgttc cgaccctgcc gcttaccgga   3060
tacctgtccg cctttctccc ttcgggaagc gtggcgcttt ctcatagctc acgctgtagg   3120
tatctcagtt cggtgtaggt cgttcgctcc aagctgggct gtgtgcacga accccccgtt   3180
cagcccgacc gctgcgcctt atccggtaac tatcgtcttg agtccaaccc ggtaagacac   3240
gacttatcgc cactggcagc agccactggt aacaggatta gcagagcgag gtatgtaggc   3300
ggtgctacag agttcttgaa gtggtggcct aactacggct acactagaag gacagtattt   3360
ggtatctgcg ctctgctgaa gccagttacc ttcggaaaaa gagttggtag ctcttgatcc   3420
ggcaaacaaa ccaccgctgg tagcggtggt ttttttgttt gcaagcagca gattacgcgc   3480
agaaaaaaag gatctcaaga agatcctttg atcttttcta cggggtctga cgctcagtgg   3540
aacgaaaact cacgttaagg gattttggtc atgagattat caaaaaggat cttcacctag   3600
atccttttaa attaaaaatg aagttttaaa tcaatctaaa gtatatatga gtaaacttgg   3660
tctgacaacc tgtcagccaa agcttgcaga gacagcggat cgcgataaga ttcctcgatg   3720
atttccacca cacgctgtgc cagctcttca tccggcagca gcgcccggc cggattgcag   3780
cgtttgcagg ggcggtaccc ttctgataaa gcatcttttg cattgaaaaa gatctgcaca   3840
ttgtcgattt gcggaactct cgatttgcag gaagggcggc aaaatatgcc ggtcgttttg   3900
accgcgtaat aaaaaactcc gtcataggcg gaatcgtttt ccgtaatcgc ccgccacatt   3960
tcaggcgtca atcgtgattt gctgttcata tcttcacccc gatctatgtc agtataacct   4020
atatgacagc cggaggtgga gaggcggaga acggcacagc aagaagacaa agaagaagag   4080
agactgttgc ctggacctcc gaaacgcgct acaattcatt tacaacacag gatggggtga   4140
gaatattgcc ggaatcagtg aagcaggtga cagaggaaag gccgatatga ttcggccttt   4200
tttatatgta cttcttagcg ggtctctaaa ataaccaaaa agcaaggact gctgaaaggg   4260
ctgacataag ccttttgccg gcggtccttt tttaattctg atttttcaaa cttagccccc   4320
tcgagaaaac cgcttgagta tcctccgctc atgttattga cctccttttc ttgatcaata   4380
tatttgtatg agcggaaaga aaatttgact agacggatgc ccctctgttg aaaatctttt   4440
tacagcatgt cagaatatga tatgatacaa ttcaaaggaa agtttaaact gttatgatta   4500
ggagtgtttg catttatgaa gaagattgca attgcggcga ttacagcgac aagcgtgctg   4560
gctctcagcg catgcagcgg gggagattct gaggttgttg cggaaacaaa agctggaaat   4620
attacaaaag aagaccttta tcaaacatta aaagacaatg ccggagcgaa ttcctccatt   4680
ttcttctgct atcaaaataa cagactcgtg attttccaaa cgagctttca aaaaagcctc   4740
```

```
tgccccttgc aaatcggatg cctgtctata aaattcccga tattggttaa acagcggcgc   4800
aatggcggcc gcatctgatg tctttgcttg gcgaatgttc atcttatttc ttcctccctc   4860
tcaataattt tttcattcta tccctttct gtaaagttta tttttcagaa tacttttatc   4920
atcatgcttt gaaaaaatat cacgataata tccattgttc tcacggaagc acacgcaggt   4980
catttgaacg aatttttcg acaggaattt gccgggactc aggagcattt aacctaaaaa   5040
agcatgacat ttcagcataa tgaacattta ctcatgtcta ttttcgttct tttctgtatg   5100
aaaatagtta tttcgagtct ctacggaaat agcgagagat gatataccta aatagagata   5160
aaatcatctc aaaaaaatgg gtctactaaa atattattcc atctattaca ataaattcac   5220
agaatagtct tttaagtaag tctactctga attttttaa aaggagaggg taactagtgg   5280
ccccaaaaaa gaaacgcaag gttatggata aaaaatacag cattggtctg gatatcggaa   5340
ccaacagcgt tgggtgggca gtaataacag atgaatacaa agtgccgtca aaaaaattta   5400
aggttctggg gaatacagat cgccacagca taaaaaagaa tctgattggg gcattgctgt   5460
ttgattcggg tgagacagct gaggccacgc gtctgaaacg tacagcaaga agacgttaca   5520
cacgtcgtaa aaatcgtatt tgctacttac aggaaatttt ttctaacgaa atggccaagg   5580
tagatgatag tttcttccat cgtctcgaag aatcttttct ggttgaggaa gataaaaaac   5640
acgaacgtca ccctatcttt ggcaatatcg tggatgaagt ggcctatcat gaaaaatacc   5700
ctacgattta tcatcttcgc aagaagttgg ttgatagtac ggacaaagcg gatctgcgtt   5760
taatccatct tgcgttagcg cacatgatca aatttcgtgg tcatttctta attgaaggtg   5820
atctgaatcc tgataactct gatgtggaca aattgtttat acaattagtg caaacctata   5880
atcagctgtt cgaggaaaac cccattaatg cctctggagt tgatgccaaa gcgattttaa   5940
gcgcgagact ttctaagtcc cggcgtctgg agaatctgat cgcccagtta ccaggggaaa   6000
agaaaaatgg tctgtttggt aatctgattg ccctcagtct ggggcttacc ccgaacttca   6060
aatccaattt tgacctggct gaggacgcaa agctgcagct gagcaaagat acttatgatg   6120
atgacctcga caatctgctc gcccagattg gtgaccaata tgcggatctg tttctggcag   6180
cgaagaatct ttcggatgct atcttgctgt cggatattct gcgtgttaat accgaaatca   6240
ccaaagcgcc tctgtctgca agtatgatca agagatacga cgagcaccac caggacctga   6300
ctcttcttaa ggcactggta cgccaacagc ttccggagaa atacaaagaa atattcttcg   6360
accagtccaa gaatggttac gcgggctaca tcgatggtgg tgcatcacag gaagagttct   6420
ataaatttat taaaccaatc cttgagaaaa tggatggcac ggaagagtta cttgttaaac   6480
ttaaccgcga agacttgctt agaaagcaac gtacattcga caacggctcc atcccacacc   6540
agattcattt aggtgaactt cacgccatct tgcgcagaca agaagatttc tatcccttct   6600
taaaagacaa tcgggagaaa atcgagaaga tcctgacgtt ccgcattccc tattatgtcg   6660
gtcccctggc acgtggtaat tctcggtttg cctggatgac gcgcaaaagt gaggaaacca   6720
tcaccccttg gaactttgaa gaagtcgtgg ataaaggtgc tagcgcgcag tcttttatag   6780
aaagaatgac gaacttcgat aaaaacttgc ccaacgaaaa agtcctgccc aagcactctc   6840
ttttatatga gtactttact gtgtacaacg aactgactaa agtgaaatac gttacggaag   6900
gtatgcgcaa acctgccttt cttagtggcg agcagaaaaa agcaattgtc gatcttctct   6960
ttaaaacgaa tcgcaaggta actgtaaaac agctgaagga agattatttc aaaaagatcg   7020
aatgctttga ttctgtcgag atctcgggtg tcgaagatcg tttcaacgct tccttaggga   7080
```

-continued cctatcatga tttgctgaag ataataaaag acaaagactt tctcgacaat gaagaaaatg 7140
aagatattct ggaggatatt gttttgacct tgaccttatt cgaagataga gagatgatcg 7200
aggagcgctt aaaaacctat gcccacctgt ttgatgacaa agtcatgaag caattaaagc 7260
gccgcagata tacggggtgg ggccgcttga gccgcaagtt gattaacggt attagagaca 7320
agcagagcgg aaaaactatc ctggatttcc tcaaatctga cggatttgcg aaccgcaatt 7380
ttatgcagct tatacatgat gattcgctta cattcaaaga ggatattcag aaggctcagg 7440
tgtctgggca aggtgattca ctccacgaac atatagcaaa tttggccggc tctcctgcga 7500
ttaagaaggg gatcctgcaa acagttaaag ttgtggatga acttgtaaaa gtaatgggcc 7560
gccacaagcc ggagaatatc gtgatagaaa tggcgcgcga gaatcaaacg acacaaaaag 7620
gtcaaaagaa ctcaagagag agaatgaagc gcattgagga ggggataaag gaacttggat 7680
ctcaaattct gaaagaacat ccagttgaaa acactcagct gcaaaatgaa aaattgtacc 7740
tgtactacct gcagaatgga agagacatgt acgtggatca ggaattggat atcaatagac 7800
tctcggacta tgacgtagat cacattgtcc ctcagagctt cctcaaggat gattctatag 7860
ataataaagt acttacgaga tcggacaaaa atcgcggtaa atcggataac gtcccatcgg 7920
aggaagtcgt taaaaagatg aaaaactatt ggcgtcaact gctgaacgcc aagctgatca 7980
cacagcgtaa gtttgataat ctgactaaag ccgaacgcgg tggtcttagt gaactcgata 8040
aagcaggatt tataaaacgg cagttagtag aaacgcgcca aattacgaaa cacgtggctc 8100
agatcctcga ttctagaatg aatacaaagt acgatgaaaa cgataaactg atccgtgaag 8160
taaaagtcat taccttaaaa tctaaacttg tgtccgattt ccgcaaagat tttcagtttt 8220
acaaggtccg ggaaatcaat aactatcacc atgcacatga tgcatattta aatgcggttg 8280
taggcacggc ccttattaag aaatacccta aactcgaaag tgagtttgtt tatggggatt 8340
ataaagtgta tgacgttcgc aaaatgatcg cgaaatcaga acaggaaatc ggtaaggcta 8400
ccgctaaata cttttttat tccaacatta tgaatttttt taagaccgaa ataactctcg 8460
cgaatggtga aatccgtaaa cggcctctta tagaaaccaa tggtgaaacg ggagaaatcg 8520
tttgggataa aggtcgtgac tttgccaccg ttcgtaaagt cctctcaatg ccgcaagtta 8580
acattgtcaa gaagacggaa gttcaaacag gggattctc caaagaatct atcctgccga 8640
agcgtaacag tgataaactt attgccagaa aaaaagattg ggatccaaaa aaatacggag 8700
gctttgattc ccctaccgtc gcgtatagtg tgctggtggt tgctaaagtc gagaaaggga 8760
aaagcaagaa attgaaatca gttaaagaac tgctgggtat tacaattatg gaaagatcgt 8820
cctttgagaa aaatccgatc gacttttag aggccaaggg gtataaggaa gtgaaaaaag 8880
atctcatcat caaattaccg aagtatagtc tttttgagct ggaaaacggc agaaaaagaa 8940
tgctggcctc cgcgggcgag ttacagaagg gaaatgagct ggcgctgcct tccaaatatg 9000
ttaattttct gtaccttgcc agtcattatg agaaactgaa gggcagcccc gaagataacg 9060
aacagaaaca attattcgtg gaacagcata agcactattt agatgaaatt atagagcaaa 9120
ttagtgaatt ttctaagcgc gttatcctcg cggatgctaa tttagacaaa gtactgtcag 9180
cttataataa acatcgggat aagccgatta gagaacaggc cgaaaatatc attcatttgt 9240
ttaccttaac caaccttgga gcaccagctg ccttcaaata tttcgatacc acaattgatc 9300
gtaaacggta tacaagtaca aaagaagtct tggacgcaac cctcattcat caatctatta 9360
ctggattata tgagacacgc attgatcttt cacagctggg cggagacaag aagaaaaaac 9420
tgaaactgca ccatcatcac catcatcatc accatcattg ataactcgag aaagcttaca 9480
taaaaaaccg gccttggccc cgccggtttt ttattatttt tcttcctccg catgttcaat 9540
ccgctccata atcgacggat ggctccctct gaaaatttta acgagaaacg gcgggttgac 9600
ccggctcagt cccgtaacgg ccaagtcctg aaacgtctca atcgccgctt cccggtttcc 9660
ggtcagctca atgccgtaac ggtcggcggc gttttcctga taccgggaga cggcattcgt 9720
aatc 9724

<210> SEQ ID NO 82
<211> LENGTH: 23
<212> TYPE: DNA
<213> ORGANISM: Bacillus licheniformis

<400> SEQUENCE: 82
gagcttcttt ttcttgagca cgg 23

<210> SEQ ID NO 83
<211> LENGTH: 1000
<212> TYPE: DNA
<213> ORGANISM: Artificial Sequence
<220> FEATURE:
<223> OTHER INFORMATION: synthetic

<400> SEQUENCE: 83
acctgtcagc caaagcttgc agagacagcg gatcgcgata agattcctcg atgatttcca 60
ccacacgctg tgccagctct tcatccggca gcagcgcccc ggccggattg cagcgtttgc 120
aggggcggta cccttctgat aaagcatctt ttgcattgaa aaagatctgc acattgtcga 180
tttgcggaac tctcgatttg caggaagggc ggcaaaatat gccggtcgtt ttgaccgcgt 240
aataaaaaac tccgtcatag gcggaatcgt tttccgtaat cgcccgccac atttcaggcg 300
tcaatcgtga tttgctgttc atatcttcac cccgatctat gtcagtataa cctatatgac 360
agccggaggt ggagaggcgg agaacggcac agcaagaaga caaagaagaa gagagactgt 420
tgcctggacc tccgaaacgc gctacaattc atttacaaca caggatgggg tgagaatatt 480
gccggaatca gtgaagcagg tgacagagga aaggccgata tgattcggcc ttttttatat 540
gtacttctta gcgggtctct aaaataacca aaaagcaagg actgctgaaa gggctgacat 600
aagccttttg ccggcggtcc ttttttaatt ctgatttttc aaacttagcc ccctcgagaa 660
aaccgcttga gtatcctccg ctcatgttat tgacctcctt ttcttgatca atatatttgt 720
atgagcggaa agaaaatttg actagacgga tgcccctctg ttgaaaatct ttttacagca 780
tgtcagaata tgatatgata caattcaaag gaaagtttaa actgttatga ttaggagtgt 840
ttgcatttat gaagaagatt gcaattgcgg cgattacagc gacaagcgtg ctggctctca 900
gcgcatgcag cgggggagat tctgaggttg ttgcggaaac aaaagctgga aatattacaa 960
aagaagacct ttatcaaaca ttaaaagaca atgccggagc 1000

<210> SEQ ID NO 84
<211> LENGTH: 9754
<212> TYPE: DNA
<213> ORGANISM: Artificial Sequence
<220> FEATURE:
<223> OTHER INFORMATION: synthetic

<400> SEQUENCE: 84
gggtgaagtg gtcaagacct cactaggcac cttaaaaata gcgcaccctg aagaagattt 60
atttgaggta gcccttgcct acctagcttc caagaaagat atcctaacag cacaagagcg 120

```
gaaagatgtt ttgttctaca tccagaacaa cctctgctaa aattcctgaa aaattttgca    180
aaaagttgtt gactttatct acaaggtgtg gcataatgtg tggatccagt tgacgtatcg    240
attcgtttta gagctagaaa tagcaagtta aaataaggct agtccgttat caacttgaaa    300
aagtggcacc gagtcggtgc gactcctgtt gatagatcca gtaatgacct cagaactcca    360
tctggatttg ttcagaacgc tcggttgccg ccgggcgttt tttattggtg agaatgtcga    420
cctcgagagt tacgctaggg ataacagggt aatataggag ctccagtcgg cttaaaccag    480
ttttcgctgg tgcgaaaaaa gagtgtcttg tgacacctaa attcaaaatc tatcggtcag    540
atttataccg atttgatttt atatattctt gaataacata cgccgagtta tcacataaaa    600
gcgggaacca atcataaaat ttaaacttca ttgcataatc cattaaactc ttaaattcta    660
cgattccttg ttcatcaata aactcaatca tttctttaat taatttatat ctatctgttg    720
ttgttttctt taataattca ttaacatcta caccgccata aactatcata tcttcttttt    780
gatatttaaa tttattagga tcgtccatgt gaagcatata tctcacaaga cctttcacac    840
ttcctgcaat ctgcggaata gtcgcattca attcttctgt taattatttt tatctgttca    900
taagatttat taccctcata catcactaga atatgataat gctctttttt catcctacct    960
tctgtatcag tatccctatc atgtaatgga gacactacaa attgaatgtg taactctttt   1020
aaatactcta accactcggc ttttgctgat tctggatata aaacaaatgt ccaattacgt   1080
cctcttgaat tttcttgtt ttcagtttct tttattacat tttcgctcat gatataataa    1140
cggtgctaat acacttaaca aaatttagtc atagataggc agcatgccag tgctgtctat   1200
ctttttttgt ttaaaatgca ccgtattcct cctttgcata ttttttttatt agaataccgg   1260
ttgcatctga tttgctaata ttatattttt ctttgattct atttaatatc tcattttctt   1320
ctgttgtaag tcttaaagta acagcaactt ttttctcttc ttttctatct acaactatca   1380
ctgtacctcc caacatctgt ttttttcact ttaacataaa aaacaacctt ttaacattaa   1440
aaacccaata tttatttatt tgtttggaca atggacactg gacacctagg ggggaggtcg   1500
tagtaccccc ctatgttttc tcccctaaat aaccccaaaa atctaagaaa aaaagacctc   1560
aaaaaggtct ttaattaaca tctcaaattt cgcatttatt ccaatttcct ttttgcgtgt   1620
gatgcgagct catcggctcc gtcgatacta tgttatacgc caactttcaa aacaactttg   1680
aaaaagctgt tttctggtat ttaaggtttt agaatgcaag gaacagtgaa ttggagttcg   1740
tcttgttata attagcttct tggggtatct ttaaatactg tagaaaagag gaaggaaata   1800
ataaatggct aaaatgagaa tatcaccgga attgaaaaaa ctgatcgaaa aataccgctg   1860
cgtaaaagat acggaaggaa tgtctcctgc taaggtatat aagctggtgg gagaaaatga   1920
aaacctatat ttaaaaatga cggacagccg gtataaaggg accacctatg atgtggaacg   1980
ggaaaaggac atgatgctat ggctggaagg aaagctgcct gttccaaagg tcctgcactt   2040
tgaacggcat gatggctgga gcaatctgct catgagtgag gccgatggcg tcctttgctc   2100
ggaagagtat gaagatgaac aaagccctga aaagattatc gagctgtatg cggagtgcat   2160
caggctcttt cactccatcg acatatcgga ttgtccctat acgaatagct tagacagccg   2220
cttagccgaa ttggattact tactgaataa cgatctggcc gatgtggatt gcgaaaactg   2280
ggaagaagac actccattta aagatccgcg cgagctgtat gatttttttaa agacggaaaa   2340
gcccgaagag gaacttgtct tttcccacgg cgacctggga gacagcaaca tctttgtgaa   2400
agatggcaaa gtaagtggct ttattgatct tgggagaagc ggcagggcgg acaagtggta   2460
tgacattgcc ttctgcgtcc ggtcgatcag ggaggatatc ggggaagaac agtatgtcga   2520
```

-continued

```
gctatttttt gacttactgg ggatcaagcc tgattgggag aaaataaaat attatatttt   2580
actggatgaa ttgttttagt gactgcagtg agatctggta atgactctct agcttgaggc   2640
atcaaataaa acgaaaggct cagtcgaaag actgggcctt tcgttttatc tgttgtttgt   2700
cggtgaacgc tctcctgagt aggacaaatc cgccgctcta gctaagcaga aggccatcct   2760
gacggatggc ctttttgcgt ttctacaaac tcttgttaac tctagagctg cctgccgcgt   2820
ttcggtgatg aagatcttcc cgatgattaa ttaattcaga acgctcggtt gccgccgggc   2880
gtttttttatg aagcttcgtt gctggcgttt ttccataggc tccgcccccc tgacgagcat   2940
cacaaaaatc gacgctcaag tcagaggtgg cgaaacccga caggactata aagataccag   3000
gcgtttcccc ctggaagctc cctcgtgcgc tctcctgttc cgaccctgcc gcttaccgga   3060
tacctgtccg cctttctccc ttcgggaagc gtggcgcttt ctcatagctc acgctgtagg   3120
tatctcagtt cggtgtaggt cgttcgctcc aagctgggct gtgtgcacga accccccgtt   3180
cagcccgacc gctgcgcctt atccggtaac tatcgtcttg agtccaaccc ggtaagacac   3240
gacttatcgc cactggcagc agccactggt aacaggatta gcagagcgag gtatgtaggc   3300
ggtgctacag agttcttgaa gtggtggcct aactacggct acactagaag gacagtattt   3360
ggtatctgcg ctctgctgaa gccagttacc ttcggaaaaa gagttggtag ctcttgatcc   3420
ggcaaacaaa ccaccgctgg tagcggtggt ttttttgttt gcaagcagca gattacgcgc   3480
agaaaaaaag gatctcaaga agatcctttg atcttttcta cggggtctga cgctcagtgg   3540
aacgaaaact cacgttaagg gattttggtc atgagattat caaaaaggat cttcacctag   3600
atccttttaa attaaaaatg aagttttaaa tcaatctaaa gtatatatga gtaaacttgg   3660
tctgacactc taatagcttc gctttgattg ttgtattatt tattttgctg atcattgtgg   3720
gctccgcttt tgtaaagtat taattcattc gcgcacgaag ccttcttccg aaaaactgca   3780
ggttcatatc gaaaggcgct ccgcttttca tatgagcctg tttttttgta atttaaaaag   3840
aatttatttc cacaataaca aaaaatgttt ataataggat aggctctgag ctgacggctg   3900
acggcgctcg gaaataaaaa ctctcccaca aatgaaactt ttatacaaca ttttcgtctt   3960
atactgttgt taaggcaatt caataacgga aaggaaaaga tcaatgttaa ataagctaag   4020
aatgttgtat gaaaaaacaa caatgaagtg gctgctcaac acttcctatt actttctcat   4080
tctggtgctg ctgtttttaa tttacggatt ccatacagca aatacaggtt catatattta   4140
taatgacttt taatggagaa gaaaacaatg aaactgattg aaacaattaa aaaataccac   4200
aaatgtgctt gatggatccg tcttattcgg aagagctgct tccggagctg agcttgttta   4260
tgttctgcgg agaaacgctt cctgcgtcag tcgccagaca gcttaaagaa agatttccaa   4320
aggctcgtgt ttttaacaca tacggcccga ccgaagcgac cgttgccgtc acttccatcg   4380
aagtaacaga cgacgtatta aacaagtatt cttctcttcc cgtcggttct gaaaagcccg   4440
aaaccgaaat cgtaatcatc aatgaagacg gaaaagccgt ccaagacggg gaaaaaggcg   4500
agatcataat taccggagca agcgtcagca aaggctattt aggcgaaaaa gcgctgacgg   4560
aaaaagcgtt tttctcttac aacggctccc ctgcttaccg caccggtgac gcaggttaca   4620
aagaaaacgg ccagctcttc ttcctcggaa gactcgattt ccaaatcaaa ctgcacggct   4680
accggattga gcttgaagaa ttcctccatt ttcttctgct atcaaaataa cagactcgtg   4740
attttccaaa cgagctttca aaaaagcctc tgccccttgc aaatcggatg cctgtctata   4800
aaattcccga tattggttaa acagcggcgc aatggcggcc gcatctgatg tctttgcttg   4860
```

```
gcgaatgttc atcttatttc ttcctccctc tcaataattt tttcattcta tccctttttct   4920
gtaaagttta tttttcagaa tacttttatc atcatgcttt gaaaaaatat cacgataata   4980
tccattgttc tcacggaagc acacgcaggt catttgaacg aattttttcg acaggaattt   5040
gccgggactc aggagcattt aacctaaaaa agcatgacat ttcagcataa tgaacattta   5100
ctcatgtcta ttttcgttct tttctgtatg aaaatagtta tttcgagtct ctacggaaat   5160
agcgagagat gatataccta aatagagata aaatcatctc aaaaaaatgg gtctactaaa   5220
atattattcc atctattaca ataaattcac agaatagtct tttaagtaag tctactctga   5280
attttttaa aaggagaggg taactagtgg ccccaaaaaa gaaacgcaag gttatggata   5340
aaaaatacag cattggtctg gatatcggaa ccaacagcgt tgggtgggca gtaataacag   5400
atgaatacaa agtgccgtca aaaaaattta aggttctggg gaatacagat cgccacagca   5460
taaaaaagaa tctgattggg gcattgctgt ttgattcggg tgagacagct gaggccacgc   5520
gtctgaaacg tacagcaaga agacgttaca cacgtcgtaa aaatcgtatt tgctacttac   5580
aggaaatttt ttctaacgaa atggccaagg tagatgatag tttcttccat cgtctcgaag   5640
aatcttttct ggttgaggaa gataaaaaac acgaacgtca ccctatcttt ggcaatatcg   5700
tggatgaagt ggcctatcat gaaaaatacc ctacgattta tcatcttcgc aagaagttgg   5760
ttgatagtac ggacaaagcg gatctgcgtt taatccatct tgcgttagcg cacatgatca   5820
aatttcgtgg tcatttctta attgaaggtg atctgaatcc tgataactct gatgtggaca   5880
aattgtttat acaattagtg caaacctata atcagctgtt cgaggaaaac cccattaatg   5940
cctctggagt tgatgccaaa gcgattttaa gcgcgagact ttctaagtcc cggcgtctgg   6000
agaatctgat cgcccagtta ccaggggaaa agaaaaatgg tctgtttggt aatctgattg   6060
ccctcagtct ggggcttacc ccgaacttca aatccaattt tgacctggct gaggacgcaa   6120
agctgcagct gagcaaagat acttatgatg atgacctcga caatctgctc gcccagattg   6180
gtgaccaata tgcggatctg tttctggcag cgaagaatct ttcggatgct atcttgctgt   6240
cggatattct gcgtgttaat accgaaatca ccaaagcgcc tctgtctgca agtatgatca   6300
agagatacga cgagcaccac caggacctga ctcttcttaa ggcactggta cgccaacagc   6360
ttccggagaa atacaaagaa atattcttcg accagtccaa gaatggttac gcgggctaca   6420
tcgatggtgg tgcatcacag gaagagttct ataaatttat taaaccaatc cttgagaaaa   6480
tggatggcac ggaagagtta cttgttaaac ttaaccgcga agacttgctt agaaagcaac   6540
gtacattcga caacggctcc atcccacacc agattcattt aggtgaactt cacgccatct   6600
tgcgcagaca agaagatttc tatcccttct taaaagacaa tcgggagaaa atcgagaaga   6660
tcctgacgtt ccgcattccc tattatgtcg gtcccctggc acgtggtaat tctcggtttg   6720
cctggatgac gcgcaaaagt gaggaaacca tcaccccttg gaactttgaa gaagtcgtgg   6780
ataaaggtgc tagcgcgcag tcttttatag aaagaatgac gaacttcgat aaaaacttgc   6840
ccaacgaaaa agtcctgccc aagcactctc ttttatatga gtactttact gtgtacaacg   6900
aactgactaa agtgaaatac gttacggaag gtatgcgcaa acctgccttt cttagtggcg   6960
agcagaaaaa agcaattgtc gatcttctct ttaaaacgaa tcgcaaggta actgtaaaac   7020
agctgaagga agattatttc aaaaagatcg aatgctttga ttctgtcgag atctcgggtg   7080
tcgaagatcg tttcaacgct tccttaggga cctatcatga tttgctgaag ataataaaag   7140
acaaagactt tctcgacaat gaagaaaatg aagatattct ggaggatatt gttttgacct   7200
tgaccttatt cgaagataga gagatgatcg aggagcgctt aaaaacctat gcccacctgt   7260
```

```
ttgatgacaa agtcatgaag caattaaagc gccgcagata tacggggtgg ggccgcttga   7320
gccgcaagtt gattaacggt attagagaca agcagagcgg aaaaactatc ctggatttcc   7380
tcaaatctga cggatttgcg aaccgcaatt ttatgcagct tatacatgat gattcgctta   7440
cattcaaaga ggatattcag aaggctcagg tgtctgggca aggtgattca ctccacgaac   7500
atatagcaaa tttggccggc tctcctgcga ttaagaaggg gatcctgcaa acagttaaag   7560
ttgtggatga acttgtaaaa gtaatgggcc gccacaagcc ggagaatatc gtgatagaaa   7620
tggcgcgcga gaatcaaacg acacaaaaag gtcaaaagaa ctcaagagag agaatgaagc   7680
gcattgagga ggggataaag gaacttggat ctcaaattct gaaagaacat ccagttgaaa   7740
acactcagct gcaaaatgaa aaattgtacc tgtactacct gcagaatgga agagacatgt   7800
acgtggatca ggaattggat atcaatagac tctcggacta tgacgtagat cacattgtcc   7860
ctcagagctt cctcaaggat gattctatag ataataaagt acttacgaga tcggacaaaa   7920
atcgcggtaa atcggataac gtcccatcgg aggaagtcgt taaaaagatg aaaaactatt   7980
ggcgtcaact gctgaacgcc aagctgatca cacagcgtaa gtttgataat ctgactaaag   8040
ccgaacgcgg tggtcttagt gaactcgata aagcaggatt tataaaacgg cagttagtag   8100
aaacgcgcca aattacgaaa cacgtggctc agatcctcga ttctagaatg aatacaaagt   8160
acgatgaaaa cgataaactg atccgtgaag taaaagtcat taccttaaaa tctaaacttg   8220
tgtccgattt ccgcaaagat tttcagtttt acaaggtccg ggaaatcaat aactatcacc   8280
atgcacatga tgcatattta aatgcggttg taggcacggc ccttattaag aaataccta   8340
aactcgaaag tgagtttgtt tatggggatt ataaagtgta tgacgttcgc aaaatgatcg   8400
cgaaatcaga acaggaaatc ggtaaggcta ccgctaaata ctttttttat tccaacatta   8460
tgaatttttt taagaccgaa ataactctcg cgaatggtga aatccgtaaa cggcctctta   8520
tagaaaccaa tggtgaaacg ggagaaatcg tttgggataa aggtcgtgac tttgccaccg   8580
ttcgtaaagt cctctcaatg ccgcaagtta acattgtcaa gaagacggaa gttcaaacag   8640
gggattctc caaagaatct atcctgccga agcgtaacag tgataaactt attgccagaa   8700
aaaaagattg ggatccaaaa aaatacggag gctttgattc ccctaccgtc gcgtatagtg   8760
tgctggtggt tgctaaagtc gagaaaggga aaagcaagaa attgaaatca gttaaagaac   8820
tgctgggtat tacaattatg gaaagatcgt cctttgagaa aaatccgatc gactttttag   8880
aggccaaggg gtataaggaa gtgaaaaaag atctcatcat caaattaccg aagtatagtc   8940
tttttgagct ggaaaacggc agaaaaagaa tgctggcctc cgcgggcgag ttacagaagg   9000
gaaatgagct ggcgctgcct tccaaatatg ttaattttct gtaccttgcc agtcattatg   9060
agaaactgaa gggcagcccc gaagataacg aacagaaaca attattcgtg gaacagcata   9120
agcactattt agatgaaatt atagagcaaa ttagtgaatt ttctaagcgc gttatcctcg   9180
cggatgctaa tttagacaaa gtactgtcag cttataataa acatcgggat aagccgatta   9240
gagaacaggc cgaaaatatc attcatttgt ttaccttaac caaccttgga gcaccagctg   9300
ccttcaaata tttcgatacc acaattgatc gtaaacggta tacaagtaca aaagaagtct   9360
tggacgcaac cctcattcat caatctatta ctggattata tgagacacgc attgatcttt   9420
cacagctggg cggagacaag aagaaaaaac tgaaactgca ccatcatcac catcatcatc   9480
accatcattg ataactcgag aaagcttaca taaaaaaccg gccttggccc cgccggtttt   9540
ttattatttt tcttcctccg catgttcaat ccgctccata atcgacggat ggctccctct   9600
```

gaaaatttta acgagaaacg gcgggttgac ccggctcagt cccgtaacgg ccaagtcctg 9660
aaacgtctca atcgccgctt cccggtttcc ggtcagctca atgccgtaac ggtcggcggc 9720
gttttcctga taccgggaga cggcattcgt aatc 9754

<210> SEQ ID NO 85
<211> LENGTH: 23
<212> TYPE: DNA
<213> ORGANISM: Artificial Sequence
<220> FEATURE:
<223> OTHER INFORMATION: synthetic

<400> SEQUENCE: 85
tccagttgac gtatcgattc cgg 23

<210> SEQ ID NO 86
<211> LENGTH: 1030
<212> TYPE: DNA
<213> ORGANISM: Artificial Sequence
<220> FEATURE:
<223> OTHER INFORMATION: synthetic

<400> SEQUENCE: 86
ctctaatagc ttcgctttga ttgttgtatt atttattttg ctgatcattg tgggctccgc 60
ttttgtaaag tattaattca ttcgcgcacg aagccttctt ccgaaaaact gcaggttcat 120
atcgaaaggc gctccgcttt tcatatgagc ctgttttttt gtaatttaaa aagaatttat 180
ttccacaata acaaaaaatg tttataatag gataggctct gagctgacgg ctgacggcgc 240
tcggaaataa aaactctccc acaaatgaaa cttttataca acattttcgt cttatactgt 300
tgttaaggca attcaataac ggaaaggaaa agatcaatgt taaataagct aagaatgttg 360
tatgaaaaaa caacaatgaa gtggctgctc aacacttcct attactttct cattctggtg 420
ctgctgtttt taatttacgg attccataca gcaaatacag gttcatatat ttataatgac 480
ttttaatgga gaagaaaaca atgaaactga ttgaaacaat taaaaaatac cacaaatgtg 540
cttgatggat ccgtcttatt cggaagagct gcttccggag ctgagcttgt ttatgttctg 600
cggagaaacg cttcctgcgt cagtcgccag acagcttaaa gaaagatttc caaaggctcg 660
tgtttttaac acatacggcc cgaccgaagc gaccgttgcc gtcacttcca tcgaagtaac 720
agacgacgta ttaaacaagt attcttctct tcccgtcggt tctgaaaagc ccgaaaccga 780
aatcgtaatc atcaatgaag acggaaaagc cgtccaagac ggggaaaaag gcgagatcat 840
aattaccgga gcaagcgtca gcaaaggcta tttaggcgaa aaagcgctga cggaaaaagc 900
gtttttctct tacaacggct cccctgctta ccgcaccggt gacgcaggtt acaaagaaaa 960
cggccagctc ttcttcctcg gaagactcga tttccaaatc aaactgcacg gctaccggat 1020
tgagcttgaa 1030

<210> SEQ ID NO 87
<211> LENGTH: 1320
<212> TYPE: DNA
<213> ORGANISM: Bacillus licheniformis

<400> SEQUENCE: 87
ttgtttttac acggtactag cagacaaaat gaaagagggc acctcgaaat cggcggtgtc 60
gatgttctat cattggcaga aagatacgga acacctcttt atgtatacga tgtcgcgctg 120
attagagagc gcgcccgaaa attccagaag gcattcaagg aagccggttt aaaagcgcag 180
gtagcgtatg caagcaaggc gttttcatcg gttgccatga ttcagcttgc cgaacaagag 240
gggctgtctc tggatgtggt atcgggagga gagcttttca ctgcgatcaa agcagggttc 300
ccagctgagc ggattcattt tcacggaaac aataagagcc ctgaagaact agccatggcg 360
ctggagcatc aaatcggctg catcgtgctc gataactttc acgagatcgc cattacagaa 420
gatctttgca agcgatcagg acaaactgta gacgttttgc tcagaatcac tccgggagtt 480
gaagcgcaca cgcacgatta tattacgacg gggcaggaag attccaaatt cggttttgat 540
ctgcataatg gacaggtcga acaagccatc gaacaagtcc tccgctcgtc tgcgtttaag 600
ctcctcggcg tgcactgcca catcggttcg caaatttttg atacggcagg atttgtcctt 660
gcagcagaca agattttcga gaagcttgcg gaatggcggg agacttactc tttcattccg 720
gaagtgctca atcttggcgg gggcttcggc atccgctata caaaagacga cgagccgctt 780
gcagctgatg tttatgttga aaaaatcatc gaggcggtca aagcaaatgc cgagcatttc 840
ggctttgaca tccctgagat ttggatcgaa ccaggccggt ctctcgtcgg tgatgcgggg 900
actacgctgt acacgatcgg ttctcaaaaa gaggtgccgg gcattcgcaa atatgtagcc 960
atcgacggcg gcatgagcga taatatcagg ccggcgcttt atgaggcaaa atatgaagca 1020
gccgtcgcca acaggatgaa cgatgcttgt catgataccg catcaatcgc aggaaaatgc 1080
tgcgaaagcg gagatatgct gatttgggat ttggaaatcc ccgaagttcg cgacggagat 1140
gtgctcgccg ttttctgcac cggtgcgtac ggctacagca tggccaacaa ctacaaccgc 1200
attccgcgcc cggccgtcgt ctttgtcgag gacggggaag cgcagctcgt cattcagaga 1260
gagacgtatg aggatatcgt caagctggat ctgccgctga aatcgaaagt caaacaataa 1320

<210> SEQ ID NO 88
<211> LENGTH: 6393
<212> TYPE: DNA
<213> ORGANISM: Artificial Sequence
<220> FEATURE:
<223> OTHER INFORMATION: synthetic

<400> SEQUENCE: 88
aagcttcata tgcaagggtt tattgttttc taaaatctga ttaccaatta gaatgaatat 60
ttcccaaata ttaaataata aaacaaaaaa attgaaaaaa gtgtttccac catttttttca 120 attttttttat aattttttta atctgttatt taaatagttt atagttaaat ttacattttc 180
attagtccat tcaatattct ctccaagata actacgaact gctaacaaaa ttctctccct 240
atgttctaat ggagaagatt cagccactgc atttcccgca atatcttttg gtatgatttt 300
acccgtgtcc atagttaaaa tcatacggca taaagttaat atagagttgg tttcatcatc 360
ctgataatta tctattaatt cctctgacga atccataatg gctcttctca catcagaaaa 420
tggaatatca ggtagtaatt cctctaagtc ataatttccg tatattcttt tattttttcg 480
ttttgcttgg taaagcatta tggttaaatc tgaatttaat tccttctgag gaatgtatcc 540
ttgttcataa agctcttgta accattctcc ataaataaat tcttgtttgg gaggatgatt 600
ccacggtacc atttcttgct gaataataat tgttaattca atatatcgta agttgctttt 660
atctcctatt ttttttgaaa taggtctaat tttttgtata agtatttctt tactttgatc 720
tgtcaatggt tcagatacga cgactaaaaa gtcaagatca ctatttggtt ttagtccact 780
ctcaactcct gatccaaaca tgtaagtacc aataaggtta ttttttaaat gtttccgaag 840
tatttttttc actttattaa tttgttcgta tgtattcaaa tatatcctcc tcactatttt 900
gattagtacc tattttatat ccatagttgt taattaaata aacttaattt agtttattta 960

-continued

```
tggatttcat tggcttctaa attttttatc tagataataa ttattttagt taattttatt   1020
ctagattata tatgatatga tctttcattt ccataaaact aaagtaagtg taaacctatt   1080
cattgtttta aaaatatctc ttgccagtca cgttacgtta ttagttatag ttattataac   1140
atgtattcac gaacgggcgc gccggtatcc gcgcttcttg agcactattt attcaaagcc   1200
gctccagatc aatagcgctt tttcagctcc ctgaggatga attcgtatat cagctgattc   1260
cggtcttctt tcggatagag cataaattcc tgtttcttct gcatggggtt tccttcaatc   1320
ctgtcgataa attttgttct cagccatgcc gttcggtaaa cctggttttc gaaagatgag   1380
atggatacgg gcagctccag cgtttccccg ttgacaaacg tgacaaacgt gttgtcatac   1440
tttgccgcgc aaaactcgtg aacatgcgca tgggaaagcc acccgcactg aggacgagtt   1500
gaggaaaatg tggggaaaag aaaaatgttg tttgagtgat ccaccatgat cggcggttta   1560
tgggaaactt taatgacttc atatgtgccc gcttttcttc ccgcatagct cgatccgaaa   1620
tagcggcagc ttctttcgat aatttgaaac ggcttcatat tgacgcggaa agtcctgtcg   1680
gtctcaagta tttttgaggc ggatttctcc ccctcaccca gaggcaggac agccattgtc   1740
gaactgttta cttcatacgt atcctttgtc atatcctctg tgctcatgtg atttccccct   1800
taaaaataaa ttcattcaaa tacagatgca ttttatttca tatagtaagt acatcaccta   1860
ttagtttgtt gtttaaacaa actaacttat tttcatctta tataacctcg tcagtatttt   1920
caatattttt tttagttttt tatgaacaca ttagatttaa taaagggaag attcgctatg   1980
tactatgttg atacttaatt taaagattaa acaaatggag tggatgaagt ggatatcgct   2040
gatcaaacct ttgtcaaaaa agtaaatcaa aagttattat taaaagaaat ccttaaaaat   2100
tcacctattt caagagcaaa attatctgaa atgactggat taaataaatc aactgtctca   2160
tcacaggtaa acacgttaat gaaagaaagt atggtatttg aaataggtca aggacaatca   2220
agtggcggaa gaagacctgt catgcttgtt tttaataaaa aggcaggata ctccgttgga   2280
atagatgttg gtgtggatta tattaatggc attttaacag accttgaagg aacaatcgtt   2340
cttgatcaat accgccattt ggaatccaat tctccagaaa taacgaaaga cattttgatt   2400
gatatgattc atcactttat tacgcaaatg ccccaatctc cgtacgggtt tattggtata   2460
ggtacttgcg tgcctggact cattgataaa gatcaaaaaa ttgttttcac tccgaactcc   2520
aactggagag atattgactt aaaatcttcg atacaagaga agtacaatgt gtctgttttt   2580
attgaaaatg aggcaaatgc tggcgcatat ggagaaaaac tatttggagc tgcaaaaaat   2640
cacgataaca ttatttacgt aagtatcagc acaggaatag ggatcggtgt tattatcaac   2700
aatcatttat atagaggagt aagcggcttc tctggagaaa tgggacatat gacaatagac   2760
tttaatggtc ctaaatgcag ttgcggaaac cgaggatgct gggaattgta tgcttcagag   2820
aaggctttat ttaaatctct tcagaccaaa gagaaaaaac tgtcctatca agatatcata   2880
aacctcgccc atctgaatga tatcggaacc ttaaatgcat tacaaaattt tggattctat   2940
ttaggaatag gccttaccaa tattctaaat actctcaacc cacaagccgt aattttaaga   3000
aatagcataa ttgaatcgca tcctatggtt ttaaattcaa tgagaagtga agtatcatca   3060
agggtttatt cccaattagg caatagctat gaattattgc catcttcctt aggacagaat   3120
gcaccggcat taggaatgtc ctccattgtg attgatcatt ttctggacat gattacaatg   3180
taattttttta tggaatggac agctcatctt taaagatgag tttttttatt ctaggagtat   3240
ttctgaagca atagtgacat ggcaccttct catatgaaaa aggagttcta aaataaaaat   3300
ctccttttttc atgtgcaaat tatttttctt tataacgaaa atatctaaat gacaatgcat   3360
```

```
atgcaagagg ggatcacata aatatatatt ttaaaaatat cccactttat ccaattttcg   3420
tttgttgaac taatgggtgc tttagttgaa gaataaaaga ccacattaaa aaatgtggtc   3480
ttttgtgttt ttttaaagga tttgagcgta gcgaaaaatc cttttctttc ttatcttgat   3540
actatataga aacaacatca tttttcaaaa ttaggtcaaa gccttgtgta tcaagggttt   3600
gatggttctt tgacaggtaa aaactccttc tgctattatt aaatactata tagaaacaac   3660
atcatttttc aaaattaggt caaagccttg tgtatcaagg gtttgatggt tctttgacag   3720
gtaaaaactc cttctgctat tattaaggtg tcgaatcaaa ataatagaat gctagagaac   3780
tagctcagaa ggagtttttt tgttgattta ttcatctgaa aatgattata gcatcctcga   3840
agataaaacc gcaacaggta aaaagcggga ttggaagggg aaaaagagac ggacgaacct   3900
catggcggag cattacgaag cgttagagag taagattggg gcaccttact atggcaaaaa   3960
ggctgaaaaa ctaattagtt gtgcagagta tctttcgttt aagagagacc cggagacggg   4020
caagttaaaa ctgtatcaag cccatttttg taaagtgagg ttatgtccga tgtgtgcgtg   4080
gcgcaggtcg ttaaaaattg cttatcacaa taagttgatc gtagaggaag ccaatagaca   4140
gtacggctgc ggatggattt ttctcacgct gacgattcga aatgtaaagg gagaacggct   4200
gaagccacaa atttctgcga tgatggaagg ctttaggaaa ctgttccagt acaaaaaagt   4260
aaaaacttcg gttcttggat ttttcagagc tttagagatt accaaaaatc atgaagaaga   4320
tacatatcat cctcattttc atgtgttgat accagtaagg aaaaattatt ttgggaaaaa   4380
ctatattaag caggcggagt ggacgagcct ttggaaaaag gcgatgaaat tggattacac   4440
tccaattgtc gatattcgtc gagtgaaagg taaagctaag attgacgctg aacagattga   4500
aaacgatgtg cggaacgcaa tgatggagca aaaagctgtt ctcgaaatct ctaaatatcc   4560
ggttaaggat acggatgttg tgcgcggtaa taaggtgact gaagacaatc tgaacacggt   4620
gctttacttg gatgatgcgt tggcagctcg aaggttaatt ggatacggtg gcattttgaa   4680
ggagatacat aaagagctga atcttggtga tgcggaggac ggcgatctgg tcaagattga   4740
ggaagaagat gacgaggttg caaatggtgc atttgaggtt atggcttatt ggcatcctgg   4800
cattaaaaat tacataatca aataaaaaaa gcagaccttt agaaggcctg ctttttaac   4860
taacccattt gtattgtgtt gaaatatgtt ttgtatggtg cactctcagt acaatctgct   4920
ctgatgccgc atagttaagc cagccccgac acccgccaac acccgctgac gcgccctgac   4980
gggcttgtct gctcccggca tccgcttaca gacaagctgt gaccgtctcc gggagctgca   5040
tgtgtcagag gttttcaccg tcatcaccga aacgcgcgag acgaaagggc ctcgtgatac   5100
gcctattttt ataggttaat gtcatgataa taatggtttc ttagcgattc acaaaaaata   5160
ggcacacgaa aaacaagtta agggatgcag tttatgcatc ccttaactta aaatactaaa   5220
aatgcccata ttttttcctc cttataaaat tagtataatt atagcacgag atctaaaagg   5280
atctaggtga agatcctttt tgataatctc atgaccaaaa tcccttaacg tgagttttcg   5340
ttccactgag cgtcagaccc cgtagaaaag atcaaaggat cttcttgaga tcctttttt   5400
ctgcgcgtaa tctgctgctt gcaaacaaaa aaaccaccgc taccagcggt ggtttgtttg   5460
ccggatcaag agctaccaac tctttttccg aaggtaactg gcttcagcag agcgcagata   5520
ccaaatactg ttcttctagt gtagccgtag ttaggccacc acttcaagaa ctctgtagca   5580
ccgcctacat acctcgctct gctaatcctg ttaccagtgg ctgctgccag tggcgataag   5640
tcgtgtctta ccgggttgga ctcaagacga tagttaccgg ataaggcgca gcggtcgggc   5700
```

tgaacggggg gttcgtgcac acagcccagc ttggagcgaa cgacctacac cgaactgaga 5760
tacctacagc gtgagctatg agaaagcgcc acgcttcccg aagggagaaa ggcggacagg 5820
tatccggtaa gcggcagggt cggaacagga gagcgcacga gggagcttcc agggggaaac 5880
gcctggtatc tttatagtcc tgtcgggttt cgccacctct gacttgagcg tcgatttttg 5940
tgatgctcgt caggggggcg gagcctatgg aaaaacgcca gcaacgcggc ctttttacgg 6000
ttcctggcct tttgctggcc ttttgctcac atgttctttc ctgcgttatc ccctgattct 6060
gtggataacc gtattaccgc ctttgagtga gctgataccg ctcgccgcag ccgaacgacc 6120
gagcgcagcg agtcagtgag cgaggaagcg gaagagcgcc caatacgcaa accgcctctc 6180
cccgcgcgtt ggccgattca ttaatgcagc tggcacgaca ggtttcccga ctggaaagcg 6240
ggcagtgagc gcaacgcaat taatgtgagt tagctcactc attaggcacc ccaggcttta 6300
cactttatgc ttccggctcg tatgttgtgt ggaattgtga gcggataaca atttcacaca 6360
ggaaacagct atgaccatga ttacgccgga tcc 6393

<210> SEQ ID NO 89
<211> LENGTH: 765
<212> TYPE: DNA
<213> ORGANISM: Artificial Sequence
<220> FEATURE:
<223> OTHER INFORMATION: synthetic

<400> SEQUENCE: 89
gtgaggagga tatatttgaa tacatacgaa caaattaata aagtgaaaaa aatacttcgg 60
aaacatttaa aaaataacct tattggtact tacatgtttg gatcaggagt tgagagtgga 120
ctaaaaccaa atagtgatct tgacttttta gtcgtcgtat ctgaaccatt gacagatcaa 180
agtaaagaaa tacttataca aaaaattaga cctatttcaa aaaaaatagg agataaaagc 240
aacttacgat atattgaatt aacaattatt attcagcaag aaatggtacc gtggaatcat 300
cctcccaaac aagaatttat ttatggagaa tggttacaag agctttatga acaaggatac 360
attcctcaga aggaattaaa ttcagattta accataatgc tttaccaagc aaaacgaaaa 420
aataaaagaa tatacggaaa ttatgactta gaggaattac tacctgatat tccattttct 480
gatgtgagaa gagccattat ggattcgtca gaggaattaa tagataatta tcaggatgat 540
gaaaccaact ctatattaac tttatgccgt atgattttaa ctatggacac gggtaaaatc 600
ataccaaaag atattgcggg aaatgcagtg gctgaatctt ctccattaga acatagggag 660
agaattttgt tagcagttcg tagttatctt ggagagaata ttgaatggac taatgaaaat 720
gtaaatttaa ctataaacta tttaaataac agattaaaaa aatta 765

<210> SEQ ID NO 90
<211> LENGTH: 1161
<212> TYPE: DNA
<213> ORGANISM: Bacillus subtilis

<400> SEQUENCE: 90
gtggatgaag tggatatcgc tgatcaaacc tttgtcaaaa aagtaaatca aaagttatta 60
ttaaaagaaa tccttaaaaa ttcacctatt tcaagagcaa aattatctga aatgactgga 120
ttaaataaat caactgtctc atcacaggta aacacgttaa tgaaagaaag tatggtattt 180
gaaataggtc aaggacaatc aagtggcgga agaagacctg tcatgcttgt ttttaataaa 240
aaggcaggat actccgttgg aatagatgtt ggtgtggatt atattaatgg cattttaaca 300
gaccttgaag gaacaatcgt tcttgatcaa taccgccatt tggaatccaa ttctccagaa 360
ataacgaaag acattttgat tgatatgatt catcacttta ttacgcaaat gccccaatct 420
ccgtacgggt ttattggtat aggtacttgc gtgcctggac tcattgataa agatcaaaaa 480
attgttttca ctccgaactc caactggaga gatattgact taaaatcttc gatacaagag 540
aagtacaatg tgtctgtttt tattgaaaat gaggcaaatg ctggcgcata tggagaaaaa 600
ctatttggag ctgcaaaaaa tcacgataac attatttacg taagtatcag cacaggaata 660
gggatcggtg ttattatcaa caatcattta tatagaggag taagcggctt ctctggagaa 720
atgggacata tgacaataga ctttaatggt cctaaatgca gttgcggaaa ccgaggatgc 780
tgggaattgt atgcttcaga gaaggcttta tttaaatctc ttcagaccaa agagaaaaaa 840
ctgtcctatc aagatatcat aaacctcgcc catctgaatg atatcggaac cttaaatgca 900
ttacaaaatt ttggattcta tttaggaata ggccttacca atattctaaa tactctcaac 960
ccacaagccg taattttaag aaatagcata attgaatcgc atcctatggt tttaaattca 1020
atgagaagtg aagtatcatc aagggtttat tcccaattag gcaatagcta tgaattattg 1080
ccatcttcct taggacagaa tgcaccggca ttaggaatgt cctccattgt gattgatcat 1140
tttctggaca tgattacaat g 1161

<210> SEQ ID NO 91
<211> LENGTH: 66
<212> TYPE: DNA
<213> ORGANISM: Bacillus subtilis

<400> SEQUENCE: 91
tgtacttact atatgaaata aaatgcatct gtatttgaat gaatttattt ttaaggggga 60
aatcac 66

<210> SEQ ID NO 92
<211> LENGTH: 576
<212> TYPE: DNA
<213> ORGANISM: Bacillus licheniformis

<400> SEQUENCE: 92
atgagcacag aggatatgac aaaggatacg tatgaagtaa acagttcgac aatggctgtc 60
ctgcctctgg gtgaggggga gaaatccgcc tcaaaaatac ttgagaccga caggactttc 120
cgcgtcaata tgaagccgtt tcaaattatc gaaagaagct gccgctattt cggatcgagc 180
tatgcgggaa gaaaagcggg cacatatgaa gtcattaaag tttcccataa accgccgatc 240
atggtggatc actcaaacaa catttttctt ttccccacat tttcctcaac tcgtcctcag 300
tgcgggtggc tttcccatgc gcatgttcac gagttttgcg cggcaaagta tgacaacacg 360
tttgtcacgt ttgtcaacgg ggaaacgctg gagctgcccg tatccatctc atctttcgaa 420
aaccaggttt accgaacggc atggctgaga acaaaattta tcgacaggat tgaaggaaac 480
cccatgcaga agaaacagga atttatgctc tatccgaaag aagaccggaa tcagctgata 540
tacgaattca tcctcaggga gctgaaaaag cgctat 576

<210> SEQ ID NO 93
<211> LENGTH: 4946
<212> TYPE: DNA
<213> ORGANISM: Artificial Sequence
<220> FEATURE:
<223> OTHER INFORMATION: synthetic

<400> SEQUENCE: 93

```
tcgcggacaa gtacggcaag acaccggccc aagtcatttt gcgctgggat ttgcaaaacg      60
gggtcgttac gattccgaag tcgactaaag cggagcggat tgcccaaaac gcggacatat     120
ttgattttga actgaccacc gaggaaatga agcaaattga cgcgctgaat gaaaacaccc     180
gtgtcggccc tgatcccgat aactttgact tttaacaaaa cggccccgtt cgacattcga     240
acggggcttt aattgaattg tgcggttaca ccgccggact ccatcatcat cagttctttt     300
ttcatatcca atccgccccg gtatcccgtg agctgcccgc ttttaccgat aacccgatgg     360
caaggcacca ccattaacag cggatttgcg ccgatcgccg cgcctactgc ccgcacagcg     420
gcctgctttt caatatgctc ggcgatatcg gaataggagc aagtgctgcc gtaagggatt     480
tcggagagcg ccttccacac tgccagctga aaaggcgtgc cggcaaggtc gacaggaaag     540
ctgaaatgag ttcgcttgcc gttcaaatac gcctgcagct gctcggcgta ttctgccaat     600
cctttgtcat cccgaatgaa aactggctgt gtaaatcttt tttcagccca agcggccaaa     660
tcctcgaagc cttgattcca tccccctgta aaacagagcc cgcgggcagt cgccccaatg     720
tgaatctgcc aacctcggca aataagcgta cgccagtata cgatttgatc gtccatatgt     780
ttacctccgt ttcatttgcc ggtacgacgt cggcgattgc ccagtcttct ttttaaacaa     840
agaggcaaaa tattccgcat tcgcaatgcc taccattgaa gcgatttctg cgatcgatcg     900
ttctgaatga gcaagcaaat cgaccgcttt ctcaatcctt ttctgcagga tgtattctgc     960
cggcgagacg cctttgattc gtttaaatgt ccgctgcagg tgaaaagggc tgatatggca    1020
cctgtcagcc aaagcttgca gagacagcgg atcgcgataa gattcctcga tgatttccac    1080
cacacgctgt gccagctctt catccggcag cagcgccccg gccggattgc agcgtttgca    1140
ggggcggtac ccttctgata aagcatcttt tgcattgaaa aagatctgca cattgtcgat    1200
ttgcggaact ctcgatttgc aggaagggcg gcaaaatatg ccggtcgttt tgaccgcgta    1260
ataaaaaact ccgtcatagg cggaatcgtt ttccgtaatc gcccgccaca tttcaggcgt    1320
caatcgtgat ttgctgttca tatcttcacc ccgatctatg tcagtataac ctatatgaca    1380
gccggaggtg gagaggcgga gaacggcaca gcaagaagac aaagaagaag agagactgtt    1440
gcctggacct ccgaaacgcg ctacaattca tttacaacac aggatggggt gagaatattg    1500
ccggaatcag tgaagcaggc ctcctaaaat aaaaatctat attttaggag gtaaaacatg    1560
aattttcaaa caatcgagct tgacacatgg tatagaaaat cttattttga ccattacatg    1620
aaggaagcga aatgttcttt cagcatcacg gcaaacgtca atgtgacaaa tttgctcgcc    1680
gtgctcaaga aaaagaagct caagctgtat ccggctttta tttatatcgt atcaagggtc    1740
attcattcgc gccctgagtt tagaacaacg tttgatgaca aaggacagct gggttattgg    1800
gaacaaatgc atccgtgcta tgcgattttt catcaggacg accaaacgtt ttccgccctc    1860
tggacggaat actcagacga tttttcgcag ttttatcatc aatatcttct ggacgccgag    1920
cgctttggag acaaaagggg cctttgggct aagccggaca tcccgcccaa tacgttttca    1980
gtttcttcta ttccatgggt gcgcttttca aacttcaatt taaaccttga taacagcgaa    2040
cacttgctgc cgattattac aaacgggaaa tacttttcag aaggcaggga aacatttttg    2100
cccgtttcct tgcaagttca ccatgcagtg tgtgacggct atcatgccgg cgcttttata    2160
aacgagttgg aacggcttgc cgccgattgt gaggagtggc ttgtgtgaca gaggaaaggc    2220
cgatatgatt cggccttttt tatatgtact tcttagcggg tctctaaaat aaccaaaaag    2280
caaggactgc tgaaagggct gacataagcc ttttgccggc ggtccttttt taattctgat    2340
ttttcaaact tagccccctc gagaaaaccg cttgagtatc ctccgctcat gttattgacc    2400
```

```
tccttttctt gatcaatata tttgtatgag cggaaagaaa atttgactag acggatgccc   2460
ctctgttgaa aatcttttta cagcatgtca gaatatgata tgatacaatt caaaggaaag   2520
tttaaactgt tatgattagg agtgtttgca tttatgaaga agattgcaat tgcggcgatt   2580
acagcgacaa gcgtgctggc tctcagcgca tgcagcgggg gagattctga ggttgttgcg   2640
gaaacaaaag ctggaaatat tacaaaagaa gacctttatc aaacattaaa agacaatgcc   2700
ggagcggacg cactgaacat gcttgttcag caaaaagtac tcgatgataa atacgatgtc   2760
tccgacaaag aaatcgacaa aaagctgaac gagtacaaaa aatcaatggg tgaccagctc   2820
aaccagctca ttgaccaaaa aggcgaagac ttcgtcaaag aacagatcaa atacgaactt   2880
ctgatgcaaa aagccgcaaa ggataacata aaagtaaccg atgatgacgt aaaagaatat   2940
tatgacggcc tgaaaggcaa aatccactta agccacattc ttgtgaaaga aaagaaaacg   3000
gctgaagaag ttgagaaaaa gctgaaaaaa ggcgaaaaat tcgaagacct tgcaaaagag   3060
tattcaactg acggtacagc cgaaaaaggc ggcgacctcg gctgggtcgg caaagacgat   3120
aacatggaca aggatttcgt caaagcggca tttgctttga aaaccggcga aatcagcgga   3180
cctgtgaaat cccaattcgg ctatcacatc attaaaaaag acgaagaacg cggcaaatat   3240
gaagacatga aaaaagagct taaaaaagaa gtccaagaac aaaagcaaaa tgatcaaact   3300
gaactgcaat ccgtcattga caaacttgtc aaagatgctg atttaaaagt aaaagacaaa   3360
gagttgaaaa aacaagtcga ccagcgtcaa gctcagacaa gcagcagcag ctgaaagagc   3420
agagaggacg gatttcctga aggaaatccg tttttttatt tttaacatct ctcactgctg   3480
tgtgatttta ctcacggcat ttggaacgcc ggctctcaac aaactttctg tagtgaaaat   3540
catgaaccaa acggatcgtc ggcctgatta acagctgaaa gctgccgatc acaaacatcc   3600
atagtcccgc cggcttcagt tcctcggaga aaaagcagaa gctcccgaca aggaataaaa   3660
ggccgatgag aaaatcgttt aatgtatgta gaactttgta tctttttttg aaaaagagtt   3720
catatcgatt gttattgttt tgcggcattg cttgatcact ccaatccttt tatttaccct   3780
gccggaagcc ggagtgaaac gccggtatac ataggattta tgaattagga aaacatatgg   3840
ggaaataaac catccaggag tgaaaaatat gcggttattc atatgtgcat cgtgcctgtt   3900
cggcttgatt gttccgtcat ttgaaacgaa agcgctgacg tttgaagaat tgccggttaa   3960
acaagcttca aaacaatggg aagttcaaat cggtaaagcc gaagccggaa acggaatggc   4020
gaaaccggaa aaaggagcgt ttcatactta tgctgtcgaa atcaaaaaca ttggacacga   4080
tgtggcttcg gcggaaattt ttgtctatcg gaacgagcct aattcttcaa cgaaattttc   4140
gctttggaac attcctcacg aaaatccggt ttctttagcc aaaagcttaa atcacggaag   4200
ctctgtcaag caccgcaatc tgcttatggc agagaatgcg accgaattgg aagtggacat   4260
gatttggacg gaaaaaggaa gcgaaggcag acttttaaag gaaacgttca ttttcaaggg   4320
agatgaatca tgaagaaaaa atggccgttc atcgtcaacg gtcttttttt aatgacttag   4380
gcagccgatc gttcggccat acgatatcga agcgacctcg aaccagcaga gctcgtcaca   4440
aaacatttgc atttaaagaa aaatacagga tgttttcacc aatatttttc tcaatgatga   4500
tacactattg acaagctgct actttgggag ggtgtttcca tagatgccga tgaagcaaaa   4560
acaccaaatg tgtcatgaga gctctctcta atcgatataa aagtagggtg aaccggggtt   4620
gtcaatctgt aaaagatctt tttttatccc gtgatacgct tttggaattc tgaatcttca   4680
agaaagtccc cagccttttg ctgatcaatc gagaacaaag gatgatacat atgaaaagaa   4740
```

tagataaaat ctaccatcag ctgctggata attttcgcga aaagaatatc aatcagcttt 4800
taaagataca agggaattcg gctaaagaaa tcgccgggca gctgcaaatg gagcgttcca 4860
atgtcagctt tgaattaaac aatctcgttc gggccaaaaa ggtgatcaag attaaaacgt 4920
tccccgtccg ctacatcccg gtggaa 4946

<210> SEQ ID NO 94
<211> LENGTH: 1341
<212> TYPE: DNA
<213> ORGANISM: Bacillus licheniformis

<400> SEQUENCE: 94
tcgcggacaa gtacggcaag acaccggccc aagtcatttt gcgctgggat ttgcaaaacg 60
gggtcgttac gattccgaag tcgactaaag cggagcggat tgcccaaaac gcggacatat 120
ttgattttga actgaccacc gaggaaatga agcaaattga cgcgctgaat gaaaacaccc 180
gtgtcggccc tgatcccgat aactttgact tttaacaaaa cggccccgtt cgacattcga 240
acggggcttt aattgaattg tgcggttaca ccgccggact ccatcatcat cagttctttt 300
ttcatatcca atccgccccg gtatcccgtg agctgcccgc ttttaccgat aacccgatgg 360
caaggcacca ccattaacag cggatttgcg ccgatcgccg cgcctactgc ccgcacagcg 420
gcctgctttt caatatgctc ggcgatatcg gaataggagc aagtgctgcc gtaagggatt 480
tcggagagcg ccttccacac tgccagctga aaaggcgtgc cggcaaggtc gacaggaaag 540
ctgaaatgag ttcgcttgcc gttcaaatac gcctgcagct gctcggcgta ttctgccaat 600
cctttgtcat cccgaatgaa aactggctgt gtaaatcttt tttcagccca agcggccaaa 660
tcctcgaagc cttgattcca tccccctgta aaacagagcc cgcgggcagt cgccccaatg 720
tgaatctgcc aacctcggca aataagcgta cgccagtata cgatttgatc gtccatatgt 780
ttacctccgt ttcatttgcc ggtacgacgt cggcgattgc ccagtcttct ttttaaacaa 840
agaggcaaaa tattccgcat tcgcaatgcc taccattgaa gcgatttctg cgatcgatcg 900
ttctgaatga gcaagcaaat cgaccgcttt ctcaatcctt ttctgcagga tgtattctgc 960
cggcgagacg cctttgattc gtttaaatgt ccgctgcagg tgaaaagggc tgatatggca 1020
cctgtcagcc aaagcttgca gagacagcgg atcgcgataa gattcctcga tgatttccac 1080
cacacgctgt gccagctctt catccggcag cagcgccccg gccggattgc agcgtttgca 1140
ggggcggtac ccttctgata aagcatcttt tgcattgaaa aagatctgca cattgtcgat 1200
ttgcggaact ctcgatttgc aggaagggcg gcaaaatatg ccggtcgttt tgaccgcgta 1260
ataaaaaact ccgtcatagg cggaatcgtt ttccgtaatc gcccgccaca tttcaggcgt 1320
caatcgtgat ttgctgttca t 1341

<210> SEQ ID NO 95
<211> LENGTH: 216
<212> TYPE: DNA
<213> ORGANISM: Bacillus licheniformis

<400> SEQUENCE: 95
atcttcaccc cgatctatgt cagtataacc tatatgacag ccggaggtgg agaggcggag 60
aacggcacag caagaagaca aagaagaaga gagactgttg cctggacctc cgaaacgcgc 120
tacaattcat ttacaacaca ggatggggtg agaatattgc cggaatcagt gaagcaggcc 180
tcctaaaata aaaatctata ttttaggagg taaaac 216

<210> SEQ ID NO 96
<211> LENGTH: 648
<212> TYPE: DNA
<213> ORGANISM: Bacillus licheniformis

<400> SEQUENCE: 96
atgaattttc aaacaatcga gcttgacaca tggtatagaa aatcttattt tgaccattac 60
atgaaggaag cgaaatgttc tttcagcatc acggcaaacg tcaatgtgac aaatttgctc 120
gccgtgctca agaaaaagaa gctcaagctg tatccggctt ttatttatat cgtatcaagg 180
gtcattcatt cgcgccctga gtttagaaca acgtttgatg acaaaggaca gctgggttat 240
tgggaacaaa tgcatccgtg ctatgcgatt tttcatcagg acgaccaaac gttttccgcc 300
ctctggacgg aatactcaga cgatttttcg cagttttatc atcaatatct tctggacgcc 360
gagcgctttg gagacaaaag gggcctttgg gctaagccgg acatcccgcc caatacgttt 420
tcagtttctt ctattccatg ggtgcgcttt tcaaacttca atttaaacct tgataacagc 480
gaacacttgc tgccgattat tacaaacggg aaatactttt cagaaggcag ggaaacattt 540
ttgcccgttt ccttgcaagt tcaccatgca gtgtgtgacg gctatcatgc cggcgctttt 600
ataaacgagt tggaacggct tgccgccgat tgtgaggagt ggcttgtg 648

<210> SEQ ID NO 97
<211> LENGTH: 149
<212> TYPE: DNA
<213> ORGANISM: Artificial Sequence
<220> FEATURE:
<223> OTHER INFORMATION: synthetic

<400> SEQUENCE: 97
aaaggccgat atgattcggc ctttttata tgtacttctt agcgggtctc taaaataacc 60
aaaaagcaag gactgctgaa agggctgaca taagcctttt gccggcggtc ctttttaat 120 tctgatttt caaacttagc cccctcgag 149

<210> SEQ ID NO 98
<211> LENGTH: 60
<212> TYPE: DNA
<213> ORGANISM: Bacillus licheniformis

<400> SEQUENCE: 98
tgacagagga aaggccgata tgattcggcc tttttatat gtacttctta gcgggtctct 60

<210> SEQ ID NO 99
<211> LENGTH: 98
<212> TYPE: DNA
<213> ORGANISM: Bacillus subtilis

<400> SEQUENCE: 99
aaaataacca aaaagcaagg actgctgaaa gggctgacat aagccttttg ccggcggtcc 60 tttttaatt ctgattttc aaacttagcc ccctcgag 98

<210> SEQ ID NO 100
<211> LENGTH: 190
<212> TYPE: DNA
<213> ORGANISM: Bacillus licheniformis

<400> SEQUENCE: 100
aaaaccgctt gagtatcctc cgctcatgtt attgacctcc ttttcttgat caatatattt 60
gtatgagcgg aaagaaaatt tgactagacg gatgcccctc tgttgaaaat ctttttacag 120
catgtcagaa tatgatatga tacaattcaa aggaaagttt aaactgttat gattaggagt 180
gtttgcattt 190

<210> SEQ ID NO 101
<211> LENGTH: 861
<212> TYPE: DNA
<213> ORGANISM: Bacillus licheniformis

<400> SEQUENCE: 101
atgaagaaga ttgcaattgc ggcgattaca gcgacaagcg tgctggctct cagcgcatgc 60
agcgggggag attctgaggt tgttgcggaa acaaaagctg gaaatattac aaaagaagac 120
ctttatcaaa cattaaaaga caatgccgga gcggacgcac tgaacatgct tgttcagcaa 180
aaagtactcg atgataaata cgatgtctcc gacaaagaaa tcgacaaaaa gctgaacgag 240
tacaaaaaat caatgggtga ccagctcaac cagctcattg accaaaaagg cgaagacttc 300
gtcaaagaac agatcaaata cgaacttctg atgcaaaaag ccgcaaagga taacataaaa 360
gtaaccgatg atgacgtaaa agaatattat gacggcctga aaggcaaaat ccacttaagc 420
cacattcttg tgaaagaaaa gaaaacggct gaagaagttg agaaaaagct gaaaaaaggc 480
gaaaaattcg aagaccttgc aaaagagtat tcaactgacg gtacagccga aaaaggcggc 540
gacctcggct gggtcggcaa agacgataac atggacaagg atttcgtcaa agcggcattt 600
gctttgaaaa ccggcgaaat cagcggacct gtgaaatccc aattcggcta tcacatcatt 660
aaaaaagacg aagaacgcgg caaatatgaa gacatgaaaa aagagcttaa aaaagaagtc 720
caagaacaaa agcaaaatga tcaaactgaa ctgcaatccg tcattgacaa acttgtcaaa 780
gatgctgatt taaaagtaaa agacaaagag ttgaaaaaac aagtcgacca gcgtcaagct 840
cagacaagca gcagcagctg a 861

<210> SEQ ID NO 102
<211> LENGTH: 34
<212> TYPE: DNA
<213> ORGANISM: Bacillus licheniformis

<400> SEQUENCE: 102
cggatttcct gaaggaaatc cgttttttta tttt 34

<210> SEQ ID NO 103
<211> LENGTH: 1484
<212> TYPE: DNA
<213> ORGANISM: Bacillus licheniformis

<400> SEQUENCE: 103
taacatctct cactgctgtg tgattttact cacggcattt ggaacgccgg ctctcaacaa 60
actttctgta gtgaaaatca tgaaccaaac ggatcgtcgg cctgattaac agctgaaagc 120
tgccgatcac aaacatccat agtcccgccg gcttcagttc ctcggagaaa aagcagaagc 180
tcccgacaag gaataaaagg ccgatgagaa aatcgtttaa tgtatgtaga actttgtatc 240 ttttttgaa aaagagttca tatcgattgt tattgttttg cggcattgct tgatcactcc 300
aatcctttta tttaccctgc cggaagccgg agtgaaacgc cggtatacat aggatttatg 360
aattaggaaa acatatgggg aaataaacca tccaggagtg aaaaatatgc ggttattcat 420
atgtgcatcg tgcctgttcg gcttgattgt tccgtcattt gaaacgaaag cgctgacgtt 480
tgaagaattg ccggttaaac aagcttcaaa acaatgggaa gttcaaatcg gtaaagccga 540
agccggaaac ggaatggcga aaccggaaaa aggagcgttt catacttatg ctgtcgaaat 600
caaaaacatt ggacacgatg tggcttcggc ggaaattttt gtctatcgga acgagcctaa 660
ttcttcaacg aaattttcgc tttggaacat tcctcacgaa aatccggttt ctttagccaa 720
aagcttaaat cacggaagct ctgtcaagca ccgcaatctg cttatggcag agaatgcgac 780
cgaattggaa gtggacatga tttggacgga aaaaggaagc gaaggcagac ttttaaagga 840
aacgttcatt ttcaagggag atgaatcatg aagaaaaaat ggccgttcat cgtcaacggt 900
ctttttttaa tgacttaggc agccgatcgt tcggccatac gatatcgaag cgacctcgaa 960
ccagcagagc tcgtcacaaa acatttgcat ttaaagaaaa atacaggatg ttttcaccaa 1020
tatttttctc aatgatgata cactattgac aagctgctac tttgggaggg tgtttccata 1080
gatgccgatg aagcaaaaac accaaatgtg tcatgagagc tctctctaat cgatataaaa 1140
gtagggtgaa ccggggttgt caatctgtaa aagatctttt tttatcccgt gatacgcttt 1200
tggaattctg aatcttcaag aaagtcccca gccttttgct gatcaatcga gaacaaagga 1260
tgatacatat gaaaagaata gataaaatct accatcagct gctggataat tttcgcgaaa 1320
agaatatcaa tcagctttta aagatacaag ggaattcggc taaagaaatc gccgggcagc 1380
tgcaaatgga gcgttccaat gtcagctttg aattaaacaa tctcgttcgg gccaaaaagg 1440
tgatcaagat taaaacgttc cccgtccgct acatcccggt ggaa 1484

<210> SEQ ID NO 104
<211> LENGTH: 20
<212> TYPE: DNA
<213> ORGANISM: Artificial Sequence
<220> FEATURE:
<223> OTHER INFORMATION: synthetic

<400> SEQUENCE: 104
tcgttctgaa tgagcaagca 20

<210> SEQ ID NO 105
<211> LENGTH: 20
<212> TYPE: DNA
<213> ORGANISM: Artificial Sequence
<220> FEATURE:
<223> OTHER INFORMATION: synthetic

<400> SEQUENCE: 105
tgttaatcag gccgacgatc 20

<210> SEQ ID NO 106
<211> LENGTH: 2676
<212> TYPE: DNA
<213> ORGANISM: Artificial Sequence
<220> FEATURE:
<223> OTHER INFORMATION: synthetic

<400> SEQUENCE: 106
tcgttctgaa tgagcaagca aatcgaccgc tttctcaatc cttttctgca ggatgtattc 60
tgccggcgag acgcctttga ttcgtttaaa tgtccgctgc aggtgaaaag ggctgatatg 120
gcacctgtca gccaaagctt gcagagacag cggatcgcga taagattcct cgatgatttc 180
caccacacgc tgtgccagct cttcatccgg cagcagcgcc ccggccggat tgcagcgttt 240
gcaggggcgg tacccttctg ataaagcatc ttttgcattg aaaaagatct gcacattgtc 300
gatttgcgga actctcgatt tgcaggaagg gcggcaaaat atgccggtcg ttttgaccgc 360
gtaataaaaa actccgtcat aggcggaatc gttttccgta atcgcccgcc acatttcagg 420

-continued

```
cgtcaatcgt gatttgctgt tcatatcttc accccgatct atgtcagtat aacctatatg    480
acagccggag gtggagaggc ggagaacggc acagcaagaa gacaaagaag aagagagact    540
gttgcctgga cctccgaaac gcgctacaat tcatttacaa cacaggatgg ggtgagaata    600
ttgccggaat cagtgaagca ggcctcctaa aataaaaatc tatattttag gaggtaaaac    660
atgaattttc aaacaatcga gcttgacaca tggtatagaa aatcttattt tgaccattac    720
atgaaggaag cgaaatgttc tttcagcatc acggcaaacg tcaatgtgac aaatttgctc    780
gccgtgctca agaaaaagaa gctcaagctg tatccggctt ttatttatat cgtatcaagg    840
gtcattcatt cgcgccctga gtttagaaca acgtttgatg acaaaggaca gctgggttat    900
tgggaacaaa tgcatccgtg ctatgcgatt tttcatcagg acgaccaaac gttttccgcc    960
ctctggacgg aatactcaga cgatttttcg cagttttatc atcaatatct tctggacgcc   1020
gagcgctttg gagacaaaag gggcctttgg gctaagccgg acatcccgcc caatacgttt   1080
tcagtttctt ctattccatg ggtgcgcttt tcaaacttca atttaaacct tgataacagc   1140
gaacacttgc tgccgattat tacaaacggg aaatactttt cagaaggcag ggaaacattt   1200
ttgcccgttt ccttgcaagt tcaccatgca gtgtgtgacg gctatcatgc cggcgctttt   1260
ataaacgagt tggaacggct tgccgccgat tgtgaggagt ggcttgtgtg acagaggaaa   1320
ggccgatatg attcggcctt ttttatatgt acttcttagc gggtctctaa aataaccaaa   1380
aagcaaggac tgctgaaagg gctgacataa gccttttgcc ggcggtcctt ttttaattct   1440
gatttttcaa acttagcccc ctcgagaaaa ccgcttgagt atcctccgct catgttattg   1500
acctcctttt cttgatcaat atatttgtat gagcggaaag aaaatttgac tagacggatg   1560
cccctctgtt gaaaatcttt ttacagcatg tcagaatatg atatgataca attcaaagga   1620
aagtttaaac tgttatgatt aggagtgttt gcatttatga agaagattgc aattgcggcg   1680
attacagcga caagcgtgct ggctctcagc gcatgcagcg ggggagattc tgaggttgtt   1740
gcggaaacaa aagctggaaa tattacaaaa gaagaccttt atcaaacatt aaaagacaat   1800
gccggagcgg acgcactgaa catgcttgtt cagcaaaaag tactcgatga taaatacgat   1860
gtctccgaca aagaaatcga caaaaagctg aacgagtaca aaaaatcaat gggtgaccag   1920
ctcaaccagc tcattgacca aaaaggcgaa gacttcgtca aagaacagat caaatacgaa   1980
cttctgatgc aaaaagccgc aaaggataac ataaaagtaa ccgatgatga cgtaaaagaa   2040
tattatgacg gcctgaaagg caaaatccac ttaagccaca ttcttgtgaa agaaaagaaa   2100
acggctgaag aagttgagaa aaagctgaaa aaaggcgaaa aattcgaaga ccttgcaaaa   2160
gagtattcaa ctgacggtac agccgaaaaa ggcggcgacc tcggctgggt cggcaaagac   2220
gataacatgg acaaggattt cgtcaaagcg gcatttgctt tgaaaaccgg cgaaatcagc   2280
ggacctgtga aatcccaatt cggctatcac atcattaaaa aagacgaaga acgcggcaaa   2340
tatgaagaca tgaaaaaaga gcttaaaaaa gaagtccaag aacaaaagca aaatgatcaa   2400
actgaactgc aatccgtcat tgacaaactt gtcaaagatg ctgatttaaa agtaaaagac   2460
aaagagttga aaaaacaagt cgaccagcgt caagctcaga caagcagcag cagctgaaag   2520
agcagagagg acggatttcc tgaaggaaat ccgttttttt atttttaaca tctctcactg   2580
ctgtgtgatt ttactcacgg catttggaac gccggctctc aacaaacttt ctgtagtgaa   2640
aatcatgaac caaacggatc gtcggcctga ttaaca                              2676
```

<210> SEQ ID NO 107
<211> LENGTH: 20

<212> TYPE: DNA
<213> ORGANISM: Artificial Sequence
<220> FEATURE:
<223> OTHER INFORMATION: synthetic

<400> SEQUENCE: 107
aacctatatg acagccggag 20

<210> SEQ ID NO 108
<211> LENGTH: 21
<212> TYPE: DNA
<213> ORGANISM: Artificial Sequence
<220> FEATURE:
<223> OTHER INFORMATION: synthetic

<400> SEQUENCE: 108
ggcaaaatcc acttaagcca c 21

<210> SEQ ID NO 109
<211> LENGTH: 20
<212> TYPE: DNA
<213> ORGANISM: Artificial Sequence
<220> FEATURE:
<223> OTHER INFORMATION: synthetic

<400> SEQUENCE: 109
aacgagttgg aacggcttgc 20

<210> SEQ ID NO 110
<211> LENGTH: 686
<212> TYPE: DNA
<213> ORGANISM: Bacillus licheniformis

<400> SEQUENCE: 110
cctcctaaaa taaaaatcta tattttagga ggtaaaacat gaattttcaa acaatcgagc 60
ttgacacatg gtatagaaaa tcttattttg accattacat gaaggaagcg aaatgttctt 120
tcagcatcac ggcaaacgtc aatgtgacaa atttgctcgc cgtgctcaag aaaaagaagc 180
tcaagctgta tccggctttt atttatatcg tatcaagggt cattcattcg cgccctgagt 240
ttagaacaac gtttgatgac aaaggacagc tgggttattg ggaacaaatg catccgtgct 300
atgcgatttt tcatcaggac gaccaaacgt tttccgccct ctggacggaa tactcagacg 360
atttttcgca gttttatcat caatatcttc tggacgccga gcgctttgga gacaaaaggg 420
gcctttgggc taagccggac atcccgccca atacgttttc agtttcttct attccatggg 480
tgcgcttttc aaacttcaat ttaaaccttg ataacagcga acacttgctg ccgattatta 540
caaacgggaa atacttttca gaaggcaggg aaacattttt gcccgtttcc ttgcaagttc 600
accatgcagt gtgtgacggc tatcatgccg gcgcttttat aaacgagttg gaacggcttg 660
ccgccgattg tgaggagtgg cttgtg 686

<210> SEQ ID NO 111
<211> LENGTH: 4260
<212> TYPE: DNA
<213> ORGANISM: Artificial Sequence
<220> FEATURE:
<223> OTHER INFORMATION: synthetic

<400> SEQUENCE: 111
tcgcggacaa gtacggcaag acaccggccc aagtcatttt gcgctgggat ttgcaaaacg 60
gggtcgttac gattccgaag tcgactaaag cggagcggat tgcccaaaac gcggacatat 120

```
ttgattttga actgaccacc gaggaaatga agcaaattga cgcgctgaat gaaaacaccc    180
gtgtcggccc tgatcccgat aactttgact tttaacaaaa cggccccgtt cgacattcga    240
acggggcttt aattgaattg tgcggttaca ccgccggact ccatcatcat cagttctttt    300
ttcatatcca atccgccccg gtatcccgtg agctgcccgc ttttaccgat aacccgatgg    360
caaggcacca ccattaacag cggatttgcg ccgatcgccg cgcctactgc ccgcacagcg    420
gcctgctttt caatatgctc ggcgatatcg gaataggagc aagtgctgcc gtaagggatt    480
tcggagagcg ccttccacac tgccagctga aaaggcgtgc cggcaaggtc gacaggaaag    540
ctgaaatgag ttcgcttgcc gttcaaatac gcctgcagct gctcggcgta ttctgccaat    600
cctttgtcat cccgaatgaa aactggctgt gtaaatcttt tttcagccca agcggccaaa    660
tcctcgaagc cttgattcca tccccctgta aaacagagcc cgcgggcagt cgccccaatg    720
tgaatctgcc aacctcggca aataagcgta cgccagtata cgatttgatc gtccatatgt    780
ttacctccgt ttcatttgcc ggtacgacgt cggcgattgc ccagtcttct ttttaaacaa    840
agaggcaaaa tattccgcat tcgcaatgcc taccattgaa gcgatttctg cgatcgatcg    900
ttctgaatga gcaagcaaat cgaccgcttt ctcaatcctt ttctgcagga tgtattctgc    960
cggcgagacg cctttgattc gtttaaatgt ccgctgcagg tgaaaagggc tgatatggca   1020
cctgtcagcc aaagcttgca gagacagcgg atcgcgataa gattcctcga tgatttccac   1080
cacacgctgt gccagctctt catccggcag cagcgccccg gccggattgc agcgtttgca   1140
ggggcggtac ccttctgata aagcatcttt tgcattgaaa aagatctgca cattgtcgat   1200
ttgcggaact ctcgatttgc aggaagggcg gcaaaatatg ccggtcgttt tgaccgcgta   1260
ataaaaaact ccgtcatagg cggaatcgtt ttccgtaatc gcccgccaca tttcaggcgt   1320
caatcgtgat ttgctgttca tatcttcacc ccgatctatg tcagtataac ctatatgaca   1380
gccggaggtg gagaggcgga gaacggcaca gcaagaagac aaagaagaag agagactgtt   1440
gcctggacct ccgaaacgcg ctacaattca tttacaacac aggatggggt gagaatattg   1500
ccggaatcag tgaagcaggt gacagaggaa aggccgatat gattcggcct tttttatatg   1560
tacttcttag cgggtctcta aaataaccaa aaagcaagga ctgctgaaag ggctgacata   1620
agccttttgc cggcggtcct tttttaattc tgatttttca aacttagccc cctcgagaaa   1680
accgcttgag tatcctccgc tcatgttatt gacctccttt tcttgatcaa tatatttgta   1740
tgagcggaaa gaaaatttga ctagacggat gcccctctgt tgaaaatctt tttacagcat   1800
gtcagaatat gatatgatac aattcaaagg aaagtttaaa ctgttatgat taggagtgtt   1860
tgcatttatg aagaagattg caattgcggc gattacagcg acaagcgtgc tggctctcag   1920
cgcatgcagc gggggagatt ctgaggttgt tgcggaaaca aaagctggaa atattacaaa   1980
agaagacctt tatcaaacat taaaagacaa tgccggagcg gacgcactga acatgcttgt   2040
tcagcaaaaa gtactcgatg ataaatacga tgtctccgac aaagaaatcg acaaaaagct   2100
gaacgagtac aaaaaatcaa tgggtgacca gctcaaccag ctcattgacc aaaaaggcga   2160
agacttcgtc aaagaacaga tcaaatacga acttctgatg caaaaagccg caaaggataa   2220
cataaaagta accgatgatg acgtaaaaga atattatgac ggcctgaaag gcaaaatcca   2280
cttaagccac attcttgtga aagaaaagaa aacggctgaa gaagttgaga aaaagctgaa   2340
aaaaggcgaa aaattcgaag accttgcaaa agagtattca actgacggta cagccgaaaa   2400
aggcggcgac ctcggctggg tcggcaaaga cgataacatg gacaaggatt tcgtcaaagc   2460
ggcatttgct ttgaaaaccg gcgaaatcag cggacctgtg aaatcccaat tcggctatca   2520
```

catcattaaa aaagacgaag aacgcggcaa atatgaagac atgaaaaaag agcttaaaaa 2580
agaagtccaa gaacaaaagc aaaatgatca aactgaactg caatccgtca ttgacaaact 2640
tgtcaaagat gctgatttaa aagtaaaaga caaagagttg aaaaaacaag tcgaccagcg 2700
tcaagctcag acaagcagca gcagctgaaa gagcagagag gacggatttc ctgaaggaaa 2760
tccgtttttt tatttttaac atctctcact gctgtgtgat tttactcacg gcatttggaa 2820
cgccggctct caacaaactt tctgtagtga aaatcatgaa ccaaacggat cgtcggcctg 2880
attaacagct gaaagctgcc gatcacaaac atccatagtc ccgccggctt cagttcctcg 2940
gagaaaaagc agaagctccc gacaaggaat aaaaggccga tgagaaaatc gtttaatgta 3000
tgtagaactt tgtatctttt tttgaaaaag agttcatatc gattgttatt gttttgcggc 3060
attgcttgat cactccaatc cttttattta ccctgccgga agccggagtg aaacgccggt 3120
atacatagga tttatgaatt aggaaaacat atggggaaat aaaccatcca ggagtgaaaa 3180
atatgcggtt attcatatgt gcatcgtgcc tgttcggctt gattgttccg tcatttgaaa 3240
cgaaagcgct gacgtttgaa gaattgccgg ttaaacaagc ttcaaaacaa tgggaagttc 3300
aaatcggtaa agccgaagcc ggaaacggaa tggcgaaacc ggaaaaagga gcgtttcata 3360
cttatgctgt cgaaatcaaa aacattggac acgatgtggc ttcggcggaa atttttgtct 3420
atcggaacga gcctaattct tcaacgaaat tttcgctttg gaacattcct cacgaaaatc 3480
cggtttcttt agccaaaagc ttaaatcacg gaagctctgt caagcaccgc aatctgctta 3540
tggcagagaa tgcgaccgaa ttggaagtgg acatgatttg gacggaaaaa ggaagcgaag 3600
gcagactttt aaaggaaacg ttcattttca agggagatga atcatgaaga aaaaatggcc 3660
gttcatcgtc aacggtcttt ttttaatgac ttaggcagcc gatcgttcgg ccatacgata 3720
tcgaagcgac ctcgaaccag cagagctcgt cacaaaacat ttgcatttaa agaaaaatac 3780
aggatgtttt caccaatatt tttctcaatg atgatacact attgacaagc tgctactttg 3840
ggagggtgtt tccatagatg ccgatgaagc aaaaacacca aatgtgtcat gagagctctc 3900
tctaatcgat ataaaagtag ggtgaaccgg ggttgtcaat ctgtaaaaga tctttttta 3960 tcccgtgata cgcttttgga attctgaatc ttcaagaaag tccccagcct tttgctgatc 4020
aatcgagaac aaaggatgat acatatgaaa agaatagata aaatctacca tcagctgctg 4080
gataattttc gcgaaaagaa tatcaatcag cttttaaaga tacaagggaa ttcggctaaa 4140
gaaatcgccg ggcagctgca aatggagcgt tccaatgtca gctttgaatt aaacaatctc 4200
gttcgggcca aaaaggtgat caagattaaa acgttccccg tccgctacat cccggtggaa 4260

<210> SEQ ID NO 112
<211> LENGTH: 1990
<212> TYPE: DNA
<213> ORGANISM: Artificial Sequence
<220> FEATURE:
<223> OTHER INFORMATION: synthetic

<400> SEQUENCE: 112
tcgttctgaa tgagcaagca aatcgaccgc tttctcaatc cttttctgca ggatgtattc 60
tgccggcgag acgcctttga ttcgtttaaa tgtccgctgc aggtgaaaag ggctgatatg 120
gcacctgtca gccaaagctt gcagagacag cggatcgcga taagattcct cgatgatttc 180
caccacacgc tgtgccagct cttcatccgg cagcagcgcc ccggccggat tgcagcgttt 240
gcaggggcgg tacccttctg ataaagcatc ttttgcattg aaaaagatct gcacattgtc 300
gatttgcgga actctcgatt tgcaggaagg gcggcaaaat atgccggtcg ttttgaccgc 360
gtaataaaaa actccgtcat aggcggaatc gttttccgta atcgcccgcc acatttcagg 420
cgtcaatcgt gatttgctgt tcatatcttc accccgatct atgtcagtat aacctatatg 480
acagccggag gtggagaggc ggagaacggc acagcaagaa gacaaagaag aagagagact 540
gttgcctgga cctccgaaac gcgctacaat tcatttacaa cacaggatgg ggtgagaata 600
ttgccggaat cagtgaagca ggtgacagag gaaaggccga tatgattcgg cctttttat 660 atgtacttct tagcgggtct ctaaaataac caaaaagcaa ggactgctga aagggctgac 720
ataagccttt tgccggcggt ccttttttaa ttctgatttt tcaaacttag ccccctcgag 780
aaaaccgctt gagtatcctc cgctcatgtt attgacctcc ttttcttgat caatatattt 840
gtatgagcgg aaagaaaatt tgactagacg gatgcccctc tgttgaaaat ctttttacag 900
catgtcagaa tatgatatga tacaattcaa aggaaagttt aaactgttat gattaggagt 960
gtttgcattt atgaagaaga ttgcaattgc ggcgattaca gcgacaagcg tgctggctct 1020
cagcgcatgc agcgggggag attctgaggt tgttgcggaa acaaaagctg gaaatattac 1080
aaaagaagac ctttatcaaa cattaaaaga caatgccgga gcggacgcac tgaacatgct 1140
tgttcagcaa aaagtactcg atgataaata cgatgtctcc gacaaagaaa tcgacaaaaa 1200
gctgaacgag tacaaaaaat caatgggtga ccagctcaac cagctcattg accaaaaagg 1260
cgaagacttc gtcaaagaac agatcaaata cgaacttctg atgcaaaaag ccgcaaagga 1320
taacataaaa gtaaccgatg atgacgtaaa agaatattat gacggcctga aaggcaaaat 1380
ccacttaagc cacattcttg tgaaagaaaa gaaaacggct gaagaagttg agaaaaagct 1440
gaaaaaaggc gaaaaattcg aagaccttgc aaaagagtat tcaactgacg gtacagccga 1500
aaaaggcggc gacctcggct gggtcggcaa agacgataac atggacaagg atttcgtcaa 1560
agcggcattt gctttgaaaa ccggcgaaat cagcggacct gtgaaatccc aattcggcta 1620
tcacatcatt aaaaaagacg aagaacgcgg caaatatgaa gacatgaaaa aagagcttaa 1680
aaaagaagtc caagaacaaa agcaaaatga tcaaactgaa ctgcaatccg tcattgacaa 1740
acttgtcaaa gatgctgatt taaaagtaaa agacaaagag ttgaaaaaac aagtcgacca 1800
gcgtcaagct cagacaagca gcagcagctg aaagagcaga gaggacggat ttcctgaagg 1860
aaatccgttt ttttattttt aacatctctc actgctgtgt gattttactc acggcatttg 1920
gaacgccggc tctcaacaaa ctttctgtag tgaaaatcat gaaccaaacg gatcgtcggc 1980
ctgattaaca 1990

<210> SEQ ID NO 113
<211> LENGTH: 20
<212> TYPE: DNA
<213> ORGANISM: Artificial Sequence
<220> FEATURE:
<223> OTHER INFORMATION: synthetic

<400> SEQUENCE: 113
gggtacctcc atggtaaagt 20

<210> SEQ ID NO 114
<211> LENGTH: 20
<212> TYPE: DNA
<213> ORGANISM: Artificial Sequence
<220> FEATURE:
<223> OTHER INFORMATION: synthetic

<400> SEQUENCE: 114
acgtattaat gcagtagccg 20

<210> SEQ ID NO 115
<211> LENGTH: 2067
<212> TYPE: DNA
<213> ORGANISM: Artificial Sequence
<220> FEATURE:
<223> OTHER INFORMATION: synthetic

<400> SEQUENCE: 115
gggtacctcc atggtaaagt ttcgacttaa agcggagatc aaaaaatagc ctggtttacc 60
attttccaca tttttaaatt tatacccctt tcaaaagtca taaaactatc atattctgta 120
ataccacttt tcggaggtga gaatatgtca tactctaata gcttcgcttt gattgttgta 180
ttatttattt tgctgatcat tgtgggctcc gcttttgtaa agtattaatt cattcgcgca 240
cgaagccttc ttccgaaaaa ctgcaggttc atatcgaaag gcgctccgct tttcatatga 300
gcctgttttt ttgtaattta aaaagaattt atttccacaa taacaaaaaa tgtttataat 360
aggataggct ctgagctgac ggctgacggc gctcggaaat aaaaactctc ccacaaatga 420
aacttttata caacattttc gtcttatact gttgttaagg caattcaata acggaaagga 480
aaagatcaat gttaaataag ctaagaatgt tgtatgaaaa aacaacaatg aagtggctgc 540
tcaacacttc ctattacttt ctcattctgg tgctgctgtt tttaatttac ggattccata 600
cagcaaatac aggttcatat atttataatg acttttaatg gagaagaaaa caatgaaact 660
gattgaaaca attaaaaaat accacaaatg tgcttgatgg atccgtctta ttcggaagag 720
ctgcttccgg agctgagctt gtttatgttc tgcggagaaa cgcttcctgc gtcagtcgcc 780
agacagctta aagaaagatt tccaaaggct cgtgttttta acacatacgg cccgaccgaa 840
gcgaccgttg ccgtcacttc catcgaagta acagacgacg tattaaacaa gtattcttct 900
cttcccgtcg gttctgaaaa gcccgaaacc gaaatcgtaa tcatcaatga agacggaaaa 960
gccgtccaag acggggaaaa aggcgagatc ataattaccg gagcaagcgt cagcaaaggc 1020
tatttaggcg aaaaagcgct gacggaaaaa gcgtttttct cttacaacgg ctcccctgct 1080
taccgcaccg gtgacgcagg ttacaaagaa aacggccagc tcttcttcct cggaagactc 1140
gatttccaaa tcaaactgca cggctaccgg attgagcttg aagaaatcga atatcaaatc 1200
aatcagtccc gatatgtgca gtcggcagtc gttattccat tctaccgcga ggagaaaatc 1260
gagtatctga tcgccatgat tgtgcctgcc gaacacgatt tcgaaaagga ataccagtta 1320
accagcgcga ttaagaaaga tttgggcagc aagctgccgg cctatatgat tccgagaaaa 1380
ttcatgtatc aaaaagagat tccgatgaca gcaaacggta aaatcgaccg caagagatta 1440
aaagaagagg taaccgtatg acgccttatg gttcatttct tttcttcatt atattaggaa 1500
ttttactggc gccgaccatc attctcggat tgaacggaaa aagcttccgc ttatataata 1560
tggcggtttc cgttctggtt ctggcgctta ttttttcgaa cagcctgcac gggctgatca 1620
tgctgtgcct gtttacgctt tggcagacgg ttctgatcaa aggctatatc gcttaccgtc 1680
taaaagcgaa cagcggcatc gtattttgtc tggctgcagc agcttctatc ctgcctctgg 1740
cactgtcaaa gctgctgccg tttttcgccg ttgacaactg ggcaacattt ctcggaatct 1800
cgtatttaac ttttaaaggg gttcagctca tcattgaaac ccgcgacggt ctcattaaaa 1860
agcagctccc aatcagcaga ctgctttact ttattctctt ttttccaacc atctcgtcag 1920
gtccgatcga caggtaccgc cgttttgaaa aagacgatca gacggtttgg acaaaggagc 1980
aatacgaaga actgctttac aaaggaatca ataaaatttt tctcggcttt ttgtacaaat 2040
tcattatcgg ctactgcatt aatacgt 2067

<210> SEQ ID NO 116
<211> LENGTH: 2767
<212> TYPE: DNA
<213> ORGANISM: Bacillus licheniformis

<400> SEQUENCE: 116
gggtacctcc atggtaaagt ttcgacttaa agcggagatc aaaaaatagc ctggtttacc 60
attttccaca tttttaaatt tatacccctt tcaaaagtca taaaactatc atattctgta 120
ataccacttt tcggaggtga gaatatgtca tactctaata gcttcgcttt gattgttgta 180
ttatttattt tgctgatcat tgtgggctcc gcttttgtaa agtattaatt cattcgcgca 240
cgaagccttc ttccgaaaaa ctgcaggttc atatcgaaag gcgctccgct tttcatatga 300
gcctgttttt ttgtaattta aaaagaattt atttccacaa taacaaaaaa tgtttataat 360
aggataggct ctgagctgac ggctgacggc gctcggaaat aaaaactctc ccacaaatga 420
aacttttata caacattttc gtcttatact gttgttaagg caattcaata acggaaagga 480
aaagatcaat gttaaataag ctaagaatgt tgtatgaaaa aacaacaatg aagtggctgc 540
tcaacacttc ctattacttt ctcattctgg tgctgctgtt tttaatttac ggattccata 600
cagcaaatac aggttcatat atttataatg acttttaatg gagaagaaaa caatgaaact 660
gattgaaaca attaaaaaat acgcgcaaac acaacccgat acccttgctt ttgtgaatga 720
agaagaaaag ctgacatacg gagagctttg gtcacaatct gagcgccttg ccgcaaggat 780
tcaaagcgaa gctttaacag atgcttctcc gatcattgtc tacggacata tgaaaccggt 840
tatggcggtt tccttcctgg cttgtgtaaa agccgggcat ccgtacattc cagttgacgt 900
atcgattccg gcagaccgga ttctgaaaat catcaacagt tcaaaagccg agcttctgct 960
caataattca ggcacttcgg ttgacacggg agatgccctc atttccgtag tggaaccggg 1020
cgttcttgaa ggagacggga tgccggagac agatcccgga cgctgggtac atggggaaga 1080
tactttttac attatctaca catccggaag cacgggaaat ccaaaaggcg tgcaaatctc 1140
agccgataac cttcagagct tcacagattg gatcacgaat gactttccgg tggaaagcgg 1200
ccaagtgttc ttaaatcaag ccccgttttc ctttgattta tcggtaatgg acctttatcc 1260
gtgcctgcag tccggaggca ccttatggac ggttacgaaa gacatgatta atcggccgaa 1320
actattgttt gaagcactga aacagtccaa cgtcaacgtc tggacatcga cgccttcatt 1380
cgcacaaatg tgcttgatgg atccgtctta ttcggaagag ctgcttccgg agctgagctt 1440
gtttatgttc tgcggagaaa cgcttcctgc gtcagtcgcc agacagctta aagaaagatt 1500
tccaaaggct cgtgttttta acacatacgg cccgaccgaa gcgaccgttg ccgtcacttc 1560
catcgaagta acagacgacg tattaaacaa gtattcttct cttcccgtcg gttctgaaaa 1620
gcccgaaacc gaaatcgtaa tcatcaatga agacggaaaa gccgtccaag acggggaaaa 1680
aggcgagatc ataattaccg gagcaagcgt cagcaaaggc tatttaggcg aaaaagcgct 1740
gacggaaaaa gcgtttttct cttacaacgg ctcccctgct taccgcaccg gtgacgcagg 1800
ttacaaagaa aacggccagc tcttcttcct cggaagactc gatttccaaa tcaaactgca 1860
cggctaccgg attgagcttg aagaaatcga atatcaaatc aatcagtccc gatatgtgca 1920
gtcggcagtc gttattccat tctaccgcga ggagaaaatc gagtatctga tcgccatgat 1980
tgtgcctgcc gaacacgatt tcgaaaagga ataccagtta accagcgcga ttaagaaaga 2040
tttgggcagc aagctgccgg cctatatgat tccgagaaaa ttcatgtatc aaaaagagat 2100
tccgatgaca gcaaacggta aaatcgaccg caagagatta aaagaagagg taaccgtatg 2160
acgccttatg gttcatttct tttcttcatt atattaggaa ttttactggc gccgaccatc 2220
attctcggat tgaacggaaa aagcttccgc ttatataata tggcggtttc cgttctggtt 2280
ctggcgctta ttttttcgaa cagcctgcac gggctgatca tgctgtgcct gtttacgctt 2340
tggcagacgg ttctgatcaa aggctatatc gcttaccgtc taaaagcgaa cagcggcatc 2400
gtattttgtc tggctgcagc agcttctatc ctgcctctgg cactgtcaaa gctgctgccg 2460
tttttcgccg ttgacaactg ggcaacattt ctcggaatct cgtatttaac ttttaaaggg 2520
gttcagctca tcattgaaac ccgcgacggt ctcattaaaa agcagctccc aatcagcaga 2580
ctgctttact ttattctctt ttttccaacc atctcgtcag gtccgatcga caggtaccgc 2640
cgttttgaaa aagacgatca gacggtttgg acaaaggagc aatacgaaga actgctttac 2700
aaaggaatca ataaaatttt tctcggcttt ttgtacaaat tcattatcgg ctactgcatt 2760
aatacgt 2767

<210> SEQ ID NO 117
<211> LENGTH: 21
<212> TYPE: DNA
<213> ORGANISM: Artificial Sequence
<220> FEATURE:
<223> OTHER INFORMATION: synthetic

<400> SEQUENCE: 117
ggatacgccg atttcaatgg c 21

<210> SEQ ID NO 118
<211> LENGTH: 20
<212> TYPE: DNA
<213> ORGANISM: Artificial Sequence
<220> FEATURE:
<223> OTHER INFORMATION: synthetic

<400> SEQUENCE: 118
ggctatgtgc tgggggaatt 20

<210> SEQ ID NO 119
<211> LENGTH: 1523
<212> TYPE: DNA
<213> ORGANISM: Artificial Sequence
<220> FEATURE:
<223> OTHER INFORMATION: synthetic

<400> SEQUENCE: 119
ggatacgccg atttcaatgg caagctgatt taaggagaga ttgtgttcaa tcatgtactg 60
gagaacaaaa tctcttttga tatgaatctt ttttaccatg attactcccc tttctaatct 120
cttatgtttc tttttatcta cattgaacat atacgatttg ttaacttttg tcaatacttt 180
taccatccat atgtttccta taggcaatat tcgtactaaa atattttata ataagagatt 240
gcgaggtttt ggccatgacg aactttggac accatttacg acaattaagg gaacggaaaa 300
aactgaccgt caatcaactg gcgatgtatt ccggcgtcag ttcggcaggc atttcgcgaa 360
tcgaaaacgg aaagcgcggc gtgccgaagc cggcgacgat cagaaaactg gcggacgctt 420
tgaaagtccc gtatgaggaa ctgatggcat ctgcaggcta tatcagcgcg tctacagtcc 480
aggaagcaag aagcagctat gattccattt acgacatcgt gtcacagtac gatttagagg 540

```
acctttctct gtttgacagc gaaaagtgga aggtgctttc aaaaaaagac atcgaaaacc    600

tggacaaata tttcgacttt ctcgtgcagg aagcaagcag ccgaaacaaa aactgaatac    660

ttctccgcgg cacactctcc tctctatcat tttcgtctgt ttacgatcct gctgttattt    720

tatcccttat gttaactttt gtcaatattt ttcctgtcta agtatttcct atagtcaaca    780

tttgtattaa aatgttcata tcatgaattt gcgggggga tggcgatgac aaggcaatca    840

taaaaagccg aatttccctt ttaggagaag ttcggctttt ttcggctgcc ttaagcggca    900

tccggattcg gcgtcttgcc tttatgatgc ttaacggggc tcagcgcacg ctcgagccat    960

cccatgaaca gatcggcgat gatcgccatc agcgccgtcg ggatcgcgcc tgctagaatg   1020

atcgctgttc cgttggtcgc gtttgatccc ctgacaatga tatccccgag gccgcctgcg   1080

ccgacaaacg tgccgatggc cgtaatgccg atcgcgatga cgagcgcggt tctgagcccc   1140

gccataatga ccgacaaggc gaggggaagc tccaccatcc ggagcacttg aaatttcgtc   1200

atgcccatcg ccttccctga ttcaagatag gcatgctcga tgctggcgat tcccgtatat   1260

gtgtttcgaa tgatcggcaa cagcgaatac aaaaacaatg aaagaatcac cgtgtttgcg   1320

ccgagcccca tgacaagcat caagacggcg agcatcgcca gcgccggaac cgtttgaatg   1380

acattagtga tggaaaagac ccatttgctg attttacggt atctggcgat gaaaatgccg   1440

gccgggatgc cgacgacggc ggcgaacaat acgccgtatg ccgacattaa aaagtggcgg   1500

taaaattccc ccagcacata gcc                                           1523
```

<210> SEQ ID NO 120
<211> LENGTH: 1922
<212> TYPE: DNA
<213> ORGANISM: Bacillus licheniformis

<400> SEQUENCE: 120

```
ggatacgccg atttcaatgg caagctgatt taaggagaga ttgtgttcaa tcatgtactg     60

gagaacaaaa tctcttttga tatgaatctt ttttaccatg attactcccc tttctaatct    120

cttatgtttc tttttatcta cattgaacat atacgatttg ttaacttttg tcaatacttt    180

taccatccat atgtttccta taggcaatat tcgtactaaa atattttata ataagagatt    240

gcgaggtttt ggccatgacg aactttggac accatttacg acaattaagg gaacggaaaa    300

aactgaccgt caatcaactg gcgatgtatt ccggcgtcag ttcggcaggc atttcgcgaa    360

tcgaaaacgg aaagcgcggc gtgccgaagc cggcgacgat cagaaaactg gcggacgctt    420

tgaaagtccc gtatgaggaa ctgatggcat ctgcaggcta tatcagcgcg tctacagtcc    480

aggaagcaag aagcagctat gattccattt acgacatcgt gtcacagtac gatttagagg    540

acctttctct gtttgacagc gaaaagtgga aggtgctttc aaaaaaagac atcgaaaacc    600

tggacaaata tttcgacttt ctcgtgcagg aagcaagcag ccgaaacaaa aactgaatac    660

ttctccgcgg cacactctcc tctctatcat tttcgtctgt ttacgatcct gctgttattt    720

tatcccttat gttaactttt gtcaatattt ttcctgtcta agtatttcct atagtcaaca    780

tttgtattaa aatgttcata tcatgaattt gcgggggga tggcgatgac aaggttcggc    840

gagcggctca aagagctgag ggaacaaaga agcctgtcgg ttaatcagct tgccatgtat    900

gccggtgtga gcgccgcagc catttccaga gccgcagcca tttccagaat cgaaaacggc    960

caccgcggcg ttcccaagcc cgcgacgatc agaaaattgg ccgaggctct gaaaatgccg   1020

tacgagcagc tcatggatat tgccggttat atgagagctg acgagattcg cgaacagccg   1080

cgcggctatg tcacgatgca ggagatcgcg gccaagcacg gcgtcgaaga cctgtggctg   1140
```

tttaaacccg agaaatggga ctgtttgtcc cgcgaagacc tgctcaacct cgaacagtat 1200
tttcattttt tggttaatga agcgaagaag cgccaatcat aaaaagccga atttcccttt 1260
taggagaagt tcggcttttt tcggctgcct taagcggcat ccggattcgg cgtcttgcct 1320
ttatgatgct taacggggct cagcgcacgc tcgagccatc ccatgaacag atcggcgatg 1380
atcgccatca gcgccgtcgg gatcgcgcct gctagaatga tcgctgttcc gttggtcgcg 1440
tttgatcccc tgacaatgat atccccgagg ccgcctgcgc cgacaaacgt gccgatggcc 1500
gtaatgccga tcgcgatgac gagcgcggtt ctgagccccg ccataatgac cgacaaggcg 1560
aggggaagct ccaccatccg gagcacttga aatttcgtca tgcccatcgc cttccctgat 1620
tcaagatagg catgctcgat gctggcgatt cccgtatatg tgtttcgaat gatcggcaac 1680
agcgaataca aaaacaatga aagaatcacc gtgtttgcgc cgagccccat gacaagcatc 1740
aagacggcga gcatcgccag cgccggaacc gtttgaatga cattagtgat ggaaaagacc 1800
catttgctga ttttacggta tctggcgatg aaaatgccgg ccgggatgcc gacgacggcg 1860
gcgaacaata cgccgtatgc cgacattaaa aagtggcggt aaaattcccc cagcacatag 1920
cc 1922

<210> SEQ ID NO 121
<211> LENGTH: 1413
<212> TYPE: DNA
<213> ORGANISM: Bacillus licheniformis

<400> SEQUENCE: 121
cgtcagttcg gcaggcattt cgcgaatcga aaacggaaag cgcggcgtgc cgaagccggc 60
gacgatcaga aaactggcgg acgctttgaa agtcccgtat gaggaactga tggcatctgc 120
aggctatatc agcgcgtcta cagtccagga agcaagaagc agctatgatt ccatttacga 180
catcgtgtca cagtacgatt tagaggacct ttctctgttt gacagcgaaa agtggaaggt 240
gctttcaaaa aaagacatcg aaaacctgga caaatatttc gactttctcg tgcaggaagc 300
aagcagccga aacaaaaact gaatacttct ccgcggcaca ctctcctctc tatcattttc 360
gtctgtttac gatcctgctg ttattttatc ccttatgtta acttttgtca atatttttcc 420
tgtctaagta tttcctatag tcaacatttg tattaaaatg ttcatatcat gaatttgcgg 480
gggggatggc gatgacaagg ttcggcgagc ggctcaaaga gctgagggaa caaagaagcc 540
tgtcggttaa tcagcttgcc atgtatgccg gtgtgagcgc cgcagccatt tccagagccg 600
cagccatttc cagaatcgaa aacggccacc gcggcgttcc caagcccgcg acgatcagaa 660
aattggccga ggctctgaaa atgccgtacg agcagctcat ggatattgcc ggttatatga 720
gagctgacga gattcgcgaa cagccgcgcg gctatgtcac gatgcaggag atcgcggcca 780
agcacggcgt cgaagacctg tggctgttta aacccgagaa atgggactgt ttgtcccgcg 840
aagacctgct caacctcgaa cagtattttc atttttggt taatgaagcg aagaagcgcc 900
aatcataaaa agccgaattt cccttttagg agaagttcgg ctttttcgg ctgccttaag 960 cggcatccgg attcggcgtc ttgcctttat gatgcttaac ggggctcagc gcacgctcga 1020
gccatcccat gaacagatcg gcgatgatcg ccatcagcgc cgtcgggatc gcgcctgcta 1080
gaatgatcgc tgttccgttg gtcgcgtttg atcccctgac aatgatatcc ccgaggccgc 1140
ctgcgccgac aaacgtgccg atggccgtaa tgccgatcgc gatgacgagc gcggttctga 1200
gccccgccat aatgaccgac aaggcgaggg gaagctccac catccggagc acttgaaatt 1260

```
tcgtcatgcc catcgccttc cctgattcaa gataggcatg ctcgatgctg gcgattcccg   1320

tatatgtgtt tcgaatgatc ggcaacagcg aatacaaaaa caatgaaaga atcaccgtgt   1380

ttgcgccgag ccccatgaca agcatcaaga cgg                                1413


<210> SEQ ID NO 122
<211> LENGTH: 2009
<212> TYPE: DNA
<213> ORGANISM: Bacillus licheniformis

<400> SEQUENCE: 122

ctctaatagc ttcgctttga ttgttgtatt atttattttg ctgatcattg tgggctccgc     60

ttttgtaaag tattaattca ttcgcgcacg aagccttctt ccgaaaaact gcaggttcat    120

atcgaaaggc gctccgcttt tcatatgagc ctgttttttt gtaatttaaa aagaatttat    180

ttccacaata acaaaaaatg tttataatag gataggctct gagctgacgg ctgacggcgc    240

tcggaaataa aaactctccc acaaatgaaa cttttataca acattttcgt cttatactgt    300

tgttaaggca attcaataac ggaaaggaaa agatcaatgt taaataagct aagaatgttg    360

tatgaaaaaa caacaatgaa gtggctgctc aacacttcct attactttct cattctggtg    420

ctgctgtttt taatttacgg attccataca gcaaatacag gttcatatat ttataatgac    480

ttttaatgga gaagaaaaca atgaaactga ttgaaacaat taaaaaatac gcgcaaacac    540

aacccgatac ccttgctttt gtgaatgaag aagaaaagct gacatacgga gagctttggt    600

cacaatctga gcgccttgcc gcaaggattc aaagcgaagc tttaacagat gcttctccga    660

tcattgtcta cggacatatg aaaccggtta tggcggtttc cttcctggct tgtgtaaaag    720

ccgggcatcc gtacattcca gttgacgtat cgattccggc agaccggatt ctgaaaatca    780

tcaacagttc aaaagccgag cttctgctca ataattcagg cacttcggtt gacacgggag    840

atgccctcat ttccgtagtg gaaccgggcg ttcttgaagg agacgggatg ccggagacag    900

atcccggacg ctgggtacat ggggaagata ctttttacat tatctacaca tccggaagca    960

cgggaaatcc aaaaggcgtg caaatctcag ccgataacct tcagagcttc acagattgga   1020

tcacgaatga ctttccggtg gaaagcggcc aagtgttctt aaatcaagcc ccgttttcct   1080

ttgatttatc ggtaatggac ctttatccgt gcctgcagtc cggaggcacc ttatggacgg   1140

ttacgaaaga catgattaat cggccgaaac tattgtttga agcactgaaa cagtccaacg   1200

tcaacgtctg gacatcgacg ccttcattcg cacaaatgtg cttgatggat ccgtcttatt   1260

cggaagagct gcttccggag ctgagcttgt ttatgttctg cggagaaacg cttcctgcgt   1320

cagtcgccag acagcttaaa gaaagatttc caaaggctcg tgtttttaac acatacggcc   1380

cgaccgaagc gaccgttgcc gtcacttcca tcgaagtaac agacgacgta ttaaacaagt   1440

attcttctct tcccgtcggt tctgaaaagc ccgaaaccga aatcgtaatc atcaatgaag   1500

acggaaaagc cgtccaagac ggggaaaaag gcgagatcat aattaccgga gcaagcgtca   1560

gcaaaggcta tttaggcgaa aaagcgctga cggaaaaagc gtttttctct tacaacggct   1620

cccctgctta ccgcaccggt gacgcaggtt acaaagaaaa cggccagctc ttcttcctcg   1680

gaagactcga tttccaaatc aaactgcacg gctaccggat tgagcttgaa gaaatcgaat   1740

atcaaatcaa tcagtcccga tatgtgcagt cggcagtcgt tattccattc taccgcgagg   1800

agaaaatcga gtatctgatc gccatgattg tgcctgccga acacgatttc gaaaaggaat   1860

accagttaac cagcgcgatt aagaaagatt tgggcagcaa gctgccggcc tatatgattc   1920

cgagaaaatt catgtatcaa aaagagattc cgatgacagc aaacggtaaa atcgaccgca   1980
```

agagattaaa agaagaggta accgtatga 2009

<210> SEQ ID NO 123
<211> LENGTH: 1557
<212> TYPE: DNA
<213> ORGANISM: Bacillus licheniformis

<400> SEQUENCE: 123
ttaattgaat tgtgcggtta caccgccgga ctccatcatc atcagttctt ttttcatatc 60
caatccgccc cggtatcccg tgagctgccc gcttttaccg ataacccgat ggcaaggcac 120
caccattaac agcggatttg cgccgatcgc cgcgcctact gcccgcacag cggcctgctt 180
ttcaatatgc tcggcgatat cggaatagga gcaagtgctg ccgtaaggga tttcggagag 240
cgccttccac actgccagct gaaaaggcgt gccggcaagg tcgacaggaa agctgaaatg 300
agttcgcttg ccgttcaaat acgcctgcag ctgctcggcg tattctgcca atcctttgtc 360
atcccgaatg aaaactggct gtgtaaatct tttttcagcc caagcggcca aatcctcgaa 420
gccttgattc catccccctg taaaacagag cccgcgggca gtcgccccaa tgtgaatctg 480
ccaacctcgg caaataagcg tacgccagta tacgatttga tcgtccatat gtttacctcc 540
gtttcatttg ccggtacgac gtcggcgatt gcccagtctt ctttttaaac aaagaggcaa 600
aatattccgc attcgcaatg cctaccattg aagcgatttc tgcgatcgat cgttctgaat 660
gagcaagcaa atcgaccgct ttctcaatcc ttttctgcag gatgtattct gccggcgaga 720
cgcctttgat tcgtttaaat gtccgctgca ggtgaaaagg gctgatatgg cacctgtcag 780
ccaaagcttg cagagacagc ggatcgcgat aagattcctc gatgatttcc accacacgct 840
gtgccagctc ttcatccggc agcagcgccc cggccggatt gcagcgtttg caggggcggt 900
acccttctga taaagcatct tttgcattga aaaagatctg cacattgtcg atttgcggaa 960
ctctcgattt gcaggaaggg cggcaaaata tgccggtcgt tttgaccgcg taataaaaaa 1020
ctccgtcata ggcggaatcg ttttccgtaa tcgcccgcca catttcaggc gtcaatcgtg 1080
atttgctgtt catatcttca ccccgatcta tgtcagtata acctatatga cagccggagg 1140
tggagaggcg gagaacggca cagcaagaag acaaagaaga agagagactg ttgcctggac 1200
ctccgaaacg cgctacaatt catttacaac acaggatggg gtgagaatat tgccggaatc 1260
agtgaagcag gtaacatctc tcactgctgt gtgattttac tcacggcatt tggaacgccg 1320
gctctcaaca aactttctgt agtgaaaatc atgaaccaaa cggatcgtcg gcctgattaa 1380
cagctgaaag ctgccgatca caaacatcca tagtcccgcc ggcttcagtt cctcggagaa 1440
aaagcagaag ctcccgacaa ggaataaaag gccgatgaga aaatcgttta atgtatgtag 1500
aactttgtat cttttttga aaaagagttc atatcgattg ttattgtttt gcggcat 1557

<210> SEQ ID NO 124
<211> LENGTH: 2814
<212> TYPE: DNA
<213> ORGANISM: Artificial Sequence
<220> FEATURE:
<223> OTHER INFORMATION: synthetic

<400> SEQUENCE: 124
ttaattgaat tgtgcggtta caccgccgga ctccatcatc atcagttctt ttttcatatc 60
caatccgccc cggtatcccg tgagctgccc gcttttaccg ataacccgat ggcaaggcac 120
caccattaac agcggatttg cgccgatcgc cgcgcctact gcccgcacag cggcctgctt 180

-continued

```
ttcaatatgc tcggcgatat cggaatagga gcaagtgctg ccgtaaggga tttcggagag    240
cgccttccac actgccagct gaaaaggcgt gccggcaagg tcgacaggaa agctgaaatg    300
agttcgcttg ccgttcaaat acgcctgcag ctgctcggcg tattctgcca atcctttgtc    360
atcccgaatg aaaactggct gtgtaaatct tttttcagcc caagcggcca aatcctcgaa    420
gccttgattc catccccctg taaaacagag cccgcgggca gtcgccccaa tgtgaatctg    480
ccaacctcgg caaataagcg tacgccagta tacgatttga tcgtccatat gtttacctcc    540
gtttcatttg ccggtacgac gtcggcgatt gcccagtctt ctttttaaac aaagaggcaa    600
aatattccgc attcgcaatg cctaccattg aagcgatttc tgcgatcgat cgttctgaat    660
gagcaagcaa atcgaccgct ttctcaatcc ttttctgcag gatgtattct gccggcgaga    720
cgcctttgat tcgtttaaat gtccgctgca ggtgaaaagg gctgatatgg cacctgtcag    780
ccaaagcttg cagagacagc ggatcgcgat aagattcctc gatgatttcc accacacgct    840
gtgccagctc ttcatccggc agcagcgccc cggccggatt gcagcgtttg caggggcggt    900
acccttctga taaagcatct tttgcattga aaaagatctg cacattgtcg atttgcggaa    960
ctctcgattt gcaggaaggg cggcaaaata tgccggtcgt tttgaccgcg taataaaaaa   1020
ctccgtcata ggcggaatcg ttttccgtaa tcgcccgcca catttcaggc gtcaatcgtg   1080
atttgctgtt catatcttca ccccgatcta tgtcagtata acctatatga cagccggagg   1140
tggagaggcg gagaacggca cagcaagaag acaaagaaga agagagactg ttgcctggac   1200
ctccgaaacg cgctacaatt catttacaac acaggatggg gtgagaatat tgccggaatc   1260
agtgaagcag gtgacagagg aaaggccgat atgattcggc ctttttttata tgtacttctt   1320
agcgggtctc taaaataacc aaaaagcaag gactgctgaa agggctgaca taagcctttt   1380
gccggcggtc cttttttaat tctgattttt caaacttagc cccctcgaga aaaccgcttg   1440
agtatcctcc gctcatgtta ttgacctcct tttcttgatc aatatatttg tatgagcgga   1500
aagaaaattt gactagacgg atgcccctct gttgaaaatc tttttacagc atgtcagaat   1560
atgatatgat acaattcaaa ggaaagttta aactgttatg attaggagtg tttgcattta   1620
tgaagaagat tgcaattgcg gcgattacag cgacaagcgt gctggctctc agcgcatgca   1680
gcgggggaga ttctgaggtt gttgcggaaa caaaagctgg aaatattaca aaagaagacc   1740
tttatcaaac attaaaagac aatgccggag cggacgcact gaacatgctt gttcagcaaa   1800
aagtactcga tgataaatac gatgtctccg acaaagaaat cgacaaaaag ctgaacgagt   1860
acaaaaaatc aatgggtgac cagctcaacc agctcattga ccaaaaaggc gaagacttcg   1920
tcaaagaaca gatcaaatac gaacttctga tgcaaaaagc cgcaaaggat aacataaaag   1980
taaccgatga tgacgtaaaa gaatattatg acggcctgaa aggcaaaatc cacttaagcc   2040
acattcttgt gaaagaaaag aaaacggctg aagaagttga gaaaaagctg aaaaaaggcg   2100
aaaaattcga agaccttgca aaagagtatt caactgacgg tacagccgaa aaaggcggcg   2160
acctcggctg ggtcggcaaa gacgataaca tggacaagga tttcgtcaaa gcggcatttg   2220
ctttgaaaac cggcgaaatc agcggacctg tgaaatccca attcggctat cacatcatta   2280
aaaaagacga agaacgcggc aaatatgaag acatgaaaaa agagcttaaa aaagaagtcc   2340
aagaacaaaa gcaaaatgat caaactgaac tgcaatccgt cattgacaaa cttgtcaaag   2400
atgctgattt aaaagtaaaa gacaaagagt tgaaaaaaca agtcgaccag cgtcaagctc   2460
agacaagcag cagcagctga aagagcagag aggacggatt tcctgaagga aatccgtttt   2520
tttattttta acatctctca ctgctgtgtg attttactca cggcatttgg aacgccggct   2580
```

ctcaacaaac tttctgtagt gaaaatcatg aaccaaacgg atcgtcggcc tgattaacag 2640
ctgaaagctg ccgatcacaa acatccatag tcccgccggc ttcagttcct cggagaaaaa 2700
gcagaagctc ccgacaagga ataaaaggcc gatgagaaaa tcgtttaatg tatgtagaac 2760
tttgtatctt tttttgaaaa agagttcata tcgattgtta ttgttttgcg gcat 2814

<210> SEQ ID NO 125
<211> LENGTH: 1309
<212> TYPE: DNA
<213> ORGANISM: Artificial Sequence
<220> FEATURE:
<223> OTHER INFORMATION: synthetic

<400> SEQUENCE: 125
ctctaatagc ttcgctttga ttgttgtatt atttattttg ctgatcattg tgggctccgc 60
ttttgtaaag tattaattca ttcgcgcacg aagccttctt ccgaaaaact gcaggttcat 120
atcgaaaggc gctccgcttt tcatatgagc ctgttttttt gtaatttaaa aagaatttat 180
ttccacaata acaaaaaatg tttataatag gataggctct gagctgacgg ctgacggcgc 240
tcggaaataa aaactctccc acaaatgaaa cttttataca acattttcgt cttatactgt 300
tgttaaggca attcaataac ggaaaggaaa agatcaatgt taaataagct aagaatgttg 360
tatgaaaaaa caacaatgaa gtggctgctc aacacttcct attactttct cattctggtg 420
ctgctgtttt taatttacgg attccataca gcaaatacag gttcatatat ttataatgac 480
ttttaatgga gaagaaaaca atgaaactga ttgaaacaat taaaaaatac cacaaatgtg 540
cttgatggat ccgtcttatt cggaagagct gcttccggag ctgagcttgt ttatgttctg 600
cggagaaacg cttcctgcgt cagtcgccag acagcttaaa gaaagatttc caaaggctcg 660
tgtttttaac acatacggcc cgaccgaagc gaccgttgcc gtcacttcca tcgaagtaac 720
agacgacgta ttaaacaagt attcttctct tcccgtcggt tctgaaaagc ccgaaaccga 780
aatcgtaatc atcaatgaag acggaaaagc cgtccaagac ggggaaaaag gcgagatcat 840
aattaccgga gcaagcgtca gcaaaggcta tttaggcgaa aaagcgctga cggaaaaagc 900
gtttttctct tacaacggct cccctgctta ccgcaccggt gacgcaggtt acaaagaaaa 960
cggccagctc ttcttcctcg gaagactcga tttccaaatc aaactgcacg gctaccggat 1020
tgagcttgaa gaaatcgaat atcaaatcaa tcagtcccga tatgtgcagt cggcagtcgt 1080
tattccattc taccgcgagg agaaaatcga gtatctgatc gccatgattg tgcctgccga 1140
acacgatttc gaaaaggaat accagttaac cagcgcgatt aagaaagatt tgggcagcaa 1200
gctgccggcc tatatgattc cgagaaaatt catgtatcaa aaagagattc cgatgacagc 1260
aaacggtaaa atcgaccgca agagattaaa agaagaggta accgtatga 1309

<210> SEQ ID NO 126
<211> LENGTH: 483
<212> TYPE: PRT
<213> ORGANISM: Bacillus licheniformis

<400> SEQUENCE: 126

Ala Asn Leu Asn Gly Thr Leu Met Gln Tyr Phe Glu Trp Tyr Met Pro
1 5 10 15

Asn Asp Gly Gln His Trp Lys Arg Leu Gln Asn Asp Ser Ala Tyr Leu
20 25 30

Ala Glu His Gly Ile Thr Ala Val Trp Ile Pro Pro Ala Tyr Lys Gly
35 40 45

```
Thr Ser Gln Ala Asp Val Gly Tyr Gly Ala Tyr Asp Leu Tyr Asp Leu
    50                  55                  60

Gly Glu Phe His Gln Lys Gly Thr Val Arg Thr Lys Tyr Gly Thr Lys
65                  70                  75                  80

Gly Glu Leu Gln Ser Ala Ile Lys Ser Leu His Ser Arg Asp Ile Asn
                85                  90                  95

Val Tyr Gly Asp Val Val Ile Asn His Lys Gly Gly Ala Asp Ala Thr
            100                 105                 110

Glu Asp Val Thr Ala Val Glu Val Asp Pro Ala Asp Arg Asn Arg Val
        115                 120                 125

Ile Ser Gly Glu His Leu Ile Lys Ala Trp Thr His Phe His Phe Pro
    130                 135                 140

Gly Arg Gly Ser Thr Tyr Ser Asp Phe Lys Trp His Trp Tyr His Phe
145                 150                 155                 160

Asp Gly Thr Asp Trp Asp Glu Ser Arg Lys Leu Asn Arg Ile Tyr Lys
                165                 170                 175

Phe Gln Gly Lys Ala Trp Asp Trp Glu Val Ser Asn Glu Asn Gly Asn
            180                 185                 190

Tyr Asp Tyr Leu Met Tyr Ala Asp Ile Asp Tyr Asp His Pro Asp Val
        195                 200                 205

Ala Ala Glu Ile Lys Arg Trp Gly Thr Trp Tyr Ala Asn Glu Leu Gln
    210                 215                 220

Leu Asp Gly Phe Arg Leu Asp Ala Val Lys His Ile Lys Phe Ser Phe
225                 230                 235                 240

Leu Arg Asp Trp Val Asn His Val Arg Glu Lys Thr Gly Lys Glu Met
                245                 250                 255

Phe Thr Val Ala Glu Tyr Trp Gln Asn Asp Leu Gly Ala Leu Glu Asn
            260                 265                 270

Tyr Leu Asn Lys Thr Asn Phe Asn His Ser Val Phe Asp Val Pro Leu
        275                 280                 285

His Tyr Gln Phe His Ala Ala Ser Thr Gln Gly Gly Gly Tyr Asp Met
    290                 295                 300

Arg Lys Leu Leu Asn Gly Thr Val Val Ser Lys His Pro Leu Lys Ser
305                 310                 315                 320

Val Thr Phe Val Asp Asn His Asp Thr Gln Pro Gly Gln Ser Leu Glu
                325                 330                 335

Ser Thr Val Gln Thr Trp Phe Lys Pro Leu Ala Tyr Ala Phe Ile Leu
            340                 345                 350

Thr Arg Glu Ser Gly Tyr Pro Gln Val Phe Tyr Gly Asp Met Tyr Gly
        355                 360                 365

Thr Lys Gly Asp Ser Gln Arg Glu Ile Pro Ala Leu Lys His Lys Ile
    370                 375                 380

Glu Pro Ile Leu Lys Ala Arg Lys Gln Tyr Ala Tyr Gly Ala Gln His
385                 390                 395                 400

Asp Tyr Phe Asp His His Asp Ile Val Gly Trp Thr Arg Glu Gly Asp
                405                 410                 415

Ser Ser Val Ala Asn Ser Gly Leu Ala Ala Leu Ile Thr Asp Gly Pro
            420                 425                 430

Gly Gly Ala Lys Arg Met Tyr Val Gly Arg Gln Asn Ala Gly Glu Thr
        435                 440                 445

Trp His Asp Ile Thr Gly Asn Arg Ser Glu Pro Val Val Ile Asn Ser
    450                 455                 460
```

```
Glu Gly Trp Gly Glu Phe His Val Asn Gly Gly Ser Val Ser Ile Tyr
465                 470                 475                 480

Val Gln Arg


<210> SEQ ID NO 127
<211> LENGTH: 9514
<212> TYPE: DNA
<213> ORGANISM: Artificial Sequence
<220> FEATURE:
<223> OTHER INFORMATION: synthetic

<400> SEQUENCE: 127

ctgggagctg atagcacagc gatttcccgc ctcctgtcgg aagcatcgcc accgtgtccc     60

gtccctccag cacgcttttg atgatcgttt cctggccttt tttaaaagca tgataaccaa    120

aatacctgcg gagcgcctga tgaagtttat ccattcctga tcaccgtttt cgacagggcc    180

aggcggattt taaaataact gtatcggccg ccgagtccct ctttaatttg tctgatttta    240

ttggtttggt tcgctatcgc ataatcggca ataattttct gttcctcttt cgacacgtac    300

tgatcgatgg aaaaagacgg atcatgaatg gcgatttcca caatgtgatc ctcgatcgtc    360

gccaatttca gctttctaat ttttgcgatc cggtctattg tataccettc ttttataaga    420

aagagcgttt ttctcgtcga ttgtgtcaga ccatcattca aaggaatgtc atgaatgagc    480

gtttgaaaaa gcggactttc accattttgg gcggattgaa taaaatggtg cagaacatcc    540

caaaacagtg catatatgta ccactcatca aggttcattt tttcggaaag ctgtctgaat    600

gtatagcccg cttttgttct ggatgtcagg gagtgaacaa aaatagcggc ctgttcatca    660

tgatttaaaa cagacagctt ctctttcagc tcttggtgaa actgggccgc tgtttcagca    720

gcattccggt ttcttaaata ctgtttaacc cagttctgaa tctgataatc ttttacgatc    780

ggcaaataca cgcgttcgcg gtaaagcttg ttggagagca cttggatcaa aagcgacatc    840

cttgcccaca tcactttggc tgccgcctga taatagccgc cgtgaaaatg gcggggccac    900

ggataaaggg caaaaaagcc ggcaagttcc gcttctcctt tttcggtgac ggtgtaagcg    960

ccgctttccg ctttttctct gaccaaagac tcctgcttca atcgttgaac gctggctgcc   1020

acctgctctc tcgacagagc cgaacaaaag ccgaagtatt ttgaaacggc aaataaaccg   1080

gcgtcctgta tcgtctgtga cgaccttttt cctttttaata aatgatagac cgcgcttgga   1140

gaacgctcac ccttcatgga tgacagaatg tcaagcacaa tcgcgtcaaa aaaatgaacc   1200

ggcatatcat cacctgcaat cttccggcaa cattcgatca tttcttcctt ttattttaac   1260

agattttgcg gagaaatcga cgtttaaact catataaaag gggtatgtta gcagtagaac   1320

ccttgtgtga taagcattct caatattttt gagttgaaat gtaagattaa caccattaca   1380

ataaggaatg ggaataggtt tcatatcgga tagatagagg gttaaaccat ttgttccaac   1440

gaagaacaat ctgggaggtt ttttattcat gccaaaatat acaattgtag acaaagatac   1500

gtgcatcgca tgcggagctt gtggtgctgc ggctcctgat atttatgatt acgacgatga   1560

gggaatcgca tttgtcaccc ttgacgacaa tcagggtgtc gtcgaagtcc ctgacgtctt   1620

agaagaagac atgatggacg cgtttgaagg ctgtcctaca gattcgatca aagttgcgga   1680

tgagccgttc gaaggcgacc cgcttaaaca cgaataaagc caaaaaacat ccggtgcaca   1740

aagtgccgga tgttttttta tgagataagc acggctttac caacaagcaa aaagaagccg   1800

gctaaagaca tccggcttct tctgcagctg acaatatccg ggaacatgca cccgatattg   1860

tcatgtttat ttatttggcc atgcggacgt tttccttcag ccgcggtttc agcgaaagga   1920
```

aaatcggcgt ggacacgagg gccacagcga tgcctttaat gaaattaaaa ggcaggattc 1980
cggccagaac tgttgtcttg agcgcctctc cagtcagcgc tggagcattt aaaaaccaag 2040
tgtaggcagg cagaaacagc agataattta aaatgctcat cgaaacggcc atcacaagcg 2100
tccctgcgaa aagagctgtg acaaaccctt tggcagaact tgattttttc agcagtacag 2160
ctgccggcag gataaacaat gttccggcaa tgaagttagc cgcctgatca atcggaacgc 2220
ccgaggcgct tcctgcaata aagtaattca gcacgttttt gatcgcttca acggcaatcc 2280
cggctcccgg accgtacaaa ataacagcga gcaatgccgg gatatcactg aaatcgattt 2340
ttaaatacgg gaatgccccc aggatcggaa agctcagcat cattaaaata aatgcgatgc 2400
tgctcagcat gctgatagag acgagacgtc tcaccttgtt gtgtttcatt ttgtcactct 2460
ctccttttcg atcacatctc acgaaaagag gaatggttct ttcccctgtc ctaaacaaaa 2520
aacccgcttt attgaaaaag cggggctgtt ttacagacag gtcaaataaa cgtttgaaaa 2580
tgttcatttc aaaacgcgcg gaacctccat cttctcccat ccagactata ctgtcggctt 2640
cggaatcgca ccgaatcctg cccataaaaa ggctcgcggg cttagagcgc ttgctcatca 2700
ccgccggtag ggaatttcac cctgccccga agattgatct tatttatttt taatactgat 2760
attattataa attaattgtg aaaaaatgta caggtgcaaa gcttattgcg ctgttttggg 2820
acatcctgca cgatatttcg gtaaactcac tttttccgca tactaaaaac cgcacattca 2880
cagttatttc atttttaatt ttcgtctttc cgcgtgaaac tcattgacac tctttatgga 2940
atatggtaaa ttatcagata tttatgacgc ttatttagga ggaaatctta catgtttcga 3000
gtattggtct cagataaaat gtccagcgac ggcctcaaac cattaatgga agcagatttt 3060
attgaaattg tagaaaagaa tgttgcggaa gcggaagacg agcttcatac gtttgacgcg 3120
ctcttggtgc ggagcgccac gaaggtaacc gaagagctgt ttaaaaagat gacttcgctg 3180
aaaatcgtcg ccagagcagg tgtcggcgtc gacaatatcg atattgacga ggcgacaaaa 3240
cacggtgtta tcgtcgtaaa cgcgccaaac gggaatacaa tttcaaccgc tgaacatacc 3300
tttgcaatgt tttcagcgtt aatgagacat attccgcagg caaacatctc cgtgaaatca 3360
agggagtgga atcgttcggc ttacgtcggt tcagagcttt acggaaaaac gctcggcatc 3420
atcggaatgg gccgcatcgg aagcgaaatc gcgagccgcg caaaagcatt cggtatgacc 3480
gttcatgtat ttgacccgtt cctgacccaa gaaagggcaa gcaagctcgg cgttaacgcg 3540
aacagctttg aagaagttct ggcatgcgcc gacatcatta cggttcatac cccgctcacg 3600
aaagaaacga agggactttt gaacaaagaa accatcgcaa aaacgaaaaa aggcgttcgt 3660
ctcgttaact gtgcaagagg cggcatcatc gatgaagcag cgcttttgga agctctggaa 3720
agcggacatg tcgctggcgc tgccttggat gtattcgaag tcgagcctcc ggtcgattca 3780
aaactgatcg atcatccgct tgtagtcgcg actcctcact tgggcgcctc aacaaaagaa 3840
gcccagctga atgtcgctgc acaagtgtcc gaagaagtcc ttcagtatgc gcaaggaaac 3900
cctgtgatgt ccgcgatcaa ccttccggcc atgacaaagg attcattcga aaaaatccag 3960
ccttatcatc agtttgccaa tacgatcgga aaccttgtgt ctcagtgcat gaatgagcct 4020
gttcaagatg tagccatcca atatgaaggc tccatcgcca aacttgaaac gtcatttatt 4080
acgaaaagcc ttttggccgg atttctgaag ccgagggtcg cggctaccgt taacgaagtg 4140
aatgccggca ccgttgcgaa agagcgcggc atcagcttca gcgaaaaaat ttcttccaat 4200
gagtcaggct atgaaaactg catctctgtg actgtcacgg gagatgtaac aacattctct 4260
ttaagagcga cgtacattcc gcacttcggc ggacgcatcg ttgccttaaa cggctttgat 4320

```
attgattttt atccggctgg acaccttgtc tacattcacc accaggataa accaggggct   4380
atcggccatg tcggacgaat tttaggagac catgacatca atatcgccac tatgcaggta   4440
ggccgaaaag aaaaaggcgg agaagcgatc atgatgcttt cctttgaccg ccaccttgag   4500
gacgatattt tagctgagct gaaaaacatc ccggatatcg tgtctgttaa agccatcgac   4560
cttccttaag tcgctgataa acagctgaca tcaatatcct attttttcaa aaaatatttt   4620
aaaaagttgt tgacttaaaa gaagctaaat gttatagtaa taaaacagaa tagtctttta   4680
agtaagtcta ctctgaattt ttttaaaagg agagggtaaa gatgaaacaa caaaaacggc   4740
tttacgcccg attgctgacg ctgttatttg cgctcatctt cttgctgcct cattctgcag   4800
ctagcgcagc aaatcttaat gggacgctga tgcagtattt tgaatggtac atgcccaatg   4860
acggccaaca ttggaagcgt ttgcaaaacg actcggcata tttggctgaa cacggtatta   4920
ctgccgtctg gattcccccg gcatataagg gaacgagcca agcggatgtg ggctacggtg   4980
cttacgacct ttatgattta ggggagtttc atcaaaaagg gacggttcgg acaaagtacg   5040
gcacaaaagg agagctgcaa tctgcgatca aaagtcttca ttcccgcgac attaacgttt   5100
acggggatgt ggtcatcaac cacaaaggcg gcgctgatgc gaccgaagat gtaaccgcgg   5160
ttgaagtcga tcccgctgac cgcaaccgcg taatttcagg agaacaccta attaaagcct   5220
ggacacattt tcattttccg ggcgcggca gcacatacag cgattttaaa tggcattggt   5280
accatttga cggaaccgat tgggacgagt cccgaaagct gaaccgcatc tataagtttc   5340
aaggaaaggc ttgggattgg gaagtttcca atgaaaacgg caactatgat tatttgatgt   5400
atgccgacat cgattatgac catcctgatg tcgcagcaga aattaagaga tggggcactt   5460
ggtatgccaa tgaactgcaa ttggacggtt tccgtcttga tgctgtcaaa cacattaaat   5520
tttctttttt gcgggattgg gttaatcatg tcagggaaaa aacggggaag gaaatgttta   5580
cggtagctga atattggcag aatgacttgg gcgcgctgga aaactatttg aacaaaacaa   5640
attttaatca ttcagtgttt gacgtgccgc ttcattatca gttccatgct gcatcgacac   5700
agggaggcgg ctatgatatg aggaaattgc tgaacggtac ggtcgtttcc aagcatccgt   5760
tgaaatcggt tacatttgtc gataaccatg atacacagcc ggggcaatcg cttgagtcga   5820
ctgtccaaac atggtttaag ccgcttgctt acgcttttat tctcacaagg gaatctggat   5880
accctcaggt tttctacggg gatatgtacg ggacgaaagg agactcccag cgcgaaattc   5940
ctgccttgaa acacaaaatt gaaccgatct taaaagcgag aaaacagtat gcgtacggag   6000
cacagcatga ttatttcgac caccatgaca ttgtcggctg gacaagggaa ggcgacagct   6060
cggttgcaaa ttcaggtttg gcggcattaa taacagacgg acccggtggg gcaaagcgaa   6120
tgtatgtcgg ccggcaaaac gccggtgaga catggcatga cattaccgga aaccgttcgg   6180
agccggttgt catcaattcg gaaggctggg gagagtttca cgtaaacggc gggtcggttt   6240
caatttatgt tcaaagatag aagcttctcg aggttaacag aggacggatt tcctgaagga   6300
aatccgtttt tttattttac agaagctgcg gaacctgaaa agaattcctt tcaggttccg   6360
tttttttag gaattctccc tgatctcaag catctggcgg ggataaatcc gctctccttt   6420
caaatcgttc cattctttga ggcgctgtac agttacgccc atttttttcgg cgatatgatg   6480
aagcgtatcc cctttccgca ctacatatgt accggtcttc gattcatcgt catgaaggcg   6540
gagtgtttgg ccggccttga gatttgaatg tttcaacccg tttattctca tgatctcctc   6600
gatggatata ccgctatcct tgctgattct ccagagcgtg tccccttttt gaacggtcac   6660
```

```
cgcaccgctc attgtcccgg cgttttgata aacgtggata gaattttgcc ggaacgcctc   6720
ctcacgaagc accgtcagcg gattgattgc atatctttta tcttcagtcc atgaaccgtg   6780
atgcatttca aaatgcaggt gggttccggt cgatattccc gtattgccga tgattccgat   6840
ttgctcgcct tttttcaccc gctccttttc ctttttcagg cgtttgctta agtgggcata   6900
aacggtttca tatccgttgt catgtttaat aaatatcact tggccgtagg agtcggattg   6960
atacgatttg cttatcgttc cgtctgcggc tgccgctact gcttcccctt cgggagcagc   7020
gatgtcaagc cccttatgct ttccgcctct cgtaccgaat tgatctgtga tctctccttt   7080
aatcggttca atccactctg aggcttccgc ccccggggca ttgacgaaaa gcgccaatcc   7140
cgaaagccat gcgatcgcga acaggaagtt ttgatgtctg agtttcttca aggttttcca   7200
tatcctccta ttacatgcat cttcggtaaa attgcccccct attcggagac agcttagtat   7260
acttccaaat caatacaatt tatacattaa aaaaagactc cgcacaggga gtcttttagt   7320
tttctatcgt catcggattc ggtgcgtacg gaacctgtac agatttcgac aggtcatagg   7380
cgccgacctt ggttatggat gcgtttttaa atttcacttt tgtgaagccg aaatctttcg   7440
cggtcaatag aaggccttcc accatcaaga catcttcggg tttattttca atattcgcgg   7500
aggaagaaaa ttgaatgatc agttcttttc cattcttttg aatatcttca atcggcgtat   7560
catcggataa aatgggtttt aaatgagtgc cgctttcttc gtttttcatc atcttaatcg   7620
cttcctgcac cgattcgtaa gattcgcttg aaggtgcaag gaaccggcgc ccgtctgagc   7680
tttcatataa atagtagcat ttttgcgtct ggtgcataat cgccatatcg gcgagcattc   7740
cgaatgtttc aaattcaaca cccgatttat cattggaaat aaacagaaca gaatcatacg   7800
atccccattt aaaggtttcg ttgatcacat ttttcagccg ttcgaaatct tcgactgata   7860
gctccggtat tttctcatca acttgaatct tcagtttttt attgtttttc tgctctttga   7920
acttcacctt atcaaggtaa gctgtgtcaa atgatgtaaa ctggtccact ccaagccggc   7980
tgtaagcgtg aagcgcatct tcaagatttg tcatgccagt gcttttctcg aggcttaccg   8040
ggacaacgac agacttggac tcgtcaagga aagcgaaggt gatatagtcg tctttttgat   8100
tctgtgagac gacaaacgta tttgcaggtt cagacttggc agcatcagcc tccgtctgca   8160
ccaattttcc gtcagaagaa atgttggcgt cggcgctgtt ttgagatctg atctgttcga   8220
ttaactgggg agtgatcagc atcagaagaa agagaaccaa aactgtagca gcaaatgcgc   8280
cgacccgttt tttcggtgat ttacgctttg gtgcgagaat cagcttttga tagatctgat   8340
ttgccgaacg attatcctta accgttggaa gttggcttag taacgccttc agccgttctt   8400
cgttccattc tgacttcttc attctttgga tcctccttca aaagctccat ctgtttacga   8460
agcactttca gaccgcggtg ctgagtggtt tttaccttgc tttcggaaaa attcaaggct   8520
tttgctgttt cactgatcga atatccttga ataaaacgca agacgataac tgatctttgg   8580
tcaagcgtac acttgtctag ggcctcgaaa atttccttta ggttttcatt ttgcatcacg   8640
atgtcctcag gcagaggctt gcggtctttt acatcttgtt tctcccagtc aaacgtcccc   8700
aaaatccgct ggcggatcgt ctgctgcttt ctgaaccagt cgatcgcaac gtgccgcgca   8760
atcgaaagaa gccaggtttt ttcgctgctc ctgccttcaa atgtttcgta agaatgcagg   8820
acgcggatgt atacttcctg aactaagtct tccgcctgat ttttgtcttt taccatataa   8880
aataaaaact gaaataaatc ctgatgatac tgatcatata ttttctgaaa ggtttcttcc   8940
acctgaaacc cctccgttca atttattgtc gtttgtcaat cttaaaaggt tacattacaa   9000
ctattacaac tatattacga acatatgaaa atggaaaggg ggttttgcga aagttaagct   9060
```

taattttaac ttaacaagca caaaagcacc cgttctaaat gaacaggtgc caaggttata 9120
ggagcccaca ttttcactaa gctgtgccct tacaaggctt tcgttctcct gaccggagcg 9180
ttgcggatcc gctgaaatga actaatttca atccgtttat gactttaagt ccaattgttg 9240
gcgaagcttt ttggaaatct ccattctctt ttcgtcagtc actaggtgat accataagcc 9300
gtcaactttt ttgtcttcac cttcaatttc tacctgctta atatctttag cagcttcttt 9360
ataagaactt tgaatatcga tcatcttgtc cagtgttaag tttgttttga tgtttttttc 9420
taatgctgcc aaaatctctt gatagtttgt taatgatttt aattgtgcac cttcatgaat 9480
aatttcgttg ataatctcac gctgacgctc ttga 9514

<210> SEQ ID NO 128
<211> LENGTH: 95
<212> TYPE: DNA
<213> ORGANISM: Artificial Sequence
<220> FEATURE:
<223> OTHER INFORMATION: synthetic

<400> SEQUENCE: 128
gtcgctgata aacagctgac atcaatatcc tattttttca aaaaatattt taaaaagttg 60
ttgacttaaa agaagctaaa tgttatagta ataaa 95

<210> SEQ ID NO 129
<211> LENGTH: 57
<212> TYPE: DNA
<213> ORGANISM: Artificial Sequence
<220> FEATURE:
<223> OTHER INFORMATION: synthetic

<400> SEQUENCE: 129
acagaatagt cttttaagta agtctactct gaattttttt aaaaggagag ggtaaag 57

<210> SEQ ID NO 130
<211> LENGTH: 87
<212> TYPE: DNA
<213> ORGANISM: Bacillus licheniformis

<400> SEQUENCE: 130
atgaaacaac aaaaacggct ttacgcccga ttgctgacgc tgttatttgc gctcatcttc 60
ttgctgcctc attctgcagc tagcgca 87

<210> SEQ ID NO 131
<211> LENGTH: 1452
<212> TYPE: DNA
<213> ORGANISM: Bacillus licheniformis

<400> SEQUENCE: 131
gcaaatctta atgggacgct gatgcagtat tttgaatggt acatgcccaa tgacggccaa 60
cattggaagc gtttgcaaaa cgactcggca tatttggctg aacacggtat tactgccgtc 120
tggattcccc cggcatataa gggaacgagc caagcggatg tgggctacgg tgcttacgac 180
ctttatgatt taggggagtt tcatcaaaaa gggacggttc ggacaaagta cggcacaaaa 240
ggagagctgc aatctgcgat caaaagtctt cattcccgcg acattaacgt ttacggggat 300
gtggtcatca accacaaagg cggcgctgat gcgaccgaag atgtaaccgc ggttgaagtc 360
gatcccgctg accgcaaccg cgtaatttca ggagaacacc taattaaagc ctggacacat 420
tttcattttc cggggcgcgg cagcacatac agcgatttta aatggcattg gtaccatttt 480
gacggaaccg attgggacga gtcccgaaag ctgaaccgca tctataagtt tcaaggaaag 540
gcttgggatt gggaagtttc caatgaaaac ggcaactatg attatttgat gtatgccgac 600
atcgattatg accatcctga tgtcgcagca gaaattaaga gatggggcac ttggtatgcc 660
aatgaactgc aattggacgg tttccgtctt gatgctgtca aacacattaa attttctttt 720
ttgcgggatt gggttaatca tgtcagggaa aaaacgggga aggaaatgtt tacggtagct 780
gaatattggc agaatgactt gggcgcgctg gaaaactatt tgaacaaaac aaattttaat 840
cattcagtgt ttgacgtgcc gcttcattat cagttccatg ctgcatcgac acagggaggc 900
ggctatgata tgaggaaatt gctgaacggt acggtcgttt ccaagcatcc gttgaaatcg 960
gttacatttg tcgataacca tgatacacag ccggggcaat cgcttgagtc gactgtccaa 1020
acatggttta agccgcttgc ttacgctttt attctcacaa gggaatctgg ataccctcag 1080
gttttctacg gggatatgta cgggacgaaa ggagactccc agcgcgaaat tcctgccttg 1140
aaacacaaaa ttgaaccgat cttaaaagcg agaaaacagt atgcgtacgg agcacagcat 1200
gattatttcg accaccatga cattgtcggc tggacaaggg aaggcgacag ctcggttgca 1260
aattcaggtt tggcggcatt aataacagac ggacccggtg ggcaaagcg aatgtatgtc 1320 ggccggcaaa acgccggtga gacatggcat gacattaccg gaaaccgttc ggagccggtt 1380
gtcatcaatt cggaaggctg gggagagttt cacgtaaacg gcgggtcggt ttcaatttat 1440
gttcaaagat ag 1452

<210> SEQ ID NO 132
<211> LENGTH: 6218
<212> TYPE: DNA
<213> ORGANISM: Artificial Sequence
<220> FEATURE:
<223> OTHER INFORMATION: synthetic

<400> SEQUENCE: 132
ggtagaggaa ttcctggtcg gccaaggcta caatccgttt ccgcttgtca ggtttacgga 60
aagggcagac gtagccgcaa gccatatttt agaggggcat gtcatcgtga tcgtcgatac 120
gtcgccaagc gtcatcatca caccgaccac tttgtttcac catgttcagc atgctgagga 180
atacagacag acgccggctg ttgggacgtt tttaaggtgg gtgcggtttt tcggtatttt 240
ggcctccacc tttttgctgc cgctttggct gctgtttgtc attcatccgt cgctcttgcc 300
tgataattta tcgtttatcg ggttgaataa agacacccat attccgatta tcatgcagat 360
tttcctggcg gatctcggcg tcgaattttt aagaatggcc gccattcata cgccgacggc 420
gctttcgact gcaatgggcc tgatcgccgc tgtattgatc ggcgatatcg cgatcaatgt 480
cggcttgttt tctcccgaag tcattttata cgtttccctc tcggcaatcg gagcctacac 540
gacaccaagc tacgagctga gcctggcgaa taaaatggtg aagctgttta tgctgatatt 600
ggtggcgctt tttaaagtgg agggatttgt catcggatta acgatcttaa ctatagtgat 660
gacttcgatc aggtcattgc gaacgcctta cttatggcct ctcctcccgt tcaatggaaa 720
agcgttttgg catgttctcg tgcgcacgtc cgttccaggg ggaaaagtca ggccgagcat 780
cgttcatccg agaaaccgct ccagacagcc gtgaagccgg cattcgaaga ggcttttccc 840
cggggaaaag cctctttttc aataatcgaa ttccggtctt tgagtaccga tgcctctgta 900
ttcattggca gagatcgcga ctgcccggag gctgcagatg ttgttctgtc ttctgatcgg 960
atagacgaca tacagcattt cgcggccgta cgggtcaatc gttgacgaat gaaggaaaac 1020
ctcagttcct ctccgccaaa atctcgtatt cgccggagct gtaataatct gcccttcata 1080

```
aggctcataa attctctgtt cataatgcgc agccggctga taaggggcgt atacatcttc   1140
aggtgcatag ccgggagcgg gggtgtaggg atagcgattt ggatacatat gataacctct   1200
ttcccacttc gtttttggt tttcatcttt aagattatat tcaggtaaat gcctatttgt   1260
atgggcgaaa atctcagctt ttcggctctt tttttattga atggacgttg tgtatgccta   1320
tttctatcaa gcgctgtttt ctgttattct ataatcaata gaatggatta gttgtttagg   1380
gaatcatttc ctttataaat caagaaaatt tggacaaatg gtggtttagt ttttaaaacg   1440
aaatgttata atacaacata agaatcgcac tatcatgaag ccggaagatg catcgggcag   1500
caaccggagc gccccttgca cctttgtcga tagagaaaga gggaatgaca attgttttta   1560
cacggtacta gcagacaaaa tgaaagaggg cacctcgaaa tcggcggtgt cgatgttcta   1620
tcattggcag aaagatacgg aacacctctt tatgtatacg atgtcgcgct gattagagag   1680
cgcgcccgaa aattccagaa ggcattcaag gaagccggtt taaaagcgca ggtagcgtat   1740
gcaagcaagg cgttttcatc ggttgccatg attcagcttg ccgaacaaga ggggctgtct   1800
ctggatgtgg tatcgggagg agagcttttc actgcgatca aagcagggtt cccagctgag   1860
cggattcatt ttcacggaaa caataagagc cctgaagaac tagccatggc gctggagcat   1920
caaatcggct gcatcgtgct cgataacttt cacgagatcg ccattacaga agatctttgc   1980
aagcgatcag gacaaactgt agacgttttg ctcagaatca ctccgggagt tgaagcgcac   2040
acgcacgatt atattacgac ggggcaggaa gattccaaat tcggttttga tctgcataat   2100
ggacaggtcg aacaagccat cgaacaagtc ctccgctcgt ctgcgtttaa gctcctcggc   2160
gtgcactgcc acatcggttc gcaaattttt gatacggcag gatttgtcct tgcagcagac   2220
aagattttcg agaagcttgc ggaatggcgg gagacttact ctttcattcc ggaagtgctc   2280
aatcttggcg ggggcttcgg catccgctat acaaaagacg acgagccgct tgcagctgat   2340
gtttatgttg aaaaaatcat cgaggcggtc aaagcaaatg ccgagcattt cggctttgac   2400
atccctgaga tttggatcga accaggccgg tctctcgtcg gtgatgcggg gactacgctg   2460
tacacgatcg gttctcaaaa agaggtgccg ggcattcgca aatatgtagc catcgacggc   2520
ggcatgagcg ataatatcag gccggcgctt tatgaggcaa aatatgaagc agccgtcgcc   2580
aacaggatga acgatgcttg tcatgatacc gcatcaatcg caggaaaatg ctgcgaaagc   2640
ggagatatgc tgatttggga tttggaaatc cccgaagttc gcgacggaga tgtgctcgcc   2700
gttttctgca ccggtgcgta cggctacagc atggccaaca actacaaccg cattccgcgc   2760
ccggccgtcg tctttgtcga ggacggggaa gcgcagctcg tcattcagag agagacgtat   2820
gaggatatcg tcaagctgga tctgccgctg aaatcgaaag tcaaacaata aaaaaatgga   2880
gattccctaa gaggggggtc tccatttta attcaagctg ataaacagct gacatcaact   2940
aaaagtttca ttaaatactt tgaaaaaagt tgttgactta aaagaagcta aatgttatag   3000
taattgtaca gaatagtctt ttaagtaagt ctactctgaa ttttttaaa aggagagggt   3060
aaagaatgaa acaacaaaaa cggctttacg cccgattgct gacgctgtta tttgcgctca   3120
tcttcttgct gcctcattct gcagctagcg cagcaaatct taatgggacg ctgatgcagt   3180
attttgaatg gtacatgccc aatgacggcc aacattggaa gcgtttgcaa aacgactcgg   3240
catatttggc tgaacacggt attactgccg tctggattcc cccggcatat aagggaacga   3300
gccaagcgga tgtgggctac ggtgcttacg acctttatga tttaggggag tttcatcaaa   3360
aagggacggt tcggacaaag tacggcacaa aaggagagct gcaatctgcg atcaaaagtc   3420
```

-continued

```
ttcattcccg cgacattaac gtttacgggg atgtggtcat caaccacaaa ggcggcgctg   3480
atgcgaccga agatgtaacc gcggttgaag tcgatcccgc tgaccgcaac cgcgtaattt   3540
caggagaaca cctaattaaa gcctggacac attttcattt tccggggcgc ggcagcacat   3600
acagcgattt taaatggcat tggtaccatt ttgacggaac cgattgggac gagtcccgaa   3660
agctgaaccg catctataag tttcaaggaa aggcttggga ttgggaagtt tccaatgaaa   3720
acggcaacta tgattatttg atgtatgccg acatcgatta tgaccatcct gatgtcgcag   3780
cagaaattaa gagatggggc acttggtatg ccaatgaact gcaattggac ggtttccgtc   3840
ttgatgctgt caaacacatt aaattttctt ttttgcggga ttgggttaat catgtcaggg   3900
aaaaaacggg gaaggaaatg tttacggtag ctgaatattg gcagaatgac ttgggcgcgc   3960
tggaaaacta tttgaacaaa acaaatttta atcattcagt gtttgacgtg ccgcttcatt   4020
atcagttcca tgctgcatcg acacagggag gcggctatga tatgaggaaa ttgctgaacg   4080
gtacggtcgt ttccaagcat ccgttgaaat cggttacatt tgtcgataac catgatacac   4140
agccggggca atcgcttgag tcgactgtcc aaacatggtt taagccgctt gcttacgctt   4200
ttattctcac aagggaatct ggataccctc aggttttcta cggggatatg tacgggacga   4260
aaggagactc ccagcgcgaa attcctgcct tgaaacacaa aattgaaccg atcttaaaag   4320
cgagaaaaca gtatgcgtac ggagcacagc atgattattt cgaccaccat gacattgtcg   4380
gctggacaag ggaaggcgac agctcggttg caaattcagg tttggcggca ttaataacag   4440
acggacccgg tggggcaaag cgaatgtatg tcggccggca aaacgccggt gagacatggc   4500
atgacattac cggaaaccgt tcggagccgg ttgtcatcaa ttcggaaggc tggggagagt   4560
ttcacgtaaa cggcgggtcg gtttcaattt atgttcaaag atagaagctt ctcgaggtta   4620
acagaggacg gatttcctga aggaaatccg ttttttattt ttcaagcacg aaaaacactt   4680
cccggtgatc gggaggtgtt ttttgttaaa aagatcatga catgcataga acagcgaccg   4740
ggctaattgt atataatatt gtgaatttaa caaaaaattt acaaaggaga tgataaaggc   4800
aatgaccagg gtgaaaagga tgagatttgc tgatttgttg gatttagagg cggagtagat   4860
gaaaccggcc aaagtatccc tactccaccg attgctccag tgcctgaagc aatgtgttga   4920
ttgtaacaca gtaaatcgtt ttacagcaat aaacattttt gtgaatattt tattgatttc   4980
ggctgtgatc tcattcccat attctgctgc ggcccatggc gcaacacagt ccggcgatca   5040
atattcaagc tttgaagaat tggagcggaa tgaagatcca gcttcttacc gaattacgga   5100
gaagaacgca agagtgccga tgctcatcat ggccatccat ggaggcggca tcgaacccgg   5160
aacgagcgaa atcgccaatg aagtgtccaa aaactattcc ctgtacttgt ttgaagggct   5220
gaaatcatca ggcaatacgg accttcacat tacaagcacg cgttttgacg agccagcggc   5280
gctcgcaatt actgcaagcc accagtatgt catgtcgctc cacggctatt acagtgaaga   5340
ccgcgatatt aaagtaggcg gcacagaccg cgctaaaatc agaatattgg ttgatgagct   5400
gaaccgctcg gggtttgccg ctgaaatgct ggggacagat gacaagtatg ccggaaccca   5460
tccgaataac atcgccaaca agtcgctttc cgggctgagc attcagcttg aaatgagcac   5520
gggtttccgc aaatctttat tcgaccggtt tacactaaaa gacagggcgg cgacgcaaaa   5580
cgaaacgttt taccgattta caaagctgct gacagatttt attcatgaaa actatgaaga   5640
agacggaggg gatttcccct ctgcaaaaat aaaacacccc cttcaagtga aaaaggaggt   5700
gtttcggcgg ttgtgttaac cgttggactc tgaggtgccg ccgccggtga atacggaaac   5760
gatggcgttc cacagagaca caaagaagtc gatcagtttt tgaagaaagt tttgtccttc   5820
```

ttcagaatcc aagaatttcg tgattttatc ctttgctttg tcaagctggt ctccaacctg 5880
gttccagtcg atattaatat ttttcatgtt attaaataaa gatataagag agtttttctg 5940
atcttctgtg agtgtcacgc caagttcgga agcagccgaa tcaatcgttt tctccaattc 6000
ctcttttgac tcgggaactc cgtttttcga gatttcttcc ttgactttgg ccatcagcgc 6060
tgacgcgttt tcactgccga ttttctcgcc aagctctgaa gtggtgacaa gctcttcatt 6120
cgcgaccttt ttcacatctt cggaaatttt ttcgcccgaa gtcgtttcat acgctttcat 6180
caatccggtt aaagcggctg tgcctgacac ttcaaacg 6218

<210> SEQ ID NO 133
<211> LENGTH: 1000
<212> TYPE: DNA
<213> ORGANISM: Artificial Sequence
<220> FEATURE:
<223> OTHER INFORMATION: synthetic

<400> SEQUENCE: 133
tcgttccggg ttcgatgccg cctccatgga tggccatgat gagcatcggc actcttgcgt 60
tcttctccgt aattcggtaa gaagctggat cttcattccg ctccaattct tcaaagcttg 120
aatattgatc gccggactgt gttgcgccat gggccgcagc agaatatggg aatgagatca 180
cagccgaaat caataaaata ttcacaaaaa tgtttattgc tgtaaaacga tttactgtgt 240
tacaatcaac acattgcttc aggcactgga gcaatcggtg gagtagggat actttggccg 300
gtttcatcta ctccgcctct aaatccaaca aatcagcaaa tctcatcctt ttcaccctgg 360
tcattgcctt tatcatctcc tttgtaaatt ttttgttaaa ttcacaatat tatatacaat 420
tagcccggtc gctgttctat gcatgtcatg atctttttaa caaaaaacac ctcccgatca 480
ccgggaagtg tttttcgtgc ttgtcattcc ctctttctct atcgacaaag gtgcaagggg 540
cgctccggtt gctgcccgat gcatcttccg gcttcatgat agtgcgattc ttatgttgta 600
ttataacatt tcgttttaaa aactaaacca ccatttgtcc aaattttctt gatttataaa 660
ggaaatgatt ccctaaacaa ctaatccatt ctattgatta tagaataaca gaaaacagcg 720
cttgatagaa ataggcatac acaacgtcca ttcaataaaa aaagagccga aaagctgaga 780
ttttcgccca tacaaatagg catttacctg aatataatct taaagatgaa aaccaaaaaa 840
cgaagtggga aagaggttat catatgtatc caaatcgcta tccctacacc cccgctcccg 900
gctatgcacc tgaagatgta tacgcccctt atcagccggc tgcgcattat gaacagagaa 960
tttatgagcc ttatgaaggg cagattatta cagctccggc 1000

<210> SEQ ID NO 134
<211> LENGTH: 1320
<212> TYPE: DNA
<213> ORGANISM: Bacillus licheniformis

<400> SEQUENCE: 134
ttgtttttac acggtactag cagacaaaat gaaagagggc acctcgaaat cggcggtgtc 60
gatgttctat cattggcaga aagatacgga acacctcttt atgtatacga tgtcgcgctg 120
attagagagc gcgcccgaaa attccagaag gcattcaagg aagccggttt aaaagcgcag 180
gtagcgtatg caagcaaggc gttttcatcg gttgccatga ttcagcttgc cgaacaagag 240
gggctgtctc tggatgtggt atcgggagga gagcttttca ctgcgatcaa agcagggttc 300
ccagctgagc ggattcattt tcacggaaac aataagagcc ctgaagaact agccatggcg 360

```
ctggagcatc aaatcggctg catcgtgctc gataactttc acgagatcgc cattacagaa    420

gatctttgca agcgatcagg acaaactgta gacgttttgc tcagaatcac tccgggagtt    480

gaagcgcaca cgcacgatta tattacgacg gggcaggaag attccaaatt cggttttgat    540

ctgcataatg gacaggtcga acaagccatc gaacaagtcc tccgctcgtc tgcgtttaag    600

ctcctcggcg tgcactgcca catcggttcg caaatttttg atacggcagg atttgtcctt    660

gcagcagaca agattttcga gaagcttgcg gaatggcggg agacttactc tttcattccg    720

gaagtgctca atcttggcgg gggcttcggc atccgctata caaaagacga cgagccgctt    780

gcagctgatg tttatgttga aaaaatcatc gaggcggtca aagcaaatgc cgagcatttc    840

ggctttgaca tccctgagat ttggatcgaa ccaggccggt ctctcgtcgg tgatgcgggg    900

actacgctgt acacgatcgg ttctcaaaaa gaggtgccgg gcattcgcaa atatgtagcc    960

atcgacggcg gcatgagcga taatatcagg ccggcgcttt atgaggcaaa atatgaagca   1020

gccgtcgcca acaggatgaa cgatgcttgt catgataccg catcaatcgc aggaaaatgc   1080

tgcgaaagcg gagatatgct gatttgggat ttggaaatcc ccgaagttcg cgacggagat   1140

gtgctcgccg ttttctgcac cggtgcgtac ggctacagca tggccaacaa ctacaaccgc   1200

attccgcgcc cggccgtcgt ctttgtcgag gacggggaag cgcagctcgt cattcagaga   1260

gagacgtatg aggatatcgt caagctggat ctgccgctga aatcgaaagt caaacaataa   1320
```

<210> SEQ ID NO 135
<211> LENGTH: 91
<212> TYPE: DNA
<213> ORGANISM: Artificial Sequence
<220> FEATURE:
<223> OTHER INFORMATION: synthetic

<400> SEQUENCE: 135

```
gctgataaac agctgacatc aactaaaagt ttcattaaat actttgaaaa aagttgttga     60

cttaaaagaa gctaaatgtt atagtaattg t                                    91
```

<210> SEQ ID NO 136
<211> LENGTH: 484
<212> TYPE: PRT
<213> ORGANISM: Artificial Sequence
<220> FEATURE:
<223> OTHER INFORMATION: synthetic

<400> SEQUENCE: 136

```
His His Asn Gly Thr Asn Gly Thr Met Met Gln Tyr Phe Glu Trp His
1               5                   10                  15

Leu Pro Asn Asp Gly Gln His Trp Asn Arg Leu Arg Asn Asp Ala Ala
            20                  25                  30

Asn Leu Lys Asn Leu Gly Ile Thr Ala Val Trp Ile Pro Pro Ala Trp
        35                  40                  45

Lys Gly Thr Ser Gln Asn Asp Val Gly Tyr Gly Ala Tyr Asp Leu Tyr
    50                  55                  60

Asp Leu Gly Glu Phe Asn Gln Lys Gly Thr Ile Arg Thr Lys Tyr Gly
65                  70                  75                  80

Thr Arg Ser Gln Leu Gln Ser Ala Ile Ala Ser Leu Gln Asn Asn Gly
                85                  90                  95

Ile Gln Val Tyr Gly Asp Val Val Met Asn His Lys Gly Gly Ala Asp
            100                 105                 110

Gly Thr Glu Trp Val Gln Ala Val Glu Val Asn Pro Ser Asn Arg Asn
        115                 120                 125
```

```
Gln Glu Val Thr Gly Glu Tyr Thr Ile Glu Ala Trp Thr Lys Phe Asp
    130                 135                 140

Phe Pro Gly Arg Gly Asn Thr His Ser Ser Phe Lys Trp Arg Trp Tyr
145                 150                 155                 160

His Phe Asp Gly Thr Asp Trp Asp Gln Ser Arg Arg Leu Asn Asn Arg
                165                 170                 175

Ile Tyr Lys Phe Thr Gly Lys Gly Trp Asp Trp Glu Val Asp Thr Glu
            180                 185                 190

Asn Gly Asn Tyr Asp Tyr Leu Met Tyr Ala Asp Val Asp Met Asp His
        195                 200                 205

Pro Glu Val Ile Asn Glu Leu Arg Arg Trp Gly Val Trp Tyr Thr Asn
    210                 215                 220

Thr Leu Asn Leu Asp Gly Phe Arg Ile Asp Ala Val Lys His Ile Lys
225                 230                 235                 240

Tyr Ser Phe Thr Arg Asp Trp Leu Asn His Val Arg Ser Thr Thr Gly
                245                 250                 255

Lys Asn Asn Met Phe Ala Val Ala Glu Phe Trp Lys Asn Asp Leu Gly
            260                 265                 270

Ala Ile Glu Asn Tyr Leu His Lys Thr Asn Trp Asn His Ser Val Phe
        275                 280                 285

Asp Val Pro Leu His Tyr Asn Leu Tyr Asn Ala Ser Lys Ser Gly Gly
    290                 295                 300

Asn Tyr Asp Met Arg Gln Ile Leu Asn Gly Thr Val Val Ser Lys His
305                 310                 315                 320

Pro Met His Ala Val Thr Phe Val Asp Asn His Asp Ser Gln Pro Ala
                325                 330                 335

Glu Ala Leu Glu Ser Phe Val Glu Ala Trp Phe Lys Pro Leu Ala Tyr
            340                 345                 350

Ala Leu Ile Leu Thr Arg Glu Gln Gly Tyr Pro Ser Val Phe Tyr Gly
        355                 360                 365

Asp Tyr Tyr Gly Ile Pro Thr His Gly Val Ala Ala Met Lys Gly Lys
    370                 375                 380

Ile Asp Pro Ile Leu Glu Ala Arg Gln Lys Tyr Ala Tyr Gly Thr Gln
385                 390                 395                 400

His Asp Tyr Leu Asp His His Asn Ile Ile Gly Trp Thr Arg Glu Gly
                405                 410                 415

Asn Ser Ala His Pro Asn Ser Gly Leu Ala Thr Ile Met Ser Asp Gly
            420                 425                 430

Pro Gly Gly Ser Lys Trp Met Tyr Val Gly Arg His Lys Ala Gly Gln
        435                 440                 445

Val Trp Arg Asp Ile Thr Gly Asn Arg Thr Gly Thr Val Thr Ile Asn
    450                 455                 460

Ala Asp Gly Trp Gly Asn Phe Ser Val Asn Gly Gly Ser Val Ser Ile
465                 470                 475                 480

Trp Val Asn Lys
```

<210> SEQ ID NO 137
<211> LENGTH: 9545
<212> TYPE: DNA
<213> ORGANISM: Artificial Sequence
<220> FEATURE:
<223> OTHER INFORMATION: synthetic

<400> SEQUENCE: 137

```
ctgggagctg atagcacagc gatttcccgc ctcctgtcgg aagcatcgcc accgtgtccc     60
gtccctccag cacgcttttg atgatcgttt cctggccttt tttaaaagca tgataaccaa    120
aatacctgcg gagcgcctga tgaagtttat ccattcctga tcaccgtttt cgacagggcc    180
aggcggattt taaaataact gtatcggccg ccgagtccct ctttaatttg tctgatttta    240
ttggtttggt tcgctatcgc ataatcggca ataattttct gttcctcttt cgacacgtac    300
tgatcgatgg aaaaagacgg atcatgaatg gcgatttcca caatgtgatc ctcgatcgtc    360
gccaatttca gctttctaat tttgcgatc  cggtctattg tataccctc  ttttataaga    420
aagagcgttt ttctcgtcga ttgtgtcaga ccatcattca aaggaatgtc atgaatgagc    480
gtttgaaaaa gcggactttc accattttgg gcggattgaa taaaatggtg cagaacatcc    540
caaaacagtg catatatgta ccactcatca aggttcattt tttcggaaag ctgtctgaat    600
gtatagcccg cttttgttct ggatgtcagg gagtgaacaa aaatagcggc ctgttcatca    660
tgatttaaaa cagacagctt ctctttcagc tcttggtgaa actgggccgc tgtttcagca    720
gcattccggt ttcttaaata ctgtttaacc cagttctgaa tctgataatc ttttacgatc    780
ggcaaataca cgcgttcgcg gtaaagcttg ttggagagca cttggatcaa aagcgacatc    840
cttgcccaca tcactttggc tgccgcctga taatagccgc cgtgaaaatg gcggggccac    900
ggataaaggg caaaaaagcc ggcaagttcc gcttctcctt tttcggtgac ggtgtaagcg    960
ccgctttccg ctttttctct gaccaaagac tcctgcttca atcgttgaac gctggctgcc   1020
acctgctctc tcgacagagc cgaacaaaag ccgaagtatt ttgaaacggc aaataaaccg   1080
gcgtcctgta tcgtctgtga cgaccttttt ccttttaata aatgatagac cgcgcttgga   1140
gaacgctcac ccttcatgga tgacagaatg tcaagcacaa tcgcgtcaaa aaaatgaacc   1200
ggcatatcat cacctgcaat cttccggcaa cattcgatca tttcttcctt ttattttaac   1260
agattttgcg gagaaatcga cgtttaaact catataaaag gggtatgtta gcagtagaac   1320
ccttgtgtga taagcattct caatattttt gagttgaaat gtaagattaa caccattaca   1380
ataaggaatg ggaataggtt tcatatcgga tagatagagg gttaaaccat ttgttccaac   1440
gaagaacaat ctgggaggtt ttttattcat gccaaaatat acaattgtag acaaagatac   1500
gtgcatcgca tgcggagctt gtggtgctgc ggctcctgat atttatgatt acgacgatga   1560
gggaatcgca tttgtcaccc ttgacgacaa tcagggtgtc gtcgaagtcc ctgacgtctt   1620
agaagaagac atgatggacg cgtttgaagg ctgtcctaca gattcgatca aagttgcgga   1680
tgagccgttc gaaggcgacc cgcttaaaca cgaataaagc caaaaaacat ccggtgcaca   1740
aagtgccgga tgttttttta tgagataagc acggctttac caacaagcaa aaagaagccg   1800
gctaaagaca tccggcttct tctgcagctg acaatatccg ggaacatgca cccgatattg   1860
tcatgtttat ttatttggcc atgcggacgt tttccttcag ccgcggtttc agcgaaagga   1920
aaatcggcgt ggacacgagg gccacagcga tgcctttaat gaaattaaaa ggcaggattc   1980
cggccagaac tgttgtcttg agcgcctctc cagtcagcgc tggagcattt aaaaaccaag   2040
tgtaggcagg cagaaacagc agataattta aaatgctcat cgaaacggcc atcacaagcg   2100
tccctgcgaa aagagctgtg acaaaccctt tggcagaact tgattttttc agcagtacag   2160
ctgccggcag gataaacaat gttccggcaa tgaagttagc cgcctgatca atcggaacgc   2220
ccgaggcgct tcctgcaata aagtaattca gcacgttttt gatcgcttca acggcaatcc   2280
cggctcccgg accgtacaaa ataacagcga gcaatgccgg gatatcactg aaatcgattt   2340
ttaaatacgg gaatgccccc aggatcggaa agctcagcat cattaaaata aatgcgatgc   2400
```

```
tgctcagcat gctgatagag acgagacgtc tcaccttgtt gtgtttcatt ttgtcactct   2460
ctccttttcg atcacatctc acgaaaagag gaatggttct ttcccctgtc ctaaacaaaa   2520
aacccgcttt attgaaaaag cggggctgtt ttacagacag gtcaaataaa cgtttgaaaa   2580
tgttcatttc aaaacgcgcg gaacctccat cttctcccat ccagactata ctgtcggctt   2640
cggaatcgca ccgaatcctg cccataaaaa ggctcgcggg cttagagcgc ttgctcatca   2700
ccgccggtag ggaatttcac cctgccccga agattgatct tatttatttt taatactgat   2760
attattataa attaattgtg aaaaaatgta caggtgcaaa gcttattgcg ctgttttggg   2820
acatcctgca cgatatttcg gtaaactcac tttttccgag ctctcgctga taaacagctg   2880
acatcaacta aaagcttcat taaatacttt gaaaaaagtt gttgacttaa aagaagctaa   2940
atgttatagt aataaaacag aatagtcttt taagtaagtc tactctgaat ttttttaaaa   3000
ggagagggta aagaatgaaa caacaaaaac ggctttacgc ccgattgctg acgctgttat   3060
ttgcgctcat cttcttgctg cctcattctg cagctagcgc acaccacaac ggaacaaacg   3120
gcacaatgat gcagtatttt gaatggcacc tgccgaatga tggacagcat tggaatagac   3180
tgagaaacga cgcagcgaac ctgaagaacc ttggcatcac ggcagtctgg attccgcctg   3240
cgtggaaagg cacatcacaa aatgatgtcg gctatggcgc atatgacctg tacgacctgg   3300
gagagttcaa ccagaaggga acaatcagaa cgaaatatgg aacaagatca caactgcaaa   3360
gcgctatcgc gagcctgcaa aataatggca tccaagttta tggcgacgtg gtcatgaacc   3420
acaaaggcgg agcagacgga acggaatggg ttcaagcggt cgaggtgaat ccgagcaaca   3480
gaaaccaaga ggttacgggc gaatacacga tcgaagcctg gacaaagttc gactttccgg   3540
gcagaggcaa tacacactca agcttcaagt ggagatggta tcactttgac ggcacggact   3600
gggatcaaag cagacgtctg aataacagaa tctataagtt tacaggcaaa ggttgggatt   3660
gggaggtgga cacagaaaac ggaaactatg actatctgat gtatgctgac gtcgacatgg   3720
atcatccgga ggtcatcaat gagctgagaa gatggggcgt ttggtacacg aacacactga   3780
acctggatgg attcagaatt gacgcagtca aacacatcaa gtactcattt acaagagact   3840
ggcttaacca cgtgagatca acaacgggaa agaacaatat gttcgccgtt gcggagtttt   3900
ggaagaatga tctgggcgca atcgagaact atcttcacaa gacgaactgg aatcatagcg   3960
tcttcgatgt cccgctgcac tacaatctgt ataatgcatc aaagtcaggc ggcaactacg   4020
atatgagaca aatcctgaat ggaacggtcg tctcaaaaca cccgatgcac gccgtcacgt   4080
ttgtcgataa tcacgattca caaccggcag aagcccttga gagctttgtt gaggcatggt   4140
tcaaaccgct ggcctatgct ctgatcctga caagagagca aggctatccg tcagtgtttt   4200
acggcgatta ctacggcatt ccgacacatg gcgtcgcagc catgaaagga aagattgatc   4260
cgattctgga ggctagacag aaatacgcct acggaacgca acacgattac cttgatcacc   4320
ataacatcat cggatggacg agagagggaa actcagcaca tcctaactca ggccttgcaa   4380
caattatgtc agatggaccg ggaggcagca aatggatgta cgttggcaga cacaaggcag   4440
gacaggtttg gagagatatc acgggcaata gaacaggaac agttacaatc aacgctgacg   4500
gctggggcaa ttttagcgtt aatggcggct cagttagcat ctgggtgaat aaatgaaaga   4560
gcagagagga cggatttcct gaaggaaatc cgttttttta ttttgcggcc gcatattccg   4620
cattcgcaat gcctaccgca tactaaaaac cgcacattca cagttatttc atttttaatt   4680
ttcgtctttc cgcgtgaaac tcattgacac tctttatgga atatggtaaa ttatcagata   4740
```

```
tttatgacgc ttatttagga ggaaatctta catgtttcga gtattggtct cagataaaat   4800
gtccagcgac ggcctcaaac cattaatgga agcagatttt attgaaattg tagaaaagaa   4860
tgttgcggaa gcggaagacg agcttcatac gtttgacgcg ctcttggtgc ggagcgccac   4920
gaaggtaacc gaagagctgt ttaaaaagat gacttcgctg aaaatcgtcg ccagagcagg   4980
tgtcggcgtc gacaatatcg atattgacga ggcgacaaaa cacggtgtta tcgtcgtaaa   5040
cgcgccaaac gggaatacaa tttcaaccgc tgaacatacc tttgcaatgt tttcagcgtt   5100
aatgagacat attccgcagg caaacatctc cgtgaaatca agggagtgga atcgttcggc   5160
ttacgtcggt tcagagcttt acggaaaaac gctcggcatc atcggaatgg gccgcatcgg   5220
aagcgaaatc gcgagccgcg caaaagcatt cggtatgacc gttcatgtat ttgacccgtt   5280
cctgacccaa gaaagggcaa gcaagctcgg cgttaacgcg aacagctttg aagaagttct   5340
ggcatgcgcc gacatcatta cggttcatac cccgctcacg aaagaaacga agggactttt   5400
gaacaaagaa accatcgcaa aaacgaaaaa aggcgttcgt ctcgttaact gtgcaagagg   5460
cggcatcatc gatgaagcag cgcttttgga agctctggaa agcggacatg tcgctggcgc   5520
tgccttggat gtattcgaag tcgagcctcc ggtcgattca aaactgatcg atcatccgct   5580
tgtagtcgcg actcctcact tgggcgcctc aacaaaagaa gcccagctga atgtcgctgc   5640
acaagtgtcc gaagaagtcc ttcagtatgc gcaaggaaac cctgtgatgt ccgcgatcaa   5700
ccttccggcc atgacaaagg attcattcga aaaaatccag ccttatcatc agtttgccaa   5760
tacgatcgga aaccttgtgt ctcagtgcat gaatgagcct gttcaagatg tagccatcca   5820
atatgaaggc tccatcgcca aacttgaaac gtcatttatt acgaaaagcc ttttggccgg   5880
atttctgaag ccgagggtcg cggctaccgt taacgaagtg aatgccggca ccgttgcgaa   5940
agagcgcggc atcagcttca gcgaaaaaat ttcttccaat gagtcaggct atgaaaactg   6000
catctctgtg actgtcacgg gagatgtaac aacattctct ttaagagcga cgtacattcc   6060
gcacttcggc ggacgcatcg ttgccttaaa cggctttgat attgattttt atccggctgg   6120
acaccttgtc tacattcacc accaggataa accaggggct atcggccatg tcggacgaat   6180
tttaggagac catgacatca atatcgccac tatgcaggta ggccgaaaag aaaaaggcgg   6240
agaagcgatc atgatgcttt cctttgaccg ccaccttgag gacgatattt tagctgagct   6300
gaaaaacatc ccggatatcg tgtctgttaa agccatcgac cttccttaaa cagaagctgc   6360
ggaacctgaa aagaattcct ttcaggttcc gtttttttta ggaattctcc ctgatctcaa   6420
gcatctggcg gggataaatc cgctctcctt tcaaatcgtt ccattctttg aggcgctgta   6480
cagttacgcc catttttttcg gcgatatgat gaagcgtatc ccctttccgc actacatatg   6540
taccggtctt cgattcatcg tcatgaaggc ggagtgtttg gccggccttg agatttgaat   6600
gtttcaaccc gtttattctc atgatctcct cgatggatat accgctatcc ttgctgattc   6660
tccagagcgt gtcccctttt tgaacggtca ccgcaccgct cattgtcccg gcgttttgat   6720
aaacgtggat agaattttgc cggaacgcct cctcacgaag caccgtcagc ggattgattg   6780
catatctttt atcttcagtc catgaaccgt gatgcatttc aaaatgcagg tgggttccgg   6840
tcgatattcc cgtattgccg atgattccga tttgctcgcc ttttttcacc cgctcctttt   6900
ccttttttcag gcgtttgctt aagtgggcat aaacggtttc atatccgttg tcatgtttaa   6960
taaatatcac ttggccgtag gagtcggatt gatacgattt gcttatcgtt ccgtctgcgg   7020
ctgccgctac tgcttcccct tcgggagcag cgatgtcaag ccccttatgc tttccgcctc   7080
tcgtaccgaa ttgatctgtg atctctcctt taatcggttc aatccactct gaggcttccg   7140
```

cccccggggc attgacgaaa agcgccaatc ccgaaagcca tgcgatcgcg aacaggaagt 7200
tttgatgtct gagtttcttc aaggttttcc atatcctcct attacatgca tcttcggtaa 7260
aattgccccc tattcggaga cagcttagta tacttccaaa tcaatacaat ttatacatta 7320
aaaaaagact ccgcacaggg agtcttttag ttttctatcg tcatcggatt cggtgcgtac 7380
ggaacctgta cagatttcga caggtcatag gcgccgacct tggttatgga tgcgttttta 7440
aatttcactt ttgtgaagcc gaaatctttc gcggtcaata gaaggccttc caccatcaag 7500
acatcttcgg gtttattttc aatattcgcg gaggaagaaa attgaatgat cagttctttt 7560
ccattctttt gaatatcttc aatcggcgta tcatcggata aaatgggttt taaatgagtg 7620
ccgctttctt cgtttttcat catcttaatc gcttcctgca ccgattcgta agattcgctt 7680
gaaggtgcaa ggaaccggcg cccgtctgag ctttcatata aatagtagca tttttgcgtc 7740
tggtgcataa tcgccatatc ggcgagcatt ccgaatgttt caaattcaac acccgattta 7800
tcattggaaa taaacagaac agaatcatac gatccccatt taaaggtttc gttgatcaca 7860
tttttcagcc gttcgaaatc ttcgactgat agctccggta ttttctcatc aacttgaatc 7920
ttcagttttt tattgttttt ctgctctttg aacttcacct tatcaaggta agctgtgtca 7980
aatgatgtaa actggtccac tccaagccgg ctgtaagcgt gaagcgcatc ttcaagattt 8040
gtcatgccag tgcttttctc gaggcttacc gggacaacga cagacttgga ctcgtcaagg 8100
aaagcgaagg tgatatagtc gtctttttga ttctgtgaga cgacaaacgt atttgcaggt 8160
tcagacttgg cagcatcagc ctccgtctgc accaatttc cgtcagaaga aatgttggcg 8220
tcggcgctgt tttgagatct gatctgttcg attaactggg gagtgatcag catcagaaga 8280
aagagaacca aaactgtagc agcaaatgcg ccgacccgtt ttttcggtga tttacgcttt 8340
ggtgcgagaa tcagcttttg atagatctga tttgccgaac gattatcctt aaccgttgga 8400
agttggctta gtaacgcctt cagccgttct tcgttccatt ctgacttctt cattctttgg 8460
atcctccttc aaaagctcca tctgtttacg aagcactttc agaccgcggt gctgagtggt 8520
ttttaccttg ctttcggaaa aattcaaggc ttttgctgtt tcactgatcg aatatccttg 8580
aataaaacgc aagacgataa ctgatctttg gtcaagcgta cacttgtcta gggcctcgaa 8640
aatttccttt aggttttcat tttgcatcac gatgtcctca ggcagaggct tgcggtcttt 8700
tacatcttgt ttctcccagt caaacgtccc caaaatccgc tggcggatcg tctgctgctt 8760
tctgaaccag tcgatcgcaa cgtgccgcgc aatcgaaaga agccaggttt tttcgctgct 8820
cctgccttca aatgtttcgt aagaatgcag gacgcggatg tatacttcct gaactaagtc 8880
ttccgcctga tttttgtctt ttaccatata aaataaaaac tgaaataaat cctgatgata 8940
ctgatcatat attttctgaa aggtttcttc cacctgaaac ccctccgttc aatttattgt 9000
cgtttgtcaa tcttaaaagg ttacattaca actattacaa ctatattacg aacatatgaa 9060
aatggaaagg gggttttgcg aaagttaagc ttaattttaa cttaacaagc acaaaagcac 9120
ccgttctaaa tgaacaggtg ccaaggttat aggagcccac attttcacta agctgtgccc 9180
ttacaaggct ttcgttctcc tgaccggagc gttgcggatc cgctgaaatg aactaatttc 9240
aatccgttta tgactttaag tccaattgtt ggcgaagctt tttggaaatc tccattctct 9300
tttcgtcagt cactaggtga taccataagc cgtcaacttt tttgtcttca ccttcaattt 9360
ctacctgctt aatatcttta gcagcttctt tataagaact ttgaatatcg atcatcttgt 9420
ccagtgttaa gtttgttttg atgtttttt ctaatgctgc caaaatctct tgatagtttg 9480
ttaatgattt taattgtgca ccttcatgaa taatttcgtt gataatctca cgctgacgct 9540
cttga 9545

<210> SEQ ID NO 138
<211> LENGTH: 93
<212> TYPE: DNA
<213> ORGANISM: Bacillus subtilis

<400> SEQUENCE: 138
tcgctgataa acagctgaca tcaactaaaa gcttcattaa atactttgaa aaaagttgtt 60
gacttaaaag aagctaaatg ttatagtaat aaa 93

<210> SEQ ID NO 139
<211> LENGTH: 58
<212> TYPE: DNA
<213> ORGANISM: Bacillus subtilis

<400> SEQUENCE: 139
acagaatagt cttttaagta agtctactct gaattttttt aaaaggagag ggtaaaga 58

<210> SEQ ID NO 140
<211> LENGTH: 1455
<212> TYPE: DNA
<213> ORGANISM: Artificial Sequence
<220> FEATURE:
<223> OTHER INFORMATION: synthetic

<400> SEQUENCE: 140
caccacaacg gaacaaacgg cacaatgatg cagtattttg aatggcacct gccgaatgat 60
ggacagcatt ggaatagact gagaaacgac gcagcgaacc tgaagaacct tggcatcacg 120
gcagtctgga ttccgcctgc gtggaaaggc acatcacaaa atgatgtcgg ctatggcgca 180
tatgacctgt acgacctggg agagttcaac cagaagggaa caatcagaac gaaatatgga 240
acaagatcac aactgcaaag cgctatcgcg agcctgcaaa ataatggcat ccaagtttat 300
ggcgacgtgg tcatgaacca caaaggcgga gcagacggaa cggaatgggt tcaagcggtc 360
gaggtgaatc cgagcaacag aaaccaagag gttacgggcg aatacacgat cgaagcctgg 420
acaaagttcg actttccggg cagaggcaat acacactcaa gcttcaagtg gagatggtat 480
cactttgacg gcacggactg ggatcaaagc agacgtctga ataacagaat ctataagttt 540
acaggcaaag gttgggattg ggaggtggac acagaaaacg gaaactatga ctatctgatg 600
tatgctgacg tcgacatgga tcatccggag gtcatcaatg agctgagaag atggggcgtt 660
tggtacacga acacactgaa cctggatgga ttcagaattg acgcagtcaa acacatcaag 720
tactcattta caagagactg gcttaaccac gtgagatcaa caacgggaaa gaacaatatg 780
ttcgccgttg cggagttttg gaagaatgat ctgggcgcaa tcgagaacta tcttcacaag 840
acgaactgga atcatagcgt cttcgatgtc ccgctgcact acaatctgta taatgcatca 900
aagtcaggcg gcaactacga tatgagacaa atcctgaatg gaacggtcgt ctcaaaacac 960
ccgatgcacg ccgtcacgtt tgtcgataat cacgattcac aaccggcaga agcccttgag 1020
agctttgttg aggcatggtt caaaccgctg gcctatgctc tgatcctgac aagagagcaa 1080
ggctatccgt cagtgtttta cggcgattac tacggcattc cgacacatgg cgtcgcagcc 1140
atgaaaggaa agattgatcc gattctggag gctagacaga aatacgccta cggaacgcaa 1200
cacgattacc ttgatcacca taacatcatc ggatggacga gagagggaaa ctcagcacat 1260
cctaactcag gccttgcaac aattatgtca gatggaccgg gaggcagcaa atggatgtac 1320
gttggcagac acaaggcagg acaggtttgg agagatatca cgggcaatag aacaggaaca 1380
gttacaatca acgctgacgg ctggggcaat tttagcgtta atggcggctc agttagcatc 1440
tgggtgaata aatga 1455

<210> SEQ ID NO 141
<211> LENGTH: 3113
<212> TYPE: DNA
<213> ORGANISM: Artificial Sequence
<220> FEATURE:
<223> OTHER INFORMATION: synthetic

<400> SEQUENCE: 141
ttgtttttac acggtactag cagacaaaat gaaagagggc acctcgaaat cggcggtgtc 60
gatgttctat cattggcaga aagatacgga acacctcttt atgtatacga tgtcgcgctg 120
attagagagc gcgcccgaaa attccagaag gcattcaagg aagccggttt aaaagcgcag 180
gtagcgtatg caagcaaggc gttttcatcg gttgccatga ttcagcttgc cgaacaagag 240
gggctgtctc tggatgtggt atcgggagga gagcttttca ctgcgatcaa agcagggttc 300
ccagctgagc ggattcattt tcacggaaac aataagagcc ctgaagaact agccatggcg 360
ctggagcatc aaatcggctg catcgtgctc gataactttc acgagatcgc cattacagaa 420
gatctttgca agcgatcagg acaaactgta gacgttttgc tcagaatcac tccgggagtt 480
gaagcgcaca cgcacgatta tattacgacg gggcaggaag attccaaatt cggttttgat 540
ctgcataatg gacaggtcga acaagccatc gaacaagtcc tccgctcgtc tgcgtttaag 600
ctcctcggcg tgcactgcca catcggttcg caaatttttg atacggcagg atttgtcctt 660
gcagcagaca agattttcga gaagcttgcg gaatggcggg agacttactc tttcattccg 720
gaagtgctca atcttggcgg gggcttcggc atccgctata caaaagacga cgagccgctt 780
gcagctgatg tttatgttga aaaaatcatc gaggcggtca aagcaaatgc cgagcatttc 840
ggctttgaca tccctgagat ttggatcgaa ccaggccggt ctctcgtcgg tgatgcgggg 900
actacgctgt acacgatcgg ttctcaaaaa gaggtgccgg gcattcgcaa atatgtagcc 960
atcgacggcg gcatgagcga taatatcagg ccggcgcttt atgaggcaaa atatgaagca 1020
gccgtcgcca acaggatgaa cgatgcttgt catgataccg catcaatcgc aggaaaatgc 1080
tgcgaaagcg gagatatgct gatttgggat ttggaaatcc ccgaagttcg cgacggagat 1140
gtgctcgccg ttttctgcac cggtgcgtac ggctacagca tggccaacaa ctacaaccgc 1200
attccgcgcc cggccgtcgt ctttgtcgag gacggggaag cgcagctcgt cattcagaga 1260
gagacgtatg aggatatcgt caagctggat ctgccgctga aatcgaaagt caaacaataa 1320
aaaaatggag attccctaag aggggggtct ccatttttaa ttcagagctc gtcgctgata 1380
aacagctgac atcaatatcc tattttttca aaaaatattt taaaaagttg ttgacttaaa 1440
agaagctaaa tgttatagta ataaaacaga atagtctttt aagtaagtct actctgaatt 1500
tttttaaaag gagagggtaa agaatgaaac aacaaaaacg gctttacgcc cgattgctga 1560
cgctgttatt tgcgctcatc ttcttgctgc ctcattctgc agctagcgca caccacaacg 1620
gaacaaacgg cacaatgatg cagtattttg aatggcacct gccgaatgat ggacagcatt 1680
ggaatagact gagaaacgac gcagcgaacc tgaagaacct tggcatcacg gcagtctgga 1740
ttccgcctgc gtggaaaggc acatcacaaa atgatgtcgg ctatggcgca tatgacctgt 1800
acgacctggg agagttcaac cagaagggaa caatcagaac gaaatatgga acaagatcac 1860
aactgcaaag cgctatcgcg agcctgcaaa ataatggcat ccaagtttat ggcgacgtgg 1920
tcatgaacca caaaggcgga gcagacggaa cggaatgggt tcaagcggtc gaggtgaatc 1980
cgagcaacag aaaccaagag gttacgggcg aatacacgat cgaagcctgg acaaagttcg 2040
actttccggg cagaggcaat acacactcaa gcttcaagtg gagatggtat cactttgacg 2100
gcacggactg ggatcaaagc agacgtctga ataacagaat ctataagttt acaggcaaag 2160
gttgggattg ggaggtggac acagaaaacg gaaactatga ctatctgatg tatgctgacg 2220
tcgacatgga tcatccggag gtcatcaatg agctgagaag atggggcgtt tggtacacga 2280
acacactgaa cctggatgga ttcagaattg acgcagtcaa acacatcaag tactcattta 2340
caagagactg gcttaaccac gtgagatcaa caacgggaaa gaacaatatg ttcgccgttg 2400
cggagttttg gaagaatgat ctgggcgcaa tcgagaacta tcttcacaag acgaactgga 2460
atcatagcgt cttcgatgtc ccgctgcact acaatctgta taatgcatca aagtcaggcg 2520
gcaactacga tatgagacaa atcctgaatg gaacggtcgt ctcaaaacac ccgatgcacg 2580
ccgtcacgtt tgtcgataat cacgattcac aaccggcaga agcccttgag agctttgttg 2640
aggcatggtt caaaccgctg gcctatgctc tgatcctgac aagagagcaa ggctatccgt 2700
cagtgtttta cggcgattac tacggcattc cgacacatgg cgtcgcagcc atgaaaggaa 2760
agattgatcc gattctggag gctagacaga aatacgccta cggaacgcaa cacgattacc 2820
ttgatcacca taacatcatc ggatggacga gagagggaaa ctcagcacat cctaactcag 2880
gccttgcaac aattatgtca gatggaccgg gaggcagcaa atggatgtac gttggcagac 2940
acaaggcagg acaggtttgg agagatatca cgggcaatag aacaggaaca gttacaatca 3000
acgctgacgg ctggggcaat tttagcgtta atggcggctc agttagcatc tgggtgaata 3060
aatgaaagag cagagaggac ggatttcctg aaggaaatcc gttttttat ttt 3113

<210> SEQ ID NO 142
<211> LENGTH: 2231
<212> TYPE: DNA
<213> ORGANISM: Artificial Sequence
<220> FEATURE:
<223> OTHER INFORMATION: synthetic

<400> SEQUENCE: 142
gtgttgtgct gaatcaatac atagaggccg gcggcgtatc gggtacaaca tctgtcaaga 60
cgtttaacgc tgatttaaag cagaaaaagc tgctgtccct tcaagatctg tttgaagaga 120
attcagattt tctgaacagg atttcaagca ttgcctatca ggaattgaaa aatcggaatc 180
cgtctgctga catggctttt ttaaaagaag ggacgagccc tcaggaagaa catttcagcc 240
gctttgcgct tcttgaaaac gaggtggaat tttattttga gaaaaaacaa gccggtcttg 300
aacagtttgt aaaaataaaa aaagaatggg taaaagatat tttaaaagac cgatatcagg 360
atatgaaaaa gaatcgtctt caggccaaac ctgatcagga gcctgttccg cttccgaagc 420
aagcgaaaat taatcccgat gaaaaagtga ttgccctcac atttgatgac ggtccgaatc 480
ccgctacaac gaataaaata ttaaacgctt tacagaagca tgaagggcat gcgaccttct 540
ttgtgcttgg aagcagagcc caatattatc ccgaaacgat aaaacggatg ctgaaggaag 600
gaaacgaagt cggcaaccat tcctgggacc atccgttatt gacaaggctg tcaaacgaaa 660
aagcgtatca ggagattaac gacacgcaag aaatgatcga aaaaatcagc ggacacctgc 720
ctgtacactt gcgtcctcca tacggcggga tcaatgattc cgtccgctcg ctttccaatc 780
tgaaggtttc attgtgggat gttgatccgg aagattggaa gtacaaaaat aagcaaaaga 840

```
ttgtcaatca tgtcatgagc catgcgggag acggaaaaat cgtcttaatg cacgatattt     900
atgcaacgtc cgcagatgct gctgaagaga ttattaaaaa gctgaaagca aaaggctatc     960
aattggtaac tgtatctcag cttgaagaag tgaagaagca gagaggctat tgaataaatg    1020
agtagaaagc gccatatcgg cgcttttctt ttggaagaaa atatagggaa aatggtactt    1080
gttaaaaatt cggaatattt atacaatatc atatgtttca cattgaaagg ggaggagaat    1140
catgaaacaa caaaaacggc tttacgcccg attgctgacg ctgttaggat cccacgtaaa    1200
cggcgggtcg gtttcaattt atgttcaaag atagaagagc aggctgacag tttgaatcgc    1260
ataggtaagg cggggatgaa atggcaacgt tatctgatgt agcaaagaaa gcaaatgtgt    1320
cgaaaatgac ggtatcgcgg gtgatcaatc atcctgagac tgtgacggat gaattgaaaa    1380
agcttgttca ttccgcaatg aaggagctca attatatacc gaactatgca gcaagagcgc    1440
tcgttcaaaa cagaacacag gtcgtcaagc tgctcatact ggaagaaatg gatacaacag    1500
aaccttatta tatgaatctg ttaacgggaa tcagccgcga gctggaccgt catcattatg    1560
ctttgcagct tgtcacaagg aaatctctca atatcggcca gtgcgacggc attattgcga    1620
cggggttgag aaaagccgat tttgaagggc tcatcaaggt ttttgaaaag cctgtcgttg    1680
tattcgggca aaatgaaatg ggctacgatt ttattgatgt taacaatgaa aaaggaacct    1740
atatggcaac acgtcacgtc attggtctgg gcgtccgcaa tgtcgtcttt tttgggatcg    1800
atttggatga gccctttgaa cgctcaaggg aaaaaggcta tcttcaggcg atggaaggca    1860
gtctgaaaaa agcagcgatt ttccggatgg aaaacagttc aaaaaaaagt gaagcacgcg    1920
cgcgggaagt gcttgcatcc tttgacgcac ctgcagcggt tgtttgcgct tcggaccgaa    1980
tcgcgctcgg ggttatccgc gcggtgcaat cgcttggtaa aagaattccg gaagatgtcg    2040
cggtcaccgg ctatgacggg gtgtttctcg accggatcgc ttcgcctcgc ctgacaaccg    2100
tcagacagcc tgttgttgaa atgggagagg cttgcgcgag aatcctgctg aaaaaaatca    2160
atgaagacgg agcgccgcaa ggcaatcaat tttttgagcc ggagcttatt gtccgcgaat    2220
cgactttgta g                                                         2231
```

```
<210> SEQ ID NO 143
<211> LENGTH: 483
<212> TYPE: PRT
<213> ORGANISM: Artificial Sequence
<220> FEATURE:
<223> OTHER INFORMATION: synthetic

<400> SEQUENCE: 143

Ala Ala Thr Asn Gly Thr Met Met Gln Tyr Phe Glu Trp Tyr Val Pro
1               5                   10                  15

Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Pro Ala Tyr Lys Gly
        35                  40                  45

Thr Ser Gln Ala Asp Val Gly Tyr Gly Pro Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110
```

```
Glu Asn Val Thr Ala Val Glu Val Asn Pro Ser Asn Arg Tyr Gln Glu
        115                 120                 125

Thr Ser Gly Glu Tyr Asn Ile Gln Ala Trp Thr Gly Phe Asn Phe Pro
    130                 135                 140

Gly Arg Gly Thr Thr Tyr Ser Asn Trp Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe His Gly Lys Ala Trp Asp Trp Pro Val Ser Ser Glu Asn Gly Asn
            180                 185                 190

Tyr Asp Tyr Leu Met Tyr Ala Asp Tyr Asp Tyr Asp His Pro Asp Val
        195                 200                 205

Val Asn Glu Met Lys Lys Trp Gly Val Trp Tyr Ala Asn Glu Val Gly
    210                 215                 220

Leu Asp Gly Tyr Arg Leu Asp Ala Val Lys His Ile Lys Phe Ser Phe
225                 230                 235                 240

Leu Lys Asp Trp Val Asp Asn Ala Arg Ala Ala Thr Gly Lys Glu Met
                245                 250                 255

Phe Thr Val Gly Glu Tyr Trp Gln Asn Asp Leu Gly Ala Leu Asn Asn
            260                 265                 270

Tyr Leu Ala Lys Val Asn Tyr Asn Gln Ser Leu Phe Asp Ala Pro Leu
        275                 280                 285

His Tyr Asn Phe Tyr Ala Ala Ser Thr Gly Gly Gly Ala Tyr Asp Met
    290                 295                 300

Arg Asn Ile Leu Asn Asn Thr Leu Val Ala Ser Asn Pro Thr Lys Ala
305                 310                 315                 320

Val Thr Leu Val Glu Asn His Asp Thr Gln Pro Gly Gln Ser Leu Glu
                325                 330                 335

Ser Thr Val Gln Pro Trp Phe Lys Pro Leu Ala Tyr Ala Phe Ile Leu
            340                 345                 350

Thr Arg Ser Gly Gly Tyr Pro Ala Val Phe Tyr Gly Asp Met Tyr Gly
        355                 360                 365

Thr Lys Gly Thr Thr Thr Tyr Glu Ile Pro Ala Leu Lys Ser Lys Ile
    370                 375                 380

Glu Pro Leu Leu Lys Ala Arg Lys Asp Tyr Ala Tyr Gly Thr Gln Arg
385                 390                 395                 400

Asp Tyr Ile Asp Asn Pro Asp Val Ile Gly Trp Thr Arg Glu Gly Asp
                405                 410                 415

Ser Thr Lys Ala Lys Ser Gly Leu Ala Thr Val Ile Thr Asp Gly Pro
            420                 425                 430

Gly Gly Ser Lys Arg Met Tyr Val Gly Thr Ser Asn Ala Gly Glu Ile
        435                 440                 445

Trp Tyr Asp Leu Thr Gly Asn Arg Thr Asp Lys Ile Thr Ile Gly Ser
    450                 455                 460

Asp Gly Tyr Ala Thr Phe Pro Val Asn Gly Gly Ser Val Ser Val Trp
465                 470                 475                 480

Val Gln Gln
```

<210> SEQ ID NO 144
<211> LENGTH: 9515
<212> TYPE: DNA
<213> ORGANISM: Artificial Sequence
<220> FEATURE:
<223> OTHER INFORMATION: synthetic

<400> SEQUENCE: 144

```
ctgggagctg atagcacagc gatttcccgc ctcctgtcgg aagcatcgcc accgtgtccc     60
gtccctccag cacgcttttg atgatcgttt cctggccttt tttaaaagca tgataaccaa    120
aatacctgcg gagcgcctga tgaagtttat ccattcctga tcaccgtttt cgacagggcc    180
aggcggattt taaaataact gtatcggccg ccgagtccct ctttaatttg tctgatttta    240
ttggtttggt tcgctatcgc ataatcggca ataattttct gttcctcttt cgacacgtac    300
tgatcgatgg aaaaagacgg atcatgaatg gcgatttcca caatgtgatc ctcgatcgtc    360
gccaatttca gctttctaat ttttgcgatc cggtctattg tatacccttc ttttataaga    420
aagagcgttt ttctcgtcga ttgtgtcaga ccatcattca aaggaatgtc atgaatgagc    480
gtttgaaaaa gcggactttc accattttgg gcggattgaa taaaatggtg cagaacatcc    540
caaaacagtg catatatgta ccactcatca aggttcattt tttcggaaag ctgtctgaat    600
gtatagcccg cttttgttct ggatgtcagg gagtgaacaa aaatagcggc ctgttcatca    660
tgatttaaaa cagacagctt ctctttcagc tcttggtgaa actgggccgc tgtttcagca    720
gcattccggt ttcttaaata ctgtttaacc cagttctgaa tctgataatc ttttacgatc    780
ggcaaataca cgcgttcgcg gtaaagcttg ttggagagca cttggatcaa aagcgacatc    840
cttgcccaca tcactttggc tgccgcctga taatagccgc cgtgaaaatg gcggggccac    900
ggataaaggg caaaaaagcc ggcaagttcc gcttctcctt tttcggtgac ggtgtaagcg    960
ccgctttccg ctttttctct gaccaaagac tcctgcttca atcgttgaac gctggctgcc   1020
acctgctctc tcgacagagc cgaacaaaag ccgaagtatt ttgaaacggc aaataaaccg   1080
gcgtcctgta tcgtctgtga cgaccttttt cctttttaata aatgatagac cgcgcttgga  1140
gaacgctcac ccttcatgga tgacagaatg tcaagcacaa tcgcgtcaaa aaaatgaacc   1200
ggcatatcat cacctgcaat cttccggcaa cattcgatca tttcttcctt ttattttaac   1260
agattttgcg gagaaatcga cgtttaaact catataaaag gggtatgtta gcagtagaac   1320
ccttgtgtga taagcattct caatattttt gagttgaaat gtaagattaa caccattaca   1380
ataaggaatg ggaataggtt tcatatcgga tagatagagg gttaaaccat ttgttccaac   1440
gaagaacaat ctgggaggtt ttttattcat gccaaaatat acaattgtag acaaagatac   1500
gtgcatcgca tgcggagctt gtggtgctgc ggctcctgat atttatgatt acgacgatga   1560
gggaatcgca tttgtcaccc ttgacgacaa tcagggtgtc gtcgaagtcc ctgacgtctt   1620
agaagaagac atgatggacg cgtttgaagg ctgtcctaca gattcgatca aagttgcgga   1680
tgagccgttc gaaggcgacc cgcttaaaca cgaataaagc caaaaaacat ccggtgcaca   1740
aagtgccgga tgttttttta tgagataagc acggctttac caacaagcaa aaagaagccg   1800
gctaaagaca tccggcttct tctgcagctg acaatatccg ggaacatgca cccgatattg   1860
tcatgtttat ttatttggcc atgcggacgt tttccttcag ccgcggtttc agcgaaagga   1920
aaatcggcgt ggacacgagg gccacagcga tgcctttaat gaaattaaaa ggcaggattc   1980
cggccagaac tgttgtcttg agcgcctctc cagtcagcgc tggagcattt aaaaaccaag   2040
tgtaggcagg cagaaacagc agataattta aaatgctcat cgaaacggcc atcacaagcg   2100
tccctgcgaa aagagctgtg acaaaccctt tggcagaact tgattttttc agcagtacag   2160
ctgccggcag gataaacaat gttccggcaa tgaagttagc cgcctgatca atcggaacgc   2220
ccgaggcgct tcctgcaata aagtaattca gcacgttttt gatcgcttca acggcaatcc   2280
```

```
cggctcccgg accgtacaaa ataacagcga gcaatgccgg gatatcactg aaatcgattt   2340
ttaaatacgg gaatgccccc aggatcggaa agctcagcat cattaaaata aatgcgatgc   2400
tgctcagcat gctgatagag acgagacgtc tcaccttgtt gtgtttcatt ttgtcactct   2460
ctccttttcg atcacatctc acgaaaagag gaatggttct ttcccctgtc ctaaacaaaa   2520
aacccgcttt attgaaaaag cggggctgtt ttacagacag gtcaaataaa cgtttgaaaa   2580
tgttcatttc aaaacgcgcg gaacctccat cttctcccat ccagactata ctgtcggctt   2640
cggaatcgca ccgaatcctg cccataaaaa ggctcgcggg cttagagcgc ttgctcatca   2700
ccgccggtag ggaatttcac cctgccccga agattgatct tatttatttt taatactgat   2760
attattataa attaattgtg aaaaaatgta caggtgcaaa gcttattgcg ctgttttggg   2820
acatcctgca cgatatttcg gtaaactcac tttttccgca tactaaaaac cgcacattca   2880
cagttatttc atttttaatt ttcgtctttc cgcgtgaaac tcattgacac tctttatgga   2940
atatggtaaa ttatcagata tttatgacgc ttatttagga ggaaatctta catgtttcga   3000
gtattggtct cagataaaat gtccagcgac ggcctcaaac cattaatgga agcagatttt   3060
attgaaattg tagaaaagaa tgttgcggaa gcggaagacg agcttcatac gtttgacgcg   3120
ctcttggtgc ggagcgccac gaaggtaacc gaagagctgt ttaaaaagat gacttcgctg   3180
aaaatcgtcg ccagagcagg tgtcggcgtc gacaatatcg atattgacga ggcgacaaaa   3240
cacggtgtta tcgtcgtaaa cgcgccaaac gggaatacaa tttcaaccgc tgaacatacc   3300
tttgcaatgt tttcagcgtt aatgagacat attccgcagg caaacatctc cgtgaaatca   3360
agggagtgga atcgttcggc ttacgtcggt tcagagcttt acggaaaaac gctcggcatc   3420
atcggaatgg gccgcatcgg aagcgaaatc gcgagccgcg caaaagcatt cggtatgacc   3480
gttcatgtat ttgacccgtt cctgacccaa gaaagggcaa gcaagctcgg cgttaacgcg   3540
aacagctttg aagaagttct ggcatgcgcc gacatcatta cggttcatac cccgctcacg   3600
aaagaaacga agggactttt gaacaaagaa accatcgcaa aaacgaaaaa aggcgttcgt   3660
ctcgttaact gtgcaagagg cggcatcatc gatgaagcag cgcttttgga agctctggaa   3720
agcggacatg tcgctggcgc tgccttggat gtattcgaag tcgagcctcc ggtcgattca   3780
aaactgatcg atcatccgct tgtagtcgcg actcctcact tgggcgcctc aacaaaagaa   3840
gcccagctga atgtcgctgc acaagtgtcc gaagaagtcc ttcagtatgc gcaaggaaac   3900
cctgtgatgt ccgcgatcaa ccttccggcc atgacaaagg attcattcga aaaaatccag   3960
ccttatcatc agtttgccaa tacgatcgga aaccttgtgt ctcagtgcat gaatgagcct   4020
gttcaagatg tagccatcca atatgaaggc tccatcgcca aacttgaaac gtcatttatt   4080
acgaaaagcc ttttggccgg atttctgaag ccgagggtcg cggctaccgt taacgaagtg   4140
aatgccggca ccgttgcgaa agagcgcggc atcagcttca gcgaaaaaat ttcttccaat   4200
gagtcaggct atgaaaactg catctctgtg actgtcacgg gagatgtaac aacattctct   4260
ttaagagcga cgtacattcc gcacttcggc ggacgcatcg ttgccttaaa cggctttgat   4320
attgattttt atccggctgg acaccttgtc tacattcacc accaggataa accaggggct   4380
atcggccatg tcggacgaat tttaggagac catgacatca atatcgccac tatgcaggta   4440
ggccgaaaag aaaaaggcgg agaagcgatc atgatgcttt cctttgaccg ccaccttgag   4500
gacgatattt tagctgagct gaaaaacatc ccggatatcg tgtctgttaa agccatcgac   4560
cttccttaag tcgctgataa acagctgaca tcaatatcct attttttcaa aaaatatttt   4620
aaaaagttgt tgacttaaaa gaagctaaat gttatagtaa taaaacagaa tagtctttta   4680
```

```
agtaagtcta ctctgaattt ttttaaaagg agagggtaaa gatgaaacaa caaaaacggc   4740
tttacgcccg attgctgacg ctgttatttg cgctcatctt cttgctgcct cattctgcag   4800
ctagcgcagc agcgacaaac ggaacaatga tgcagtattt cgagtggtat gtacctaacg   4860
acggccagca atggaacaga ctgagaacag atgcccctta cttgtcatct gttggtatta   4920
cagcagtatg gacaccgccg gcttataagg gcacgtctca agcagatgtg gggtacggcc   4980
cgtacgatct gtatgattta ggcgagttta atcaaaaagg tacagtcaga acgaagtatg   5040
gcacaaaagg agaacttaaa tctgctgtca acacgctgca ttcaaatgga atccaagtgt   5100
atggtgatgt cgtgatgaat cataaagcag gtgctgatta tacagaaaac gtaacggcgg   5160
tggaggtgaa tccgtctaat agatatcagg aaacgagcgg cgaatataat attcaggcat   5220
ggacaggctt caactttccg ggcagaggaa caacgtattc taactggaaa tggcagtggt   5280
tccattttga tggaacggat tgggaccaga gcagaagcct ctctagaatc ttcaaattcc   5340
atggaaaggc gtgggactgg ccggtttctt cagaaaacgg aaattatgac tatctgatgt   5400
acgcggacta tgattatgac catccggatg tcgtgaatga aatgaaaaag tggggcgtct   5460
ggtatgccaa cgaagttggg ttagatggat acagacttga cgcggtcaaa catattaaat   5520
ttagctttct caaagactgg gtggataacg caagagcagc gacgggaaaa gaaatgttta   5580
cggttggcga atattggcaa aatgatttag ggccctgaa taactacctg gcaaaggtaa   5640
attacaacca atctcttttt gatgcgccgt tgcattacaa cttttacgct gcctcaacag   5700
ggggtggagc gtacgatatg agaaatattc ttaataacac gttagtcgca agcaatccga   5760
caaaggctgt tacgttagtt gagaatcatg acacacagcc tggacaatca ctggaatcaa   5820
cagtccaacc gtggtttaaa ccgttagcct acgcgtttat tctcacgaga agcggaggct   5880
atcctgcggt attttatgga gatatgtacg gtacaaaagg aacgacaaca tatgagatcc   5940
ctgctcttaa atctaaaatc gaacctttgc ttaaggctag aaaagactat gcttatggaa   6000
cacagagaga ctatattgat aacccggatg tcattggctg gacgagagaa ggggactcaa   6060
cgaaagccaa gagcggtctg gccacagtga ttacagatgg gccgggcggt tcaaaaagaa   6120
tgtatgttgg cacgagcaat gcgggtgaaa tctggtatga tttgacaggg aatagaacag   6180
ataaaatcac gattggaagc gatggctatg caacatttcc tgtcaatggg ggctcagttt   6240
cagtatgggt gcagcaatga aagcttctcg aggttaacag aggacggatt tcctgaagga   6300
aatccgtttt tttattttac agaagctgcg gaacctgaaa agaattcctt tcaggttccg   6360
tttttttag gaattctccc tgatctcaag catctggcgg ggataaatcc gctctccttt   6420
caaatcgttc cattctttga ggcgctgtac agttacgccc attttttcgg cgatatgatg   6480
aagcgtatcc cctttccgca ctacatatgt accggtcttc gattcatcgt catgaaggcg   6540
gagtgtttgg ccggccttga gatttgaatg tttcaacccg tttattctca tgatctcctc   6600
gatggatata ccgctatcct tgctgattct ccagagcgtg tccccttttt gaacggtcac   6660
cgcaccgctc attgtcccgg cgttttgata aacgtggata gaattttgcc ggaacgcctc   6720
ctcacgaagc accgtcagcg gattgattgc atatctttta tcttcagtcc atgaaccgtg   6780
atgcatttca aaatgcaggt gggttccggt cgatattccc gtattgccga tgattccgat   6840
ttgctcgcct tttttcaccc gctccttttc ctttttcagg cgtttgctta agtgggcata   6900
aacggtttca tatccgttgt catgtttaat aaatatcact tggccgtagg agtcggattg   6960
atacgatttg cttatcgttc cgtctgcggc tgccgctact gcttcccctt cgggagcagc   7020
```

-continued

```
gatgtcaagc cccttatgct ttccgcctct cgtaccgaat tgatctgtga tctctccttt   7080
aatcggttca atccactctg aggcttccgc ccccggggca ttgacgaaaa gcgccaatcc   7140
cgaaagccat gcgatcgcga acaggaagtt ttgatgtctg agtttcttca aggttttcca   7200
tatcctccta ttacatgcat cttcggtaaa attgccccct attcggagac agcttagtat   7260
acttccaaat caatacaatt tatacattaa aaaaagactc cgcacaggga gtcttttagt   7320
tttctatcgt catcggattc ggtgcgtacg gaacctgtac agatttcgac aggtcatagg   7380
cgccgacctt ggttatggat gcgtttttaa atttcacttt tgtgaagccg aaatctttcg   7440
cggtcaatag aaggccttcc accatcaaga catcttcggg tttattttca atattcgcgg   7500
aggaagaaaa ttgaatgatc agttcttttc cattcttttg aatatcttca atcggcgtat   7560
catcggataa aatgggtttt aaatgagtgc cgctttcttc gtttttcatc atcttaatcg   7620
cttcctgcac cgattcgtaa gattcgcttg aaggtgcaag gaaccggcgc ccgtctgagc   7680
tttcatataa atagtagcat ttttgcgtct ggtgcataat cgccatatcg gcgagcattc   7740
cgaatgtttc aaattcaaca cccgatttat cattggaaat aaacagaaca gaatcatacg   7800
atccccattt aaaggtttcg ttgatcacat ttttcagccg ttcgaaatct tcgactgata   7860
gctccggtat tttctcatca acttgaatct tcagtttttt attgttttttc tgctctttga   7920
acttcacctt atcaaggtaa gctgtgtcaa atgatgtaaa ctggtccact ccaagccggc   7980
tgtaagcgtg aagcgcatct tcaagatttg tcatgccagt gcttttctcg aggcttaccg   8040
ggacaacgac agacttggac tcgtcaagga aagcgaaggt gatatagtcg tctttttgat   8100
tctgtgagac gacaaacgta tttgcaggtt cagacttggc agcatcagcc tccgtctgca   8160
ccaattttcc gtcagaagaa atgttggcgt cggcgctgtt ttgagatctg atctgttcga   8220
ttaactgggg agtgatcagc atcagaagaa agagaaccaa aactgtagca gcaaatgcgc   8280
cgacccgttt tttcggtgat ttacgctttg gtgcgagaat cagcttttga tagatctgat   8340
ttgccgaacg attatcctta accgttggaa gttggcttag taacgccttc agccgttctt   8400
cgttccattc tgacttcttc attctttgga tcctccttca aaagctccat ctgtttacga   8460
agcactttca gaccgcggtg ctgagtggtt tttaccttgc tttcggaaaa attcaaggct   8520
tttgctgttt cactgatcga atatccttga ataaaacgca agacgataac tgatctttgg   8580
tcaagcgtac acttgtctag ggcctcgaaa atttccttta ggttttcatt ttgcatcacg   8640
atgtcctcag gcagaggctt gcggtctttt acatcttgtt tctcccagtc aaacgtcccc   8700
aaaatccgct ggcggatcgt ctgctgcttt ctgaaccagt cgatcgcaac gtgccgcgca   8760
atcgaaagaa gccaggtttt ttcgctgctc ctgccttcaa atgtttcgta agaatgcagg   8820
acgcggatgt atacttcctg aactaagtct tccgcctgat tttgtcttt taccatataa    8880
aataaaaact gaaataaatc ctgatgatac tgatcatata ttttctgaaa ggtttcttcc   8940
acctgaaacc cctccgttca atttattgtc gtttgtcaat cttaaaaggt tacattacaa   9000
ctattacaac tatattacga acatatgaaa atggaaaggg ggttttgcga aagttaagct   9060
taattttaac ttaacaagca caaaagcacc cgttctaaat gaacaggtgc caaggttata   9120
ggagcccaca ttttcactaa gctgtgccct tacaaggctt tcgttctcct gaccggagcg   9180
ttgcggatcc gctgaaatga actaatttca atccgtttat gactttaagt ccaattgttg   9240
gcgaagcttt ttggaaatct ccattctctt ttcgtcagtc actaggtgat accataagcc   9300
gtcaactttt ttgtcttcac cttcaatttc tacctgctta atatctttag cagcttcttt   9360
ataagaactt tgaatatcga tcatcttgtc cagtgttaag tttgttttga tgtttttttc   9420
```

taatgctgcc aaaatctctt gatagtttgt taatgatttt aattgtgcac cttcatgaat 9480
aatttcgttg ataatctcac gctgacgctc ttgac 9515

<210> SEQ ID NO 145
<211> LENGTH: 1452
<212> TYPE: DNA
<213> ORGANISM: Artificial Sequence
<220> FEATURE:
<223> OTHER INFORMATION: synthetic

<400> SEQUENCE: 145
gcagcgacaa acggaacaat gatgcagtat ttcgagtggt atgtacctaa cgacggccag 60
caatggaaca gactgagaac agatgcccct tacttgtcat ctgttggtat tacagcagta 120
tggacaccgc cggcttataa gggcacgtct caagcagatg tggggtacgg cccgtacgat 180
ctgtatgatt taggcgagtt taatcaaaaa ggtacagtca gaacgaagta tggcacaaaa 240
ggagaactta aatctgctgt caacacgctg cattcaaatg gaatccaagt gtatggtgat 300
gtcgtgatga atcataaagc aggtgctgat tatacagaaa acgtaacggc ggtggaggtg 360
aatccgtcta atagatatca ggaaacgagc ggcgaatata atattcaggc atggacaggc 420
ttcaactttc cgggcagagg aacaacgtat tctaactgga aatggcagtg gttccatttt 480
gatggaacgg attgggacca gagcagaagc ctctctagaa tcttcaaatt ccatggaaag 540
gcgtgggact ggccggtttc ttcagaaaac ggaaattatg actatctgat gtacgcggac 600
tatgattatg accatccgga tgtcgtgaat gaaatgaaaa agtggggcgt ctggtatgcc 660
aacgaagttg ggttagatgg atacagactt gacgcggtca aacatattaa atttagcttt 720
ctcaaagact gggtggataa cgcaagagca gcgacgggaa aagaaatgtt tacggttggc 780
gaatattggc aaaatgattt aggggccctg aataactacc tggcaaaggt aaattacaac 840
caatctcttt ttgatgcgcc gttgcattac aacttttacg ctgcctcaac agggggtgga 900
gcgtacgata tgagaaatat tcttaataac acgttagtcg caagcaatcc gacaaaggct 960
gttacgttag ttgagaatca tgacacacag cctggacaat cactggaatc aacagtccaa 1020
ccgtggttta aaccgttagc ctacgcgttt attctcacga gaagcggagg ctatcctgcg 1080
gtattttatg gagatatgta cggtacaaaa ggaacgacaa catatgagat ccctgctctt 1140
aaatctaaaa tcgaaccttt gcttaaggct agaaaagact atgcttatgg aacacagaga 1200
gactatattg ataacccgga tgtcattggc tggacgagag aaggggactc aacgaaagcc 1260
aagagcggtc tggccacagt gattacagat gggccgggcg gttcaaaaag aatgtatgtt 1320
ggcacgagca atgcgggtga aatctggtat gatttgacag ggaatagaac agataaaatc 1380
acgattggaa gcgatggcta tgcaacattt cctgtcaatg gggctcagt ttcagtatgg 1440 gtgcagcaat ga 1452

<210> SEQ ID NO 146
<211> LENGTH: 9214
<212> TYPE: DNA
<213> ORGANISM: Artificial Sequence
<220> FEATURE:
<223> OTHER INFORMATION: synthetic

<400> SEQUENCE: 146
catcggacag ctcttgcttg atatcttcaa aatgacgccg gctcatgtca tgtcaacttt 60
tgtcgtatct ggagcgatcc ttgacggatt cggcatttac gaccgtttta tcgaatttgc 120
cggtgccggg gctacagtcc cgattgtcag cttcggccac tctcttttgc acggcgcgat 180
gcaccaggct gagaaacatg gctttatcgg aatcggcatg gggatatttg aactgacatc 240
tgccggtata tctgccgcta tcttgttcgc ttttcttgtt gccgtgattt ttaaaccgaa 300
aggataaagg aaaatgccag caaaacgcaa ggtcattttg gtcacagacg gcgatatata 360
cgctgcaaaa gcaatcgaat atgcagcaag aaaaacgggt ggccgctgca tttcccaatc 420
ggcggggaat ccgagcgtta aaacaggacc ggagcttgta accatgatcc tgcaaacccc 480
tcatgatcct gtattcgtca tgtttgatga ttccggactt caaggtgaag gcccgggaga 540
gacagctatg aaatatgtag cgatgcatcc cgatatcgag gtgctcggag tcatcgccgt 600
cgcttcaaaa actcattatg cagagtggac gagagtcgat gtatcaatcg atgcagaagg 660
cgaactgaca gagtacggcg tcgataaaca cggggtcaaa gagttcgatg tcaaacgaat 720
gaatggtgat acagtctatt gccttgacca gctggatgtt ccgatcattg tcggaatcgg 780
tgatatcggt aagatgaaca gaaaagacga tgtggaaaaa ggttcgccga ttacaatgaa 840
agcggtcgag ctcattttag aaaggagcgg gtatcatgag tgctcaaaag caagagaaga 900
cgaacgtatt ccttgatcct tctaagaatg aagcgtattt caagaagcgg gtcggcatgg 960
gagaaagctt tgaccttggc gtacggaagg tctttattct cggacatgaa gttcagcttt 1020
attatgtcaa cggattgtgc gacacacaat acatcattca cctgttaaga gaactggtgc 1080
atctgaatga taaagaaaaa gaatcgggcg aggtcgaaga catcgtcgaa aacaggcttt 1140
tgaaccagca ggtttcaaaa gcggaaacgc ttgatgaagc tgtcgaccaa gtgttgtcag 1200
gactggttgc catcatcgtc gaagatgcgg gctttgcttt tatcatcgat gtcagaagct 1260
acccgggcag aacgccggaa gaacctgata cagaaaaagt cgtacgcggt gcaagggacg 1320
gactcgtcga gaacatcatc gtcaacacag ccctgattag acgccggatc agagatgagc 1380
gcttgcgcta caaaatgctt catatcggtg aacgctctaa aacagacatc tgcctctgct 1440
atttggaaga cgttgcagat cccgatcttg ttgaagtatt aaaaaaagaa attgaagatg 1500
tgaagatcga cgggctgccg atgtcggata aatcggtaga ggaattcctg gtcggccaag 1560
gctacaatcc gtttccgctt gtcaggttta cggaaagggc agacgtagcc gcaagccata 1620
ttttagaggg gcatgtcatc gtgatcgtcg atacgtcgcc aagcgtcatc atcacaccga 1680
ccactttgtt tcaccatgtt cagcatgctg aggaatacag acagacgccg gctgttggga 1740
cgtttttaag gtgggtgcgg tttttcggta ttttggcctc cacctttttg ctgccgcttt 1800
ggctgctgtt tgtcattcat ccgtcgctct tgcctgataa tttatcgttt atcgggttga 1860
ataaagacac ccatattccg attatcatgc agattttcct ggcggatctc ggcgtcgaat 1920
ttttaagaat ggccgccatt catacgccga cggcgctttc gactgcaatg ggcctgatcg 1980
ccgctgtatt gatcggcgat atcgcgatca atgtcggctt gttttctccc gaagtcattt 2040
tatacgtttc cctctcggca atcggagcct acacgacacc aagctacgag ctgagcctgg 2100
cgaataaaat ggtgaagctg tttatgctga tattggtggc gctttttaaa gtggagggat 2160
ttgtcatcgg attaacgatc ttaactatag tgatgacttc gatcaggtca ttgcgaacgc 2220
cttacttatg gcctctcctc ccgttcaatg gaaaagcgtt ttggcatgtt ctcgtgcgca 2280
cgtccgttcc agggggaaaa gtcaggccga gcatcgttca tccgagaaac cgctccagac 2340
agccgtgaag ccggcattcg aagaggcttt tccccgggga aaagcctctt tttcaataat 2400
cgaattccgg tctttgagta ccgatgcctc tgtattcatt ggcagagatc gcgactgccc 2460
ggaggctgca gatgttgttc tgtcttctga tcggatagac gacatacagc atttcgcggc 2520

```
cgtacgggtc aatcgttgac gaatgaagga aaacctcagt tcctctccgc caaaatctcg   2580
tattcgccgg agctgtaata atctgccctt cataaggctc ataaattctc tgttcataat   2640
gcgcagccgg ctgataaggg gcgtatacat cttcaggtgc atagccggga gcgggggtgt   2700
agggatagcg atttggatac atatgataac ctctttccca cttcgttttt tggttttcat   2760
ctttaagatt atattcaggt aaatgcctat ttgtatgggc gaaaatctca gcttttcggc   2820
tcttttttta ttgaatggac gttgtgtatg cctatttcta tcaagcgctg ttttctgtta   2880
ttctataatc aatagaatgg attagttgtt tagggaatca tttcctttat aaatcaagaa   2940
aatttggaca aatggtggtt tagtttttaa aacgaaatgt tataatacaa cataagaatc   3000
gcactatcat gaagccggaa gatgcatcgg gcagcaaccg gagcgcccct tgcacctttg   3060
tcgatagaga aagagggaat gacaattgtt tttacacggt actagcagac aaaatgaaag   3120
agggcacctc gaaatcggcg gtgtcgatgt tctatcattg gcagaaagat acggaacacc   3180
tctttatgta tacgatgtcg cgctgattag agagcgcgcc cgaaaattcc agaaggcatt   3240
caaggaagcc ggtttaaaag cgcaggtagc gtatgcaagc aaggcgtttt catcggttgc   3300
catgattcag cttgccgaac aagaggggct gtctctggat gtggtatcgg gaggagagct   3360
tttcactgcg atcaaagcag ggttcccagc tgagcggatt cattttcacg gaaacaataa   3420
gagccctgaa gaactagcca tggcgctgga gcatcaaatc ggctgcatcg tgctcgataa   3480
ctttcacgag atcgccatta cagaagatct ttgcaagcga tcaggacaaa ctgtagacgt   3540
tttgctcaga atcactccgg gagttgaagc gcacacgcac gattatatta cgacggggca   3600
ggaagattcc aaattcggtt ttgatctgca taatggacag gtcgaacaag ccatcgaaca   3660
agtcctccgc tcgtctgcgt ttaagctcct cggcgtgcac tgccacatcg gttcgcaaat   3720
ttttgatacg gcaggatttg tccttgcagc agacaagatt ttcgagaagc ttgcggaatg   3780
gcgggagact tactctttca ttccggaagt gctcaatctt ggcgggggct tcggcatccg   3840
ctatacaaaa gacgacgagc cgcttgcagc tgatgtttat gttgaaaaaa tcatcgaggc   3900
ggtcaaagca aatgccgagc atttcggctt tgacatccct gagatttgga tcgaaccagg   3960
ccggtctctc gtcggtgatg cggggactac gctgtacacg atcggttctc aaaaagaggt   4020
gccgggcatt cgcaaatatg tagccatcga cggcggcatg agcgataata tcaggccggc   4080
gctttatgag gcaaaatatg aagcagccgt cgccaacagg atgaacgatg cttgtcatga   4140
taccgcatca atcgcaggaa aatgctgcga aagcggagat atgctgattt gggatttgga   4200
aatccccgaa gttcgcgacg gagatgtgct cgccgttttc tgcaccggtg cgtacggcta   4260
cagcatggcc aacaactaca accgcattcc gcgcccggcc gtcgtctttg tcgaggacgg   4320
ggaagcgcag ctcgtcattc agagagagac gtatgaggat atcgtcaagc tggatctgcc   4380
gctgaaatcg aaagtcaaac aataaaaaaa tggagattcc ctaagagggg ggtctccatt   4440
tttaattcaa gctgataaac agctgacatc aactaaaagt ttcattaaat actttgaaaa   4500
aagttgttga cttaaaagaa gctaaatgtt atagtaattg tacagaatag tcttttaagt   4560
aagtctactc tgaatttttt taaaaggaga gggtaaagat gaaacaacaa aaacggcttt   4620
acgcccgatt gctgacgctg ttatttgcgc tcatcttctt gctgcctcat tctgcagcta   4680
gcgcagcagc gacaaacgga acaatgatgc agtatttcga gtggtatgta cctaacgacg   4740
gccagcaatg gaacagactg agaacagatg cccccttactt gtcatctgtt ggtattacag   4800
cagtatggac accgccggct tataagggca cgtctcaagc agatgtgggg tacggcccgt   4860
```

acgatctgta tgatttaggc gagtttaatc aaaaaggtac agtcagaacg aagtatggca 4920
caaaaggaga acttaaatct gctgtcaaca cgctgcattc aaatggaatc caagtgtatg 4980
gtgatgtcgt gatgaatcat aaagcaggtg ctgattatac agaaaacgta acggcggtgg 5040
aggtgaatcc gtctaataga tatcaggaaa cgagcggcga atataatatt caggcatgga 5100
caggcttcaa ctttccgggc agaggaacaa cgtattctaa ctggaaatgg cagtggttcc 5160
attttgatgg aacggattgg gaccagagca gaagcctctc tagaatcttc aaattccatg 5220
gaaaggcgtg ggactggccg gtttcttcag aaaacggaaa ttatgactat ctgatgtacg 5280
cggactatga ttatgaccat ccggatgtcg tgaatgaaat gaaaaagtgg ggcgtctggt 5340
atgccaacga agttgggtta gatggataca gacttgacgc ggtcaaacat attaaattta 5400
gctttctcaa agactgggtg gataacgcaa gagcagcgac gggaaaagaa atgtttacgg 5460
ttggcgaata ttggcaaaat gatttagggg ccctgaataa ctacctggca aaggtaaatt 5520
acaaccaatc tctttttgat gcgccgttgc attacaactt ttacgctgcc tcaacagggg 5580
gtggagcgta cgatatgaga aatattctta ataacacgtt agtcgcaagc aatccgacaa 5640
aggctgttac gttagttgag aatcatgaca cacagcctgg acaatcactg gaatcaacag 5700
tccaaccgtg gtttaaaccg ttagcctacg cgtttattct cacgagaagc ggaggctatc 5760
ctgcggtatt ttatggagat atgtacggta caaaaggaac gacaacatat gagatccctg 5820
ctcttaaatc taaaatcgaa cctttgctta aggctagaaa agactatgct tatggaacac 5880
agagagacta tattgataac ccggatgtca ttggctggac gagagaaggg gactcaacga 5940
aagccaagag cggtctggcc acagtgatta cagatgggcc gggcggttca aaaagaatgt 6000
atgttggcac gagcaatgcg ggtgaaatct ggtatgattt gacagggaat agaacagata 6060
aaatcacgat tggaagcgat ggctatgcaa catttcctgt caatgggggc tcagtttcag 6120
tatgggtgca gcaatgaaag cttctcgagg ttaacagagg acggatttcc tgaaggaaat 6180
ccgttttttt attttcaagc acgaaaaaca cttcccggtg atcgggaggt gtttttttgtt 6240
aaaaagatca tgacatgcat agaacagcga ccgggctaat tgtatataat attgtgaatt 6300
taacaaaaaa tttacaaagg agatgataaa ggcaatgacc agggtgaaaa ggatgagatt 6360
tgctgatttg ttggatttag aggcggagta gatgaaaccg gccaaagtat ccctactcca 6420
ccgattgctc cagtgcctga agcaatgtgt tgattgtaac acagtaaatc gttttacagc 6480
aataaacatt tttgtgaata ttttattgat ttcggctgtg atctcattcc catattctgc 6540
tgcggcccat ggcgcaacac agtccggcga tcaatattca agctttgaag aattggagcg 6600
gaatgaagat ccagcttctt accgaattac ggagaagaac gcaagagtgc cgatgctcat 6660
catggccatc catggaggcg gcatcgaacc cggaacgagc gaaatcgcca atgaagtgtc 6720
caaaaactat tccctgtact tgtttgaagg gctgaaatca tcaggcaata cggaccttca 6780
cattacaagc acgcgttttg acgagccagc ggcgctcgca attactgcaa gccaccagta 6840
tgtcatgtcg ctccacggct attacagtga agaccgcgat attaaagtag gcggcacaga 6900
ccgcgctaaa atcagaatat tggttgatga gctgaaccgc tcggggtttg ccgctgaaat 6960
gctggggaca gatgacaagt atgccggaac ccatccgaat aacatcgcca acaagtcgct 7020
ttccgggctg agcattcagc ttgaaatgag cacgggtttc cgcaaatctt tattcgaccg 7080
gtttacacta aaagacaggg cggcgacgca aaacgaaacg ttttaccgat ttacaaagct 7140
gctgacagat tttattcatg aaaactatga agaagacgga ggggatttcc cctctgcaaa 7200
aataaaacac ccccttcaag tgaaaaagga ggtgtttcgg cggttgtgtt aaccgttgga 7260

```
ctctgaggtg ccgccgccgg tgaatacgga aacgatggcg ttccacagag acacaaagaa   7320
gtcgatcagt ttttgaagaa agttttgtcc ttcttcagaa tccaagaatt tcgtgatttt   7380
atcctttgct ttgtcaagct ggtctccaac ctggttccag tcgatattaa tatttttcat   7440
gttattaaat aaagatataa gagagttttt ctgatcttct gtgagtgtca cgccaagttc   7500
ggaagcagcc gaatcaatcg ttttctccaa ttcctctttt gactcgggaa ctccgttttt   7560
cgagatttct tccttgactt tggccatcag cgctgacgcg ttttcactgc cgattttctc   7620
gccaagctct gaagtggtga caagctcttc attcgcgacc tttttcacat cttcggaaat   7680
tttttcgccc gaagtcgttt catacgcttt catcaatccg gttaaagcgg ctgtgcctga   7740
cacttcaaac ggagcggtga catagacttt ggcgtctttt acaccggccg tcatcagcgc   7800
gttcaaatac atctcatctg taattctgct gatattgtgt gtctgaactt ccaaaccggt   7860
gcctttttc gctacggtaa ttgaagaaga agaaatcgct cttgttccga tttgtgcttt    7920
cggtatataa tcccctaaat atttatgctc ctcatcattt gtcacctcga tgatggtcgc   7980
attttcaggc gcattcattt cttttaatac tttttgtctg tcctggcttg acaagtcttt   8040
ccccagcgtg acgatgacat cacccactgc ggcgtcagcg aagctgacct gcgggaaaat   8100
gagcagacac aatgctgtaa agattcctag tatcgatttt ttcaagctca atgccctcct   8160
taaaaatgca ggcttcaggc agaattgctg tacttttaaa gaagcctgcc ggaacggaaa   8220
taatgcgttc cgaaatatag acggatgaaa gatgagtgag gtttcaaaga aaaaaagaga   8280
gaattttctc ttcaagtcaa atgccctccc ggcatcgtat ctcgccgctc ttttatcatt   8340
catgattttc acaggcgatt caaccttttt ttaaaatttt ttacaaaaac gatacaagag   8400
cggcgtttat ttcggtcgat tggctctctg cttcttcaat atgatataat gacccttgtg   8460
aaatgaaagg agagaatcaa gatggctaaa aaaggataca tacaactgac aaacggcaaa   8520
aaaatcgagt ttgaactata tccggatgcg gcgccgggaa ctgtcgccaa ctttgaaaaa   8580
cttgcaaacg aagggttcta tgacgggctg aagttccacc gcgtcatccc gggcttcgtc   8640
agccagggag gctgcccgca cggcaccgga acaggcggac ctggatatac gattaaatgc   8700
gagacagaag ggaatccgca caaacacgaa gccggttctc tctcaatggc tcacgcagga   8760
aaagataccg gaggcagcca atttttatc gtccatgagc ctcagccgca cttgaacggc    8820
gttcacaccg ttttcggaaa ggtcacatca ggccttgatg ccgtcacttc aatggagcag   8880
ggacaaggca tggaaaaagt cgaagtattt gatgcataat cagagagcgc aaaaaacagc   8940
ccgcttagcc gggctgtttt tttgtctgta acggtgttta ttttccaggt gcaacaggac   9000
ttgaggccga ttcttcgtcc acatcctgat aggaaataac gatgctaata aataaaataa   9060
ttgtgaaaaa atgacccttt atgtaaaata tattcaagtg aagagctaga tagagaacgc   9120
aatctgtaaa aaaggaaggg gcgtaagggg tgagcgtaaa aatcccatcg acggcagtcg   9180
gcgtaaaaat taatgactgg tataacgcga tacg                               9214
```

<210> SEQ ID NO 147
<211> LENGTH: 483
<212> TYPE: PRT
<213> ORGANISM: Artificial Sequence
<220> FEATURE:
<223> OTHER INFORMATION: synthetic

<400> SEQUENCE: 147

```
Ala Ala Thr Asn Gly Thr Met Met Gln Tyr Phe Glu Trp Tyr Val Pro
1               5                   10                  15
```

```
Asn Asp Gly Gln Gln Trp Asn Arg Leu Arg Thr Asp Ala Pro Tyr Leu
            20                  25                  30

Ser Ser Val Gly Ile Thr Ala Val Trp Thr Pro Pro Ala Tyr Lys Gly
        35                  40                  45

Thr Ser Gln Ala Asp Val Gly Tyr Gly Pro Tyr Asp Leu Tyr Asp Leu
    50                  55                  60

Gly Glu Phe Asn Gln Lys Gly Thr Val Arg Thr Lys Tyr Gly Thr Lys
65                  70                  75                  80

Gly Glu Leu Lys Ser Ala Val Asn Thr Leu His Ser Asn Gly Ile Gln
                85                  90                  95

Val Tyr Gly Asp Val Val Met Asn His Lys Ala Gly Ala Asp Tyr Thr
            100                 105                 110

Glu Asn Val Thr Ala Val Glu Val Asn Pro Ser Asn Arg Asn Gln Glu
        115                 120                 125

Thr Ser Gly Glu Tyr Asn Ile Gln Ala Trp Thr Gly Phe Asn Phe Pro
    130                 135                 140

Gly Arg Gly Thr Thr Tyr Ser Asn Phe Lys Trp Gln Trp Phe His Phe
145                 150                 155                 160

Asp Gly Thr Asp Trp Asp Gln Ser Arg Ser Leu Ser Arg Ile Phe Lys
                165                 170                 175

Phe Thr Gly Lys Ala Trp Asp Trp Pro Val Ser Ser Glu Asn Gly Asn
            180                 185                 190

Tyr Asp Tyr Leu Met Tyr Ala Asp Tyr Asp Tyr Asp His Pro Asp Val
        195                 200                 205

Val Asn Glu Met Lys Lys Trp Gly Val Trp Tyr Ala Asn Glu Val Gly
    210                 215                 220

Leu Asp Gly Tyr Arg Leu Asp Ala Val Lys His Ile Lys Phe Ser Phe
225                 230                 235                 240

Leu Lys Asp Trp Val Asp Asn Ala Arg Ala Ala Thr Gly Lys Glu Met
                245                 250                 255

Phe Thr Val Gly Glu Tyr Trp Gln Asn Asp Leu Gly Ala Leu Asn Asn
            260                 265                 270

Tyr Leu Ala Lys Val Asn Tyr Asn Gln Ser Leu Phe Asp Ala Pro Leu
        275                 280                 285

His Tyr Asn Phe Tyr Ala Ala Ser Thr Gly Gly Gly Tyr Tyr Asp Met
    290                 295                 300

Arg Asn Ile Leu Asn Asn Thr Leu Val Ala Ser Asn Pro Thr Lys Ala
305                 310                 315                 320

Val Thr Leu Val Glu Asn His Asp Thr Gln Pro Gly Gln Ser Leu Glu
                325                 330                 335

Ser Thr Val Gln Pro Trp Phe Lys Pro Leu Ala Tyr Ala Phe Ile Leu
            340                 345                 350

Thr Arg Ser Gly Gly Tyr Pro Ser Val Phe Tyr Gly Asp Met Tyr Gly
        355                 360                 365

Thr Lys Gly Thr Thr Thr Arg Glu Ile Pro Ala Leu Lys Ser Lys Ile
    370                 375                 380

Glu Pro Leu Leu Lys Ala Arg Lys Asp Tyr Ala Tyr Gly Thr Gln Arg
385                 390                 395                 400

Asp Tyr Ile Asp Asn Pro Asp Val Ile Gly Trp Thr Arg Glu Gly Asp
                405                 410                 415

Ser Thr Lys Ala Lys Ser Gly Leu Ala Thr Val Ile Thr Asp Gly Pro
            420                 425                 430
```

Gly Gly Ser Lys Arg Met Tyr Val Gly Thr Ser Asn Ala Gly Glu Ile
        435                 440                 445

Trp Tyr Asp Leu Thr Gly Asn Asn Ser Thr Lys Ile Thr Ile Gly Ser
    450                 455                 460

Asp Gly Tyr Ala Thr Phe Pro Val Asn Lys Gly Ser Val Ser Val Trp
465                 470                 475                 480

Val Gln Gln

<210> SEQ ID NO 148
<211> LENGTH: 9516
<212> TYPE: DNA
<213> ORGANISM: Artificial Sequence
<220> FEATURE:
<223> OTHER INFORMATION: synthetic

<400> SEQUENCE: 148
ctgggagctg atagcacagc gatttcccgc ctcctgtcgg aagcatcgcc accgtgtccc 60
gtccctccag cacgcttttg atgatcgttt cctggccttt tttaaaagca tgataaccaa 120
aatacctgcg gagcgcctga tgaagtttat ccattcctga tcaccgtttt cgacagggcc 180
aggcggattt taaaataact gtatcggccg ccgagtccct ctttaatttg tctgatttta 240
ttggtttggt tcgctatcgc ataatcggca ataattttct gttcctcttt cgacacgtac 300
tgatcgatgg aaaaagacgg atcatgaatg gcgatttcca caatgtgatc ctcgatcgtc 360
gccaatttca gctttctaat ttttgcgatc cggtctattg tatacccttc ttttataaga 420
aagagcgttt ttctcgtcga ttgtgtcaga ccatcattca aaggaatgtc atgaatgagc 480
gtttgaaaaa gcggactttc accattttgg gcggattgaa taaaatggtg cagaacatcc 540
caaaacagtg catatatgta ccactcatca aggttcattt tttcggaaag ctgtctgaat 600
gtatagcccg cttttgttct ggatgtcagg gagtgaacaa aaatagcggc ctgttcatca 660
tgatttaaaa cagacagctt ctctttcagc tcttggtgaa actgggccgc tgtttcagca 720
gcattccggt ttcttaaata ctgtttaacc cagttctgaa tctgataatc ttttacgatc 780
ggcaaataca cgcgttcgcg gtaaagcttg ttggagagca cttggatcaa aagcgacatc 840
cttgcccaca tcactttggc tgccgcctga taatagccgc cgtgaaaatg gcggggccac 900
ggataaaggg caaaaaagcc ggcaagttcc gcttctcctt tttcggtgac ggtgtaagcg 960
ccgctttccg ctttttctct gaccaaagac tcctgcttca atcgttgaac gctggctgcc 1020
acctgctctc tcgacagagc cgaacaaaag ccgaagtatt ttgaaacggc aaataaaccg 1080
gcgtcctgta tcgtctgtga cgaccttttt ccttttaata aatgatagac cgcgcttgga 1140
gaacgctcac ccttcatgga tgacagaatg tcaagcacaa tcgcgtcaaa aaaatgaacc 1200
ggcatatcat cacctgcaat cttccggcaa cattcgatca tttcttcctt ttattttaac 1260
agattttgcg gagaaatcga cgtttaaact catataaaag ggtatgttta gcagtagaac 1320
ccttgtgtga taagcattct caatattttt gagttgaaat gtaagattaa caccattaca 1380
ataaggaatg ggaataggtt tcatatcgga tagatagagg gttaaaccat ttgttccaac 1440
gaagaacaat ctgggaggtt ttttattcat gccaaaatat acaattgtag acaaagatac 1500
gtgcatcgca tgcggagctt gtggtgctgc ggctcctgat atttatgatt acgacgatga 1560
gggaatcgca tttgtcaccc ttgacgacaa tcagggtgtc gtcgaagtcc ctgacgtctt 1620
agaagaagac atgatggacg cgtttgaagg ctgtcctaca gattcgatca aagttgcgga 1680
tgagccgttc gaaggcgacc cgcttaaaca cgaataaagc caaaaaacat ccggtgcaca 1740
aagtgccgga tgttttttta tgagataagc acggctttac caacaagcaa aaagaagccg 1800
gctaaagaca tccggcttct tctgcagctg acaatatccg ggaacatgca cccgatattg 1860
tcatgtttat ttatttggcc atgcggacgt tttccttcag ccgcggtttc agcgaaagga 1920
aaatcggcgt ggacacgagg gccacagcga tgcctttaat gaaattaaaa ggcaggattc 1980
cggccagaac tgttgtcttg agcgcctctc cagtcagcgc tggagcattt aaaaaccaag 2040
tgtaggcagg cagaaacagc agataattta aaatgctcat cgaaacggcc atcacaagcg 2100
tccctgcgaa aagagctgtg acaaaccctt tggcagaact tgatttttttc agcagtacag 2160
ctgccggcag gataaacaat gttccggcaa tgaagttagc cgcctgatca atcggaacgc 2220
ccgaggcgct tcctgcaata aagtaattca gcacgttttt gatcgcttca acggcaatcc 2280
cggctcccgg accgtacaaa ataacagcga gcaatgccgg gatatcactg aaatcgattt 2340
ttaaatacgg gaatgccccc aggatcggaa agctcagcat cattaaaata aatgcgatgc 2400
tgctcagcat gctgatagag acgagacgtc tcaccttgtt gtgtttcatt ttgtcactct 2460
ctccttttcg atcacatctc acgaaaaagag gaatggttct ttcccctgtc ctaaacaaaa 2520
aacccgcttt attgaaaaag cggggctgtt ttacagacag gtcaaataaa cgtttgaaaa 2580
tgttcatttc aaaacgcgcg gaacctccat cttctcccat ccagactata ctgtcggctt 2640
cggaatcgca ccgaatcctg cccataaaaa ggctcgcggg cttagagcgc ttgctcatca 2700
ccgccggtag ggaatttcac cctgccccga agattgatct tatttatttt taatactgat 2760
attattataa attaattgtg aaaaaatgta caggtgcaaa gcttattgcg ctgttttggg 2820
acatcctgca cgatatttcg gtaaactcac tttttccgca tactaaaaac cgcacattca 2880
cagttatttc atttttaatt ttcgtctttc cgcgtgaaac tcattgacac tctttatgga 2940
atatggtaaa ttatcagata tttatgacgc ttatttagga ggaaatctta catgtttcga 3000
gtattggtct cagataaaat gtccagcgac ggcctcaaac cattaatgga agcagatttt 3060
attgaaattg tagaaaagaa tgttgcggaa gcggaagacg agcttcatac gtttgacgcg 3120
ctcttggtgc ggagcgccac gaaggtaacc gaagagctgt ttaaaaagat gacttcgctg 3180
aaaatcgtcg ccagagcagg tgtcggcgtc gacaatatcg atattgacga ggcgacaaaa 3240
cacggtgtta tcgtcgtaaa cgcgccaaac gggaatacaa tttcaaccgc tgaacatacc 3300
tttgcaatgt tttcagcgtt aatgagacat attccgcagg caaacatctc cgtgaaatca 3360
agggagtgga atcgttcggc ttacgtcggt tcagagcttt acggaaaaac gctcggcatc 3420
atcggaatgg gccgcatcgg aagcgaaatc gcgagccgcg caaaagcatt cggtatgacc 3480
gttcatgtat ttgacccgtt cctgacccaa gaaagggcaa gcaagctcgg cgttaacgcg 3540
aacagctttg aagaagttct ggcatgcgcc gacatcatta cggttcatac cccgctcacg 3600
aaagaaacga agggactttt gaacaaagaa accatcgcaa aaacgaaaaa aggcgttcgt 3660
ctcgttaact gtgcaagagg cggcatcatc gatgaagcag cgcttttgga agctctggaa 3720
agcggacatg tcgctggcgc tgccttggat gtattcgaag tcgagcctcc ggtcgattca 3780
aaactgatcg atcatccgct tgtagtcgcg actcctcact tgggcgcctc aacaaaagaa 3840
gcccagctga atgtcgctgc acaagtgtcc gaagaagtcc ttcagtatgc gcaaggaaac 3900
cctgtgatgt ccgcgatcaa ccttccggcc atgacaaagg attcattcga aaaaatccag 3960
ccttatcatc agtttgccaa tacgatcgga aaccttgtgt ctcagtgcat gaatgagcct 4020
gttcaagatg tagccatcca atatgaaggc tccatcgcca aacttgaaac gtcatttatt 4080
acgaaaagcc ttttggccgg atttctgaag ccgagggtcg cggctaccgt taacgaagtg 4140

```
aatgccggca ccgttgcgaa agagcgcggc atcagcttca gcgaaaaaat ttcttccaat   4200
gagtcaggct atgaaaactg catctctgtg actgtcacgg gagatgtaac aacattctct   4260
ttaagagcga cgtacattcc gcacttcggc ggacgcatcg ttgccttaaa cggctttgat   4320
attgattttt atccggctgg acaccttgtc tacattcacc accaggataa accaggggct   4380
atcggccatg tcggacgaat tttaggagac catgacatca atatcgccac tatgcaggta   4440
ggccgaaaag aaaaaggcgg agaagcgatc atgatgcttt cctttgaccg ccaccttgag   4500
gacgatattt tagctgagct gaaaaacatc ccggatatcg tgtctgttaa agccatcgac   4560
cttccttaag tcgctgataa acagctgaca tcaatatcct atttttttcaa aaaatatttt   4620
aaaaagttgt tgacttaaaa gaagctaaat gttatagtaa taaaacagaa tagtctttta   4680
agtaagtcta ctctgaattt ttttaaaagg agagggtaaa gaatgaaaca acaaaaacgg   4740
ctttacgccc gattgctgac gctgttattt gcgctcatct tcttgctgcc tcattctgca   4800
gctagcgcag cagcgacaaa cggaacaatg atgcagtatt tcgagtggta tgtacctaac   4860
gacggccagc aatggaacag actgagaaca gatgcccctt acttgtcatc tgttggtatt   4920
acagcagtat ggacaccgcc ggcttataag ggcacgtctc aagcagatgt ggggtacggc   4980
ccgtacgatc tgtatgattt aggcgagttt aatcaaaaag gtacagtcag aacgaagtat   5040
ggcacaaaag gagaacttaa atctgctgtc aacacgctgc attcaaatgg aatccaagtg   5100
tatggtgatg tcgtgatgaa tcataaagca ggtgctgatt atacagaaaa cgtaacggcg   5160
gtggaggtga atccgtctaa tagaaatcag gaaacgagcg gcgaatataa tattcaggca   5220
tggacaggct tcaactttcc gggcagagga acaacgtatt ctaacttcaa atggcagtgg   5280
ttccattttg atggaacgga ttgggaccag agcagaagcc tctctagaat cttcaaattc   5340
acgggaaagg cgtgggactg gccggtttct tcagaaaacg gaaattatga ctatctgatg   5400
tacgcggact acgattatga ccatccggat gtcgtgaatg aaatgaaaaa gtggggcgtc   5460
tggtatgcca acgaagttgg gttagatgga tacagacttg acgcggtcaa acatattaaa   5520
tttagctttc tcaaagactg ggtggataac gcaagagcag cgacgggaaa agaaatgttt   5580
acggttggcg aatattggca aaatgattta ggggccctga ataactacct ggcaaaggta   5640
aattacaacc aatctctttt tgatgcgccg ttgcattaca acttttacgc tgcctcaaca   5700
gggggtggat attacgatat gagaaatatt cttaataaca cgttagtcgc aagcaatccg   5760
acaaaggctg ttacgttagt tgagaatcat gacacacagc ctggacaatc actggaatca   5820
acagtccaac cgtggtttaa accgttagcc tacgcgttta ttctcacgag aagcggaggc   5880
tatccttctg tattttatgg agatatgtac ggtacaaaag gaacgacaac aagagagatc   5940
cctgctctta aatctaaaat cgaacctttg cttaaggcta gaaaagacta tgcttatgga   6000
acacagagag actatattga taacccggat gtcattggct ggacgagaga aggggactca   6060
acgaaagcca agagcggtct ggccacagtg attacagatg ggccgggcgg ttcaaaaaga   6120
atgtatgttg gcacgagcaa tgcgggtgaa atctggtatg atttgacagg gaataactca   6180
acaaaaatca cgattggaag cgatggctat gcaacatttc ctgtcaataa aggctcagtt   6240
tcagtatggg tgcagcaata gaagcttctc gaggttaaca gaggacggat ttcctgaagg   6300
aaatccgttt ttttatttta cagaagctgc ggaacctgaa aagaattcct ttcaggttcc   6360
gtttttttta ggaattctcc ctgatctcaa gcatctggcg gggataaatc cgctctcctt   6420
tcaaatcgtt ccattctttg aggcgctgta cagttacgcc catttttttcg gcgatatgat   6480
```

```
gaagcgtatc ccctttccgc actacatatg taccggtctt cgattcatcg tcatgaaggc   6540
ggagtgtttg gccggccttg agatttgaat gtttcaaccc gtttattctc atgatctcct   6600
cgatggatat accgctatcc ttgctgattc tccagagcgt gtccccttt tgaacggtca   6660
ccgcaccgct cattgtcccg gcgttttgat aaacgtggat agaattttgc cggaacgcct   6720
cctcacgaag caccgtcagc ggattgattg catatctttt atcttcagtc catgaaccgt   6780
gatgcatttc aaaatgcagg tgggttccgg tcgatattcc cgtattgccg atgattccga   6840
tttgctcgcc ttttttcacc cgctcctttt cctttttcag gcgtttgctt aagtgggcat   6900
aaacggtttc atatccgttg tcatgtttaa taaatatcac ttggccgtag gagtcggatt   6960
gatacgattt gcttatcgtt ccgtctgcgg ctgccgctac tgcttcccct tcgggagcag   7020
cgatgtcaag ccccttatgc tttccgcctc tcgtaccgaa ttgatctgtg atctctcctt   7080
taatcggttc aatccactct gaggcttccg cccccggggc attgacgaaa agcgccaatc   7140
ccgaaagcca tgcgatcgcg aacaggaagt tttgatgtct gagtttcttc aaggttttcc   7200
atatcctcct attacatgca tcttcggtaa aattgccccc tattcggaga cagcttagta   7260
tacttccaaa tcaatacaat ttatacatta aaaaaagact ccgcacaggg agtcttttag   7320
ttttctatcg tcatcggatt cggtgcgtac ggaacctgta cagatttcga caggtcatag   7380
gcgccgacct tggttatgga tgcgttttta aatttcactt ttgtgaagcc gaaatctttc   7440
gcggtcaata gaaggccttc caccatcaag acatcttcgg gtttattttc aatattcgcg   7500
gaggaagaaa attgaatgat cagttctttt ccattctttt gaatatcttc aatcggcgta   7560
tcatcggata aaatgggttt taaatgagtg ccgctttctt cgtttttcat catcttaatc   7620
gcttcctgca ccgattcgta agattcgctt gaaggtgcaa ggaaccggcg cccgtctgag   7680
ctttcatata aatagtagca tttttgcgtc tggtgcataa tcgccatatc ggcgagcatt   7740
ccgaatgttt caaattcaac acccgattta tcattggaaa taaacagaac agaatcatac   7800
gatccccatt taaaggtttc gttgatcaca tttttcagcc gttcgaaatc ttcgactgat   7860
agctccggta ttttctcatc aacttgaatc ttcagttttt tattgttttt ctgctctttg   7920
aacttcacct tatcaaggta agctgtgtca aatgatgtaa actggtccac tccaagccgg   7980
ctgtaagcgt gaagcgcatc ttcaagattt gtcatgccag tgcttttctc gaggcttacc   8040
gggacaacga cagacttgga ctcgtcaagg aaagcgaagg tgatatagtc gtctttttga   8100
ttctgtgaga cgacaaacgt atttgcaggt tcagacttgg cagcatcagc ctccgtctgc   8160
accaatttc cgtcagaaga aatgttggcg tcggcgctgt tttgagatct gatctgttcg   8220
attaactggg gagtgatcag catcagaaga aagagaacca aaactgtagc agcaaatgcg   8280
ccgacccgtt ttttcggtga tttacgcttt ggtgcgagaa tcagcttttg atagatctga   8340
tttgccgaac gattatcctt aaccgttgga agttggctta gtaacgcctt cagccgttct   8400
tcgttccatt ctgacttctt cattctttgg atcctccttc aaaagctcca tctgtttacg   8460
aagcactttc agaccgcggt gctgagtggt ttttaccttg ctttcggaaa aattcaaggc   8520
ttttgctgtt tcactgatcg aatatccttg aataaaacgc aagacgataa ctgatctttg   8580
gtcaagcgta cacttgtcta gggcctcgaa aatttccttt aggttttcat tttgcatcac   8640
gatgtcctca ggcagaggct tgcggtcttt tacatcttgt ttctcccagt caaacgtccc   8700
caaaatccgc tggcggatcg tctgctgctt tctgaaccag tcgatcgcaa cgtgccgcgc   8760
aatcgaaaga agccaggttt tttcgctgct cctgccttca aatgtttcgt aagaatgcag   8820
gacgcggatg tatacttcct gaactaagtc ttccgcctga tttttgtctt ttaccatata   8880
```

```
aaataaaaac tgaaataaat cctgatgata ctgatcatat attttctgaa aggtttcttc   8940

cacctgaaac ccctccgttc aatttattgt cgtttgtcaa tcttaaaagg ttacattaca   9000

actattacaa ctatattacg aacatatgaa aatggaaagg gggttttgcg aaagttaagc   9060

ttaattttaa cttaacaagc acaaaagcac ccgttctaaa tgaacaggtg ccaaggttat   9120

aggagcccac attttcacta agctgtgccc ttacaaggct ttcgttctcc tgaccggagc   9180

gttgcggatc cgctgaaatg aactaatttc aatccgttta tgactttaag tccaattgtt   9240

ggcgaagctt tttggaaatc tccattctct tttcgtcagt cactaggtga taccataagc   9300

cgtcaacttt tttgtcttca ccttcaattt ctacctgctt aatatcttta gcagcttctt   9360

tataagaact ttgaatatcg atcatcttgt ccagtgttaa gtttgttttg atgttttttt   9420

ctaatgctgc caaaatctct tgatagtttg ttaatgattt taattgtgca ccttcatgaa   9480

taatttcgtt gataatctca cgctgacgct cttgac                            9516
```

```
<210> SEQ ID NO 149
<211> LENGTH: 1452
<212> TYPE: DNA
<213> ORGANISM: Artificial Sequence
<220> FEATURE:
<223> OTHER INFORMATION: synthetic

<400> SEQUENCE: 149

gcagcgacaa acggaacaat gatgcagtat ttcgagtggt atgtacctaa cgacggccag     60

caatggaaca gactgagaac agatgcccct tacttgtcat ctgttggtat tacagcagta    120

tggacaccgc cggcttataa gggcacgtct caagcagatg tggggtacgg cccgtacgat    180

ctgtatgatt taggcgagtt taatcaaaaa ggtacagtca gaacgaagta tggcacaaaa    240

ggagaactta aatctgctgt caacacgctg cattcaaatg gaatccaagt gtatggtgat    300

gtcgtgatga atcataaagc aggtgctgat tatacagaaa acgtaacggc ggtggaggtg    360

aatccgtcta atagaaatca ggaaacgagc ggcgaatata atattcaggc atggacaggc    420

ttcaactttc cgggcagagg aacaacgtat tctaacttca aatggcagtg gttccatttt    480

gatggaacgg attgggacca gagcagaagc ctctctagaa tcttcaaatt cacgggaaag    540

gcgtgggact ggccggtttc ttcagaaaac ggaaattatg actatctgat gtacgcggac    600

tacgattatg accatccgga tgtcgtgaat gaaatgaaaa agtggggcgt ctggtatgcc    660

aacgaagttg ggttagatgg atacagactt gacgcggtca aacatattaa atttagcttt    720

ctcaaagact gggtggataa cgcaagagca gcgacgggaa aagaaatgtt tacggttggc    780

gaatattggc aaaatgattt aggggccctg aataactacc tggcaaaggt aaattacaac    840

caatctcttt ttgatgcgcc gttgcattac aacttttacg ctgcctcaac agggggtgga    900

tattacgata tgagaaatat tcttaataac acgttagtcg caagcaatcc gacaaaggct    960

gttacgttag ttgagaatca tgacacacag cctggacaat cactggaatc aacagtccaa   1020

ccgtggttta aaccgttagc ctacgcgttt attctcacga gaagcggagg ctatccttct   1080

gtattttatg gagatatgta cggtacaaaa ggaacgacaa caagagagat ccctgctctt   1140

aaatctaaaa tcgaaccttt gcttaaggct agaaaagact atgcttatgg aacacagaga   1200

gactatattg ataacccgga tgtcattggc tggacgagag aaggggactc aacgaaagcc   1260

aagagcggtc tggccacagt gattacagat gggccgggcg gttcaaaaag aatgtatgtt   1320

ggcacgagca atgcgggtga aatctggtat gatttgacag ggaataactc aacaaaaatc   1380
```

acgattggaa gcgatggcta tgcaacattt cctgtcaata aaggctcagt ttcagtatgg 1440
gtgcagcaat ag 1452

<210> SEQ ID NO 150
<211> LENGTH: 9215
<212> TYPE: DNA
<213> ORGANISM: Artificial Sequence
<220> FEATURE:
<223> OTHER INFORMATION: synthetic

<400> SEQUENCE: 150
catcggacag ctcttgcttg atatcttcaa aatgacgccg gctcatgtca tgtcaacttt 60
tgtcgtatct ggagcgatcc ttgacggatt cggcatttac gaccgtttta tcgaatttgc 120
cggtgccggg gctacagtcc cgattgtcag cttcggccac tctcttttgc acggcgcgat 180
gcaccaggct gagaaacatg gctttatcgg aatcggcatg gggatatttg aactgacatc 240
tgccggtata tctgccgcta tcttgttcgc ttttcttgtt gccgtgattt ttaaaccgaa 300
aggataaagg aaaatgccag caaaacgcaa ggtcattttg gtcacagacg gcgatatata 360
cgctgcaaaa gcaatcgaat atgcagcaag aaaaacgggt ggccgctgca tttcccaatc 420
ggcggggaat ccgagcgtta aaacaggacc ggagcttgta accatgatcc tgcaaacccc 480
tcatgatcct gtattcgtca tgtttgatga ttccggactt caaggtgaag gcccgggaga 540
gacagctatg aaatatgtag cgatgcatcc cgatatcgag gtgctcggag tcatcgccgt 600
cgcttcaaaa actcattatg cagagtggac gagagtcgat gtatcaatcg atgcagaagg 660
cgaactgaca gagtacggcg tcgataaaca cggggtcaaa gagttcgatg tcaaacgaat 720
gaatggtgat acagtctatt gccttgacca gctggatgtt ccgatcattg tcggaatcgg 780
tgatatcggt aagatgaaca gaaaagacga tgtggaaaaa ggttcgccga ttacaatgaa 840
agcggtcgag ctcattttag aaaggagcgg gtatcatgag tgctcaaaag caagagaaga 900
cgaacgtatt ccttgatcct tctaagaatg aagcgtattt caagaagcgg gtcggcatgg 960
gagaaagctt tgaccttggc gtacggaagg tctttattct cggacatgaa gttcagcttt 1020
attatgtcaa cggattgtgc gacacacaat acatcattca cctgttaaga gaactggtgc 1080
atctgaatga taaagaaaaa gaatcgggcg aggtcgaaga catcgtcgaa aacaggcttt 1140
tgaaccagca ggtttcaaaa gcggaaacgc ttgatgaagc tgtcgaccaa gtgttgtcag 1200
gactggttgc catcatcgtc gaagatgcgg gctttgcttt tatcatcgat gtcagaagct 1260
acccgggcag aacgccggaa gaacctgata cagaaaaagt cgtacgcggt gcaagggacg 1320
gactcgtcga gaacatcatc gtcaacacag ccctgattag acgccggatc agagatgagc 1380
gcttgcgcta caaaatgctt catatcggtg aacgctctaa aacagacatc tgcctctgct 1440
atttggaaga cgttgcagat cccgatcttg ttgaagtatt aaaaaaagaa attgaagatg 1500
tgaagatcga cgggctgccg atgtcggata aatcggtaga ggaattcctg gtcggccaag 1560
gctacaatcc gtttccgctt gtcaggttta cggaaagggc agacgtagcc gcaagccata 1620
ttttagaggg gcatgtcatc gtgatcgtcg atacgtcgcc aagcgtcatc atcacaccga 1680
ccactttgtt tcaccatgtt cagcatgctg aggaatacag acagacgccg gctgttggga 1740
cgtttttaag gtgggtgcgg tttttcggta ttttggcctc caccttttg ctgccgcttt 1800 ggctgctgtt tgtcattcat ccgtcgctct tgcctgataa tttatcgttt atcgggttga 1860
ataaagacac ccatattccg attatcatgc agattttcct ggcggatctc ggcgtcgaat 1920
ttttaagaat ggccgccatt catacgccga cggcgctttc gactgcaatg ggcctgatcg 1980

```
ccgctgtatt gatcggcgat atcgcgatca atgtcggctt gttttctccc gaagtcattt   2040
tatacgtttc cctctcggca atcggagcct acacgacacc aagctacgag ctgagcctgg   2100
cgaataaaat ggtgaagctg tttatgctga tattggtggc gctttttaaa gtggagggat   2160
ttgtcatcgg attaacgatc ttaactatag tgatgacttc gatcaggtca ttgcgaacgc   2220
cttacttatg gcctctcctc ccgttcaatg gaaaagcgtt ttggcatgtt ctcgtgcgca   2280
cgtccgttcc agggggaaaa gtcaggccga gcatcgttca tccgagaaac cgctccagac   2340
agccgtgaag ccggcattcg aagaggcttt tccccgggga aaagcctctt tttcaataat   2400
cgaattccgg tctttgagta ccgatgcctc tgtattcatt ggcagagatc gcgactgccc   2460
ggaggctgca gatgttgttc tgtcttctga tcggatagac gacatacagc atttcgcggc   2520
cgtacgggtc aatcgttgac gaatgaagga aaacctcagt tcctctccgc caaaatctcg   2580
tattcgccgg agctgtaata atctgccctt cataaggctc ataaattctc tgttcataat   2640
gcgcagccgg ctgataaggg gcgtatacat cttcaggtgc atagccggga gcgggggtgt   2700
agggatagcg atttggatac atatgataac ctctttccca cttcgttttt tggttttcat   2760
ctttaagatt atattcaggt aaatgcctat ttgtatgggc gaaaatctca gcttttcggc   2820
tcttttttta ttgaatggac gttgtgtatg cctatttcta tcaagcgctg ttttctgtta   2880
ttctataatc aatagaatgg attagttgtt tagggaatca tttcctttat aaatcaagaa   2940
aatttggaca aatggtggtt tagtttttaa aacgaaatgt tataatacaa cataagaatc   3000
gcactatcat gaagccggaa gatgcatcgg gcagcaaccg gagcgcccct tgcacctttg   3060
tcgatagaga aagagggaat gacaattgtt tttacacggt actagcagac aaaatgaaag   3120
agggcacctc gaaatcggcg gtgtcgatgt tctatcattg gcagaaagat acggaacacc   3180
tctttatgta tacgatgtcg cgctgattag agagcgcgcc cgaaaattcc agaaggcatt   3240
caaggaagcc ggtttaaaag cgcaggtagc gtatgcaagc aaggcgtttt catcggttgc   3300
catgattcag cttgccgaac aagaggggct gtctctggat gtggtatcgg gaggagagct   3360
tttcactgcg atcaaagcag ggttcccagc tgagcggatt cattttcacg gaaacaataa   3420
gagccctgaa gaactagcca tggcgctgga gcatcaaatc ggctgcatcg tgctcgataa   3480
ctttcacgag atcgccatta cagaagatct ttgcaagcga tcaggacaaa ctgtagacgt   3540
tttgctcaga atcactccgg gagttgaagc gcacacgcac gattatatta cgacggggca   3600
ggaagattcc aaattcggtt ttgatctgca taatggacag gtcgaacaag ccatcgaaca   3660
agtcctccgc tcgtctgcgt ttaagctcct cggcgtgcac tgccacatcg gttcgcaaat   3720
ttttgatacg gcaggatttg tccttgcagc agacaagatt ttcgagaagc ttgcggaatg   3780
gcgggagact tactctttca ttccggaagt gctcaatctt ggcgggggct tcggcatccg   3840
ctatacaaaa gacgacgagc cgcttgcagc tgatgtttat gttgaaaaaa tcatcgaggc   3900
ggtcaaagca aatgccgagc atttcggctt tgacatccct gagatttgga tcgaaccagg   3960
ccggtctctc gtcggtgatg cggggactac gctgtacacg atcggttctc aaaaagaggt   4020
gccgggcatt cgcaaatatg tagccatcga cggcggcatg agcgataata tcaggccggc   4080
gctttatgag gcaaaatatg aagcagccgt cgccaacagg atgaacgatg cttgtcatga   4140
taccgcatca atcgcaggaa aatgctgcga aagcggagat atgctgattt gggatttgga   4200
aatccccgaa gttcgcgacg gagatgtgct cgccgttttc tgcaccggtg cgtacggcta   4260
cagcatggcc aacaactaca accgcattcc gcgcccggcc gtcgtctttg tcgaggacgg   4320
```

-continued

```
ggaagcgcag ctcgtcattc agagagagac gtatgaggat atcgtcaagc tggatctgcc   4380
gctgaaatcg aaagtcaaac aataaaaaaa tggagattcc ctaagagggg ggtctccatt   4440
tttaattcaa gctgataaac agctgacatc aactaaaagt ttcattaaat actttgaaaa   4500
aagttgttga cttaaaagaa gctaaatgtt atagtaattg tacagaatag tcttttaagt   4560
aagtctactc tgaatttttt taaaaggaga gggtaaagaa tgaaacaaca aaaacggctt   4620
tacgcccgat tgctgacgct gttatttgcg ctcatcttct tgctgcctca ttctgcagct   4680
agcgcagcag cgacaaacgg aacaatgatg cagtatttcg agtggtatgt acctaacgac   4740
ggccagcaat ggaacagact gagaacagat gccccttact tgtcatctgt tggtattaca   4800
gcagtatgga caccgccggc ttataagggc acgtctcaag cagatgtggg gtacggcccg   4860
tacgatctgt atgatttagg cgagtttaat caaaaaggta cagtcagaac gaagtatggc   4920
acaaaaggag aacttaaatc tgctgtcaac acgctgcatt caaatggaat ccaagtgtat   4980
ggtgatgtcg tgatgaatca taaagcaggt gctgattata cagaaaacgt aacggcggtg   5040
gaggtgaatc cgtctaatag aaatcaggaa acgagcggcg aatataatat tcaggcatgg   5100
acaggcttca actttccggg cagaggaaca acgtattcta acttcaaatg gcagtggttc   5160
cattttgatg gaacggattg ggaccagagc agaagcctct ctagaatctt caaattcacg   5220
ggaaaggcgt gggactggcc ggtttcttca gaaaacggaa attatgacta tctgatgtac   5280
gcggactacg attatgacca tccggatgtc gtgaatgaaa tgaaaaagtg gggcgtctgg   5340
tatgccaacg aagttgggtt agatggatac agacttgacg cggtcaaaca tattaaattt   5400
agctttctca aagactgggt ggataacgca agagcagcga cgggaaaaga aatgtttacg   5460
gttggcgaat attggcaaaa tgatttaggg gccctgaata actacctggc aaaggtaaat   5520
tacaaccaat ctctttttga tgcgccgttg cattacaact tttacgctgc ctcaacaggg   5580
ggtggatatt acgatatgag aaatattctt aataacacgt tagtcgcaag caatccgaca   5640
aaggctgtta cgttagttga gaatcatgac acacagcctg gacaatcact ggaatcaaca   5700
gtccaaccgt ggtttaaacc gttagcctac gcgtttattc tcacgagaag cggaggctat   5760
ccttctgtat tttatggaga tatgtacggt acaaaaggaa cgacaacaag agagatccct   5820
gctcttaaat ctaaaatcga acctttgctt aaggctagaa aagactatgc ttatggaaca   5880
cagagagact atattgataa cccggatgtc attggctgga cgagagaagg ggactcaacg   5940
aaagccaaga gcggtctggc cacagtgatt acagatgggc cgggcggttc aaaaagaatg   6000
tatgttggca cgagcaatgc gggtgaaatc tggtatgatt tgacagggaa taactcaaca   6060
aaaatcacga ttggaagcga tggctatgca acatttcctg tcaataaagg ctcagtttca   6120
gtatgggtgc agcaatagaa gcttctcgag gttaacagag gacggatttc ctgaaggaaa   6180
tccgtttttt tattttcaag cacgaaaaac acttcccggt gatcgggagg tgtttttttgt   6240
taaaaagatc atgacatgca tagaacagcg accgggctaa ttgtatataa tattgtgaat   6300
ttaacaaaaa atttacaaag gagatgataa aggcaatgac cagggtgaaa aggatgagat   6360
ttgctgattt gttggattta gaggcggagt agatgaaacc ggccaaagta tccctactcc   6420
accgattgct ccagtgcctg aagcaatgtg ttgattgtaa cacagtaaat cgttttacag   6480
caataaacat ttttgtgaat attttattga tttcggctgt gatctcattc ccatattctg   6540
ctgcggccca tggcgcaaca cagtccggcg atcaatattc aagctttgaa gaattggagc   6600
ggaatgaaga tccagcttct taccgaatta cggagaagaa cgcaagagtg ccgatgctca   6660
tcatggccat ccatggaggc ggcatcgaac ccggaacgag cgaaatcgcc aatgaagtgt   6720
```

ccaaaaacta ttccctgtac ttgtttgaag ggctgaaatc atcaggcaat acggaccttc 6780
acattacaag cacgcgtttt gacgagccag cggcgctcgc aattactgca agccaccagt 6840
atgtcatgtc gctccacggc tattacagtg aagaccgcga tattaaagta ggcggcacag 6900
accgcgctaa aatcagaata ttggttgatg agctgaaccg ctcggggttt gccgctgaaa 6960
tgctggggac agatgacaag tatgccggaa cccatccgaa taacatcgcc aacaagtcgc 7020
tttccgggct gagcattcag cttgaaatga gcacgggttt ccgcaaatct ttattcgacc 7080
ggtttacact aaaagacagg gcggcgacgc aaaacgaaac gttttaccga tttacaaagc 7140
tgctgacaga ttttattcat gaaaactatg aagaagacgg aggggatttc ccctctgcaa 7200
aaataaaaca ccccccttcaa gtgaaaaagg aggtgtttcg gcggttgtgt taaccgttgg 7260
actctgaggt gccgccgccg gtgaatacgg aaacgatggc gttccacaga gacacaaaga 7320
agtcgatcag tttttgaaga aagttttgtc cttcttcaga atccaagaat ttcgtgattt 7380
tatcctttgc tttgtcaagc tggtctccaa cctggttcca gtcgatatta atatttttca 7440
tgttattaaa taaagatata agagagtttt tctgatcttc tgtgagtgtc acgccaagtt 7500
cggaagcagc cgaatcaatc gttttctcca attcctcttt tgactcggga actccgtttt 7560
tcgagatttc ttccttgact ttggccatca gcgctgacgc gttttcactg ccgattttct 7620
cgccaagctc tgaagtggtg acaagctctt cattcgcgac ctttttcaca tcttcggaaa 7680
ttttttcgcc cgaagtcgtt tcatacgctt tcatcaatcc ggttaaagcg gctgtgcctg 7740
acacttcaaa cggagcggtg acatagactt tggcgtcttt tacaccggcc gtcatcagcg 7800
cgttcaaata catctcatct gtaattctgc tgatattgtg tgtctgaact tccaaaccgg 7860
tgcctttttt cgctacggta attgaagaag aagaaatcgc tcttgttccg atttgtgctt 7920
tcggtatata atcccctaaa tatttatgct cctcatcatt tgtcacctcg atgatggtcg 7980
cattttcagg cgcattcatt tcttttaata ctttttgtct gtcctggctt gacaagtctt 8040
tccccagcgt gacgatgaca tcacccactg cggcgtcagc gaagctgacc tgcgggaaaa 8100
tgagcagaca caatgctgta aagattccta gtatcgattt tttcaagctc aatgccctcc 8160
ttaaaaatgc aggcttcagg cagaattgct gtacttttaa agaagcctgc cggaacggaa 8220
ataatgcgtt ccgaaatata gacggatgaa agatgagtga ggtttcaaag aaaaaaagag 8280
agaattttct cttcaagtca aatgccctcc cggcatcgta tctcgccgct cttttatcat 8340
tcatgatttt cacaggcgat tcaacctttt tttaaaattt tttacaaaaa cgatacaaga 8400
gcggcgttta tttcggtcga ttggctctct gcttcttcaa tatgatataa tgacccttgt 8460
gaaatgaaag gagagaatca agatggctaa aaaaggatac atacaactga caaacggcaa 8520
aaaaatcgag tttgaactat atccggatgc ggcgccggga actgtcgcca actttgaaaa 8580
acttgcaaac gaagggttct atgacgggct gaagttccac cgcgtcatcc cgggcttcgt 8640
cagccaggga ggctgcccgc acggcaccgg aacaggcgga cctggatata cgattaaatg 8700
cgagacagaa gggaatccgc acaaacacga agccggttct ctctcaatgg ctcacgcagg 8760
aaaagatacc ggaggcagcc aatttttat cgtccatgag cctcagccgc acttgaacgg 8820
cgttcacacc gttttcggaa aggtcacatc aggccttgat gccgtcactt caatggagca 8880
gggacaaggc atggaaaaag tcgaagtatt tgatgcataa tcagagagcg caaaaaacag 8940
cccgcttagc cgggctgttt ttttgtctgt aacggtgttt attttccagg tgcaacagga 9000
cttgaggccg attcttcgtc cacatcctga taggaaataa cgatgctaat aaataaaata 9060

```
attgtgaaaa aatgaccctt tatgtaaaat atattcaagt gaagagctag atagagaacg    9120

caatctgtaa aaaaggaagg ggcgtaaggg gtgagcgtaa aaatcccatc gacggcagtc    9180

ggcgtaaaaa ttaatgactg gtataacgcg atacg                               9215


<210> SEQ ID NO 151
<211> LENGTH: 485
<212> TYPE: PRT
<213> ORGANISM: Artificial Sequence
<220> FEATURE:
<223> OTHER INFORMATION: synthetic

<400> SEQUENCE: 151

His His Asn Gly Thr Asn Gly Thr Met Met Gln Tyr Phe Glu Trp Tyr
1               5                   10                  15

Leu Pro Asn Asp Gly Asn His Trp Asn Arg Leu Asn Ser Asp Ala Ser
            20                  25                  30

Asn Leu Lys Ser Lys Gly Ile Thr Ala Val Trp Ile Pro Pro Ala Trp
        35                  40                  45

Lys Gly Ala Ser Gln Asn Asp Val Gly Tyr Gly Ala Tyr Asp Leu Tyr
    50                  55                  60

Asp Leu Gly Glu Phe Asn Gln Lys Gly Thr Val Arg Thr Lys Tyr Gly
65                  70                  75                  80

Thr Arg Ser Gln Leu Gln Ala Ala Val Thr Ser Leu Lys Asn Asn Gly
                85                  90                  95

Ile Gln Val Tyr Gly Asp Val Val Met Asn His Lys Gly Gly Ala Asp
            100                 105                 110

Ala Thr Glu Met Val Arg Ala Val Glu Val Asn Pro Asn Asn Arg Asn
        115                 120                 125

Gln Glu Val Thr Gly Glu Tyr Thr Ile Glu Ala Trp Thr Arg Phe Asp
    130                 135                 140

Phe Pro Gly Arg Gly Asn Thr His Ser Ser Phe Lys Trp Arg Trp Tyr
145                 150                 155                 160

His Phe Asp Gly Val Asp Trp Asp Gln Ser Arg Arg Leu Asn Asn Arg
                165                 170                 175

Ile Tyr Lys Phe Arg Gly His Gly Lys Ala Trp Asp Trp Glu Val Asp
            180                 185                 190

Thr Glu Asn Gly Asn Tyr Asp Tyr Leu Leu Tyr Ala Asp Ile Asp Met
        195                 200                 205

Asp His Pro Glu Val Val Asn Glu Leu Arg Asn Trp Gly Val Trp Tyr
    210                 215                 220

Thr Asn Thr Leu Gly Leu Asp Gly Phe Arg Ile Asp Ala Val Lys His
225                 230                 235                 240

Ile Lys Tyr Ser Phe Thr Arg Asp Trp Ile Asn His Val Arg Ser Ala
                245                 250                 255

Thr Gly Lys Asn Met Phe Ala Val Ala Glu Phe Trp Lys Asn Asp Leu
            260                 265                 270

Gly Ala Ile Glu Asn Tyr Leu Gln Lys Thr Asn Trp Asn His Ser Val
        275                 280                 285

Phe Asp Val Pro Leu His Tyr Asn Leu Tyr Asn Ala Ser Lys Ser Gly
    290                 295                 300

Gly Asn Tyr Asp Met Arg Asn Ile Phe Asn Gly Thr Val Val Gln Arg
305                 310                 315                 320

His Pro Ser His Ala Val Thr Phe Val Asp Asn His Asp Ser Gln Pro
                325                 330                 335
```

```
Glu Glu Ala Leu Glu Ser Phe Val Glu Glu Trp Phe Lys Pro Leu Ala
            340                 345                 350

Tyr Ala Leu Thr Leu Thr Arg Glu Gln Gly Tyr Pro Ser Val Phe Tyr
        355                 360                 365

Gly Asp Tyr Tyr Gly Ile Pro Thr His Gly Val Pro Ala Met Arg Ser
    370                 375                 380

Lys Ile Asp Pro Ile Leu Glu Ala Arg Gln Lys Tyr Ala Tyr Gly Lys
385                 390                 395                 400

Gln Asn Asp Tyr Leu Asp His His Asn Ile Ile Gly Trp Thr Arg Glu
                405                 410                 415

Gly Asn Thr Ala His Pro Asn Ser Gly Leu Ala Thr Ile Met Ser Asp
            420                 425                 430

Gly Ala Gly Gly Ser Lys Trp Met Phe Val Gly Arg Asn Lys Ala Gly
        435                 440                 445

Gln Val Trp Ser Asp Ile Thr Gly Asn Arg Thr Gly Thr Val Thr Ile
    450                 455                 460

Asn Ala Asp Gly Trp Gly Asn Phe Ser Val Asn Gly Gly Ser Val Ser
465                 470                 475                 480

Ile Trp Val Asn Lys
                485


<210> SEQ ID NO 152
<211> LENGTH: 9522
<212> TYPE: DNA
<213> ORGANISM: Artificial Sequence
<220> FEATURE:
<223> OTHER INFORMATION: synthetic

<400> SEQUENCE: 152

ctgggagctg atagcacagc gatttcccgc ctcctgtcgg aagcatcgcc accgtgtccc     60

gtccctccag cacgcttttg atgatcgttt cctggccttt tttaaaagca tgataaccaa    120

aatacctgcg gagcgcctga tgaagtttat ccattcctga tcaccgtttt cgacagggcc    180

aggcggattt taaaataact gtatcggccg ccgagtccct ctttaatttg tctgatttta    240

ttggtttggt tcgctatcgc ataatcggca ataattttct gttcctcttt cgacacgtac    300

tgatcgatgg aaaaagacgg atcatgaatg gcgatttcca caatgtgatc ctcgatcgtc    360

gccaatttca gctttctaat ttttgcgatc cggtctattg tataccottc ttttataaga    420

aagagcgttt ttctcgtcga ttgtgtcaga ccatcattca aaggaatgtc atgaatgagc    480

gtttgaaaaa gcggactttc accattttgg gcggattgaa taaaatggtg cagaacatcc    540

caaaacagtg catatatgta ccactcatca aggttcattt tttcggaaag ctgtctgaat    600

gtatagcccg cttttgttct ggatgtcagg gagtgaacaa aaatagcggc ctgttcatca    660

tgatttaaaa cagacagctt ctctttcagc tcttggtgaa actgggccgc tgtttcagca    720

gcattccggt ttcttaaata ctgtttaacc cagttctgaa tctgataatc ttttacgatc    780

ggcaaataca cgcgttcgcg gtaaagcttg ttggagagca cttggatcaa aagcgacatc    840

cttgcccaca tcactttggc tgccgcctga taatagccgc cgtgaaaatg gcggggccac    900

ggataaaggg caaaaaagcc ggcaagttcc gcttctcctt tttcggtgac ggtgtaagcg    960

ccgctttccg ctttttctct gaccaaagac tcctgcttca atcgttgaac gctggctgcc   1020

acctgctctc tcgacagagc cgaacaaaag ccgaagtatt ttgaaacggc aaataaaccg   1080

gcgtcctgta tcgtctgtga cgaccttttt ccttttaata aatgatagac cgcgcttgga   1140

gaacgctcac ccttcatgga tgacagaatg tcaagcacaa tcgcgtcaaa aaaatgaacc   1200
```

```
ggcatatcat cacctgcaat cttccggcaa cattcgatca tttcttcctt ttattttaac   1260

agattttgcg gagaaatcga cgtttaaact catataaaag ggtatgtta gcagtagaac    1320

ccttgtgtga taagcattct caatattttt gagttgaaat gtaagattaa caccattaca   1380

ataaggaatg ggaataggtt tcatatcgga tagatagagg gttaaaccat ttgttccaac   1440

gaagaacaat ctgggaggtt ttttattcat gccaaaatat acaattgtag acaaagatac   1500

gtgcatcgca tgcggagctt gtggtgctgc ggctcctgat atttatgatt acgacgatga   1560

gggaatcgca tttgtcaccc ttgacgacaa tcagggtgtc gtcgaagtcc ctgacgtctt   1620

agaagaagac atgatggacg cgtttgaagg ctgtcctaca gattcgatca aagttgcgga   1680

tgagccgttc gaaggcgacc cgcttaaaca cgaataaagc caaaaaacat ccggtgcaca   1740

aagtgccgga tgttttttta tgagataagc acggctttac caacaagcaa aaagaagccg   1800

gctaaagaca tccggcttct tctgcagctg acaatatccg ggaacatgca cccgatattg   1860

tcatgtttat ttatttggcc atgcggacgt tttccttcag ccgcggtttc agcgaaagga   1920

aaatcggcgt ggacacgagg gccacagcga tgcctttaat gaaattaaaa ggcaggattc   1980

cggccagaac tgttgtcttg agcgcctctc cagtcagcgc tggagcattt aaaaaccaag   2040

tgtaggcagg cagaaacagc agataattta aaatgctcat cgaaacggcc atcacaagcg   2100

tccctgcgaa aagagctgtg acaaaccctt tggcagaact tgattttttc agcagtacag   2160

ctgccggcag gataaacaat gttccggcaa tgaagttagc cgcctgatca atcggaacgc   2220

ccgaggcgct tcctgcaata aagtaattca gcacgttttt gatcgcttca acggcaatcc   2280

cggctcccgg accgtacaaa ataacagcga gcaatgccgg gatatcactg aaatcgattt   2340

ttaaatacgg gaatgccccc aggatcggaa agctcagcat cattaaaata aatgcgatgc   2400

tgctcagcat gctgatagag acgagacgtc tcaccttgtt gtgtttcatt ttgtcactct   2460

ctccttttcg atcacatctc acgaaaagag gaatggttct ttcccctgtc ctaaacaaaa   2520

aacccgcttt attgaaaaag cggggctgtt ttacagacag gtcaaataaa cgtttgaaaa   2580

tgttcatttc aaaacgcgcg gaacctccat cttctcccat ccagactata ctgtcggctt   2640

cggaatcgca ccgaatcctg cccataaaaa ggctcgcggg cttagagcgc ttgctcatca   2700

ccgccggtag ggaatttcac cctgccccga agattgatct tatttatttt taatactgat   2760

attattataa attaattgtg aaaaaatgta caggtgcaaa gcttattgcg ctgttttggg   2820

acatcctgca cgatatttcg gtaaactcac tttttccgca tactaaaaac cgcacattca   2880

cagttatttc atttttaatt ttcgtctttc cgcgtgaaac tcattgacac tctttatgga   2940

atatggtaaa ttatcagata tttatgacgc ttatttagga ggaaatctta catgtttcga   3000

gtattggtct cagataaaat gtccagcgac ggcctcaaac cattaatgga agcagatttt   3060

attgaaattg tagaaaagaa tgttgcggaa gcggaagacg agcttcatac gtttgacgcg   3120

ctcttggtgc ggagcgccac gaaggtaacc gaagagctgt ttaaaaagat gacttcgctg   3180

aaaatcgtcg ccagagcagg tgtcggcgtc gacaatatcg atattgacga ggcgacaaaa   3240

cacggtgtta tcgtcgtaaa cgcgccaaac gggaatacaa tttcaaccgc tgaacatacc   3300

tttgcaatgt tttcagcgtt aatgagacat attccgcagg caaacatctc cgtgaaatca   3360

agggagtgga atcgttcggc ttacgtcggt tcagagcttt acggaaaaac gctcggcatc   3420

atcggaatgg gccgcatcgg aagcgaaatc gcgagccgcg caaaagcatt cggtatgacc   3480

gttcatgtat ttgacccgtt cctgacccaa gaaagggcaa gcaagctcgg cgttaacgcg   3540
```

aacagctttg aagaagttct ggcatgcgcc gacatcatta cggttcatac cccgctcacg 3600
aaagaaacga agggactttt gaacaaagaa accatcgcaa aaacgaaaaa aggcgttcgt 3660
ctcgttaact gtgcaagagg cggcatcatc gatgaagcag cgcttttgga agctctggaa 3720
agcggacatg tcgctggcgc tgccttggat gtattcgaag tcgagcctcc ggtcgattca 3780
aaactgatcg atcatccgct tgtagtcgcg actcctcact tgggcgcctc aacaaaagaa 3840
gcccagctga atgtcgctgc acaagtgtcc gaagaagtcc ttcagtatgc gcaaggaaac 3900
cctgtgatgt ccgcgatcaa ccttccggcc atgacaaagg attcattcga aaaaatccag 3960
ccttatcatc agtttgccaa tacgatcgga aaccttgtgt ctcagtgcat gaatgagcct 4020
gttcaagatg tagccatcca atatgaaggc tccatcgcca aacttgaaac gtcatttatt 4080
acgaaaagcc ttttggccgg atttctgaag ccgagggtcg cggctaccgt taacgaagtg 4140
aatgccggca ccgttgcgaa agagcgcggc atcagcttca gcgaaaaaat ttcttccaat 4200
gagtcaggct atgaaaactg catctctgtg actgtcacgg gagatgtaac aacattctct 4260
ttaagagcga cgtacattcc gcacttcggc ggacgcatcg ttgccttaaa cggctttgat 4320
attgattttt atccggctgg acaccttgtc tacattcacc accaggataa accaggggct 4380
atcggccatg tcggacgaat tttaggagac catgacatca atatcgccac tatgcaggta 4440
ggccgaaaag aaaaaggcgg agaagcgatc atgatgcttt cctttgaccg ccaccttgag 4500
gacgatattt tagctgagct gaaaaacatc ccggatatcg tgtctgttaa agccatcgac 4560
cttccttaag tcgctgataa acagctgaca tcaatatcct attttttcaa aaaatatttt 4620
aaaaagttgt tgacttaaaa gaagctaaat gttatagtaa taaaacagaa tagtctttta 4680
agtaagtcta ctctgaattt ttttaaaagg agagggtaaa gaatgaaaca acaaaaacgg 4740
ctttacgccc gattgctgac gctgttattt gcgctcatct tcttgctgcc tcattctgca 4800
gctagcgcac atcataacgg tacgaacggg acaatgatgc aatactttga atggtatcta 4860
cctaatgacg gaaatcattg gaatcgatta aactctgatg cgagtaacct taaaagcaaa 4920
gggattacag cggtgtggat tcctccagca tggaagggcg cttctcaaaa tgacgtagga 4980
tacggagcct atgacctgta tgatctggga gaatttaatc aaaaaggtac cgtccgtaca 5040
aaatatggaa cacgtagtca gttacaagct gcggtaacct ccttaaaaaa taatggaatt 5100
caagtatatg gtgacgttgt tatgaatcac aaaggtggcg cagacgctac tgaaatggta 5160
agggccgttg aagtgaatcc caataaccgt aaccaagaag tgactggtga atataccatt 5220
gaagcttgga ctagatttga ttttccaggg cgaggaaata ctcattctag ctttaaatgg 5280
agatggtatc attttgatgg tgtggattgg gatcagtcac gtagactgaa caatcgcatc 5340
tataaattta gaggtcatgg caaagcttgg gattgggaag ttgatacgga aaatggtaat 5400
tatgattatt tactatacgc tgatattgat atggatcacc cagaagtagt aaatgaatta 5460
agaaattggg gtgtttggta cacaaacaca ttaggactcg atggatttag aatagatgcg 5520
gttaaacata taaagtatag ctttacgcgc gattggatta atcacgttag aagtgcaaca 5580
ggtaaaaata tgtttgcggt tgctgagttt tggaagaatg atttaggtgc aattgaaaac 5640
tatctgcaga aaacaaactg gaaccattca gtctttgatg tgccgttaca ttataatctt 5700
tataatgcat caaaaagcgg agggaactat gatatgcgaa acatatttaa tggaacggtt 5760
gttcaacgac atccaagtca tgctgtaaca tttgttgata atcatgattc gcagcctgaa 5820
gaagcattag aatcttttgt tgaagaatgg tttaaaccat tagcgtatgc gcttacatta 5880
acgcgtgaac aaggataccc ttctgtattt tacggagatt attatgggat tccaacacat 5940
ggagtgccag caatgagatc aaaaatcgat ccgattttag aagcacgtca aaagtatgca 6000
tacggaaaac aaaatgatta cttagaccat cataatatca ttggttggac gcgtgaaggg 6060
aatacagcac accccaattc aggtctagct accatcatgt ctgatggagc gggtggaagt 6120
aagtggatgt ttgttgggcg taataaggct ggtcaagtat ggagtgatat tacaggaaac 6180
cgtacaggta cggttacaat caatgcagac ggttggggca atttctctgt gaatggaggg 6240
tcagtttcta tttgggtcaa caaataaaag cttctcgagg ttaacagagg acggatttcc 6300
tgaaggaaat ccgttttttt attttacaga agctgcggaa cctgaaaaga attcctttca 6360
ggttccgttt tttttaggaa ttctccctga tctcaagcat ctggcgggga taaatccgct 6420
ctcctttcaa atcgttccat tctttgaggc gctgtacagt tacgcccatt ttttcggcga 6480
tatgatgaag cgtatcccct ttccgcacta catatgtacc ggtcttcgat tcatcgtcat 6540
gaaggcggag tgtttggccg gccttgagat ttgaatgttt caacccgttt attctcatga 6600
tctcctcgat ggatataccg ctatccttgc tgattctcca gagcgtgtcc ccttttttgaa 6660
cggtcaccgc accgctcatt gtcccggcgt tttgataaac gtggatagaa ttttgccgga 6720
acgcctcctc acgaagcacc gtcagcggat tgattgcata tcttttatct tcagtccatg 6780
aaccgtgatg catttcaaaa tgcaggtggg ttccggtcga tattcccgta ttgccgatga 6840
ttccgatttg ctcgcctttt ttcacccgct ccttttcctt tttcaggcgt ttgcttaagt 6900
gggcataaac ggtttcatat ccgttgtcat gtttaataaa tatcacttgg ccgtaggagt 6960
cggattgata cgatttgctt atcgttccgt ctgcggctgc cgctactgct tccccttcgg 7020
gagcagcgat gtcaagcccc ttatgctttc cgcctctcgt accgaattga tctgtgatct 7080
ctcctttaat cggttcaatc cactctgagg cttccgcccc cggggcattg acgaaaagcg 7140
ccaatcccga aagccatgcg atcgcgaaca ggaagttttg atgtctgagt ttcttcaagg 7200
ttttccatat cctcctatta catgcatctt cggtaaaatt gccccctatt cggagacagc 7260
ttagtatact tccaaatcaa tacaatttat acattaaaaa aagactccgc acagggagtc 7320
ttttagtttt ctatcgtcat cggattcggt gcgtacggaa cctgtacaga tttcgacagg 7380
tcataggcgc cgaccttggt tatggatgcg tttttaaatt tcacttttgt gaagccgaaa 7440
tctttcgcgg tcaatagaag gccttccacc atcaagacat cttcgggttt attttcaata 7500
ttcgcggagg aagaaaattg aatgatcagt tcttttccat tcttttgaat atcttcaatc 7560
ggcgtatcat cggataaaat gggttttaaa tgagtgccgc tttcttcgtt tttcatcatc 7620
ttaatcgctt cctgcaccga ttcgtaagat tcgcttgaag gtgcaaggaa ccggcgcccg 7680
tctgagcttt catataaata gtagcatttt tgcgtctggt gcataatcgc catatcggcg 7740
agcattccga atgtttcaaa ttcaacaccc gatttatcat tggaaataaa cagaacagaa 7800
tcatacgatc cccatttaaa ggtttcgttg atcacatttt tcagccgttc gaaatcttcg 7860
actgatagct ccggtatttt ctcatcaact tgaatcttca gtttttttatt gtttttctgc 7920
tctttgaact tcaccttatc aaggtaagct gtgtcaaatg atgtaaactg gtccactcca 7980
agccggctgt aagcgtgaag cgcatcttca agatttgtca tgccagtgct tttctcgagg 8040
cttaccggga caacgacaga cttggactcg tcaaggaaag cgaaggtgat atagtcgtct 8100
ttttgattct gtgagacgac aaacgtattt gcaggttcag acttggcagc atcagcctcc 8160
gtctgcacca attttccgtc agaagaaatg ttggcgtcgg cgctgttttg agatctgatc 8220
tgttcgatta actggggagt gatcagcatc agaagaaaga gaaccaaaac tgtagcagca 8280
aatgcgccga cccgtttttt cggtgattta cgctttggtg cgagaatcag cttttgatag 8340
atctgatttg ccgaacgatt atccttaacc gttggaagtt ggcttagtaa cgccttcagc 8400
cgttcttcgt tccattctga cttcttcatt ctttggatcc tccttcaaaa gctccatctg 8460
tttacgaagc actttcagac cgcggtgctg agtggttttt accttgcttt cggaaaaatt 8520
caaggctttt gctgtttcac tgatcgaata tccttgaata aaacgcaaga cgataactga 8580
tctttggtca agcgtacact tgtctagggc ctcgaaaatt tcctttaggt tttcattttg 8640
catcacgatg tcctcaggca gaggcttgcg gtcttttaca tcttgtttct cccagtcaaa 8700
cgtccccaaa atccgctggc ggatcgtctg ctgctttctg aaccagtcga tcgcaacgtg 8760
ccgcgcaatc gaaagaagcc aggtttttttc gctgctcctg ccttcaaatg tttcgtaaga 8820
atgcaggacg cggatgtata cttcctgaac taagtcttcc gcctgatttt tgtcttttac 8880
catataaaat aaaaactgaa ataaatcctg atgatactga tcatatattt tctgaaaggt 8940
ttcttccacc tgaaacccct ccgttcaatt tattgtcgtt tgtcaatctt aaaaggttac 9000
attacaacta ttacaactat attacgaaca tatgaaaatg gaaagggggt tttgcgaaag 9060
ttaagcttaa ttttaactta acaagcacaa aagcacccgt tctaaatgaa caggtgccaa 9120
ggttatagga gcccacattt tcactaagct gtgcccttac aaggctttcg ttctcctgac 9180
cggagcgttg cggatccgct gaaatgaact aatttcaatc cgtttatgac tttaagtcca 9240
attgttggcg aagcttttttg gaaatctcca ttctcttttc gtcagtcact aggtgatacc 9300
ataagccgtc aactttttttg tcttcacctt caatttctac ctgcttaata tctttagcag 9360
cttctttata agaactttga atatcgatca tcttgtccag tgttaagttt gttttgatgt 9420 tttttctaa tgctgccaaa atctcttgat agtttgttaa tgattttaat tgtgcacctt 9480
catgaataat ttcgttgata atctcacgct gacgctcttg ac 9522

<210> SEQ ID NO 153
<211> LENGTH: 1458
<212> TYPE: DNA
<213> ORGANISM: Artificial Sequence
<220> FEATURE:
<223> OTHER INFORMATION: synthetic

<400> SEQUENCE: 153
catcataacg gtacgaacgg gacaatgatg caatactttg aatggtatct acctaatgac 60
ggaaatcatt ggaatcgatt aaactctgat gcgagtaacc ttaaaagcaa agggattaca 120
gcggtgtgga ttcctccagc atggaagggc gcttctcaaa atgacgtagg atacggagcc 180
tatgacctgt atgatctggg agaatttaat caaaaaggta ccgtccgtac aaaatatgga 240
acacgtagtc agttacaagc tgcggtaacc tccttaaaaa ataatggaat tcaagtatat 300
ggtgacgttg ttatgaatca caaaggtggc gcagacgcta ctgaaatggt aagggccgtt 360
gaagtgaatc ccaataaccg taaccaagaa gtgactggtg aatataccat tgaagcttgg 420
actagatttg attttccagg gcgaggaaat actcattcta gctttaaatg gagatggtat 480
cattttgatg gtgtggattg ggatcagtca cgtagactga acaatcgcat ctataaattt 540
agaggtcatg gcaaagcttg ggattgggaa gttgatacgg aaaatggtaa ttatgattat 600
ttactatacg ctgatattga tatggatcac ccagaagtag taaatgaatt aagaaattgg 660
ggtgtttggt acacaaacac attaggactc gatggattta gaatagatgc ggttaaacat 720
ataaagtata gctttacgcg cgattggatt aatcacgtta gaagtgcaac aggtaaaaat 780
atgtttgcgg ttgctgagtt ttggaagaat gatttaggtg caattgaaaa ctatctgcag 840
aaaacaaact ggaaccattc agtctttgat gtgccgttac attataatct ttataatgca 900
tcaaaaagcg gagggaacta tgatatgcga aacatattta atggaacggt tgttcaacga 960
catccaagtc atgctgtaac atttgttgat aatcatgatt cgcagcctga agaagcatta 1020
gaatcttttg ttgaagaatg gtttaaacca ttagcgtatg cgcttacatt aacgcgtgaa 1080
caaggatacc cttctgtatt ttacggagat tattatggga ttccaacaca tggagtgcca 1140
gcaatgagat caaaaatcga tccgatttta gaagcacgtc aaaagtatgc atacggaaaa 1200
caaaatgatt acttagacca tcataatatc attggttgga cgcgtgaagg gaatacagca 1260
caccccaatt caggtctagc taccatcatg tctgatggag cgggtggaag taagtggatg 1320
tttgttgggc gtaataaggc tggtcaagta tggagtgata ttacaggaaa ccgtacaggt 1380
acggttacaa tcaatgcaga cggttggggc aatttctctg tgaatggagg gtcagtttct 1440
atttgggtca acaaataa 1458

<210> SEQ ID NO 154
<211> LENGTH: 9219
<212> TYPE: DNA
<213> ORGANISM: Artificial Sequence
<220> FEATURE:
<223> OTHER INFORMATION: synthetic

<400> SEQUENCE: 154
catcggacag ctcttgcttg atatcttcaa aatgacgccg gctcatgtca tgtcaacttt 60
tgtcgtatct ggagcgatcc ttgacggatt cggcatttac gaccgtttta tcgaatttgc 120
cggtgccggg gctacagtcc cgattgtcag cttcggccac tctcttttgc acggcgcgat 180
gcaccaggct gagaaacatg gctttatcgg aatcggcatg gggatatttg aactgacatc 240
tgccggtata tctgccgcta tcttgttcgc ttttcttgtt gccgtgattt ttaaaccgaa 300
aggataaagg aaaatgccag caaaacgcaa ggtcattttg gtcacagacg gcgatatata 360
cgctgcaaaa gcaatcgaat atgcagcaag aaaaacgggt ggccgctgca tttcccaatc 420
ggcggggaat ccgagcgtta aaacaggacc ggagcttgta accatgatcc tgcaaacccc 480
tcatgatcct gtattcgtca tgtttgatga ttccggactt caaggtgaag gcccgggaga 540
gacagctatg aaatatgtag cgatgcatcc cgatatcgag gtgctcggag tcatcgccgt 600
cgcttcaaaa actcattatg cagagtggac gagagtcgat gtatcaatcg atgcagaagg 660
cgaactgaca gagtacggcg tcgataaaca cggggtcaaa gagttcgatg tcaaacgaat 720
gaatggtgat acagtctatt gccttgacca gctggatgtt ccgatcattg tcggaatcgg 780
tgatatcggt aagatgaaca gaaaagacga tgtggaaaaa ggttcgccga ttacaatgaa 840
agcggtcgag ctcatttttag aaaggagcgg gtatcatgag tgctcaaaag caagagaaga 900
cgaacgtatt ccttgatcct tctaagaatg aagcgtattt caagaagcgg gtcggcatgg 960
gagaaagctt tgaccttggc gtacggaagg tctttattct cggacatgaa gttcagcttt 1020
attatgtcaa cggattgtgc gacacacaat acatcattca cctgttaaga gaactggtgc 1080
atctgaatga taaagaaaaa gaatcgggcg aggtcgaaga catcgtcgaa aacaggcttt 1140
tgaaccagca ggtttcaaaa gcggaaacgc ttgatgaagc tgtcgaccaa gtgttgtcag 1200
gactggttgc catcatcgtc gaagatgcgg gctttgcttt tatcatcgat gtcagaagct 1260
acccgggcag aacgccggaa gaacctgata cagaaaaagt cgtacgcggt gcaagggacg 1320
gactcgtcga gaacatcatc gtcaacacag ccctgattag acgccggatc agagatgagc 1380

```
gcttgcgcta caaaatgctt catatcggtg aacgctctaa aacagacatc tgcctctgct   1440
atttggaaga cgttgcagat cccgatcttg ttgaagtatt aaaaaaagaa attgaagatg   1500
tgaagatcga cgggctgccg atgtcggata aatcggtaga ggaattcctg gtcggccaag   1560
gctacaatcc gtttccgctt gtcaggttta cggaaagggc agacgtagcc gcaagccata   1620
ttttagaggg gcatgtcatc gtgatcgtcg atacgtcgcc aagcgtcatc atcacaccga   1680
ccactttgtt tcaccatgtt cagcatgctg aggaatacag acagacgccg gctgttggga   1740
cgtttttaag gtgggtgcgg tttttcggta ttttggcctc cacctttttg ctgccgcttt   1800
ggctgctgtt tgtcattcat ccgtcgctct tgcctgataa tttatcgttt atcgggttga   1860
ataaagacac ccatattccg attatcatgc agattttcct ggcggatctc ggcgtcgaat   1920
ttttaagaat ggccgccatt catacgccga cggcgctttc gactgcaatg ggcctgatcg   1980
ccgctgtatt gatcggcgat atcgcgatca atgtcggctt gttttctccc gaagtcattt   2040
tatacgtttc cctctcggca atcggagcct acacgacacc aagctacgag ctgagcctgg   2100
cgaataaaat ggtgaagctg tttatgctga tattggtggc gctttttaaa gtggagggat   2160
ttgtcatcgg attaacgatc ttaactatag tgatgacttc gatcaggtca ttgcgaacgc   2220
cttacttatg gcctctcctc ccgttcaatg gaaaagcgtt ttggcatgtt ctcgtgcgca   2280
cgtccgttcc agggggaaaa gtcaggccga gcatcgttca tccgagaaac cgctccagac   2340
agccgtgaag ccggcattcg aagaggcttt tccccgggga aaagcctctt tttcaataat   2400
cgaattccgg tctttgagta ccgatgcctc tgtattcatt ggcagagatc gcgactgccc   2460
ggaggctgca gatgttgttc tgtcttctga tcggatagac gacatacagc atttcgcggc   2520
cgtacgggtc aatcgttgac gaatgaagga aaacctcagt tcctctccgc caaaatctcg   2580
tattcgccgg agctgtaata atctgccctt cataaggctc ataaattctc tgttcataat   2640
gcgcagccgg ctgataaggg gcgtatacat cttcaggtgc atagccggga gcgggggtgt   2700
agggatagcg atttggatac atatgataac ctctttccca cttcgttttt tggttttcat   2760
ctttaagatt atattcaggt aaatgcctat ttgtatgggc gaaaatctca gcttttcggc   2820
tcttttttta ttgaatggac gttgtgtatg cctatttcta tcaagcgctg ttttctgtta   2880
ttctataatc aatagaatgg attagttgtt tagggaatca tttcctttat aaatcaagaa   2940
aatttggaca aatggtggtt tagtttttaa aacgaaatgt tataatacaa cataagaatc   3000
gcactatcat gaagccggaa gatgcatcgg gcagcaaccg gagcgcccct tgcacctttg   3060
tcgatagaga aagagggaat gacaattgtt tttacacggt actagcagac aaaatgaaag   3120
agggcacctc gaaatcggcg gtgtcgatgt tctatcattg gcagaaagat acggaacacc   3180
tctttatgta tacgatgtcg cgctgattag agagcgcgcc cgaaaattcc agaaggcatt   3240
caaggaagcc ggtttaaaag cgcaggtagc gtatgcaagc aaggcgtttt catcggttgc   3300
catgattcag cttgccgaac aagaggggct gtctctggat gtggtatcgg gaggagagct   3360
tttcactgcg atcaaagcag ggttcccagc tgagcggatt cattttcacg gaaacaataa   3420
gagccctgaa gaactagcca tggcgctgga gcatcaaatc ggctgcatcg tgctcgataa   3480
ctttcacgag atcgccatta cagaagatct ttgcaagcga tcaggacaaa ctgtagacgt   3540
tttgctcaga atcactccgg gagttgaagc gcacacgcac gattatatta cgacggggca   3600
ggaagattcc aaattcggtt ttgatctgca taatggacag gtcgaacaag ccatcgaaca   3660
agtcctccgc tcgtctgcgt ttaagctcct cggcgtgcac tgccacatcg gttcgcaaat   3720
ttttgatacg gcaggatttg tccttgcagc agacaagatt ttcgagaagc ttgcggaatg   3780
```

gcgggagact tactctttca ttccggaagt gctcaatctt ggcgggggct tcggcatccg 3840
ctatacaaaa gacgacgagc cgcttgcagc tgatgtttat gttgaaaaaa tcatcgaggc 3900
ggtcaaagca aatgccgagc atttcggctt tgacatccct gagatttgga tcgaaccagg 3960
ccggtctctc gtcggtgatg cggggactac gctgtacacg atcggttctc aaaaagaggt 4020
gccgggcatt cgcaaatatg tagccatcga cggcggcatg agcgataata tcaggccggc 4080
gctttatgag gcaaaatatg aagcagccgt cgccaacagg atgaacgatg cttgtcatga 4140
taccgcatca atcgcaggaa aatgctgcga aagcggagat atgctgattt gggatttgga 4200
aatccccgaa gttcgcgacg gagatgtgct cgccgttttc tgcaccggtg cgtacggcta 4260
cagcatggcc aacaactaca accgcattcc gcgcccggcc gtcgtctttg tcgaggacgg 4320
ggaagcgcag ctcgtcattc agagagagac gtatgaggat atcgtcaagc tggatctgcc 4380
gctgaaatcg aaagtcaaac aataaaaaaa tggagattcc ctaagagggg ggtctccatt 4440
tttaattcaa gctgataaac agctgacatc aactaaaagt ttcattaaat actttgaaaa 4500
aagttgttga cttaaaagaa gctaaatgtt atagtaattg tacagaatag tcttttaagt 4560
aagtctactc tgaatttttt taaaaggaga gggtaaagaa tgaaacaaca aaaacggctt 4620
tacgcccgat tgctgacgct gttatttgcg ctcatcttct tgctgcctca ttctgcagct 4680
agcgcacatc ataacggtac gaacgggaca atgatgcaat actttgaatg gtatctacct 4740
aatgacggaa atcattggaa tcgattaaac tctgatgcga gtaaccttaa aagcaaaggg 4800
attacagcgg tgtggattcc tccagcatgg aagggcgctt ctcaaaatga cgtaggatac 4860
ggagcctatg acctgtatga tctgggagaa tttaatcaaa aaggtaccgt ccgtacaaaa 4920
tatggaacac gtagtcagtt acaagctgcg gtaacctcct taaaaaataa tggaattcaa 4980
gtatatggtg acgttgttat gaatcacaaa ggtggcgcag acgctactga aatggtaagg 5040
gccgttgaag tgaatcccaa taaccgtaac caagaagtga ctggtgaata taccattgaa 5100
gcttggacta gatttgattt tccagggcga ggaaatactc attctagctt taaatggaga 5160
tggtatcatt ttgatggtgt ggattgggat cagtcacgta gactgaacaa tcgcatctat 5220
aaatttagag gtcatggcaa agcttgggat tgggaagttg atacggaaaa tggtaattat 5280
gattatttac tatacgctga tattgatatg gatcacccag aagtagtaaa tgaattaaga 5340
aattggggtg tttggtacac aaacacatta ggactcgatg gatttagaat agatgcggtt 5400
aaacatataa agtatagctt tacgcgcgat tggattaatc acgttagaag tgcaacaggt 5460
aaaaatatgt ttgcggttgc tgagttttgg aagaatgatt taggtgcaat tgaaaactat 5520
ctgcagaaaa caaactggaa ccattcagtc tttgatgtgc cgttacatta taatctttat 5580
aatgcatcaa aaagcggagg gaactatgat atgcgaaaca tatttaatgg aacggttgtt 5640
caacgacatc caagtcatgc tgtaacattt gttgataatc atgattcgca gcctgaagaa 5700
gcattagaat cttttgttga agaatggttt aaaccattag cgtatgcgct tacattaacg 5760
cgtgaacaag gataccctte tgtattttac ggagattatt atgggattcc aacacatgga 5820
gtgccagcaa tgagatcaaa aatcgatccg attttagaag cacgtcaaaa gtatgcatac 5880
ggaaaacaaa atgattactt agaccatcat aatatcattg gttggacgcg tgaagggaat 5940
acagcacacc ccaattcagg tctagctacc atcatgtctg atggagcggg tggaagtaag 6000
tggatgtttg ttgggcgtaa taaggctggt caagtatgga gtgatattac aggaaaccgt 6060
acaggtacgg ttacaatcaa tgcagacggt tggggcaatt tctctgtgaa tggagggtca 6120

```
gtttctattt gggtcaacaa ataaaagctt ctcgaggtta acagaggacg gatttcctga   6180
aggaaatccg tttttttatt ttagcacgaa aaacacttcc cggtgatcgg gaggtgtttt   6240
ttgttaaaaa gatcatgaca tgcatagaac agcgaccggg ctaattgtat ataatattgt   6300
gaatttaaca aaaaatttac aaaggagatg ataaaggcaa tgaccagggt gaaaaggatg   6360
agatttgctg atttgttgga tttagaggcg gagtagatga aaccggccaa agtatcccta   6420
ctccaccgat tgctccagtg cctgaagcaa tgtgttgatt gtaacacagt aaatcgtttt   6480
acagcaataa acatttttgt gaatatttta ttgatttcgg ctgtgatctc attcccatat   6540
tctgctgcgg cccatggcgc aacacagtcc ggcgatcaat attcaagctt tgaagaattg   6600
gagcggaatg aagatccagc ttcttaccga attacggaga agaacgcaag agtgccgatg   6660
ctcatcatgg ccatccatgg aggcggcatc gaacccggaa cgagcgaaat cgccaatgaa   6720
gtgtccaaaa actattccct gtacttgttt gaagggctga aatcatcagg caatacggac   6780
cttcacatta caagcacgcg ttttgacgag ccagcggcgc tcgcaattac tgcaagccac   6840
cagtatgtca tgtcgctcca cggctattac agtgaagacc gcgatattaa agtaggcggc   6900
acagaccgcg ctaaaatcag aatattggtt gatgagctga accgctcggg gtttgccgct   6960
gaaatgctgg ggacagatga caagtatgcc ggaacccatc cgaataacat cgccaacaag   7020
tcgctttccg ggctgagcat tcagcttgaa atgagcacgg gtttccgcaa atctttattc   7080
gaccggttta cactaaaaga cagggcggcg acgcaaaacg aaacgtttta ccgatttaca   7140
aagctgctga cagattttat tcatgaaaac tatgaagaag acggaggga tttcccctct   7200
gcaaaaataa aacacccct tcaagtgaaa aaggaggtgt ttcggcggtt gtgttaaccg   7260
ttggactctg aggtgccgcc gccggtgaat acggaaacga tggcgttcca cagagacaca   7320
aagaagtcga tcagtttttg aagaaagttt tgtccttctt cagaatccaa gaatttcgtg   7380
attttatcct ttgctttgtc aagctggtct ccaacctggt tccagtcgat attaatattt   7440
ttcatgttat taaataaaga tataagagag tttttctgat cttctgtgag tgtcacgcca   7500
agttcggaag cagccgaatc aatcgttttc tccaattcct cttttgactc gggaactccg   7560
tttttcgaga tttcttcctt gactttggcc atcagcgctg acgcgttttc actgccgatt   7620
ttctcgccaa gctctgaagt ggtgacaagc tcttcattcg cgaccttttt cacatcttcg   7680
gaaatttttt cgcccgaagt cgtttcatac gctttcatca atccggttaa agcggctgtg   7740
cctgacactt caaacggagc ggtgacatag actttggcgt cttttacacc ggccgtcatc   7800
agcgcgttca aatacatctc atctgtaatt ctgctgatat tgtgtgtctg aacttccaaa   7860
ccggtgcctt ttttcgctac ggtaattgaa gaagaagaaa tcgctcttgt tccgatttgt   7920
gctttcggta tataatcccc taaatattta tgctcctcat catttgtcac ctcgatgatg   7980
gtcgcatttt caggcgcatt catttctttt aatacttttt gtctgtcctg gcttgacaag   8040
tctttcccca gcgtgacgat gacatcaccc actgcggcgt cagcgaagct gacctgcggg   8100
aaaatgagca gacacaatgc tgtaaagatt cctagtatcg attttttcaa gctcaatgcc   8160
ctccttaaaa atgcaggctt caggcagaat tgctgtactt ttaaagaagc ctgccggaac   8220
ggaaataatg cgttccgaaa tatagacgga tgaaagatga gtgaggtttc aaagaaaaaa   8280
agagagaatt ttctcttcaa gtcaaatgcc ctcccggcat cgtatctcgc cgctctttta   8340
tcattcatga ttttcacagg cgattcaacc ttttttaaa atttttaca aaaacgatac    8400
aagagcggcg tttatttcgg tcgattggct ctctgcttct tcaatatgat ataatgaccc   8460
ttgtgaaatg aaaggagaga atcaagatgg ctaaaaaagg atacatacaa ctgacaaacg   8520
```

```
gcaaaaaaat cgagtttgaa ctatatccgg atgcggcgcc gggaactgtc gccaactttg   8580

aaaaacttgc aaacgaaggg ttctatgacg ggctgaagtt ccaccgcgtc atcccgggct   8640

tcgtcagcca gggaggctgc ccgcacggca ccggaacagg cggacctgga tatacgatta   8700

aatgcgagac agaagggaat ccgcacaaac acgaagccgg ttctctctca atggctcacg   8760

caggaaaaga taccggaggc agccaatttt ttatcgtcca tgagcctcag ccgcacttga   8820

acggcgttca caccgttttc ggaaaggtca catcaggcct tgatgccgtc acttcaatgg   8880

agcagggaca aggcatggaa aaagtcgaag tatttgatgc ataatcagag agcgcaaaaa   8940

acagcccgct tagccgggct gttttttgt ctgtaacggt gtttattttc caggtgcaac    9000

aggacttgag gccgattctt cgtccacatc ctgataggaa ataacgatgc taataaataa   9060

aataattgtg aaaaaatgac cctttatgta aaatatattc aagtgaagag ctagatagag   9120

aacgcaatct gtaaaaaagg aaggggcgta aggggtgagc gtaaaaatcc catcgacggc   9180

agtcggcgta aaaattaatg actggtataa cgcgatacg                          9219
```

<210> SEQ ID NO 155
<211> LENGTH: 286
<212> TYPE: PRT
<213> ORGANISM: Bacillus licheniformis

<400> SEQUENCE: 155

```
Met Lys Lys Ile Ala Ile Ala Ala Ile Thr Ala Thr Ser Val Leu Ala
1               5                   10                  15

Leu Ser Ala Cys Ser Gly Gly Asp Ser Glu Val Val Ala Glu Thr Lys
            20                  25                  30

Ala Gly Asn Ile Thr Lys Glu Asp Leu Tyr Gln Thr Leu Lys Asp Asn
        35                  40                  45

Ala Gly Ala Asp Ala Leu Asn Met Leu Val Gln Gln Lys Val Leu Asp
    50                  55                  60

Asp Lys Tyr Asp Val Ser Asp Lys Glu Ile Asp Lys Lys Leu Asn Glu
65                  70                  75                  80

Tyr Lys Lys Ser Met Gly Asp Gln Leu Asn Gln Leu Ile Asp Gln Lys
                85                  90                  95

Gly Glu Asp Phe Val Lys Glu Gln Ile Lys Tyr Glu Leu Leu Met Gln
            100                 105                 110

Lys Ala Ala Lys Asp Asn Ile Lys Val Thr Asp Asp Asp Val Lys Glu
        115                 120                 125

Tyr Tyr Asp Gly Leu Lys Gly Lys Ile His Leu Ser His Ile Leu Val
    130                 135                 140

Lys Glu Lys Lys Thr Ala Glu Glu Val Glu Lys Lys Leu Lys Lys Gly
145                 150                 155                 160

Glu Lys Phe Glu Asp Leu Ala Lys Glu Tyr Ser Thr Asp Gly Thr Ala
                165                 170                 175

Glu Lys Gly Gly Asp Leu Gly Trp Val Gly Lys Asp Asp Asn Met Asp
            180                 185                 190

Lys Asp Phe Val Lys Ala Ala Phe Ala Leu Lys Thr Gly Glu Ile Ser
        195                 200                 205

Gly Pro Val Lys Ser Gln Phe Gly Tyr His Ile Ile Lys Lys Asp Glu
    210                 215                 220

Glu Arg Gly Lys Tyr Glu Asp Met Lys Lys Glu Leu Lys Lys Glu Val
225                 230                 235                 240

Gln Glu Gln Lys Gln Asn Asp Gln Thr Glu Leu Gln Ser Val Ile Asp
```

```
                245                 250                 255

Lys Leu Val Lys Asp Ala Asp Leu Lys Val Lys Asp Lys Glu Leu Lys
            260                 265                 270

Lys Gln Val Asp Gln Arg Gln Ala Gln Thr Ser Ser Ser Ser
        275                 280                 285


<210> SEQ ID NO 156
<211> LENGTH: 134
<212> TYPE: PRT
<213> ORGANISM: Bacillus licheniformis

<400> SEQUENCE: 156

Met Ala Met Thr Arg Phe Gly Glu Arg Leu Lys Glu Leu Arg Glu Gln
1               5                   10                  15

Arg Ser Leu Ser Val Asn Gln Leu Ala Met Tyr Ala Gly Val Ser Ala
            20                  25                  30

Ala Ala Ile Ser Arg Ile Glu Asn Gly His Arg Gly Val Pro Lys Pro
        35                  40                  45

Ala Thr Ile Arg Lys Leu Ala Glu Ala Leu Lys Met Pro Tyr Glu Gln
    50                  55                  60

Leu Met Asp Ile Ala Gly Tyr Met Arg Ala Asp Glu Ile Arg Glu Gln
65                  70                  75                  80

Pro Arg Gly Tyr Val Thr Met Gln Glu Ile Ala Ala Lys His Gly Val
                85                  90                  95

Glu Asp Leu Trp Leu Phe Lys Pro Glu Lys Trp Asp Cys Leu Ser Arg
            100                 105                 110

Glu Asp Leu Leu Asn Leu Glu Gln Tyr Phe His Phe Leu Val Asn Glu
        115                 120                 125

Ala Lys Lys Arg Gln Ser
    130


<210> SEQ ID NO 157
<211> LENGTH: 140
<212> TYPE: PRT
<213> ORGANISM: Bacillus licheniformis

<400> SEQUENCE: 157

Met Ala Met Thr Arg Phe Gly Glu Arg Leu Lys Glu Leu Arg Glu Gln
1               5                   10                  15

Arg Ser Leu Ser Val Asn Gln Leu Ala Met Tyr Ala Gly Val Ser Ala
            20                  25                  30

Ala Ala Ile Ser Arg Ala Ala Ala Ile Ser Arg Ile Glu Asn Gly His
        35                  40                  45

Arg Gly Val Pro Lys Pro Ala Thr Ile Arg Lys Leu Ala Glu Ala Leu
    50                  55                  60

Lys Met Pro Tyr Glu Gln Leu Met Asp Ile Ala Gly Tyr Met Arg Ala
65                  70                  75                  80

Asp Glu Ile Arg Glu Gln Pro Arg Gly Tyr Val Thr Met Gln Glu Ile
                85                  90                  95

Ala Ala Lys His Gly Val Glu Asp Leu Trp Leu Phe Lys Pro Glu Lys
            100                 105                 110

Trp Asp Cys Leu Ser Arg Glu Asp Leu Leu Asn Leu Glu Gln Tyr Phe
        115                 120                 125

His Phe Leu Val Asn Glu Ala Lys Lys Arg Gln Ser
    130                 135                 140
```

```
<210> SEQ ID NO 158
<211> LENGTH: 423
<212> TYPE: DNA
<213> ORGANISM: Bacillus licheniformis

<400> SEQUENCE: 158

atggcgatga caaggttcgg cgagcggctc aaagagctga gggaacaaag aagcctgtcg      60

gttaatcagc ttgccatgta tgccggtgtg agcgccgcag ccatttccag agccgcagcc     120

atttccagaa tcgaaaacgg ccaccgcggc gttcccaagc ccgcgacgat cagaaaattg     180

gccgaggctc tgaaaatgcc gtacgagcag ctcatggata ttgccggtta tatgagagct     240

gacgagattc gcgaacagcc gcgcggctat gtcacgatgc aggagatcgc ggccaagcac     300

ggcgtcgaag acctgtggct gtttaaaccc gagaaatggg actgtttgtc ccgcgaagac     360

ctgctcaacc tcgaacagta ttttcatttt ttggttaatg aagcgaagaa gcgccaatca     420

taa                                                                   423
```

COMPOSITIONS AND METHODS FOR ENHANCED PROTEIN PRODUCTION IN BACILLUS LICHENIFORMIS

CROSS-REFERENCE TO RELATED APPLICATIONS

The present application is a U.S. National Stage Application under 35 U.S.C. § 371 of International Application No. PCT/US2021/013420, filed Jan. 14, 2021, which claims priority to U.S. Provisional Patent Application No. 62/961,234, filed Jan. 15, 2020, all of which are incorporated herein by reference in their entirety.

FIELD

The present disclosure is generally related to the fields of bacteriology, microbiology, genetics, molecular biology, enzymology, industrial protein production the like. Certain embodiments of the disclosure are therefore related to compositions and methods for constructing *Bacillus licheniformis* cells/strains having enhanced protein production phenotypes.

REFERENCE TO A SEQUENCE LISTING

The contents of the electronic submission of the text file Sequence Listing, named "NB41684-WO-PCT_Sequence-Listing.txt" was created on Jan. 7, 2021 and is 425 KB in size, which is hereby incorporated by reference in its entirety.

BACKGROUND

Gram-positive bacteria such as *Bacillus subtilis, Bacillus licheniformis* and *Bacillus amyloliquefaciens* are frequently used as microbial factories for the production of industrial relevant proteins, due to their excellent fermentation properties and high yields (e.g., up to 25 grams per liter culture; Van Dijl and Hecker, 2013). For example, *B. subtilis* is well known for its production of α-amylases (Jensen et al., 2000; Raul et al., 2014) and proteases (Brode et al., 1996) necessary for food, textile, laundry, medical instrument cleaning, pharmaceutical industries and the like (Westers et al., 2004). Because these non-pathogenic Gram-positive bacteria produce proteins that completely lack toxic by-products (e.g., lipopolysaccharides; LPS, also known as endotoxins) they have obtained the "Qualified Presumption of Safety" (QPS) status of the European Food Safety Authority, and many of their products gained a "Generally Recognized As Safe" (GRAS) status from the US Food and Drug Administration (Olempska-Beer et al., 2006; Earl et al., 2008; Caspers et al., 2010).

Thus, the production of proteins (e.g., enzymes, antibodies, receptors, etc.) in microbial host cells is of particular interest in the biotechnological arts. Likewise, the optimization of *Bacillus* host cells for the production and secretion of one or more protein(s) of interest is of high relevance, particularly in the industrial biotechnology setting, wherein small improvements in protein yield are quite significant when the protein is produced in large industrial quantities. More particularly. *B. licheniformis* is a *Bacillus* species host cell of high industrial importance, and as such, the ability to modify and engineer *B. licheniformis* host cells for enhanced/increased protein expression/production is highly desirable for construction of new and improved *B. licheniformis* production strains. The present disclosure is thus related to the highly desirable and unmet need for obtaining and constructing *B. licheniformis* cells (e.g., protein production host cells) having increased protein production capabilities.

SUMMARY

The present disclosure is generally related to compositions and methods for obtaining *B. licheniformis* cells (e.g., protein production hosts) comprising enhanced protein production capabilities. Certain embodiments of the disclosure are therefore related to methods for constructing such modified *B. licheniformis* cells/strains producing increased amounts of one or more proteins of interest.

Thus, certain embodiments of the disclosure are directed to methods for producing an increased amount of an endogenous protein of interest (POT) in a modified *Bacillus licheniformis* cell comprising (a) obtaining parental *B. licheniformis* cell expressing a POI and modifying the parental cell by introducing therein a polynucleotide comprising a native prsA promoter operably linked to a native prsA open reading frame (ORF), and (b) fermenting the modified cell of step (a) under suitable conditions for the production of the POI, wherein the modified cell produces an increased amount of the POT relative to the parental cell when fermented under the same conditions. In particular embodiments of the methods, the introduced polynucleotide of step (a) comprises a native prsA promoter comprising at least 95% sequence identity to SEQ ID NO: 100. In other embodiments of the methods, the introduced polynucleotide of step (a) comprises a native prsA ORF comprising at least 90% sequence identity to SEQ ID NO: 101. In other embodiments, the introduced polynucleotide encodes a native prsA protein comprising about 90% sequence identity to SEQ ID NO: 155. In certain preferred embodiments, the parental cell comprises an endogenous (wild-type) prsA gene encoding a native prsA protein, wherein the introduced polynucleotide thereby encodes a second ($2^{nd}$) copy of a prsA protein comprising about 90% sequence identity to SEQ ID NO: 155. In other embodiments, the introduced polynucleotide of step (a) is integrated into the genome of the modified *B. licheniformis* cell. In yet other embodiments of the methods, the protein of interest (POI) is a protease or an amylase. In other embodiments, the modified cell comprises a deleted or disrupted dltA gene comprising at least 90% sequence identity to SEQ ID NO: 122. In other embodiments, the modified cell comprises a deleted or disrupted rghR2 gene comprising at least 90% sequence identity to SEQ ID NO: 121 or SEQ ID NO: 158. In other embodiments, the modified cell comprises a deleted or disrupted dltA gene comprising at least 90% sequence identity to SEQ ID NO: 122 and a deleted or disrupted rghR2 gene comprising at least 90% sequence identity to SEQ ID NO: 121 or SEQ ID NO: 158.

In certain other embodiments, the disclosure is related to methods for producing an increased amount of a heterologous protein of interest (POI) in a modified *Bacillus licheniformis* cell comprising (a) introducing into a parental *B. licheniformis* cell (i) an expression cassette encoding a POI and (ii) a polynucleotide comprising a native prsA promoter operably linked to a native prsA open reading frame (ORF), and (b) fermenting the modified cell of step (a) under suitable conditions for the production of the POT, wherein the modified cell produces an increased amount of the POT relative to the parental cell when fermented under the same conditions. In particular embodiments of the methods, the introduced polynucleotide of step (a)(ii) comprises a native prsA promoter comprising at least 95% sequence identity to SEQ ID NO: 100. In certain other embodiments, the introduced polynucleotide of step (a)(ii) comprises a native prsA ORF comprises at least 90% sequence identity to SEQ ID NO: 101. In yet other embodiments of the methods, the endogenous prsA gene encodes a native prsA protein comprising about 90% sequence identity to SEQ ID NO: 155. In certain other embodiments, the introduced polynucleotide of step (a)(ii) is integrated into the genome of the modified *B. licheniformis* cell. In certain preferred embodiments, the parental cell comprises an endogenous (wild-type) prsA gene encoding a native prsA protein, wherein the introduced polynucleotide step (a)(ii) thereby encodes a second ($2^{nd}$) copy of a prsA protein comprising about 90% sequence identity to SEQ ID NO: 155. In particular embodiments, the protein of interest (POI) is a protease or an amylase. In other embodiments, the modified cell comprises a deleted or disrupted dltA gene comprising at least 90% sequence identity to SEQ ID NO: 122. In other embodiments, the modified cell comprises a deleted or disrupted rghR2 gene comprising at least 90% sequence identity to SEQ ID NO: 121 or SEQ ID NO: 158. In certain preferred embodiments, the modified cell comprises a deleted or disrupted dltA gene comprising at least 90% sequence identity to SEQ ID NO: 122 and a deleted or disrupted rghR2 gene comprising at least 90% sequence identity to SEQ ID NO: 121 or SEQ ID NO: 158.

Other embodiments of the disclosure are directed to modified *Bacillus licheniformis* cells/strains derived from parental *B. licheniformis* cells/strains comprising an endogenous prsA gene encoding a native prsA protein. Thus, in certain embodiments, a modified *B. licheniformis* cell of the disclosure comprises an introduced polynucleotide comprising a native prsA promoter operably linked to a native prsA open reading frame (ORF). In particular embodiments, the introduced polynucleotide comprises a native prsA promoter comprising at least 95% sequence identity to SEQ ID NO: 100. In other embodiments, the introduced polynucleotide comprises a native prsA ORF comprising at least 90% sequence identity to SEQ ID NO: 101. In yet other embodiments, the introduced polynucleotide encodes a native prsA protein comprising about 90% sequence identity to SEQ ID NO: 155. In certain other embodiments, the introduced polynucleotide encoding a native prsA protein is integrated into the genome of the modified *B. licheniformis* cell. In another embodiment, the modified cell comprises a deleted or disrupted dltA gene comprising at least 90% sequence identity to SEQ ID NO: 122. In another embodiment, the modified cell comprises a deleted or disrupted rghR2 gene comprising at least 90% sequence identity to SEQ ID NO: 121 or SEQ ID NO: 158. In a preferred embodiment, the modified cell comprises a deleted or disrupted dltA gene comprising at least 90% sequence identity to SEQ ID NO: 122 and a deleted or disrupted rghR2 gene comprising at least 90% sequence identity to SEQ ID NO: 121 or SEQ ID NO: 158. In certain other embodiments, the modified cell comprises an introduced expression construct encoding a heterologous protein of interest (POT). In other embodiments, the heterologous POI is a protease or an amylase. Certain embodiments of the disclosure are therefore directed to obtaining, isolating, purifying and like a protein of interest produced by a modified *B. licheniformis* cell of the disclosure.

Certain other embodiments of the disclosure are therefore directed to modified *Bacillus licheniformis* cells producing an increased amount of a protein of interest (POI), relative to a parental *B. licheniformis* cell from they were derived. Thus, in certain embodiments, the disclosure relates to a modified *Bacillus licheniformis* cell producing an increased amount of a protein of interest (POI) relative to a parental *B. licheniformis* cell, wherein modified cell is derived from a parental *B. licheniformis* cell expressing a POT, wherein the modified cell comprises an introduced polynucleotide comprising a native prsA promoter operably linked to a native prsA open reading frame (ORF) and comprises a deleted or disrupted rghR2 gene comprising at least 90% sequence identity to SEQ ID NO: 121 or SEQ ID NO: 158, wherein the modified cell produces an increased amount of the POT relative to the parental strain when fermented under the same condition. In another embodiment, the modified *Bacillus licheniformis* cell comprises a deleted or disrupted dltA gene comprising at least 90% sequence identity to SEQ ID NO: 122. In yet another embodiment, the native prsA promoter comprises at least 95% sequence identity to SEQ ID NO: 100. In certain other embodiments, the native prsA ORF comprises at least 90% sequence identity to SEQ ID NO: 101. In another embodiment, the native prsA protein comprises about 90% sequence identity to SEQ ID NO: 155. In particular embodiments, the protein of interest (POT) is a protease or an amylase. Certain other embodiments of the disclosure are therefore directed to obtaining, isolating, purifying and like a protein of interest produced by a modified *B. licheniformis* cell.

In other embodiments, the disclosure relates to a modified *Bacillus licheniformis* cell producing an increased amount of a protein of interest (POI) relative to a parental *B. licheniformis* cell, wherein modified cell is derived from a parental *B. licheniformis* cell expressing a POI, wherein the modified cell comprises an introduced polynucleotide comprising a native prsA promoter operably linked to a native prsA open reading frame (ORF) and comprises a deleted or disrupted dltA gene comprising at least 90% sequence identity to SEQ ID NO: 122, wherein the modified cell produces an increased amount of the POI relative to the parental strain when fermented under the same condition. In other embodiments, the modified cell further comprises a deleted or disrupted rghR2 gene comprising at least 90% sequence identity to SEQ ID NO: 121 or SEQ ID NO: 158. In yet another embodiment, the native prsA promoter comprises at least 95% sequence identity to SEQ ID NO: 100. In certain other embodiments, the native prsA ORF comprises at least 90% sequence identity to SEQ ID NO: 101. In another embodiment, the native prsA protein comprises about 90% sequence identity to SEQ ID NO: 155. In particular embodiments, the protein of interest (POI) is a protease or an amylase. Certain other embodiments of the disclosure are therefore directed to obtaining, isolating, purifying and like a protein of interest produced by a modified *B. licheniformis* cell.

BRIEF DESCRIPTION OF THE BIOLOGICAL SEQUENCES

SEQ ID NO: 1 is an amino acid sequence encoding a native *S. pyogenes* Cas9 protein.

SEQ ID NO: 2 is a nucleic acid sequence encoding the Cas9 protein of SEQ ID NO: 1, which nucleic sequence has been codon optimized for expression in *Bacillus* sp. cells.

SEQ ID NO: 3 is the amino acid sequence of a synthetic N-terminal nuclear localization signal (NLS).

SEQ ID NO: 4 is the amino acid sequence of a synthetic C-terminal nuclear localization signal (NLS).

SEQ ID NO: 5 is the amino acid sequence of a synthetic deca-histidine tag.

SEQ ID NO: 6 is a *B. subtilis* aprE promoter sequence.

SEQ ID NO: 7 is a synthetic terminator nucleic acid sequence.

SEQ ID NO: 8 is a forward primer nucleic acid sequence.

SEQ ID NO: 9 is a reverse primer nucleic acid sequence.

SEQ ID NO: 10 is a synthetic pKB320 backbone nucleic acid sequence.

SEQ ID NO: 11 is a synthetic pKB320 nucleic acid sequence.

SEQ ID NO: 12 is a primer nucleic acid sequence.

SEQ ID NO: 13 is a primer nucleic acid sequence.

SEQ ID NO: 14 is a primer nucleic acid sequence.

SEQ ID NO: 15 is a primer nucleic acid sequence.

SEQ ID NO: 16 is a primer nucleic acid sequence.

SEQ ID NO: 17 is a primer nucleic acid sequence.

SEQ ID NO: 18 is a primer nucleic acid sequence.

SEQ ID NO: 19 is a primer nucleic acid sequence.

SEQ ID NO: 20 is a primer nucleic acid sequence.

SEQ ID NO: 21 is a primer nucleic acid sequence.

SEQ ID NO: 22 is a primer nucleic acid sequence.

SEQ ID NO: 23 is a primer nucleic acid sequence.

SEQ ID NO: 24 is a primer nucleic acid sequence.

SEQ ID NO: 25 is a synthetic pRF694 nucleic acid sequence.

SEQ ID NO: 26 is a synthetic pRF801 nucleic acid sequence.

SEQ ID NO: 27 is a synthetic pRF806 nucleic acid sequence.

SEQ ID NO: 28 is a *B. licheniformis* target site 1 (TS1) nucleic acid sequence.

SEQ ID NO: 29 is a *B. licheniformis* target site 2 (TS2) nucleic acid sequence.

SEQ ID NO: 30 is a *B. licheniformis* serA1 open reading frame (ORF) sequence.

SEQ ID NO: 31 is a target site 1 PAM sequence comprising nucleotides "AGG".

SEQ ID NO: 32 is a nucleic acid sequence encoding variable targeting (VT) site 1.

SEQ ID NO: 33 is a synthetic nucleic acid sequence encoding a CER domain.

SEQ ID NO: 34 is a synthetic guide RNA (gRNA) sequence targeting site 1.

SEQ ID NO: 35 is a synthetic spac promoter nucleic acid sequence.

SEQ ID NO: 36 is a synthetic t0 terminator nucleic acid sequence.

SEQ ID NO: 37 is a *B. licheniformis* serA1 homology arm 1 nucleic acid sequence.

SEQ ID NO: 38 is a synthetic serA1 homology arm 1 forward primer sequence.

SEQ ID NO: 39 is a synthetic serA1 homology arm 1 reverse primer sequence.

SEQ ID NO: 40 is a *B. licheniformis* serA1 homology arm 2 nucleic acid sequence.

SEQ ID NO: 41 is a synthetic serA1 homology arm 2 forward primer sequence.

SEQ ID NO: 42 is a synthetic serA1 homology arm 2 forward primer sequence.

SEQ ID NO: 43 is an expression cassette encoding a target site 1 (TS1) gRNA.

SEQ ID NO: 44 is a synthetic serA1 deletion editing template.

SEQ ID NO: 45 is a *B. licheniformis* rghR1 open reading frame (ORF) sequence.

SEQ ID NO: 46 is a target site 2 PAM sequence comprising nucleotides "CGG".

SEQ ID NO: 47 is a synthetic guide RNA (gRNA) sequence targeting site 2.

SEQ ID NO: 48 is a *B. licheniformis* rghR1 homology arm 1 nucleic acid sequence.

SEQ ID NO: 49 is a synthetic rghR1 homology arm 1 forward primer sequence.

SEQ ID NO: 50 is a synthetic rghR1 homology arm 1 reverse primer sequence.

SEQ ID NO: 51 is a *B. licheniformis* rghR1 homology arm 2 nucleic acid sequence.

SEQ ID NO: 52 is a synthetic rghR1 homology arm 2 forward primer sequence.

SEQ ID NO: 53 is a synthetic rghR1 homology arm 2 reverse primer sequence.

SEQ ID NO: 54 is an expression cassette encoding a target site 2 (TS2) gRNA.

SEQ ID NO: 55 is a synthetic rghR1 deletion editing template.

SEQ ID NO: 56 is an amino acid sequence encoding Cas9 (Y155H) variant protein.

SEQ ID NO: 57 is a synthetic Y155H forward primer sequence.

SEQ ID NO: 58 is a synthetic Y155H reverse primer sequence.

SEQ ID NO: 59 is a synthetic pRF827 nucleic acid sequence.

SEQ ID NO: 60 is an expression cassette encoding a variant Cas9 (Y155H) protein of SEQ ID NO: 56.

SEQ ID NO: 61 is a synthetic pRF856 nucleic acid sequence.

SEQ ID NO: 62 is a synthetic pRF862 nucleic acid sequence.

SEQ ID NO: 63 is a synthetic Y155H fragment sequence.

SEQ ID NO: 64 is a synthetic Y155H fragment forward primer sequence.

SEQ ID NO: 65 is a synthetic Y155H fragment reverse primer sequence.

SEQ ID NO: 66 is a synthetic pRF694 fragment sequence.

SEQ ID NO: 67 is a synthetic pRF694 fragment forward primer sequence.

SEQ ID NO: 68 is a synthetic pRF694 fragment reverse primer sequence.

SEQ ID NO: 69 is a synthetic pRF869 nucleic acid sequence.

SEQ ID NO: 70 is a *B. licheniformis* rghR2 open reading frame (ORF) sequence.

SEQ ID NO: 71 is a synthetic rghR2$_{stop}$ fragment.

SEQ ID NO: 72 is a synthetic rghR2$_{stop}$ editing template.

SEQ ID NO: 73 is an expression cassette encoding a rghR2 gRNA.

SEQ ID NO: 74 is a synthetic fragment forward primer.

SEQ ID NO: 75 is a synthetic fragment reverse primer.

SEQ ID NO: 76 is a synthetic pRF862 backbone forward primer.

SEQ ID NO: 77 is a synthetic pRF862 backbone reverse primer.

SEQ ID NO: 78 is a synthetic pRF879 nucleic acid sequence.

SEQ ID NO: 79 is a *B. licheniformis* pRF879 target site and PAM nucleic acid sequence.

SEQ ID NO: 80 is a synthetic pRF879 editing template sequence.

SEQ ID NO: 81 is a synthetic pRF946 nucleic acid sequence.

SEQ ID NO: 82 is a *B. licheniformis* pR946 target site and PAM nucleic acid sequence.

SEQ ID NO: 83 is a synthetic pR946 editing template sequence.

SEQ ID NO: 84 is a synthetic pZM221 nucleic acid sequence.

SEQ ID NO: 85 is a synthetic pZM221 target site and PAM nucleic acid sequence.

SEQ ID NO: 86 is a synthetic pZM221 editing template sequence.

SEQ ID NO: 87 is a *B. licheniformis* lysA open reading frame (ORF) sequence.

SEQ ID NO: 88 is a synthetic pBl.comK nucleic acid sequence.

SEQ ID NO: 89 is a synthetic spectinomycin marker nucleic acid sequence.

SEQ ID NO: 90 is a *B. subtilis* xylR nucleic acid sequence.

SEQ ID NO: 91 is a *B. subtilis* xylAp nucleic acid sequence.

SEQ ID NO: 92 is a synthetic comK nucleic acid sequence.

SEQ ID NO: 93 is a synthetic cat_prsA nucleic acid sequence.

SEQ ID NO: 94 is a *B. licheniformis* cat upstream nucleic acid sequence.

SEQ ID NO: 95 is a *B. licheniformis* cat promoter nucleic acid sequence.

SEQ ID NO: 96 is a *B. licheniformis* catH nucleic acid sequence.

SEQ ID NO: 97 is a synthetic dual terminator nucleic acid sequence.

SEQ ID NO: 98 is a *B. licheniformis* catH terminator nucleic acid sequence.

SEQ ID NO: 99 is a *B. subtilis* spoVG terminator nucleic acid sequence.

SEQ ID NO: 100 is a *B. licheniformis* prsA promoter nucleic acid sequence.

SEQ ID NO: 101 is a *B. licheniformis* prsA open reading frame (ORF) sequence.

SEQ ID NO: 102 *B. licheniformis* amyL terminator nucleic acid sequence.

SEQ ID NO: 103 is a *B. licheniformis* cat downstream nucleic acid sequence.

SEQ ID NO: 104 is a synthetic forward primer nucleic acid sequence.

SEQ ID NO: 105 is a synthetic reverse primer nucleic acid sequence.

SEQ ID NO: 106 is a synthetic prsA ($2^{nd}$ copy) verification nucleic acid sequence.

SEQ ID NO: 107 is a synthetic primer sequence.

SEQ ID NO: 108 is a synthetic primer sequence.

SEQ ID NO: 109 is a synthetic primer sequence.

SEQ ID NO: 110 is a *B. licheniformis* deleted catHP and catH encoding nucleic acid sequence.

SEQ ID NO: 111 is a synthetic prsA ($2^{nd}$ copy) expression cassette in cat catH deletion SEQ ID NO: 112 is a synthetic catH ($2^{nd}$ copy) deletion verification PCR product.

SEQ ID NO: 113 is a synthetic forward primer sequence.

SEQ ID NO: 114 is a synthetic reverse primer sequence.

SEQ ID NO: 115 is a synthetic dltA-2 verification PCR product.

SEQ ID NO: 116 is a synthetic dltA-2 parental verification PCR product.

SEQ ID NO: 117 is a synthetic forward primer sequence.

SEQ ID NO: 118 is a synthetic reverse primer sequence.

SEQ ID NO: 119 is a synthetic rghR2 deletion verification PCR product.

SEQ ID NO: 120 is a *B. licheniformis* parental rghR2 deletion verification PCR product.

SEQ ID NO: 121 is a *B. licheniformis* parental rghR2 locus.

SEQ ID NO: 122 is a *B. licheniformis* parental dltA locus.

SEQ ID NO: 123 is a *B. licheniformis* parental cat locus.

SEQ ID NO: 124 is a synthetic cat 2x prsA locus

SEQ ID NO: 125 is a synthetic dltA-2 locus.

SEQ ID NO: 126 is an amino acid sequence of a *B. licheniformis* Amylase 1 protein.

SEQ ID NO: 127 is a synthetic serA1 Amylase 1 cassette.

SEQ ID NO: 128 is a synthetic p3 promoter sequence.

SEQ ID NO: 129 is a synthetic modified aprE 5'-UTR sequence.

SEQ ID NO: 130 is a *B. licheniformis* nucleic acid sequence encoding an amyL signal sequence.

SEQ ID NO: 131 is a *B. licheniformis* nucleic acid sequence encoding the Amylase 1 protein of SEQ ID NO: 126.

SEQ ID NO: 132 is a synthetic lysA Amylase 1 cassette.

SEQ ID NO: 133 is a synthetic lysA parental locus nucleic acid sequence.

SEQ ID NO: 134 is a *B. licheniformis* nucleic acid sequence encoding lysA.

SEQ ID NO: 135 is a synthetic p2 promoter sequence.

SEQ ID NO: 136 is an amino acid sequence of an Amylase 2 protein.

SEQ ID NO: 137 is a synthetic serA1 Amylase 2 cassette.

SEQ ID NO: 138 is a *B. subtilis* rrnI promoter sequence.

SEQ ID NO: 139 is a *B. subtilis* aprE 5'-UTR sequence.

SEQ ID NO: 140 is a synthetic nucleic acid sequence encoding the Amylase 2 protein of SEQ ID NO: 136.

SEQ ID NO: 141 is a synthetic amyL or lysA Amylase 2 cassette.

SEQ ID NO: 142 is a synthetic amyL parental locus.

SEQ ID NO: 143 is an amino acid sequence of an Amylase 3 protein.

SEQ ID NO: 144 is a synthetic serA1 Amylase 3 cassette.

SEQ ID NO: 145 is a synthetic nucleic acid sequence encoding the Amylase 3 protein of SEQ ID NO: 143.

SEQ ID NO: 146 is a synthetic lysA Amylase 3 cassette.

SEQ ID NO: 147 is an amino acid sequence of an Amylase 4 protein.

SEQ ID NO: 148 is a synthetic serA1 Amylase 4 cassette.

SEQ ID NO: 149 is a synthetic nucleic acid sequence encoding the Amylase 4 protein of SEQ ID NO: 147.

SEQ ID NO: 150 is a synthetic lysA Amylase 4 cassette.

SEQ ID NO: 151 is an amino acid sequence of an Amylase 5 protein.

SEQ ID NO: 152 is a synthetic serA1 Amylase 5 cassette.

SEQ ID NO: 153 is a synthetic nucleic acid sequence encoding the Amylase 5 protein of SEQ ID NO: 151.

SEQ ID NO: 154 is a synthetic lysA Amylase 5 cassette.

SEQ ID NO: 155 is the amino acid sequence of a native *B. licheniformis* prsA protein.

SEQ ID NO: 156 is the amino acid sequence of a native *B. licheniformis* RghR2 protein.

SEQ ID NO: 157 is the amino acid sequence of a variant *B. licheniformis* RghR2 protein.

SEQ ID NO: 158 is the nucleic acid sequence of a variant *B. licheniformis* rghR2 gene encoding the variant RghR2 protein of SEQ ID NO: 157.

DETAILED DESCRIPTION

The present disclosure is generally related to compositions and methods for obtaining *B. licheniformis* cells (e.g., protein production hosts) comprising enhanced protein production capabilities. Certain embodiments of the disclosure are related to genetically modified *Bacillus licheniformis* cells/strains derived from parental *B. licheniformis* cells/strains. Thus, certain other embodiments of the disclosure are directed to methods for constructing such modified *B. licheniformis* cells/strains producing increased amounts of one or more proteins of interest.

For example, certain embodiments of the disclosure are directed to methods for producing an increased amount of a protein of interest (POT) in a modified *Bacillus licheniformis* cell comprising (a) modifying a parental *B. licheniformis* cell expressing a POI by introducing therein a polynucleotide comprising a native prsA promoter operably linked to a native prsA open reading frame (ORF) and (b) fermenting the modified cell under suitable conditions for the production of the POT, wherein the modified cell produces an increased amount of the POI relative to the parental cell when fermented under the same conditions. In certain embodiments, the modified cell further comprises a deleted or disrupted dltA gene comprising at least 90% sequence identity to SEQ ID NO: 122 and/or a deleted or disrupted rghR2 gene comprising at least 90% sequence identity to SEQ ID NO: 121. In certain embodiments, the protein of interest (POI) is an enzyme. In certain embodiments, the enzyme is a protease or an amylase.

Other embodiments of the disclosure are directed to modified *Bacillus licheniformis* cells/strains derived from parental *B. licheniformis* cells/strains comprising an endogenous prsA gene encoding a native prsA protein. Thus, in certain embodiments, a modified *B. licheniformis* cell of the disclosure comprises an introduced polynucleotide comprising a native prsA promoter operably linked to a native prsA open reading frame (ORF). In particular embodiments, the introduced polynucleotide encodes a native prsA protein comprising about 90% sequence identity to SEQ ID NO: 155. In other embodiments, the modified cell comprises a deleted or disrupted dltA gene comprising at least 90% sequence identity to SEQ ID NO: 122 and/or a deleted or disrupted rghR2 gene comprising at least 90% sequence identity to SEQ ID NO: 121 or SEQ ID NO: 158.

Certain embodiments of the disclosure are therefore directed to obtaining, isolating, purifying and like a protein of interest produced by a modified *B. licheniformis* cell of the disclosure.

I. Definitions

In view of the modified *B. licheniformis* cells of the disclosure and methods thereof described herein, the following terms and phrases are defined. Terms not defined herein should be accorded their ordinary meaning as used in the art.

Unless defined otherwise, all technical and scientific terms used herein have the same meaning as commonly understood by one of ordinary skill in the art to which the present compositions and methods apply. Although any methods and materials similar or equivalent to those described herein can also be used in the practice or testing of the present compositions and methods, representative illustrative methods and materials are now described. All publications and patents cited herein are incorporated by reference in their entirety.

It is further noted that the claims may be drafted to exclude any optional element. As such, this statement is intended to serve as antecedent basis for use of such exclusive terminology as "solely," "only", "excluding", "not including" and the like, in connection with the recitation of claim elements, or use of a "negative" limitation or proviso thereof.

As will be apparent to those of skill in the art upon reading this disclosure, each of the individual embodiments described and illustrated herein has discrete components and features which may be readily separated from or combined with the features of any of the other several embodiments without departing from the scope or spirit of the present compositions and methods described herein. Any recited method can be carried out in the order of events recited or in any other order which is logically possible.

As used herein. "the genus *Bacillus*" includes all species within the genus "*Bacillus*" as known to those of skill in the art, including but not limited to *B. subtilis, B. licheniformis, B. lentus, B. brevis, B. stearothermophilus, B. alkalophilus, B. amyloliquefaciens, B. clausii, B. halodurans, B. megaterium, B. coagulans, B. circulans, B. lautus*, and *B. thuringiensis*. It is recognized that the genus *Bacillus* continues to undergo taxonomical reorganization. Thus, it is intended that the genus include species that have been reclassified, including but not limited to such organisms as *B. stearothermophilus*, which is now named "*Geobacillus stearothermophilus*".

As used herein, a "parental cell" refers to an "unmodified cell" (e.g., such as an unmodified *B. licheniformis* parental cell).

As used herein, a "modified cell" or a "daughter cell" may be used interchangeably and refer to recombinant *B. licheniformis* cells that comprise at least one genetic modification which is not present in the "parental cell" from which the modified (daughter) cell is derived.

In certain embodiments, the "unmodified" *B. licheniformis* (parental) cell may be referred to as a "control cell", particularly when being compared with, or relative to, a 'modified' *B. licheniformis* (daughter) cell.

As used herein, when the expression and/or production of a protein of interest (POI) in an "unmodified" (parental) cell is being compared to the expression and/or production of the same POI in a "modified" (daughter) cell, it will be understood that the "modified" and "unmodified" cells are grown/cultivated/fermented under the same conditions (e.g., the same conditions such as media, temperature. pH and the like).

As used herein, a "host cell" refers to a cell that has the capacity to act as a host or expression vehicle for a newly introduced DNA sequence. This, in certain embodiments of the disclosure, the host cells are *Bacillus* sp. or *E. coli* cells.

As used herein, a "native *B. licheniformis* prsA promoter" of the disclosure comprises about 95% sequence identity to SEQ ID NO: 100. In certain embodiments, a native *B. licheniformis* prsA promoter comprises about 95%, 96%, 97%, 98%, 99% or 100% sequence identity to SEQ ID NO: 100.

As used herein, a "native *B. licheniformis* prsA open reading frame (ORF)" comprises about 90% or greater sequence identity to SEQ ID NO: 101. In certain embodiments, a native *B. licheniformis* prsA ORF comprises about 90%, 91%, 92%, 93%, 94%, 95%, 96%, 97%, 98%, 99% or 100% sequence identity to SEQ ID NO: 101.

The prsA gene of *Bacillus subtilis* has been described in Kontinen and Sarvas (1993) and PCT Publication No. WO1994/019471, which publications suggest that the prsA gene is involved in protein secretion (i.e., encoding a component of the cellular secretion machinery), wherein the prsA gene product is a membrane-associated lipoprotein.

As used herein, a "native *B. licheniformis* prsA protein" comprises about 90% or greater sequence identity to SEQ ID NO: 155 and comprises peptidyl-prolyl cis-trans isomerase activity (EC 5.2.1.8). In certain embodiments, a native *B. licheniformis* prsA protein comprises about 90%, 91%, 92%, 93%, 94%, 95%, 96%, 97%, 98%, 99% or 100% sequence identity to SEQ ID NO: 155.

As used herein, a "parental *B. licheniformis* cell comprises an endogenous (wild-type) prsA gene encoding a native prsA protein", and as such, when a polynucleotide encoding a prsA protein comprising about 90% sequence identity to SEQ ID NO: 155 is introduced into a modified *B. licheniformis* cell of the disclosure, the introduced polynucleotide may be referred to herein as a second ($2^{nd}$) prsA copy. For example, a modified *B. licheniformis* cell of the disclosure comprising an introduced polynucleotide encoding a prsA protein comprising about 90% sequence identity to SEQ ID NO: 155, may be referred to herein as a two (2) copy prsA (modified) *B. licheniformis* cell, which comprises a first ($1^{st}$) endogenous (wild-type) prsA gene encoding a native prsA protein, and a second ($2^{nd}$) introduced polynucleotide encoding a prsA protein.

In *B. subtilis*, the dlt operon comprises five (5) ORFs (dltA, dltB, dltC, dltD and dltE) encoding the proteins named DltA, DltB, DltC, DltD and DltE, respectively (May et al., 2005). For example, as described in by May et al. (2005), the DltA protein is a D-alanine:D-alanyl carrier protein ligase involved in the incorporation of D-Ala into the lipoteichoic acid of the cell wall.

As used herein, a "dltA gene" comprises about 90% sequence identity to SEQ ID NO: 122. In certain embodiments, a dltA gene comprises about 90%, 91%, 92%, 93%, 94%, 95%, 96%, 97%, 98%, 99% or 100% sequence identity to SEQ ID NO: 155.

The *B. subtilis* rghR gene encodes a transcriptional regulatory protein named RghR, which has been described in the art as a repressor of rapG, rapH (Hayashi et al., 2006) and rapD (Ogura and Fujita, 2007). In contrast, as recently described in PCT Publication No. WO2018/156705, *B. licheniformis* encodes two (2) homologues of the RghR transcriptional regulatory protein, named RghR1 and RghR2. As set forth hereinafter, certain embodiments of the disclosure are related to *B. licheniformis* cells comprising a modified (e.g., deleted or disrupted) rghr2 gene.

As used herein, a "*B. licheniformis* rghR2 gene" suitable for genetic modifications described herein can be a wild-type *B. licheniformis* rghR2 gene (SEQ ID NO: 121) encoding a native RhgR2 protein comprising about 90% sequence identity to SEQ ID NO: 156 (e.g., about 90%, 91%, 92%, 93%, 94%, 95%, 96%, 97%, 98%, 99% or 100% sequence identity to SEQ ID NO: 156), or it can be a variant *B. licheniformis* rghR2 gene (SEQ ID NO: 158) encoding a variant RhgR2 protein comprising about 90% sequence identity to SEQ ID NO: 157 (e.g., about 90%, 91%, 92%, 93%, 94%, 95%, 96%, 97%, 98%, 99% or 100% sequence identity to SEQ ID NO: 156). For example, as presented in SEQ ID NO: 157, the variant RhgR2 protein comprises a six (6) amino acid residue repeat of "Ala-Ala-Ala-Ile-Ser-Arg" at amino acid residues 36-41 of SEQ ID NO: 157, which six (6) amino acid repeat is not present in the native RghR2 protein (i.e., amino acid residues 1-134 of SEQ ID NO: 156).

Thus, in certain other embodiments, a rghR2 gene, or open reading frame thereof, comprises about 90% sequence identity to a native rghR2 gene (e.g., about 90%, 91%, 92%, 93%, 94%, 95%, 96%, 97%, 98%, 99% or 100% sequence identity to SEQ ID NO: 121); or comprises about 901% sequence identity to a variant rghR2 gene (e.g., about 90%, 91%, 92%, 93%, 94%, 95%, 96%, 97%, 98%, 99% or 100% sequence identity to SEQ ID NO: 158).

As used herein, a parental *B. licheniformis* strain named "BF140" or "BF140 (ΔserA_ΔlysA)" comprises a serA gene deletion (ΔserA) and lysA gene deletion (ΔlysA).

As used herein, a modified *B. licheniformis* strain named "BF561" or "BF561 ($2^{nd}$ copy prsA)" was derived from the parental strain BF140, wherein the modified BF561 strain comprises an introduced $2^{nd}$ copy of a wild-type *B. licheniformis* prsA gene encoding a native prsA protein.

As used herein, a modified *B. licheniformis* strain named "BF598" or "BF598 (ΔdltA_$2^{nd}$ copy prsA)" was derived from the BF561 strain, wherein the modified BF598 further comprises a deletion of the *B. licheniformis* dltA gene.

As used herein, a modified *B. licheniformis* strain named "BF602" or "BF602 (ΔrghR2_$2^{nd}$ copy prsA)" was derived from the BF561 strain, wherein the modified BF602 further comprises a deletion of the *B. licheniformis* rghR2 gene.

As used herein, a modified *B. licheniformis* strain named "BF613" or "BF613 (ΔrghR2_ΔdltA_$2^{nd}$ copy prsA)" was derived from the BF598 (ΔdltA_$2^{nd}$ copy prsA) strain, wherein the modified BF613 further comprises a deletion of the *B. licheniformis* rghR2 gene.

As used herein, "amylase 1" is a native *B. licheniformis* α-amylase commonly referred to in the art as AmyL and comprises an amino acid sequence of SEQ ID NO: 126.

As used herein, "amylase 2" is a variant *Bacillus* sp. α-amylase comprising SEQ ID NO: 136, as generally described in International PCT Publication No. WO2018/184004 (incorporated herein by reference in its entirety).

As used herein, "amylase 3" is a variant Cytophaga sp. α-amylase comprising SEQ ID NO: 143, as generally described in International PCT Publication Nos. WO2014/164777; WO2012/164800 and WO2014/164834 (each incorporated herein by reference in its entirety).

As used herein, "amylase 4" is a variant Cytophaga sp. α-amylase comprising SEQ ID NO: 147, as generally described in International PCT Publication Nos. WO2014/164777; WO2012/164800 and WO2014/164834 (each incorporated herein by reference in its entirety).

As used herein, "amylase 5" is a variant *Bacillus* sp. 707 alkaline α-amylase comprising SEQ ID NO: 151, as generally described in International PCT Publication No. WO2008/153805 and US Patent Publication No. US2014/0057324 (each incorporated herein by reference in its entirety).

As used herein, a variant Cas9 protein herein named "Cas9 Y155H" has been described in PCT Publication No. WO2019/118463 (incorporated herein by reference in its entirety).

As used herein, the terms "modification" and "genetic modification" are used interchangeably and include: (a) the introduction, substitution, or removal of one or more nucleotides in a gene (or an ORF thereof), or the introduction, substitution, or removal of one or more nucleotides in a regulatory element required for the transcription or translation of the gene or ORF thereof. (b) a gene disruption. (c) a gene conversion, (d) a gene deletion, (e) the down-regulation of a gene, (f) specific mutagenesis and/or (g) random mutagenesis of any one or more the genes disclosed herein.

As used herein, an "increased amount", when used in phrases such as "a modified host cell 'expresses/produces an increased amount' of one or more proteins of interest relative to the (unmodified) parental host cell", particularly refers to an "increased amount" of any protein of interest (POI) expressed/produced in the modified host cell, which "increased amount" is always relative to the (unmodified)

parental *B. licheniformis* cells expressing/producing the same POI, wherein the modified and unmodified cells are grown/cultured/fermented under the same conditions (e.g., the same conditions such as media, temperature, pH and the like). For example, an increased amount of a POI may be an endogenous *Bacillus* sp. POT, or a heterologous POI expressed in a modified *Bacillus* sp. cell of the disclosure.

As used herein, "increasing" protein production or "increased" protein production is meant an increased amount of protein produced (e.g., a protein of interest). The protein may be produced inside the host cell, or secreted (or transported) into the culture medium. In certain embodiments, the protein of interest is produced (secreted) into the culture medium. Increased protein production may be detected for example, as higher maximal level of protein or enzymatic activity (e.g., such as protease activity, amylase activity, cellulase activity, hemicellulase activity and the like), or total extracellular protein produced as compared to the parental host cell.

As used herein, the term "expression" refers to the transcription and stable accumulation of sense (mRNA) or anti-sense RNA, derived from a nucleic acid molecule of the disclosure. Expression may also refer to translation of mRNA into a polypeptide. Thus, the term "expression" includes any step involved in the production of the polypeptide including, but not limited to, transcription, post-transcriptional modification, translation, post-translational modification, secretion and the like.

As used herein, "nucleic acid" refers to a nucleotide or poly nucleotide sequence, and fragments or portions thereof, as well as to DNA, cDNA, and RNA of genomic or synthetic origin, which may be double-stranded or single-stranded, whether representing the sense or antisense strand. It will be understood that as a result of the degeneracy of the genetic code, a multitude of nucleotide sequences may encode a given protein.

It is understood that the polynucleotides (or nucleic acid molecules) described herein include "genes", "vectors" and "plasmids".

Accordingly, the term "gene", refers to a polynucleotide that codes for a particular sequence of amino acids, which comprise all, or part of a protein coding sequence, and may include regulatory (non-transcribed) DNA sequences, such as promoter sequences, which determine for example the conditions under which the gene is expressed. The transcribed region of the gene may include untranslated regions (UTRs), including introns, 5'-untranslated regions (UTRs), and 3'-UTRs, as well as the coding sequence.

As used herein, the term "coding sequence" refers to a nucleotide sequence, which directly specifies the amino acid sequence of its (encoded) protein product. The boundaries of the coding sequence are generally determined by an open reading frame (hereinafter, "ORF"), which usually begins with an ATG start codon. The coding sequence typically includes DNA, cDNA, and recombinant nucleotide sequences.

The term "promoter" as used herein refers to a nucleic acid sequence capable of controlling the expression of a coding sequence or functional RNA. In general, a coding sequence is located 3' (downstream) to a promoter sequence. Promoters may be derived in their entirety from a native gene, or be composed of different elements derived from different promoters found in nature, or even comprise synthetic nucleic acid segments. It is understood by those skilled in the art that different promoters may direct the expression of a gene in different cell types, or at different stages of development, or in response to different environmental or physiological conditions. Promoters which cause a gene to be expressed in most cell types at most times are commonly referred to as "constitutive promoters". It is further recognized that since in most cases the exact boundaries of regulatory sequences have not been completely defined. DNA fragments of different lengths may have identical promoter activity.

The term "operably linked" as used herein refers to the association of nucleic acid sequences on a single nucleic acid fragment so that the function of one is affected by the other. For example, a promoter is operably linked with a coding sequence (e.g., an ORF) when it is capable of affecting the expression of that coding sequence (i.e., that the coding sequence is under the transcriptional control of the promoter). Coding sequences can be operably linked to regulatory sequences in sense or antisense orientation.

A nucleic acid is "operably linked" when it is placed into a functional relationship with another nucleic acid sequence. For example, DNA encoding a secretory leader (i.e., a signal peptide), is operably linked to DNA for a polypeptide if it is expressed as a pre-protein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, "a functional promoter sequence controlling the expression of a gene of interest (or open reading frame thereof) linked to the gene of interest's protein coding sequence" refers to a promoter sequence which controls the transcription and translation of the coding sequence in *Bacillus. For example, in certain embodiments, the present disclosure is directed to a polynucleotide comprising a* 5' promoter (or 5' promoter region, or tandem 5' promoters and the like), wherein the promoter region is operably linked to a nucleic acid sequence (e.g., an ORF) encoding a protein.

As used herein, "suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences. RNA processing site, effector binding site and stem-loop structure.

As used herein, the term "introducing", as used in phrases such as "introducing into a bacterial cell" or "introducing into a *B. licheniformis* cell at least one polynucleotide open reading frame (ORF), or a gene thereof, or a vector thereof, includes methods known in the art for introducing polynucleotides into a cell, including, but not limited to protoplast fusion, natural or artificial transformation (e.g., calcium chloride, electroporation), transduction, transfection, conjugation and the like (e.g., see Ferrari et al., 1989).

As used herein, "transformed" or "transformation" mean a cell has been transformed by use of recombinant DNA techniques. Transformation typically occurs by insertion of one or more nucleotide sequences (e.g., a polynucleotide, an ORF or gene) into a cell. The inserted nucleotide sequence may be a heterologous nucleotide sequence (i.e., a sequence that is not naturally occurring in cell that is to be transformed). Transformation therefore generally refers to introducing an exogenous DNA into a host cell so that the DNA is maintained as a chromosomal integrant or a self-replicating extrachromosomal vector.

As used herein, “transforming DNA”, “transforming sequence”, and “DNA construct” refer to DNA that is used to introduce sequences into a host cell or organism. Transforming DNA is DNA used to introduce sequences into a host cell or organism. The DNA may be generated in vitro by PCR or any other suitable techniques. In some embodiments, the transforming DNA comprises an incoming sequence, while in other embodiments it further comprises an incoming sequence flanked by homology boxes. In yet a further embodiment, the transforming DNA comprises other non-homologous sequences, added to the ends (i.e., stuffer sequences or flanks). The ends can be closed such that the transforming DNA forms a closed circle, such as, for example, insertion into a vector.

As used herein, “disruption of a gene” or a “gene disruption”, are used interchangeably and refer broadly to any genetic modification that substantially prevents a host cell from producing a functional gene product (e.g., a protein). Thus, as used herein, a gene disruption includes, but is not limited to, frameshift mutations, premature stop codons (i.e., such that a functional protein is not made), substitutions eliminating or reducing activity of the protein internal deletions (such that a functional protein is not made), insertions disrupting the coding sequence, mutations removing the operable link between a native promoter required for transcription and the open reading frame, and the like.

As used herein “an incoming sequence” refers to a DNA sequence that is introduced into the *Bacillus* sp. chromosome. In some embodiments, the incoming sequence is part of a DNA construct. In other embodiments, the incoming sequence encodes one or more proteins of interest. In some embodiments, the incoming sequence comprises a sequence that may or may not already be present in the genome of the cell to be transformed (i.e., it may be either a homologous or heterologous sequence). In some embodiments, the incoming sequence encodes one or more proteins of interest, a gene, and/or a mutated or modified gene. In alternative embodiments, the incoming sequence encodes a functional wild-type gene or operon, a functional mutant gene or operon, or a nonfunctional gene or operon. In some embodiments, the non-functional sequence may be inserted into a gene to disrupt function of the gene. In another embodiment, the incoming sequence includes a selective marker. In a further embodiment the incoming sequence includes two homology boxes.

As used herein, “homology box” refers to a nucleic acid sequence, which is homologous to a sequence in the *Bacillus* chromosome. More specifically, a homology box is an upstream or downstream region having between about 80 and 100% sequence identity, between about 90 and 100% sequence identity, or between about 95 and 100% sequence identity with the immediate flanking coding region of a gene or part of a gene to be deleted, disrupted, inactivated, down-regulated and the like, according to the invention. These sequences direct where in the *Bacillus* chromosome a DNA construct is integrated and directs what part of the *Bacillus* chromosome is replaced by the incoming sequence. While not meant to limit the present disclosure, a homology box may include about between 1 base pair (bp) to 200 kilobases (kb). Preferably, a homology box includes about between 1 bp and 10.0 kb; between 1 bp and 5.0 kb; between 1 bp and 2.5 kb; between 1 bp and 1.0 kb, and between 0.25 kb and 2.5 kb. A homology box may also include about 10.0 kb, 5.0 kb, 2.5 kb, 2.0 kb, 1.5 kb, 1.0 kb, 0.5 kb, 0.25 kb and 0.1 kb. In some embodiments, the 5' and 3' ends of a selective marker are flanked by a homology box wherein the homology box comprises nucleic acid sequences immediately flanking the coding region of the gene.

As used herein, the term “selectable marker-encoding nucleotide sequence” refers to a nucleotide sequence which is capable of expression in the host cells and where expression of the selectable marker confers to cells containing the expressed gene the ability to grow in the presence of a corresponding selective agent or lack of an essential nutrient.

As used herein, the terms “selectable marker” and “selective marker” refer to a nucleic acid (e.g., a gene) capable of expression in host cell which allows for ease of selection of those hosts containing the vector. Examples of such selectable markers include, but are not limited to, antimicrobials. Thus, the term “selectable marker” refers to genes that provide an indication that a host cell has taken up an incoming DNA of interest or some other reaction has occurred. Typically, selectable markers are genes that confer antimicrobial resistance or a metabolic advantage on the host cell to allow cells containing the exogenous DNA to be distinguished from cells that have not received any exogenous sequence during the transformation.

A “residing selectable marker” is one that is located on the chromosome of the microorganism to be transformed. A residing selectable marker encodes a gene that is different from the selectable marker on the transforming DNA construct. Selective markers are well known to those of skill in the art. As indicated above, the marker can be an antimicrobial resistance marker (e.g., $amp^R$, $phleo^R$, $spec^R$, $kan^R$, $ery^R$, $tet^R$, $cmp^R$ and $neo^R$ (see e.g., Guerot-Fleury, 1995; Palmeros et al., 2000; and Trieu-Cuot et al., 1983). In some embodiments, the present invention provides a chloramphenicol resistance gene (e.g., the gene present on pC194, as well as the resistance gene present in the *Bacillus licheniformis* genome). This resistance gene is particularly useful in the present invention, as well as in embodiments involving chromosomal amplification of chromosomally integrated cassettes and integrative plasmids (See e.g., Albertini and Galizzi, 1985; Stahl and Ferrari, 1984). Other markers useful in accordance with the invention include, but are not limited to auxotrophic markers, such as serine, lysine, tryptophan; and detection markers, such as β-galactosidase.

As defined herein, a host cell “genome”, a bacterial (host) cell “genome”, or a *Bacillus* sp. (host) cell “genome” includes chromosomal and extrachromosomal genes.

As used herein, the terms “plasmid”, “vector” and “cassette” refer to extrachromosomal elements, often carrying genes which are typically not part of the central metabolism of the cell, and usually in the form of circular double-stranded DNA molecules. Such elements may be autonomously replicating sequences, genome integrating sequences, phage or nucleotide sequences, linear or circular, of a single-stranded or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell.

As used herein, the term “plasmid” refers to a circular double-stranded (ds) DNA construct used as a cloning vector, and which forms an extrachromosomal self-replicating genetic element in many bacteria and some eukaryotes. In some embodiments, plasmids become incorporated into the genome of the host cell. in some embodiments plasmids exist in a parental cell and are lost in the daughter cell.

A used herein, a "transformation cassette" refers to a specific vector comprising a gene (or ORF thereof), and having elements in addition to the foreign gene that facilitate transformation of a particular host cell.

As used herein, the term "vector" refers to any nucleic acid that can be replicated (propagated) in cells and can carry new genes or DNA segments into cells. Thus, the term refers to a nucleic acid construct designed for transfer between different host cells. Vectors include viruses, bacteriophage, pro-viruses, plasmids, phagemids, transposons, and artificial chromosomes such as YACs (yeast artificial chromosomes). BACs (bacterial artificial chromosomes), PLACs (plant artificial chromosomes), and the like, that are "episomes" (i.e., replicate autonomously or can integrate into a chromosome of a host organism).

An "expression vector" refers to a vector that has the ability to incorporate and express heterologous DNA in a cell. Many prokaryotic and eukaryotic expression vectors are commercially available and know to one skilled in the art. Selection of appropriate expression vectors is within the knowledge of one skilled in the art.

As used herein, the terms "expression cassette" and "expression vector" refer to a nucleic acid construct generated recombinantly or synthetically, with a series of specified nucleic acid elements that permit transcription of a particular nucleic acid in a target cell (i.e., these are vectors or vector elements, as described above). The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In some embodiments. DNA constructs also include a series of specified nucleic acid elements that permit transcription of a particular nucleic acid in a target cell. In certain embodiments, a DNA construct of the disclosure comprises a selective marker and an inactivating chromosomal or gene or DNA segment as defined herein.

As used herein, a "targeting vector" is a vector that includes polynucleotide sequences that are homologous to a region in the chromosome of a host cell into which the targeting vector is transformed and that can drive homologous recombination at that region. For example, targeting vectors find use in introducing mutations into the chromosome of a host cell through homologous recombination. In some embodiments, the targeting vector comprises other non-homologous sequences, e.g., added to the ends (i.e., stuffer sequences or flanking sequences). The ends can be closed such that the targeting vector forms a closed circle, such as, for example, insertion into a vector. For example, in certain embodiments, a parental *B. licheniformis* (host) cell is modified (e.g., transformed) by introducing therein one or more "targeting vectors".

As used herein, the term "protein of interest" or "POI" refers to a polypeptide of interest that is desired to be expressed in a modified *B. licheniformis* (daughter) host cell, wherein the POI is preferably expressed at increased levels (i.e., relative to the "unmodified" (parental) cell). Thus, as used herein, a POI may be an enzyme, a substrate-binding protein, a surface-active protein, a structural protein, a receptor protein, and the like. In certain embodiments, a modified cell of the disclosure produces an increased amount of a heterologous protein of interest or an endogenous protein of interest relative to the parental cell. In particular embodiments, an increased amount of a protein of interest produced by a modified cell of the disclosure is at least a 0.5% increase, at least a 1.0% increase, at least a 5.0% increase, or a greater than 5.0% increase, relative to the parental cell.

Similarly, as defined herein, a "gene of interest" or "GOI" refers a nucleic acid sequence (e.g., a poly nucleotide, a gene or an ORF) which encodes a POI. A "gene of interest" encoding a "protein of interest" may be a naturally occurring gene, a mutated gene or a synthetic gene.

As used herein, the terms "polypeptide" and "protein" are used interchangeably, and refer to polymers of any length comprising amino acid residues linked by peptide bonds. The conventional one (1) letter or three (3) letter codes for amino acid residues are used herein. The polypeptide may be linear or branched, it may comprise modified amino acids, and it may be interrupted by non-amino acids. The term polypeptide also encompasses an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art.

In certain embodiments, a gene of the instant disclosure encodes a commercially relevant industrial protein of interest, such as an enzyme (e.g., a acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases. β-glucosidases, glucuronidases, glycosyl hydrolases, hemicellulases, hexose oxidases, hydrolases, invertases, isomerases, laccases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof).

As used herein, a "variant" polypeptide refers to a polypeptide that is derived from a parent (or reference) polypeptide by the substitution, addition, or deletion of one or more amino acids, typically by recombinant DNA techniques. Variant polypeptides may differ from a parent polypeptide by a small number of amino acid residues and may be defined by their level of primary amino acid sequence homology/identity with a parent (reference) polypeptide.

Preferably, variant polypeptides have at least 70%, at least 75%, at least 80%, at least 85%, at least 90%, at least 91%, at least 92%, at least 93%, at least 94%, at least 95%, at least 96%, at least 97%, at least 98%, or even at least 99% amino acid sequence identity with a parent (reference) polypeptide sequence. As used herein, a "variant" polynucleotide refers to a polynucleotide encoding a variant polypeptide, wherein the "variant polynucleotide" has a specified degree of sequence homology/identity with a parent polynucleotide, or hybridizes with a parent polynucleotide (or a complement thereof) under stringent hybridization conditions. Preferably, a variant polynucleotide has at least 70%, at least 75%, at least 80%, at least 85%, at least 90%, at least 91%, at least 92%, at least 93%, at least 94%, at least 95%, at least 96%, at least 97%, at least 98%, or even at least 99% nucleotide sequence identity with a parent (reference) polynucleotide sequence.

As used herein, a "mutation" refers to any change or alteration in a nucleic acid sequence. Several types of mutations exist, including point mutations, deletion mutations, silent mutations, frame shift mutations, splicing mutations and the like. Mutations may be performed specifically (e.g., via site directed mutagenesis) or randomly (e.g., via chemical agents, passage through repair minus bacterial strains).

As used herein, in the context of a polypeptide or a sequence thereof, the term "substitution" means the replacement (i.e., substitution) of one amino acid with another amino acid.

As defined herein, an "endogenous gene" refers to a gene in its natural location in the genome of an organism.

As defined herein, a "heterologous" gene, a "non-endogenous" gene, or a "foreign" gene refer to a gene (or ORF) not normally found in the host organism, but that is introduced into the host organism by gene transfer. As used herein, the term "foreign" gene(s) comprise native genes (or ORFs) inserted into a non-native organism and/or chimeric genes inserted into a native or non-native organism.

As defined herein, a "heterologous control sequence", refers to a gene expression control sequence (e.g., a promoter or enhancer) which does not function in nature to regulate (control) the expression of the gene of interest. Generally, heterologous nucleic acid sequences are not endogenous (native) to the cell, or a part of the genome in which they are present, and have been added to the cell, by infection, transfection, transformation, microinjection, electroporation, and the like. A "heterologous" nucleic acid construct may contain a control sequence/DNA coding (ORF) sequence combination that is the same as, or different, from a control sequence/DNA coding sequence combination found in the native host cell.

As used herein, the terms "signal sequence" and "signal peptide" refer to a sequence of amino acid residues that may participate in the secretion or direct transport of a mature protein or precursor form of a protein. The signal sequence is typically located N-terminal to the precursor or mature protein sequence. The signal sequence may be endogenous or exogenous. A signal sequence is normally absent from the mature protein. A signal sequence is typically cleaved from the protein by a signal peptidase after the protein is transported.

The term "derived" encompasses the terms "originated" "obtained," "obtainable," and "created," and generally indicates that one specified material or composition finds its origin in another specified material or composition, or has features that can be described with reference to the another specified material or composition.

As used herein, the term "homology" relates to homologous polynucleotides or polypeptides. If two or more polynucleotides or two or more polypeptides are homologous, this means that the homologous polynucleotides or polypeptides have a "degree of identity" of at least 60%, more preferably at least 70%, even more preferably at least 85%, still more preferably at least 90%, more preferably at least 95%, and most preferably at least 98%. Whether two polynucleotide or polypeptide sequences have a sufficiently high degree of identity to be homologous as defined herein, can suitably be investigated by aligning the two sequences using a computer program known in the art, such as "GAP" provided in the GCG program package (Program Manual for the Wisconsin Package, Version 8, August 1994, Genetics Computer Group, 575 Science Drive, Madison, Wisconsin, USA 53711) (Needleman and Wunsch, (1970). Using GAP with the following settings for DNA sequence comparison: GAP creation penalty of 5.0 and GAP extension penalty of 0.3.

As used herein, the term "percent (%) identity" refers to the level of nucleic acid or amino acid sequence identity between the nucleic acid sequences that encode a polypeptide or the polypeptide's amino acid sequences, when aligned using a sequence alignment program.

As used herein, "specific productivity" is total amount of protein produced per cell per time over a given time period.

As defined herein, the terms "purified", "isolated" or "enriched" are meant that a biomolecule (e.g., a polypeptide or polynucleotide) is altered from its natural state by virtue of separating it from some, or all of, the naturally occurring constituents with which it is associated in nature. Such isolation or purification may be accomplished by art-recognized separation techniques such as ion exchange chromatography, affinity chromatography, hydrophobic separation, dialysis, protease treatment, ammonium sulphate precipitation or other protein salt precipitation, centrifugation, size exclusion chromatography, filtration, microfiltration, gel electrophoresis or separation on a gradient to remove whole cells, cell debris, impurities, extraneous proteins, or enzymes undesired in the final composition. It is further possible to then add constituents to a purified or isolated biomolecule composition which provide additional benefits, for example, activating agents, anti-inhibition agents, desirable ions, compounds to control pH or other enzymes or chemicals.

As used herein, the term "ComK polypeptide" is defined as the product of a comK gene; a transcription factor that acts as the final auto-regulatory control switch prior to competence development, involved with activation of the expression of late competence genes involved in DNA-binding and uptake and in recombination (Liu and Zuber, 1998, Hamoen et al., 1998). An exemplary ComK nucleic acid is set forth in SEQ ID NO: 92.

As used herein, "recombinant" includes reference to a cell or vector, that has been modified by the introduction of a heterologous nucleic acid sequence or that the cell is derived from a cell so modified. Thus, for example, recombinant cells express genes that are not found in identical form within the native (non-recombinant) form of the cell or express native genes that are otherwise abnormally expressed, under expressed or not expressed at all as a result of deliberate human intervention. "Recombination". "recombining" or generating a "recombined" nucleic acid is generally the assembly of two or more nucleic acid fragments wherein the assembly gives rise to a chimeric gene.

As used herein, a "flanking sequence" refers to any sequence that is either upstream or downstream of the sequence being discussed (e.g., for genes A-B-C, gene B is flanked by the A and C gene sequences). In certain embodiments, the incoming sequence is flanked by a homology box on each side. In another embodiment, the incoming sequence and the homology boxes comprise a unit that is flanked by stuffer sequence on each side. In some embodiments, a flanking sequence is present on only a single side (either 3' or 5'), but in preferred embodiments, it is on each side of the sequence being flanked. The sequence of each homology box is homologous to a sequence in the *Bacillus* chromosome. These sequences direct where in the *Bacillus* chromosome the new construct gets integrated and what part of the *Bacillus* chromosome will be replaced by the incoming sequence. In other embodiments, the 5' and 3' ends of a selective marker are flanked by a polynucleotide sequence comprising a section of the inactivating chromosomal segment. In some embodiments, a flanking sequence is present on only a single side (either 3' or 5'), while in other embodiments, it is present on each side of the sequence being flanked.

II. Modified *Bacillus licheniformis* Cells Comprising Enhanced Protein Production Phenotypes As generally set forth in the Examples section below, Applicant constructed and introduced a series of host modifications into a parental *B. licheniformis* strain. More particularly, as presented in Examples below (e.g., see TABLE 18), the parental *B. licheniformis* strain used in this example comprises deletions of the serA1 gene (SEQ ID NO: 30) and the lysA gene (SEQ ID NO: 87), and was named BF140 (ΔserA_ΔlysA). Applicant subsequently introduced certain genetic modifications into the parental *B. licheniformis* strain (BF140), including (1) the introduction of a $2^{nd}$ copy of a wild-type *B. licheniformis* prsA gene encoding a native prsA protein (named BF561; $2^{nd}$ copy prsA), (2) the deletion of the *B. licheniformis* dltA gene (named BF598; ΔdltA_$2^{nd}$ copy prsA), (3) the deletion of the *B. licheniformis* rghR2 gene (named BF602; ΔrghR2_$2^{nd}$ copy prsA) and (4) the combined deletion of the *B. licheniformis* rghR2 gene and dltA gene (named BF613; ΔrghR2_ΔdltA_$2^{nd}$ copy prsA).

Following the construction of the modified strains above, a series of α-amylase expression cassettes were introduced into the modified *B. licheniformis* strains (BF561, BF598, BF602 and BF613) and the parental *B. licheniformis* strain (BF140). More particularly, as presented in Example 4 below, two (2) copies of five (5) different α-amylase expression cassettes (i.e., "amylase 1", "amylase 2" "amylase 3", "amylase 4" and "amylase 5") were introduced into the *B. licheniformis* strains.

As further described below in Example 5, the parental (BF140) and modified (BF561, BF598. BF602 and BF613) *B. licheniformis* strains containing two (2) copies of expression cassettes for amylases 1-5 were assayed for production of amylases (e.g., see TABLE 19). For example, all five (5) of the amylases tested from a diverse group of α-amylases demonstrate an improvement in α-amylase production in the BF613 modified background (ΔrghR2_ΔdltA_$2^{nd}$ copy prsA) comprising the deleted dltA-2 (ΔdltA-2) allele (SEQ ID NO: 125), the deleted rghR2 (ΔrghR2) allele (SEQ ID NO: 80) and the insertion of a second copy of the native prsA gene controlled by the native prsA promoter (SEQ ID NO: 124), compared to the unmodified parental host BF140. For amylase 2 and amylase 3, the improvement in a α-amylase production in the BF602 modified background (ΔrghR2_$2^{nd}$ copy prsA), comprising the deleted rghR2 (ΔrghR2) allele (SEQ ID NO: 80) and the second copy of the native prsA gene controlled by the native prsA promoter (SEQ ID NO: 124), is nearly as good as the productivity improvement seen in the BF613 modified host. This observation suggests that for some amylases the productivity improvement only requires the presence of these two (2) alleles (i.e., ΔrghR2_$2^{nd}$ copy prsA), and that the presence of the ΔdltA-2 allele is not harmful to this improvement.

III. Molecular Biology

As generally set forth above, certain embodiments of the disclosure are related to modified *Bacillus licheniformis* (daughter) cells derived from parental *B. licheniformis* cells. More particularly, certain embodiments of the disclosure are related to modified *Bacillus* (daughter) cells and methods thereof for producing and constructing such modified *Bacillus* (host) cells (e.g., protein production host cells, cell factories) having increased protein production capabilities, increased secondary metabolite production capabilities and the like.

In certain embodiments, a modified *B. licheniformis* cell of the disclosure comprises an introduced $2^{nd}$ copy of gene or ORF encoding a native prsA protein. In other embodiments, a modified *B. licheniformis* cell of the disclosure comprises a deleted dltA gene. In certain other embodiments, a modified *B. licheniformis* cell of the disclosure comprises an introduced $2^{nd}$ copy of gene or ORF encoding a native prsA protein and a deleted dltA gene. In other embodiments, a modified *B. licheniformis* cell of the disclosure comprises a deleted rghR2 gene. In certain other embodiments, a modified *B. licheniformis* cell of the disclosure comprises an introduced $2^{nd}$ copy of gene or ORF encoding a native prsA protein and a deleted rghR2 gene. In other embodiments, a modified *B. licheniformis* cell of the disclosure comprises a deleted dltA gene and a deleted rghR2 gene. In certain other embodiments, a modified *B. licheniformis* cell of the disclosure comprises an introduced $2^{nd}$ copy of gene or ORF encoding a native prsA protein, a deleted dltA gene and a deleted rghR2 gene.

Thus, certain embodiments of the disclosure provide compositions and methods for genetically modifying (altering) a parental *Bacillus* cell of the disclosure to generate modified *Bacillus* cells thereof, and more particularly, modified *Bacillus* cells which produce an increased amount of endogenous and/or heterologous proteins of interest relative to (unmodified) parental *B. licheniformis* cells.

Thus, certain embodiments of the disclosure are directed to methods for genetically modifying *Bacillus* cells, wherein the modification comprises (a) the introduction, substitution, or removal of one or more nucleotides in a gene (or an ORF thereof), or the introduction, substitution, or removal of one or more nucleotides in a regulatory element required for the transcription or translation of the gene or ORF thereof, (b) a gene disruption, (c) a gene conversion, (d) a gene deletion, (e) a gene down-regulation, (f) site specific mutagenesis and/or (g) random mutagenesis.

In certain embodiments, a modified *Bacillus* cell of the disclosure is constructed by reducing or eliminating the expression of a gene set forth above, using methods well known in the art, for example, insertions, disruptions, replacements, or deletions. The portion of the gene to be modified or inactivated may be, for example, the coding region or a regulatory element required for expression of the coding region.

An example of such a regulatory or control sequence may be a promoter sequence or a functional part thereof, (i.e., a part which is sufficient for affecting expression of the nucleic acid sequence). Other control sequences for modification include, but are not limited to, a leader sequence, a propeptidic sequence, a signal sequence, a transcription terminator, a transcriptional activator and the like.

In certain other embodiments a modified *Bacillus* cell is constructed by gene deletion to eliminate or reduce the expression of at least one of the aforementioned genes of the disclosure. Gene deletion techniques enable the partial or complete removal of the gene(s), thereby eliminating their expression, or expressing a non-functional (or reduced activity) protein product. In such methods, the deletion of the gene(s) may be accomplished by homologous recombination using a plasmid that has been constructed to contiguously contain the 5' and 3' regions flanking the gene. The contiguous 5' and 3' regions may be introduced into a *Bacillus* cell, for example, on a temperature-sensitive plasmid, such as pE194, in association with a second selectable marker at a permissive temperature to allow the plasmid to become established in the cell. The cell is then shifted to a non-permissive temperature to select for cells that have the plasmid integrated into the chromosome at one of the homologous flanking regions. Selection for integration of the plasmid is effected by selection for the second selectable marker. After integration, a recombination event at the second homologous flanking region is stimulated by shifting the cells to the permissive temperature for several generations without selection. The cells are plated to obtain single colonies and the colonies are examined for loss of both selectable markers (see, e.g., Perego, 1993). Thus, a person of skill in the art may readily identify nucleotide regions in the gene's coding sequence and/or the gene's non-coding sequence suitable for complete or partial deletion.

In other embodiments, a modified *Bacillus* cell of the disclosure is constructed by introducing, substituting, or removing one or more nucleotides in the gene or a regulatory element required for the transcription or translation thereof. For example, nucleotides may be inserted or removed so as to result in the introduction of a stop codon, the removal of the start codon, or a frame-shift of the open reading frame. Such a modification may be accomplished by site-directed mutagenesis or PCR generated mutagenesis in accordance with methods known in the art (e.g., see, Botstein and Shortle, 1985; Lo et al., 1985; Higuchi et al., 1988; Shimada, 1996; Ho et al., 1989; Horton et al., 1989 and Sarkar and Sommer, 1990). Thus, in certain embodiments, a gene of the disclosure is inactivated by complete or partial deletion.

In another embodiment, a modified *Bacillus* cell is constructed by the process of gene conversion (e.g., see Iglesias and Trautner, 1983). For example, in the gene conversion method, a nucleic acid sequence corresponding to the gene(s) is mutagenized in vitro to produce a defective nucleic acid sequence, which is then transformed into the parental *Bacillus* cell to produce a defective gene. By homologous recombination, the defective nucleic acid sequence replaces the endogenous gene. It may be desirable that the defective gene or gene fragment also encodes a marker which may be used for selection of transformants containing the defective gene. For example, the defective gene may be introduced on a non-replicating or temperature-sensitive plasmid in association with a selectable marker. Selection for integration of the plasmid is effected by selection for the marker under conditions not permitting plasmid replication. Selection for a second recombination event leading to gene replacement is effected by examination of colonies for loss of the selectable marker and acquisition of the mutated gene (Perego, 1993). Alternatively, the defective nucleic acid sequence may contain an insertion, substitution, or deletion of one or more nucleotides of the gene, as described below.

In other embodiments, a modified *Bacillus* cell is constructed by established anti-sense techniques using a nucleotide sequence complementary to the nucleic acid sequence of the gene (Parish and Stoker, 1997). More specifically, expression of the gene by a *Bacillus* cell may be reduced (down-regulated) or eliminated by introducing a nucleotide sequence complementary to the nucleic acid sequence of the gene, which may be transcribed in the cell and is capable of hybridizing to the mRNA produced in the cell. Under conditions allowing the complementary anti-sense nucleotide sequence to hybridize to the mRNA, the amount of protein translated is thus reduced or eliminated. Such anti-sense methods include, but are not limited to RNA interference (RNAi), small interfering RNA (siRNA), microRNA (miRNA), antisense oligonucleotides, and the like, all of which are well known to the skilled artisan.

In other embodiments, a modified *Bacillus* cell is produced/constructed via CRiSPR-Cas9 editing. For example, a gene encoding a protein of interest can be edited or disrupted (or deleted or down-regulated) by means of nucleic acid guided endonucleases, that find their target DNA by binding either a guide RNA (e.g., Cas9) and Cpf1 or a guide DNA (e.g., NgAgo), which recruits the endonuclease to the target sequence on the DNA, wherein the endonuclease can generate a single or double stranded break in the DNA. This targeted DNA break becomes a substrate for DNA repair, and can recombine with a provided editing template to disrupt or delete the gene. For example, the gene encoding the nucleic acid guided endonuclease (for this purpose Cas9 from *S. pyogenes*) or a codon optimized gene encoding the Cas9 nuclease is operably linked to a promoter active in the *Bacillus* cell and a terminator active in *Bacillus* cell, thereby creating a *Bacillus* Cas9 expression cassette. Likewise, one or more target sites unique to the gene of interest are readily identified by a person skilled in the art. For example, to build a DNA construct encoding a gRNA-directed to a target site within the gene of interest, the variable targeting domain (VT) will comprise nucleotides of the target site which are 5' of the (PAM) proto-spacer adjacent motif (TGG), which nucleotides are fused to DNA encoding the Cas9 endonuclease recognition domain for *S. pyogenes* Cas9 (CER). The combination of the DNA encoding a VT domain and the DNA encoding the CER domain thereby generate a DNA encoding a gRNA. Thus, a *Bacillus* expression cassette for the gRNA is created by operably linking the DNA encoding the gRNA to a promoter active in *Bacillus* cells and a terminator active in *Bacillus* cells.

In certain embodiments, the DNA break induced by the endonuclease is repaired/replaced with an incoming sequence. For example, to precisely repair the DNA break generated by the Cas9 expression cassette and the gRNA expression cassette described above, a nucleotide editing template is provided, such that the DNA repair machinery of the cell can utilize the editing template. For example, about 500 bp 5' of targeted gene can be fused to about 500 bp 3' of the targeted gene to generate an editing template, which template is used by the *Bacillus* host's machinery to repair the DNA break generated by the RGEN.

The Cas9 expression cassette, the gRNA expression cassette and the editing template can be co-delivered to filamentous fungal cells using many different methods (e.g., protoplast fusion, electroporation, natural competence, or induced competence). The transformed cells are screened by PCR amplifying the target gene locus, by amplifying the locus with a forward and reverse primer. These primers can amplify the wild-type locus or the modified locus that has been edited by the RGEN. These fragments are then sequenced using a sequencing primer to identify, edited colonies.

In yet other embodiments, a modified *Bacillus* cell is constructed by random or specific mutagenesis using methods well known in the art, including, but not limited to, chemical mutagenesis (see, e.g., Hopwood, 1970) and transposition (see, e.g., Youngman et al., 1983). Modification of the gene may be performed by subjecting the parental cell to mutagenesis and screening for mutant cells in which expression of the gene has been reduced or eliminated. The mutagenesis, which may be specific or random, may be performed, for example, by use of a suitable physical or chemical mutagenizing agent, use of a suitable oligonucleotide, or subjecting the DNA sequence to PCR generated mutagenesis. Furthermore, the mutagenesis may be performed by use of any combination of these mutagenizing methods.

Examples of a physical or chemical mutagenizing agent suitable for the present purpose include ultraviolet (UV) irradiation, hydroxylamine, N-methyl-N'-nitro-N-nitrosoguanidine (MNNG), N-methyl-N'-nitrosoguanidine (NTG), O-methyl hydroxylamine, nitrous acid, ethyl methane sulphonate (EMS), sodium bisulphite, formic acid, and nucleotide analogues. When such agents are used, the mutagenesis is typically performed by incubating the parental cell to be mutagenized in the presence of the mutagenizing agent of choice under suitable conditions, and selecting for mutant cells exhibiting reduced or no expression of the gene.

In certain other embodiments, a modified *Bacillus* cell comprises a deletion of an endogenous gene. In other embodiments, a modified *Bacillus* cell comprises a disruption of an endogenous gene. In certain embodiments, a polynucleotide disruption cassette of the disclosure comprises a marker gene.

In other embodiments, a modified *Bacillus* cell comprises a down-regulated endogenous gene. For example, in certain embodiments, down-regulating one or more genes set forth above comprises deleting or disrupting the gene's upstream or downstream regulatory elements.

PCT Publication No. WO2003/083125 discloses methods for modifying *Bacillus* cells, such as the creation of *Bacillus* deletion strains and DNA constructs using PCR fusion to bypass *E. coli.*

PCT Publication No. WO2002/14490 discloses methods for modifying *Bacillus* cells including (1) the construction and transformation of an integrative plasmid (pComK), (2) random mutagenesis of coding sequences, signal sequences and pro-peptide sequences, (3) homologous recombination, (4) increasing transformation efficiency by adding non-homologous flanks to the transformation DNA, (5) optimizing double cross-over integrations, (6) site directed mutagenesis and (7) marker-less deletion.

Those of skill in the art are well aware of suitable methods for introducing polynucleotide sequences into bacterial cells (e.g., *E. coli* and *Bacillus* spp.) (e.g., Ferrari et al., 1989, Saunders et al., 1984; Hoch et al., 1967; Mann et al., 1986; Holubova, 1985; Chang et al., 1979; Vorobjeva et al., 1980; Smith et al., 1986; Fisher et. al., 1981 and McDonald, 1984). Indeed, such methods as transformation including protoplast transformation and congression, transduction, and protoplast fusion are known and suited for use in the present disclosure. Methods of transformation are particularly preferred to introduce a DNA construct of the present disclosure into a host cell.

In addition to commonly used methods, in some embodiments, host cells are directly transformed (i.e., an intermediate cell is not used to amplify, or otherwise process, the DNA construct prior to introduction into the host cell). Introduction of the DNA construct into the host cell includes those physical and chemical methods known in the art to introduce DNA into a host cell, without insertion into a plasmid or vector. Such methods include, but are not limited to, calcium chloride precipitation, electroporation, naked DNA, liposomes and the like. In additional embodiments, DNA constructs are co-transformed with a plasmid without being inserted into the plasmid. In further embodiments, a selective marker is deleted or substantially excised from the modified *Bacillus* strain by methods known in the art (e.g., Stahl et al., 1984 and Palmeros et al., 2000). In some embodiments, resolution of the vector from a host chromosome leaves the flanking regions in the chromosome, while removing the indigenous chromosomal region.

Promoters and promoter sequence regions for use in the expression of genes, open reading frames (ORFs) thereof and/or variant sequences thereof in *Bacillus* cells are generally known on one of skill in the art. Promoter sequences of the disclosure of the disclosure are generally chosen so that they are functional in the *Bacillus* cells (e.g., *B. licheniformis* cells, *B. subtilis* cells and the like). Certain exemplary *Bacillus* promoter sequences are presented in Table 6. Likewise, promoters useful for driving gene expression in *Bacillus* cells include, but are not limited to, the *B. subtilis* alkaline protease (aprE) promoter (Stahl et al., 1984), the α-amylase promoter of *B. subtilis* (Yang et al., 1983), the α-amylase promoter of *B. amyloliquefaciens* (Tarkinen et al., 1983), the neutral protease (nprE) promoter from *B. subtilis* (Yang et al., 1984), a mutant aprE promoter (PCT Publication No. WO2001/51643) or any other promoter from *B. licheniformis* or other related Bacilli. In certain other embodiments, the promoter is a ribosomal protein promoter or a ribosomal RNA promoter (e.g., the rmI promoter) disclosed in U.S. Patent Publication No. 2014/0329309. Methods for screening and creating promoter libraries with a range of activities (promoter strength) in *Bacillus* cells is describe in PCT Publication No. WO2003/089604.

IV. Culturing *Bacillus* Cells for Production of a Protein of Interest

In other embodiments, the present disclosure provides methods for increasing the protein productivity of a modified bacterial cell, as compared (i.e., relative) to an unmodified (parental) cell. In certain embodiments, the instant disclosure is directed to methods of producing a protein of interest (POI) comprising fermenting/cultivating a modified bacterial cell, wherein the modified cell secrets the POI into the culture medium. Fermentation methods well known in the art can be applied to ferment the modified and unmodified *Bacillus* cells of the disclosure.

In some embodiments, the cells are cultured under batch or continuous fermentation conditions. A classical batch fermentation is a closed system, where the composition of the medium is set at the beginning of the fermentation and is not altered during the fermentation. At the beginning of the fermentation, the medium is inoculated with the desired organism(s). In this method, fermentation is permitted to occur without the addition of any components to the system. Typically, a batch fermentation qualifies as a "batch" with respect to the addition of the carbon source, and attempts are often made to control factors such as pH and oxygen concentration. The metabolite and biomass compositions of the batch system change constantly up to the time the fermentation is stopped. Within typical batch cultures, cells can progress through a static lag phase to a high growth log phase, and finally to a stationary phase, where growth rate is diminished or halted. If untreated, cells in the stationary phase eventually die. In general, cells in log phase are responsible for the bulk of production of product.

A suitable variation on the standard batch system is the "fed-batch fermentation" system. In this variation of a typical batch system, the substrate is added in increments as the fermentation progresses. Fed-batch systems are useful when catabolite repression likely inhibits the metabolism of the cells and where it is desirable to have limited amounts of substrate in the medium. Measurement of the actual substrate concentration in fed-batch systems is difficult and is therefore estimated on the basis of the changes of measurable factors, such as pH, dissolved oxygen and the partial pressure of waste gases, such as $CO_2$. Batch and fed-batch fermentations are common and known in the art.

Continuous fermentation is an open system where a defined fermentation medium is added continuously to a bioreactor, and an equal amount of conditioned medium is removed simultaneously for processing. Continuous fermentation generally maintains the cultures at a constant high density, where cells are primarily in log phase growth. Continuous fermentation allows for the modulation of one or more factors that affect cell growth and/or product concentration. For example, in one embodiment, a limiting nutrient, such as the carbon source or nitrogen source, is maintained at a fixed rate and all other parameters are allowed to moderate. In other systems, a number of factors affecting growth can be altered continuously while the cell concentration, measured by media turbidity, is kept constant. Continuous systems strive to maintain steady state growth conditions. Thus, cell loss due to medium being drawn off should be balanced against the cell growth rate in the fermentation. Methods of modulating nutrients and growth factors for continuous fermentation processes, as well as techniques for maximizing the rate of product formation, are well known in the art of industrial microbiology.

Thus, in certain embodiments, a POI produced by a transformed (modified) host cell may be recovered from the culture medium by conventional procedures including separating the host cells from the medium by centrifugation or filtration, or if necessary, disrupting the cells and removing the supernatant from the cellular fraction and debris. Typically, after clarification, the proteinaceous components of the supernatant or filtrate are precipitated by means of a salt, e.g., ammonium sulfate.

The precipitated proteins are then solubilized and may be purified by a variety of chromatographic procedures, e.g., ion exchange chromatography, gel filtration.

V. Proteins of Interest Produced by Modified (Host) Cells

A protein of interest (POI) of the instant disclosure can be any endogenous or heterologous protein, and it may be a variant of such a POI. The protein can contain one or more disulfide bridges or is a protein whose functional form is a monomer or a multimer. i.e., the protein has a quaternary structure and is composed of a plurality of identical (homologous) or non-identical (heterologous) subunits, wherein the POI or a variant POI thereof is preferably one with properties of interest.

For example, as set forth in the Examples below, the modified *Bacillus* cells of the disclosure produce an increased amount of endogenous and/or heterologous proteins of interests. Thus, in certain embodiments, a modified cell of the disclosure expresses an endogenous POI, a heterologous POI or a combination of one or more of such POIs. For example, in certain embodiments, a modified *Bacillus* (daughter) cell of the disclosure produces an increased amount of an endogenous POI relative to a parental *Bacillus* cell. In other embodiments, a modified *Bacillus* (daughter) cell of the disclosure produces an increased amount of a heterologous POI relative to a parental *Bacillus* cell.

Thus, in certain embodiments, a modified *Bacillus* (daughter) cell of the disclosure produces an increased amount of a POI relative to a parental *Bacillus* (control) cell, wherein the increased amount of the POI is at least about a 0.01% increase, at least about a 0.10% increase, at least about a 0.50% increase, at least about a 1.0% increase, at least about a 2.0% increase, at least about a 3.0% increase, at least about a 4.0% increase, at least about a 5.0% increase, or an increase greater than 5.0%. In certain embodiments, the increased amount of the POI is determined by assaying enzymatic activity and/or by assaying/quantifying the specific productivity (Qp) thereof. Likewise, one skilled in the art may utilize other routine methods and techniques known in the art for detecting, assaying, measuring, etc. the expression or production of one or more proteins of interest.

In certain embodiments, a modified *Bacillus* cell of the disclosure exhibits an increased specific productivity (Qp) of a POI relative the (unmodified) parental *Bacillus* cell. For example, the detection of specific productivity (Qp) is a suitable method for evaluating protein production. The specific productivity (Qp) can be determined using the following equation:

$$\text{“}Qp=gP/g\text{DCW}\cdot hr\text{”}$$

wherein, “gP” is grams of protein produced in the tank; “gDCW” is grams of dry cell weight (DCW) in the tank and “hr” is fermentation time in hours from the time of inoculation, which includes the time of production as well as growth time.

Thus, in certain other embodiments, a modified *Bacillus* cell of the disclosure comprises a specific productivity (Qp) increase of at least about 0.1%, at least about 1%, at least about 5%, at least about 6%, at least about 7%, at least about 8%, at least about 9%, or at least about 10% or more as compared to the unmodified (parental) cell.

In certain embodiments, a POI or a variant POI thereof is selected from the group consisting of acetyl esterases, aminopeptidases, amylases, arabinases, arabinofuranosidases, carbonic anhydrases, carboxypeptidases, catalases, cellulases, chitinases, chymosins, cutinases, deoxyribonucleases, epimerases, esterases, α-galactosidases, β-galactosidases, α-glucanases, glucan lysases, endo-β-glucanases, glucoamylases, glucose oxidases, α-glucosidases, β-glucosidases, glucuronidases, glycosyl hydrolases, hemicellulases, hexose oxidases, hydrolases, invertases, isomerases, laccases, ligases, lipases, lyases, mannosidases, oxidases, oxidoreductases, pectate lyases, pectin acetyl esterases, pectin depolymerases, pectin methyl esterases, pectinolytic enzymes, perhydrolases, polyol oxidases, peroxidases, phenoloxidases, phytases, polygalacturonases, proteases, peptidases, rhamno-galacturonases, ribonucleases, transferases, transport proteins, transglutaminases, xylanases, hexose oxidases, and combinations thereof.

Thus, in certain embodiments, a POI or a variant POI thereof is an enzyme selected from Enzyme Commission (EC) Number EC 1, EC 2, EC 3, EC 4, EC 5 or EC 6.

For example, in certain embodiments a POI is an oxidoreductase enzyme, including, but not limited to, an EC 1 (oxidoreductase) enzyme selected from EC 1.10.3.2 (e.g., a laccase), EC 1.10.3.3 (e.g., L-ascorbate oxidase), EC 1.1.1.1 (e.g., alcohol dehydrogenase), EC 1.11.1.10 (e.g., chloride peroxidase), EC 1.11.1.17 (e.g., peroxidase), EC 1.1.1.27 (e.g., L-lactate dehydrogenase), EC 1.1.1.47 (e.g., glucose 1-dehydrogenase), EC 1.1.3.X (e.g., glucose oxidase), EC 1.1.3.10 (e.g., pyranose oxidase), EC 1.13.11.X (e.g., dioxygenase), EC 1.13.11.12 (e.g., lineolate 13S-lipozygenase), EC 1.1.3.13 (e.g., alcohol oxidase), EC 1.14.14.1 (e.g., monooxygenase), EC 1.14.18.1 (e.g., monophenol monooxigenase) EC 1.15.1.1 (e.g., superoxide dismutase), EC 1.1.5.9 (formerly EC 1.1.99.10, e.g., glucose dehydrogenase), EC 1.1.99.18 (e.g., cellobiose dehydrogenase), EC 1.1.99.29 (e.g., pyranose dehydrogenase), EC 1.2.1.X (e.g., fatty acid reductase), EC 1.2.1.10 (e.g., acetaldehyde dehydrogenase), EC 1.5.3.X (e.g., fructosyl amine reductase), EC 1.8.1.X (e.g., disulfide reductase) and EC 1.8.3.2 (e.g., thiol oxidase).

In certain embodiments a POI is a transferase enzyme, including, but not limited to, an EC 2 (transferase) enzyme selected from EC 2.3.2.13 (e.g., transglutaminase), EC 2.4.1.X (e.g., hexosyltransferase), EC 2.4.1.40 (e.g., alternasucrase), EC 2.4.1.18 (e.g., 1.4 alpha-glucan branching enzyme), EC 2.4.1.19 (e.g., cyclomaltodextrin glucanotransferase), EC 2.4.1.2 (e.g., dextrin dextranase), EC 2.4.1.20 (e.g., cellobiose phosphorylase), EC 2.4.1.25 (e.g., 4-alpha-glucanotransferase), EC 2.4.1.333 (e.g., 1,2-beta-oligoglucan phosphor transferase), EC 2.4.1.4 (e.g., amylosucrase), EC 2.4.1.5 (e.g., dextransucrase), EC 2.4.1.69 (e.g., galactoside 2-alpha-L-fucosyl transferase), EC 2.4.1.9 (e.g., inulosucrase), EC 2.7.1.17 (e.g., xylulokinase), EC 2.7.7.89 (formerly EC 3.1.4.15, e.g., [glutamine synthetase]-adenylyl-L-tyrosine phosphorylase), EC 2.7.9.4 (e.g., alpha glucan kinase) and EC 2.7.9.5 (e.g., phosphoglucan kinase).

In other embodiments a POI is a hydrolase enzyme, including, but not limited to, an EC 3 (hydrolase) enzyme selected from EC 3.1.X.X (e.g., an esterase), EC 3.1.1.1 (e.g., pectinase), EC 3.1.1.14 (e.g., chlorophyllase), EC 3.1.1.20 (e.g., tannase), EC 3.1.1.23 (e.g., glycerol-ester acylhydrolase), EC 3.1.1.26 (e.g., galactolipase), EC 3.1.1.32 (e.g., phospholipase A1), EC 3.1.1.4 (e.g., phospholipase A2), EC 3.1.1.6 (e.g., acetylesterase), EC 3.1.1.72 (e.g., acetylxylan esterase). EC 3.1.1.73 (e.g., feruloyl esterase), EC 3.1.1.74 (e.g., cutinase), EC 3.1.1.86 (e.g., rhamnogalacturonan acetylesterase), EC 3.1.1.87 (e.g., fumosin B1 esterase), EC 3.1.26.5 (e.g., ribonuclease P), EC 3.1.3.X (e.g., phosphoric monoester hydrolase), EC 3.1.30.1 (e.g., *Aspergillus* nuclease Si), EC 3.1.30.2 (e.g., *Serratia marcescens* nuclease), EC 3.1.3.1 (e.g., alkaline phosphatase), EC 3.1.3.2 (e.g., acid phosphatase), EC 3.1.3.8 (e.g., 3-phytase), EC 3.1.4.1 (e.g., phosphodiesterase 1), EC 3.1.4.11 (e.g., phosphoinositide phospholipase C), EC 3.1.4.3 (e.g., phospholipase C), EC 3.1.4.4 (e.g., phospholipase D), EC 3.1.6.1 (e.g., arylsufatase), EC 3.1.8.2 (e.g., diisopropyl-fluorophosphatase), EC 3.2.1.10 (e.g., oligo-1,6-glucosidase), EC 3.2.1.101 (e.g., mannan endo-1,6-alpha-mannosidase), EC 3.2.1.11 (e.g., alpha-1,6-glucan-6-glucanohydrolase), EC 3.2.1.131 (e.g., xylan alpha-1,2-glucuronosidase), EC 3.2.1.132 (e.g., chitosan N-acetylglucosaminohydrolase), EC 3.2.1.139 (e.g., alpha-glucuronidase), EC 3.2.1.14 (e.g., chitinase), EC 3.2.1.151 (e.g., xyloglucan-specific endo-beta-1,4-glucanase), EC 3.2.1.155 (e.g., xyloglucan-specific exo-beta-1,4-glucanase), EC 3.2.1.164 (e.g., galactan endo-1,6-beta-galactosidase), EC 3.2.1.17 (e.g., lysozyme), EC 3.2.1.171 (e.g., rhamnogalacturonan hydrolase). EC 3.2.1.174 (e.g., rhamnogalacturonan rhamnohydrolase), EC 3.2.1.2 (e.g., beta-amylase), EC 3.2.1.20 (e.g., alpha-glucosidase), EC 3.2.1.22 (e.g., alpha-galactosidase), EC 3.2.1.25 (e.g., beta-mannosidase), EC 3.2.1.26 (e.g., beta-fructofiranosidase), EC 3.2.1.37 (e.g., xylan 1,4-beta-xylosidase), EC 3.2.1.39 (e.g., glucan endo-1,3-beta-D-glucosidase), EC 3.2.1.40 (e.g., alpha-L-rhamnosidase), EC 3.2.1.51 (e.g., alpha-L-fucosidase), EC 3.2.1.52 (e.g., beta-N-Acetylhexosaminidase), EC 3.2.1.55 (e.g., alpha-N-arabinofuranosidase), EC 3.2.1.58 (e.g., glucan 1,3-beta-glucosidase), EC 3.2.1.59 (e.g., glucan endo-1,3-alpha-glucosidase), EC 3.2.1.67 (e.g., galacturan 1,4-alpha-galacturonidase), EC 3.2.1.68 (e.g., isoamylase), EC 3.2.1.7 (e.g., 1-beta-D-fructan fructanohydrolase), EC 3.2.1.74 (e.g., glucan 1,4-β-glucosidase), EC 3.2.1.75 (e.g., glucan endo-1,6-beta-glucosidase), EC 3.2.1.77 (e.g., mannan 1,2-(1,3)-alpha-mannosidase), EC 3.2.1.80 (e.g., fructan beta-fructosidase), EC 3.2.1.82 (e.g., exo-poly-alpha-galacturonosidase), EC 3.2.1.83 (e.g., kappa-carrageenase), EC 3.2.1.89 (e.g., arabinogalactan endo-1,4-beta-galactosidase), EC 3.2.1.91 (e.g., cellulose 1,4-beta-cellobiosidase), EC 3.2.1.96 (e.g., mannosyl-glycoprotein endo-beta-N-acetylglucosaminidase), EC 3.2.1.99 (e.g., arabinan endo-1,5-alpha-L-arabinanase), EC 3.4.X.X (e.g., peptidase), EC 3.4.11.X (e.g., aminopeptidase), EC 3.4.11.1 (e.g., leucyl aminopeptidase), EC 3.4.11.18 (e.g., methionyl aminopeptidase), EC 3.4.13.9 (e.g., Xaa-Pro dipeptidase), EC 3.4.14.5 (e.g., dipeptidyl-peptidase IV), EC 3.4.16.X (e.g., serine-type carboxypeptidase), EC 3.4.16.5 (e.g., carboxypeptidase C), EC 3.4.19.3 (e.g., pyroglutamyl-peptidase 1), EC 3.4.21.X (e.g., serine endopeptidase), EC 3.4.21.1 (e.g., chymotrypsin), EC 3.4.21.19 (e.g., glutamyl endopeptidase), EC 3.4.21.26 (e.g., prolyl oligopeptidase), EC 3.4.21.4 (e.g., trypsin), EC 3.4.21.5 (e.g., thrombin), EC 3.4.21.63 (e.g., oryzin). EC 3.4.21.65 (e.g., thermomycolin), EC 3.4.21.80 (e.g., streptogrisin A), EC 3.4.22.X (e.g., cysteine endopeptidase), EC 3.4.22.14 (e.g., actinidain), EC 3.4.22.2 (e.g., papain), EC 3.4.22.3 (e.g., ficain), EC 3.4.22.32 (e.g., stem bromelain), EC 3.4.22.33 (e.g., fruit bromelain), EC 3.4.22.6 (e.g., chymopapain), EC 3.4.23.1 (e.g., pepsin A), EC 3.4.23.2 (e.g., pepsin B), EC 3.4.23.22 (e.g., endothiapepsin), EC 3.4.23.23 (e.g., mucorpepsin), EC 3.4.23.3 (e.g., gastricsin), EC 3.4.24.X (e.g., metalloendopeptidase), EC 3.4.24.39 (e.g., deuterolysin), EC 3.4.24.40 (e.g., serralysin), EC 3.5.1.1 (e.g., asparaginase), EC 3.5.1.11 (e.g., penicillin amidase), EC 3.5.1.14 (e.g., N-acyl-aliphatic-L-amino acid amidohydrolase), EC 3.5.1.2 (e.g., L-glutamine amidohydrolase), EC 3.5.1.28 (e.g., N-acetylmuramoyl-L-alanine amidase), EC 3.5.1.4 (e.g., amidase), EC 3.5.1.44 (e.g., protein-L-glutamine amidohydrolase), EC 3.5.1.5 (e.g., urease), EC 3.5.1.52 (e.g., peptide-N(4)-(N-acetyl-beta-glucosaminyl)asparagine amidase), EC 3.5.1.81 (e.g., N-Acyl-D-amino-acid deacylase), EC 3.5.4.6 (e.g., AMP deaminase) and EC 3.5.5.1 (e.g., nitrilase).

In other embodiments a POI is a lyase enzyme, including, but not limited to, an EC 4 (lyase) enzyme selected from EC 4.1.2.10 (e.g., mandelonitrile lyase), EC 4.1.3.3 (e.g., N-acetylneuraminate lyase), EC 4.2.1.1 (e.g., carbonate dehydratase), EC 4.2.2.- (e.g., rhamnogalacturonan lyase), EC 4.2.2.10 (e.g., pectin lyase), EC 4.2.2.22 (e.g., pectate trisaccharide-lyase), EC 4.2.2.23 (e.g., rhamnogalacturonan endolyase) and EC 4.2.2.3 (e.g., mannuronate-specific alginate lyase).

In certain other embodiments a POI is an isomerase enzyme, including, but not limited to, an EC 5 (isomerase) enzyme selected from EC 5.1.3.3 (e.g., aldose 1-epimerase), EC 5.1.3.30 (e.g., D-psicose 3-epimerase), EC 5.4.99.11 (e.g., isomaltulose synthase) and EC 5.4.99.15 (e.g., (1-+4)-α-D-glucan 1-α-D-glucosylmutase).

In yet other embodiments, a POI is a ligase enzyme, including, but not limited to, an EC 6 (ligase) enzyme selected from EC 6.2.1.12 (e.g., 4-coumarate:coenzyme A ligase) and EC 6.3.2.28 (e.g., L-amino-acid alpha-ligase)9

Thus, in certain embodiments, industrial protease producing *Bacillus* host cells provide particularly preferred expression hosts. Likewise, in certain other embodiments, industrial amylase producing *Bacillus* host cells provide particularly preferred expression hosts.

For example, there are two general types of proteases which are typically secreted by *Bacillus* spp., namely neutral (or "metalloproteases") and alkaline (or "serine") proteases.

For example, *Bacillus* subtilisin proteins (enzymes) are exemplary serine proteases for use in the present disclosure. A wide variety of *Bacillus* subtilisins have been identified and sequenced, for example, subtilisin 168, subtilisin BPN', subtilisin Carlsberg, subtilisin DY, subtilisin 147 and subtilisin 309 (e.g., WO 1989/06279 and Stahl et al., 1984). In some embodiments of the present disclosure, the modified *Bacillus* cells produce mutant (i.e., variant) proteases. Numerous references provide examples of variant proteases, such as PCT Publication Nos. WO1999/20770; WO1999/20726; WO1999/20769; WO1989/06279; U.S. RE34,606; U.S. Pat. Nos. 4,914,031; 4,980,288; 5,208,158; 5,310,675; 5,336,611; 5,399,283; 5,441,882; 5,482,849; 5,631,217; 5,665,587; 5,700,676; 5,741,694; 5,858,757; 5,880,080; 6,197,567 and 6,218,165. Thus, in certain embodiments, a modified *Bacillus* cells of the disclosure comprises an expression construct encoding a protease.

In certain other embodiments, a modified *Bacillus* cells of the disclosure comprises an expression construct encoding an amylase. A wide variety of amylase enzymes and variants thereof are known to one skilled in the art. For example, International PCT Publication NO. WO2006/037484 and WO 2006/037483 describe variant α-amylases having improved solvent stability, Publication No. WO1994/18314 discloses oxidatively stable α-amylase variants, Publication No. WO1999/19467, WO2000/29560 and WO2000/60059 disclose Termamyl-like α-amylase variants, Publication No. WO2008/112459 discloses α-amylase variants derived from *Bacillus* sp. number 707, Publication No. WO1999/43794 discloses maltogenic α-amylase variants, Publication No. WO1990/11352 discloses hyper-thermostable α-amylase variants, Publication No. WO2006/089107 discloses α-amylase variants having granular starch hydrolyzing activity.

In other embodiments, a POI or variant POI expressed and produced in a modified cell of the disclosure is a peptide, a peptide hormone, a growth factor, a clotting factor, a chemokine, a cytokine, a lymphokine, an antibody, a receptor, an adhesion molecule, a microbial antigen (e.g., HBV surface antigen, HPV E7, etc.), variants thereof, fragments thereof and the like. Other types of proteins (or variants thereof) of interest may be those that are capable of providing nutritional value to a food or to a crop. Non-limiting examples include plant proteins that can inhibit the formation of anti-nutritive factors and plant proteins that have a more desirable amino acid composition (e.g., a higher lysine content than a non-transgenic plant).

There are various assays known to those of ordinary skill in the art for detecting and measuring activity of intracellularly and extracellularly expressed proteins. In particular, for proteases, there are assays based on the release of acid-soluble peptides from casein or hemoglobin measured as absorbance at 280 nm or colorimetrically, using the Folin method (e.g., Bergmeyer et al., 1984). Other assays involve the solubilization of chromogenic substrates (See e.g., Ward, 1983). Other exemplary assays include succinyl-Ala-Ala-Pro-Phe-para-nitroanilide assay (SAAPFpNA) and the 2,4,6-trinitrobenzene sulfonate sodium salt assay (TNBS assay). Numerous additional references known to those in the art provide suitable methods (See e.g., Wells et al., 1983; Christianson et al., 1994 and Hsia et al., 1999).

International PCT Publication No. WO2014/164777 discloses Ceralpha α-amylase activity assays useful for amylase activities described herein.

Means for determining the levels of secretion of a protein of interest in a host cell and detecting expressed proteins include the use of immunoassays with either polyclonal or monoclonal antibodies specific for the protein. Examples include enzyme-linked immunosorbent assay (ELISA), radioimmunoassay (RIA), fluorescence immunoassay (FIA), and fluorescent activated cell sorting (FACS).

VI. Exemplary Embodiments

Non-limiting embodiments of the disclosure include, but are not limited to:

1. A method for producing an increased amount of a protein of interest (POI) in a modified *Bacillus licheniformis* cell comprising (a) modifying a parental *B. licheniformis* cell expressing a POI by introducing therein a polynucleotide comprising a native prsA promoter sequence operably linked to a native prsA open reading frame (ORF) sequence, and (b) fermenting the modified cell under suitable conditions for the production of the POI, wherein the modified cell produces an increased amount of the POI relative to the parental cell when fermented under the same conditions.

2. A method for producing an increased amount of a protein of interest (POI) in a modified *Bacillus licheniformis* cell comprising (a) modifying a parental *B. licheniformis* cell by introducing therein (i) an expression cassette encoding a POI and (ii) a polynucleotide comprising a native prsA promoter sequence operably linked to a native prsA open reading frame (ORF) sequence, and (b) fermenting the modified cell under suitable conditions for the production of the POI, wherein the modified cell produces an increased amount of the POI relative to the parental cell when fermented under the same conditions.

3. The method of embodiment 1 or embodiment 2, wherein the introduced polynucleotide comprises a native prsA promoter sequence comprising at least 95% sequence identity to SEQ ID NO: 100.

4. The method of embodiment 1 or embodiment 2, wherein the introduced polynucleotide comprises a native prsA ORF comprises at least 90% sequence identity to SEQ ID NO: 101.

5. The method of embodiment 1 or embodiment 2, wherein the parental cell comprises an endogenous prsA gene encoding a native prsA protein.

6. The method of embodiment 5, wherein the endogenous prsA gene encodes a native prsA protein comprising about 90% sequence identity to SEQ ID NO: 155.

7. The method of embodiment 1 or embodiment 2, wherein the introduced polynucleotide is integrated into the genome of the modified *B. licheniformis* cell.

8. The method of embodiment 1 or embodiment 2, wherein the modified cell further comprises a deleted or disrupted dltA gene comprising at least 90% sequence identity to SEQ ID NO: 122.

9. The method of embodiment 1 or embodiment 2, wherein the modified cell further comprises a deleted or disrupted rghR2 gene comprising at least 90% sequence identity to SEQ ID NO: 121 or SEQ ID NO: 158.

10. The method of embodiment 1 or embodiment 2, wherein the modified cell further comprises a deleted or disrupted dltA gene comprising at least 90% sequence identity to SEQ ID NO: 122 and a deleted or disrupted rghR2 gene comprising at least 90% sequence identity to SEQ ID NO: 121 or SEQ ID NO: 158.

11. The method of embodiment 1 or embodiment 2, wherein the POI is an enzyme.

12. The method of embodiment 11, wherein the enzyme is a protease or an amylase.

13. A modified *Bacillus licheniformis* cell derived from a parental *B. licheniformis* cell, wherein the modified cell comprises an introduced polynucleotide comprising a native prsA promoter sequence operably linked to a native prsA open reading frame (ORF) sequence.

14. A modified *Bacillus licheniformis* cell derived from a parental *B. licheniformis* comprising an endogenous prsA gene encoding a native prsA protein, wherein the modified cell comprises an introduced polynucleotide comprising a native prsA promoter sequence operably linked to a native prsA open reading frame (ORF) sequence.

15. The modified cell of embodiment 13 or embodiment 14, wherein the introduced polynucleotide comprises a native prsA promoter comprising at least 95% sequence identity to SEQ ID NO: 100.

16. The modified cell of embodiment 13 or embodiment 14, wherein the introduced polynucleotide comprises a native prsA ORF comprises at least 90% sequence identity to SEQ ID NO: 101.

17. The modified cell of embodiment 13 or embodiment 14, wherein the introduced polynucleotide encodes a native prsA protein comprising about 90% sequence identity to SEQ ID NO: 155.

18. The modified cell of embodiment 13 or embodiment 14, wherein the introduced polynucleotide is integrated into the genome of the modified *B. licheniformis* cell.

19. The modified cell of embodiment 13 or embodiment 14, comprising a deleted or disrupted dltA gene comprising at least 90% sequence identity to SEQ ID NO: 122.

20. The modified cell of embodiment 13 or embodiment 14, comprising a deleted or disrupted rghR2 gene comprising at least 90% sequence identity to SEQ ID NO: 121 or SEQ ID NO: 158.

21. The modified cell of embodiment 13 or embodiment 14, comprising a deleted or disrupted dltA gene comprising at least 90% sequence identity to SEQ ID NO: 122 and a deleted or disrupted rghR2 gene comprising at least 90% sequence identity to SEQ ID NO: 121 or SEQ ID NO: 158.

22. The modified cell of embodiment 13 or embodiment 14, comprising an introduced expression cassette encoding a heterologous protein of interest (POI).

23. The modified cell of embodiment 22, wherein the POI is an enzyme.

24. The modified cell of embodiment 13 or embodiment 14, wherein the parental cell expresses an endogenous POI.

25. A protein of interest produced by the modified cell of embodiment 22 or embodiment 24.

26. A modified *Bacillus licheniformis* cell producing an increased amount of a protein of interest (POI) relative to a parental *B. licheniformis* cell, wherein the modified cell is derived from a parental *B. licheniformis* cell expressing a POI, wherein the modified cell comprises an introduced polynucleotide comprising a native prsA promoter sequence operably linked to a native prsA open reading frame (ORF) sequence and comprises a deleted or disrupted rghR2 gene comprising at least 90% sequence identity to SEQ ID NO: 121 or SEQ ID NO: 158, wherein the modified cell produces an increased amount of the POI relative to the parental strain when fermented under the same condition.

27. The modified cell of embodiment 26, further comprising a deleted or disrupted dltA gene comprising at least 90% sequence identity to SEQ ID NO: 122.

28. A modified *Bacillus licheniformis* cell producing an increased amount of a protein of interest (POI) relative to a parental *B. licheniformis* cell, wherein modified cell is derived from a parental *B. licheniformis* cell expressing a POI, wherein the modified cell comprises an introduced polynucleotide comprising a native prsA promoter operably linked to a native prsA open reading frame (ORF) and comprises a deleted or disrupted dltA gene comprising at least 90% sequence identity to SEQ ID NO: 122, wherein the modified cell produces an increased amount of the POI relative to the parental strain when fermented under the same condition.

29. The modified cell of embodiment 28, further comprising a deleted or disrupted rghR2 gene comprising at least 90% sequence identity to SEQ ID NO: 121 or SEQ ID NO: 158.

30. The modified cell of embodiment 26 or embodiment 28, wherein the native prsA promoter comprises at least 95% sequence identity to SEQ ID NO: 100.

31. The modified cell of embodiment 26 or embodiment 28, wherein the native prsA ORF comprises at least 90% sequence identity to SEQ ID NO: 101.

32. The modified cell of embodiment 26 or embodiment 28, wherein the native prsA protein comprises about 90% sequence identity to SEQ ID NO: 155.

33. The modified cell of embodiment 26 or embodiment 28, wherein the POI is an enzyme.

34. The modified cell of embodiment 33, wherein the enzyme is a protease or an amylase.

35. A protein of interest produced by the modified cell of embodiment 26 or embodiment 28.

EXAMPLES

Certain aspects of the present invention may be further understood in light of the following examples, which should not be construed as limiting. Modifications to materials and methods will be apparent to those skilled in the art.

Example 1

Construction of Cas9 Vectors Targeting rghR2 Pathway Genes

The Cas9 protein from *S. pyogenes* (SEQ ID NO: 1) was codon optimized for *Bacillus* (SEQ ID NO: 2) with the addition of an N-terminal nuclear localization sequence (NLS; "APKKKRKV"; SEQ ID NO: 3), a C-terminal NLS ("KKKKLK"; SEQ ID NO: 4), a deca-histidine tag ("HHHHHHHHHH"; SEQ ID NO: 5), the aprE promoter from *B. subtilis* (SEQ ID NO: 6) and a terminator sequence (SEQ ID NO: 7) and was amplified using Q5 DNA polymerase (NEB) per

| | | |
|---|---|---|
| Forward | ATATATGAGTAAACTTGGTCTGACA GAATTCCTCCATTTTCTTCTGCTAT | SEQ ID NO: 8 |
| Reverse | TGCGGCCGCGAATTCGATTACGAAT GCCGTCTCCC | SEQ ID NO: 9 |

manufacturer's instructions with the forward (SEQ ID NO: 8) and reverse (SEQ ID NO: 9) primer pair set forth below in TABLE 1.

Table 1

Forward and Reverse Primer Pair

The backbone (SEQ ID NO: 10) of plasmid pKB320 (SEQ ID NO: 11) was amplified using Q5

| | | |
|---|---|---|
| Forward | GGGAGACGGCATTCGTAATCGAATT CGCGGCCGCA | SEQ ID NO: 12 |
| Reverse | ATAGCAGAAGAAAATGGAGGAATTC TGTCAGACCAAGTTTACTCATATAT | SEQ ID NO: 13 |

DNA polymerase (NEB) per manufacturer's instructions with the forward (EQ ID NO: 12) and reverse (SEQ ID NO: 13) primer pair set forth below in TABLE 2.

Table 2

Forward and Reverse Primer Pair

The PCR products were purified using Zymo clean and concentrate 5 columns per manufacturer's instructions. Subsequently, the PCR products were assembled using prolonged overlap extension PCR (POE-PCR) with Q5 Polymerase (NEB) mixing the two fragments at equimolar ratio. The POE-PCR reactions were cycled: 98° C. for five (5) seconds, 64° C. for ten (10) seconds, 72° C. for four (4) minutes and fifteen (15) seconds for 30 cycles. Five (5) µl of the POE-PCR (DNA) was transformed into Top10 *E. coli* (Invitrogen) per manufacturer's instructions and selected on lysogeny (L) Broth (Miller recipe; 1% (w/v) Tryptone, 0.5% Yeast extract (w/v), 1% NaCl (w/v)), containing fifty (50) µg/ml kanamycin sulfate and solidified with 1.5% Agar. Colonies were allowed to grow for eighteen (18) hours at 37° C. Colonies were picked and plasmid DNA prepared using Qiaprep DNA miniprep kit per manufacturer's instructions and eluted in fifty-five (55) µl of ddH2O. The plasmid DNA was Sanger sequenced to verify correct assembly, using the sequencing primers set forth below in TABLE 3.

TABLE 3

| SEQUENCING PRIMERS | | |
|---|---|---|
| Reverse | CCGACTGGAGCTCCTATATTACC | SEQ ID NO: 14 |
| Reverse | GCTGTGGCGATCTGTATTCC | SEQ ID NO: 15 |
| Forward | GTCTTTTAAGTAAGTCTACTCT | SEQ ID NO: 16 |
| Forward | CCAAAGCGATTTTAAGCGCG | SEQ ID NO: 17 |
| Forward | CCTGGCACGTGGTAATTCTC | SEQ ID NO: 18 |
| Forward | GGATTTCCTCAAATCTGACG | SEQ ID NO: 19 |
| Forward | GTAGAAACGCGCCAAATTACG | SEQ ID NO: 20 |
| Forward | GCTGGTGGTTGCTAAAGTCG | SEQ ID NO: 21 |
| Forward | GGACGCAACCCTCATTCATC | SEQ ID NO: 22 |
| Reverse | CAGGCATCCGATTTGCAAGG | SEQ ID NO: 23 |
| Forward | GCAAGCAGCAGATTACGCG | SEQ ID NO: 24 |

The correctly assembled plasmid, pRF694 (SEQ ID NO: 25) was used to construct plasmids pRF801 (SEQ ID NO: 26) and pRF806 (SEQ ID NO: 27) for editing the *B. licheniformis* genome at target site 1 (TS1; SEQ ID NO: 28) and target site 2 (TS2; SEQ ID NO: 29) as described below.

The serA1 open reading frame (SEQ ID NO: 30) of *B. licheniformis* contains a unique target site, target site 1 (TS1; SEQ ID NO: 28) in the reverse orientation. The target site lies adjacent to a protospacer adjacent motif (SEQ ID NO: 31) in the reverse orientation. The target site can be converted into the DNA encoding a variable targeting domain (SEQ ID NO: 32).

The DNA sequence encoding the VT domain (SEQ ID NO: 32) is operably fused to the DNA sequence encoding the Cas9 endonuclease recognition domain (CER, SEQ ID NO: 33) such that when transcribed by RNA polymerase of the bacterial cell, it produces a functional gRNA targeting target site 1 (SEQ ID NO: 34). The DNA encoding the gRNA was operably linked to a promoter operable in *Bacillus* sp. cells (e.g., the spac promoter; SEQ ID NO: 35) and a terminator operable in *Bacillus* sp. cells (e.g., the t0 terminator of phage lambda; SEQ ID NO: 36), such that the promoter was positioned upstream (5') of the DNA encoding the gRNA (SEQ ID NO: 33) and the terminator is positioned downstream (3') of the DNA encoding the gRNA (SEQ ID NO: 33).

An editing template to delete the serA1 gene in response to Cas9/gRNA cleavage was created by amplification of two homology arms from *B. licheniformis* genomic DNA (gDNA). The first fragment corresponds to the 500 bp directly upstream of the serA1 open reading frame (SEQ ID NO: 37). This fragment was amplified using Q5 DNA polymerase per the manufacturer's instructions and the forward (SEQ ID NO: 38) and reverse (SEQ ID NO: 39) primers listed in TABLE 4 below. The primers incorporate 18 bp homologous to the 5' end of the second fragment on the 3' end of the first fragment and 20 bp homologous to pRF694 to the 5' end of first fragment.

TABLE 4

| FORWARD AND REVERSE PRIMER PAIR | | |
|---|---|---|
| Forward | TGAGTAAACTTGGTCTGACAAATGGTTCTT TCCCCTGTCC | SEQ ID NO: 38 |
| Reverse | AGGTTCCGCAGCTTCTGTGTAAGATTTCCT CCTAAATAAGCGTCAT | SEQ ID NO: 39 |

The second fragment corresponds to the 500 bp directly downstream of the 3' end of the serA1 open reading frame (SEQ ID NO: 40). This fragment was amplified using Q5 DNA polymerase per manufacturer's instructions and the forward (SEQ ID NO: 41) and reverse (SEQ ID NO: 42) primers listed in TABLE 5 below. The primers incorporate 28 bp homologous to the 3' end of the first fragment on the 5' end of the second fragment and 21 bp homologous to pRF694 on the 3' end of the second fragment.

TABLE 5

| FORWARD AND REVERSE PRIMER PAIR | | |
|---|---|---|
| Forward | ATGACGCTTATTTAGGAGGAAATCTTACACA GAAGCTGCGGAACCT | SEQ ID NO: 41 |
| Reverse | CAGAAGAAAATGGAGGAATTCGAATATCGAC CGGAACCCAC | SEQ ID NO: 42 |

The DNA encoding the target site 1 gRNA expression cassette (SEQ ID NO: 43), the first (SEQ ID NO: 37) and second homology arms (SEQ ID NO: 40) were assembled into pRF694 (SEQ ID NO: 25) using standard molecular biology techniques generating pRF801 (SEQ ID NO: 26), an *E. coli-B. licheniformis* shuttle plasmid containing a Cas9 expression cassette (SEQ ID NO: 2), a gRNA expression cassette (SEQ ID NO: 43) encoding a gRNA targeting target site 1 within the serA1 open-reading frame and an editing template (SEQ ID NO: 44) composed of the first (SEQ ID NO: 37) and second (SEQ ID NO: 40) homology arms. The plasmid was verified by Sanger sequencing with the oligos set forth in TABLE 3.

The rghR1 open reading frame of *B. licheniformis* (SEQ ID NO: 45) contains a unique target site on the reverse strand, target site 2 (TS2; SEQ ID NO: 29). The target site lies adjacent to a protospacer adjacent motif (SEQ ID NO:

46) on the reverse strand. The DNA sequence encoding the target site (SEQ ID NO: 29) is operably fused to the DNA sequence encoding the Cas9 endonuclease recognition domain (CER, SEQ ID NO: 33) such that when transcribed by RNA polymerase of the bacterial cell it produces a functional gRNA targeting target site 2 (SEQ ID NO: 47). The DNA encoding the gRNA was operably linked to a promoter operable in *Bacillus* sp. cells (e.g., the spac promoter from *B. subtilis*; SEQ ID NO: 35) and a terminator operable in *Bacillus* sp. cells (e.g., the t0 terminator of phage lambda; SEQ ID NO: 36), such that the promoter was positioned 5' of the DNA encoding the gRNA (SEQ ID NO: 47) and the terminator is positioned 3' of the DNA encoding the gRNA (SEQ ID NO: 47).

An editing template to modify the rghR1 gene in response to Cas9/gRNA cleavage was created by amplification of two homology arms from *B. licheniformis* genomic DNA (gDNA). The first fragment corresponds to the 500 bp directly upstream of the rghR1 open reading frame (SEQ ID NO: 48). This fragment was amplified using Q5 DNA polymerase per the manufacturer's instructions and the primers listed in TABLE 6 below. The primers incorporate 23 bp homologous to the 5' end of the second fragment on the 3' end of the first fragment and 20 bp homologous to pRF694 to the 5' end of first fragment.

TABLE 6

| | FORWARD AND REVERSE PRIMER PAIR |
|---|---|
| Forward | TGAGTAAACTTGGTCTGACATTGATA TTCAGCACCCTGCG SEQ ID NO: 49 |
| Reverse | TGTGCCGCGGAGAAGTATGGCCAAAA CCTCGCAATCTC SEQ ID NO: 50 |

The second fragment corresponds to the 500 bp directly downstream of the 3' end of the rghR1 open reading frame (SEQ ID NO: 51). This fragment was amplified using Q5 DNA polymerase per manufacturer's instructions and the primers listed in TABLE 7 below. The primers incorporate 20 bp homologous to the 3' end of the first fragment on the 5' end of the second fragment and 21 bp homologous to pRF694 on the 3' end of the second fragment.

TABLE 7

| | FORWARD AND REVERSE PRIMER PAIR |
|---|---|
| Forward | GAGATTGCGAGGTTTTGGCCATACTT CTCCGCGGCACA SEQ ID NO: 52 |
| Reverse | CAGAAGAAAATGGAGGAATTCATTTC TCGGGTTTAAACAGCCAC SEQ ID NO: 53 |

The DNA encoding the target site 2 gRNA expression cassette (SEQ ID NO: 54), the first (SEQ ID NO: 48) and second homology arms (SEQ ID NO: 51) were assembled into pRF694 (SEQ ID NO: 25) using standard molecular biology techniques generating pRF806 (SEQ ID NO: 27), an *E. coli-B. licheniformis* shuttle plasmid containing a Cas9 expression cassette (SEQ ID NO: 2), a gRNA expression cassette (SEQ ID NO: 54) encoding a gRNA targeting target site 2 within the rghR1 open-reading frame and an editing template (SEQ ID NO: 55) composed of the first (SEQ ID NO: 48) and second (SEQ ID NO: 51) homology arms. The plasmid was verified by sanger sequence with the oligos set forth in TABLE 3.

Example 2

Construction of Cas9 Y155H Variant and Associated Targeting Plasmids

In the present example, the Y155H variant of *S. pyogenes* Cas9 (SEQ ID NO: 56) is constructed in the pRF801 (SEQ ID NO: 26) and pRF806 plasmids (SEQ ID NO: 27). To introduce the Y155H variant in the pRF801 plasmid (SEQ ID NO: 26), or the pRF806 plasmid (SEQ ID NO: 27), site-directed mutagenesis was performed using Quikchange mutagenesis kit per the manufacturer's instructions and the oligos in TABLE 8 below using pRF801 (SEQ ID NO: 26) or pRF806 (SEQ ID NO: 27) as template DNA.

TABLE 8

| | FORWARD AND REVERSE PRIMER PAIR |
|---|---|
| Forward | GATCTGCGTTTAATCCATCTTGCG TTAGCGCAC SEQ ID NO: 57 |
| Reverse | GTGCGCTAACGCAAGATGGATTAA ACGCAGATC SEQ ID NO: 58 |

The resultant products of the reaction, pRF827 (SEQ ID NO: 59) contained a Cas9 Y155H variant expression cassette (SEQ ID NO: 60), a gRNA expression cassette (SEQ ID NO: 43) encoding a gRNA targeting target site 1 within the serA1 open-reading frame, and an editing template (SEQ ID NO: 44) composed of the first (SEQ ID NO: 37) and second (SEQ ID NO: 40) homology arms; or pRF856 (SEQ ID NO: 61) which contained a Cas9 Y155H variant expression cassette (SEQ ID NO: 60), a gRNA expression cassette (SEQ ID NO: 54) targeting target site 2 within the rghR1 open reading frame and an editing template (SEQ ID NO: 55) composed of the first (SEQ ID NO: 48) and second (SEQ ID NO: 51) homology arms. The plasmid DNAs were Sanger sequenced to verify correct assembly, using the sequencing primers set forth in TABLE 3.

Construction of Plasmid pRF862

Plasmid pRF862 (SEQ ID NO: 62) was constructed by moving a fragment (SEQ ID NO: 63) of the Cas9 open-reading frame containing the Y155H substitution from pRF827 (SEQ ID NO: 59) amplified using the primers set forth in TABLE 9.

TABLE 9

| | FORWARD AND REVERSE PRIMER PAIR | |
|---|---|---|
| Forward | CACGTCGTAAAAATCGTATT | SEQ ID NO: 64 |
| Reverse | CAAACAGACCATTITTCTTT | SEQ ID NO: 65 |

A second fragment (SEQ ID NO: 66) was amplified from pRF694 (SEQ ID NO: 25) such that it contained the entire plasmid except the fragment contained on the pRF827 fragment above (SEQ ID NO: 63). This fragment shared homology with the 5' and 3' ends of the pRF827 fragment (SEQ ID NO: 60) for assembly and was amplified using the primers set forth in TABLE 10.

TABLE 10

| | FORWARD AND REVERSE PRIMER PAIR | |
|---|---|---|
| Forward | AAAGAAAAATGGTCTGTTTG | SEQ ID NO: 67 |
| Reverse | AATACGATTTTTACGACGTG | SEQ ID NO: 68 |

The two fragments were assembled using NEBuilder according to manufacturer's instructions and transformed into *E. coli* competent cells. Plasmid sequence was verified by the method of Sanger as set forth in TABLE 3. A sequence verified isolate was stored as plasmid pRF862 (SEQ ID NO: 62).

pRF869 (SEQ ID NO: 69), a plasmid that targets the rghR2 ORF (SEQ ID NO: 70) and inserts three (3) in-frame stop codons, was constructed using two parts. The first part (SEQ ID NO: 71) containing the editing template (SEQ ID NO: 72) to modify the rghR2 ORF (SEQ ID NO: 70), and a gRNA expression cassette (SEQ ID NO: 73) targeting the rghR2 ORF (SEQ ID NO 70) was synthesized by IDT and was amplified for assembly using the primers set forth in TABLE 11.

TABLE 11

| FORWARD AND REVERSE PRIMER PAIR | | |
|---|---|---|
| Forward | CGTGCGGCCGCGAATTC | SEQ ID NO: 74 |
| Reverse | CCTGATACCGGGAGACGGCATTCGTAATC | SEQ ID NO: 75 |

The synthetic fragment was inserted into pRF862 (SEQ ID NO: 62) by amplifying pRF862 using the primers set forth in TABLE 12.

TABLE 12

| FORWARD AND REVERSE PRIMER PAIR | | |
|---|---|---|
| Forward | GAATTCGCGGCCGCACG | SEQ ID NO: 76 |
| Reverse | GATTACGAATGCCGTCTCCCGGTATCAGG | SEQ ID NO: 77 |

The two parts were assembled using NEBuilder according to manufacturer's instructions and transformed into *E. coli*. Plasmid sequence was verified by the method of Sanger as set forth in TABLE 3. A sequence verified isolate was stored as pRF869 (SEQ ID NO: 69).

Several additional Cas9 plasmids were assembled as described above in Examples 1 and 2. Those plasmids are listed below in TABLE 13, along with the target site sequence and the editing template effect.

TABLE 13

ADDITIONAL CAS9 PLASMIDS FOR EDITING B. LICHENIFORMIS CELLS

| Plasmid | SEQ ID | arget site and TPAM sequence | Target and PAM SEQ ID | Editing template effect | Editing template SEQ ID |
|---|---|---|---|---|---|
| pRF879 | 78 | GCGAGCGGCTCAAAGAGCTGAGG | 79 | ΔrghR2 | 80 |
| pRF946 | 81 | GAGCTTCTTTTTCTTGAGCACGG | 82 | Δcat | 83 |
| pZM221 | 84 | TCCAGTTGACGTATCGATTCCGG | 85 | ΔdltA-2 | 86 |

For all plasmids, rolling-circle amplification (RCA) was used to amplify and make the plasmids suitable substrates for transformation using the TruPrime RCA kit (Sygnis).

Example 3

Construction of Modified Host Strains

In the present example, a series of host modifications were introduced into a parental *B. licheniformis* strain. The parental *B. licheniformis* strain contains deletions of the serA1 (SEQ ID NO: 30) and the lysA genes (SEQ ID NO: 87) and is named BF140.

A version of BF140 containing the pBl.comK plasmid (SEQ ID NO: 88) (Liu and Zuber, 1998, Hamoen et al., 1998) which contains a spectinomycin marker (SEQ ID NO: 89), the DNA encoding the XylR repressor (SEQ ID NO: 90) and the xylA promoter (SEQ ID NO: 91) of *B. subtilis* operably linked to the DNA encoding the *B. licheniformis* ComK protein (SEQ ID NO: 92), was transformed with a linear PCR product targeting the catH locus for integration of a second copy of the prsA gene of *B. licheniformis* (SEQ ID NO: 93). The construct contains an upstream homology arm to the catH locus (SEQ ID NO: 94) operably linked to the catH promoter (SEQ ID NO: 95), the DNA encoding the CatH protein (SEQ ID NO: 96) operably linked to a dual terminator (SEQ ID NO: 97) composed of the catH terminator (SEQ ID NO: 98) operably linked to the spoVG terminator of *B. subtilis* (SEQ ID NO: 99).

The construct then contains the prsA promoter of *B. licheniformis* (SEQ ID NO: 100) operably linked to the prsA coding sequence (SEQ ID NO: 101) operably linked to the terminator from the amyL gene of *B. licheniformis* (SEQ ID NO: 102) operably linked to a downstream homology arm for the catH locus (SEQ ID NO: 103). Briefly. BF140/pBl.comK competent cells were generated. The BF140/pBl.comK strain was grown overnight in L broth containing one hundred (100) ppm spectinomycin at 37° C. with 250 RPM shaking. The culture was diluted the next day to an $OD_{600}$ of 0.7 of fresh L broth containing one hundred (100) ppm spectinomycin. This new culture was grown for one (1) hour at 37° C., 250 RPM shaking. D-xylose was added to 0.1% $w \cdot v^{-1}$. The culture was grown for an additional four (4) hours at 37° C. and 250 RPM shaking. The cells were harvested at 1700·g for seven (7) minutes. The cells were resuspended in ¼ volume of the spent culture medium containing 10% $v \cdot v^{-1}$ DMSO. One hundred (100) µl of cells were mixed with ten (10) µl of the catH::[catH prsAp-prsA] integration fragment (SEQ ID NO: 94). The cell/DNA mixture was incubated at 1400 RPM, 37° C. for one and a half (1.5) hours. The mixture was then plated on L agar plates contain ten (10) ppm chloramphenicol. The inoculated plates were incubated at 37° C. for forty-eight (48) hours.

Colonies that formed on L agar containing ten (10) ppm chloramphenicol were screened using colony PCR to confirm the modification of the catH locus using primers listed in TABLE 14 and standard PCR techniques.

TABLE 14

| FORWARD AND REVERSE PRIMER PAIR | | |
|---|---|---|
| Forward | TCGTTCTGAATGAGCAAGCA | SEQ ID NO: 104 |
| Reverse | TGTTAATCAGGCCGACGATC | SEQ ID NO: 105 |

This PCR product, a 2676 bp fragment (SEQ ID NO: 106), was sequenced using the method of Sanger and the primers listed in TABLE 15.

TABLE 15

| SANGER SEQUENCING PRIMERS | | |
|---|---|---|
| 1915 | AACCTATATGACAGCCGGAG | SEQ ID NO: 107 |
| 1916 | GGCAAAATCCACTTAAGCCAC | SEQ ID NO: 108 |
| 1054 | AACGAGTTGGAACGGCTTGC | SEQ ID NO: 109 |

An isolate with the correct catH::[catH prsAp-prsA]integration (SEQ ID NO: 93) was stored as strain BF547.

A version of BF547 containing the pBl.comK plasmid (SEQ ID NO: 88) was made competent as described above. One hundred (100) μl of competent cells were mixed with five (5) μl of pRF946 (SEQ ID NO: 81) RCA and incubated at 1400 RPM, 37° C. for one and a half (1.5) hours. The mixture was plated on L agar plates containing twenty (20) ppm kanamycin to select for plasmid transformation. The plates were incubated at 37° C. for forty-eight (48) hours.

Colonies that formed on L agar containing twenty (20) ppm kanamycin were screened for colony PCR to confirm the deletion of the DNA encoding the 3' end of the catH promoter and the DNA encoding the CatH protein (SEQ ID NO: 110), while retaining the catH::[prsAp-prsA]cassette (SEQ ID NO: 111) using standard PCR techniques and primers listed in above TABLE 14.

Correct colonies containing the catH::[prsAp-prsA]cassette (SEQ ID NO: 111) produced a PCR product of 1990 bp (SEQ ID NO: 112), as opposed to the parent colonies containing the catH::[catH prsAp-prsA] cassette (SEQ ID NO: 93, which produced a PCR product of 2676 bp in length (SEQ ID NO: 106). The difference was assessed visually using standard gel electrophoresis techniques. Isolates with the correct sized PCR product were sequenced using primer 1915 (SEQ ID NO: 107) and primer 1916 (SEQ ID NO: 108) in TABLE 15 above.

A sequence verified isolate that contained catH::[prsAp-prsA]cassette (SEQ ID NO: 111) and was phenotypically sensitive to chloramphenicol (10 ppm) was stored as BF561.

A version of BF561 containing the pBl.comK plasmid (SEQ ID NO: 88) was made competent as described above. One hundred (100) μl of competent cells were mixed with five (5) μl of either pZM221 (SEQ ID NO: 84) or pRF879 (SEQ ID NO: 78) RCA and incubated at 1400 RPM and 37° C. for one and a half (1.5) hours. The mixtures were plated on L agar plates containing twenty (20) ppm kanamycin to select for cells transformed with the plasmid.

For cells transformed with pZM221 (SEQ ID NO: 84) that formed colonies on the L agar plates containing twenty (20) ppm kanamycin, the colonies were screened for the ΔdltA-2 allele (SEQ ID NO: 86), a deletion of 700 bp of the dltA coding sequence using standard PCR techniques and the primers in TABLE 16.

TABLE 16

| FORWARD AND REVERSE PRIMER PAIR | | |
|---|---|---|
| Forward | GGGTACCTCCATGGTAAAGT | SEQ ID NO: 113 |
| Reverse | ACGTATTAATGCAGTAGCCG | SEQ ID NO: 114 |

Colonies with the ΔdltA-2 allele produce a PCR product of 2067 bp (SEQ ID NO: 115) with the primers in TABLE 16, while the parental cells containing the intact dltA gene produce a PCR product of 2767 bp (SEQ ID NO: 116). This can be differentiated using standard electrophoresis techniques. A colony containing the 700 bp internal deletion of dltA (SEQ ID NO: 86) was stored as BF598.

For cells transformed with pRF879 (SEQ IN NO: 78) that formed colonies on the L agar plates containing twenty (20) ppm kanamycin the colonies were screened for the ΔrghR2 allele (SEQ ID NO: 80), a deletion of the rghR2 coding sequence except for the first nine (9) and last nine (9) bp, using standard PCR techniques and the primers in TABLE 17 below.

TABLE 17

| FORWARD AND REVERSE PRIMER PAIR | | |
|---|---|---|
| Forward | GGATACGCCGATTTCAATGGC | SEQ ID NO: 117 |
| Reverse | GGCTATGTGCTGGGGGAATT | SEQ ID NO: 118 |

Colonies with the ΔrghR2 allele (SEQ ID NO: 80) produce a PCR product of 1523 bp (SEQ ID NO: 119) using the primers in TABLE 17, while the parental cells containing the intact rghR2 gene produce a PCR product of 1922 bp (SEQ ID NO: 120). The difference between these two products can be differentiated using standard electrophoresis techniques. A colony containing the deletion of the rghR2 gene (SEQ ID NO: 84) was stored as BF602.

A version of BF598 containing the pBl.comK plasmid (SEQ ID NO: 88) was made competent as described above. One hundred (100) μl of competent cells were mixed with five (5) μl of pRF879 (SEQ ID NO: 78) RCA and incubated at 1400 RPM and 37° C. for lone and a half (1.5) hours. The mixtures were plated on L agar plates containing twenty (20) ppm kanamycin to select for cells transformed with the plasmid.

For cells transformed with pRF879 (SEQ IN NO: 78) that formed colonies on the L agar plates containing twenty (20) ppm kanamycin the colonies were screened for the ΔrghR2 allele (SEQ ID NO: 80), a deletion of the rghR2 coding sequence except for the first nine (9) and last nine (9) bp, using standard PCR techniques and the primers in TABLE 17 above.

Colonies with the ΔrghR2 allele (SEQ ID NO: 80) produce a PCR product of 1523 bp (SEQ ID NO: 119) using the primers in TABLE 17, while the parental cells containing the intact rghR2 gene produce a PCR product of 1922 bp (SEQ ID NO: 120). The difference between these two products can be differentiated using standard electrophoresis techniques. A colony containing the deletion of the rghR2 gene (SEQ ID NO: 80) was stored as BF613. TABLE 18 below indicates the modified host strains created in the present example, with the SEQ ID number for the three (3) modified loci in the example.

TABLE 18

MODIFIED HOST STRAINS

| Strain | Relative genotype | rghR2 allele SEQ ID | dltA allele SEQ ID | catH locus SEQ ID NO |
|---|---|---|---|---|
| BF140 | ΔlysA_ΔserA pBl.comKsyn | 121 | 122 | 123 |
| BF561 | BF140 cat::[prsAp-prsA] | 121 | 122 | 124 |
| BF598 | BF561 ΔdltA-2 | 121 | 125 | 125 |
| BF602 | BF561 ΔrghR2 | 80 | 122 | 125 |
| BF613 | BF598 ΔrghR2 | 80 | 125 | 125 |

Example 4

Construction of Amylase Expressing Strains in Modified Host Strains

In the present example a series of amylase and amylase variant expression cassettes were introduced into the strain lineages listed in Example 2, TABLE 18 above.

Amylase 1

Amylase 1 (SEQ ID NO: 126) is the native alpha amylase of *B. licheniformis*, commonly referred to as AmyL. The first cassette of amylase 1 (SEQ ID NO: 127) was integrated into the serA1 locus (SEQ ID NO: 44) and contains the serA1 ORF (SEQ ID NO: 30) and the synthetic p3 promoter (SEQ ID NO: 128) operably linked to the DNA encoding the modified *B. subtilis* aprE 5' UTR (SEQ ID NO: 129) operably linked to the DNA encoding the *B. licheniformis* AmyL signal sequence (SEQ ID NO: 130) operably linked to the DNA encoding amylase 1 (SEQ ID NO: 131) operably linked to the *B. licheniformis* amyL transcriptional terminator (SEQ ID NO: 102). The second cassette (SEQ ID NO: 132) of amylase 1, integrated in the lysA locus (SEQ ID NO: 133), contains the DNA encoding LysA (SEQ ID NO: 134) and the synthetic p2 promoter (SEQ ID NO: 135) operably linked to the DNA encoding the modified *B. subtilis* aprE 5' UTR (SEQ ID NO: 129) operably linked to the DNA encoding the *B. licheniformis* AmyL signal sequence (SEQ ID NO: 130) operably linked to the DNA encoding amylase 1 (SEQ ID NO: 131) operably linked to the *B. licheniformis* amyL transcriptional terminator (SEQ ID NO: 102).

Amylase 2

Amylase 2 (SEQ ID NO: 136) is a variant *Bacillus* sp. α-amylase described in PCT Publication No. WO2018/184004 (incorporated herein by reference in its entirety). The first cassette of amylase 2 (SEQ ID NO: 137) was integrated into the serA1 locus (SEQ ID NO: 44) and contains the serA1 ORF (SEQ ID NO: 30) and the *B. subtilis* rrnI promoter (SEQ ID NO: 138) operably linked to the DNA encoding the *B. subtilis* aprE 5' UTR (SEQ ID NO: 139) operably linked to the DNA encoding the *B. licheniformis* Amy L signal sequence (SEQ ID NO: 130) operably linked to the DNA encoding amylase 2 (SEQ ID NO: 140) operably linked to the *B. licheniformis* amyL transcriptional terminator (SEQ ID NO: 102). The second cassette of amylase 2 (SEQ ID NO: 141), integrated in the lysA locus (SEQ ID NO: 133) or the amyL locus (SEQ ID NO: 142), contains the DNA encoding LysA (SEQ ID NO: 134) and the synthetic p3 promoter (SEQ ID NO: 128) operably linked to the DNA encoding the *B. subtilis* aprE 5' UTR (SEQ ID NO: 139) operably linked to the DNA encoding the *B. licheniformis* AmyL signal sequence (SEQ ID NO: 130) operably linked to the DNA encoding amylase 2 (SEQ ID NO: 140) operably linked to the *B. licheniformis* amyL transcriptional terminator (SEQ ID NO: 102).

Amylase 3

Amylase 3 (SEQ ID NO: 143) is a variant Cytophaga sp. α-amylase (e.g., see PCT Publication Nos. WO2014/164777; WO2012/164800 and WO2014/16483, each incorporated herein by reference in its entirety). The first cassette of amylase 3 (SEQ ID NO: 144) was integrated into the serA1 locus (SEQ ID NO: 44) and contains the serA1 ORF (SEQ ID NO: 30) and the synthetic p3 promoter (SEQ ID NO: 128) operably linked to the DNA encoding the modified *B. subtilis* aprE 5' UTR (SEQ ID NO: 129) operably linked to the DNA encoding the *B. licheniformis* AmyL signal sequence (SEQ ID NO: 130) operably linked to the DNA encoding amylase 3 (SEQ ID NO: 145) operably linked to the *B. licheniformis* amyL transcriptional terminator (SEQ ID NO: 102). The second cassette of amylase 3 (SEQ ID NO: 146), integrated in the lysA locus (SEQ ID NO: 133), contains the DNA encoding LysA (SEQ ID NO: 134) and the synthetic p2 promoter (SEQ ID NO: 135) operably linked to the DNA encoding the modified *B. subtilis* aprE 5' UTR (SEQ ID NO: 129) operably linked to the DNA encoding the *B. licheniformis* AmyL signal sequence (SEQ ID NO: 130) operably linked to the DNA encoding amylase 3 (SEQ ID NO: 145) operably linked to the *B. licheniformis* amyL transcriptional terminator (SEQ ID NO: 102).

Amylase 4

Amylase 4 (SEQ ID NO: 147) is a variant Cytophaga sp. α-amylase (e.g., see PCT Publication Nos. WO2014/164777, WO2012/164800 and WO2014/16483, each incorporated herein by reference in its entirety). The first cassette of amylase 4 (SEQ ID NO: 148) was integrated into the serA1 locus (SEQ ID NO: 44) and contains the serA1 ORF (SEQ ID NO: 30) and the synthetic p3 promoter (SEQ ID NO: 128) operably linked to the DNA encoding the *B. subtilis* aprE 5' UTR (SEQ ID NO: 139) operably linked to the DNA encoding the *B. licheniformis* AmyL signal sequence (SEQ ID NO: 130) operably linked to the DNA encoding amylase 4 (SEQ ID NO: 149) operably linked to the *B. licheniformis* amyL transcriptional terminator (SEQ ID NO: 129). The second cassette of amylase 4 (SEQ ID NO: 150), integrated in the lysA locus (SEQ ID NO: 133), contains the DNA encoding LysA (SEQ ID NO: 134) and the synthetic p2 promoter (SEQ ID NO: 135) operably linked to the DNA encoding the *B. subtilis* aprE 5' UTR (SEQ ID NO: 139) operably linked to the DNA encoding the *B. licheniformis* AmyL signal sequence (SEQ ID NO: 130) operably linked to the DNA encoding amylase 4 (SEQ ID NO: 149) operably linked to the *B. licheniformis* amyL transcriptional terminator (SEQ ID NO: 102).

Amylase 5

Amylase 5 (SEQ ID NO: 151) is a variant *Bacillus* sp. 707 α-amylase (see PCT Publication No. WO2008/153805 and US Patent Publication No. US2014/0057324). The first cassette of amylase 5 (SEQ ID NO: 152) was integrated into the serA1 locus (SEQ ID NO: 44) and contains the serA1 ORF (SEQ ID NO: 30) and the synthetic p3 promoter (SEQ ID NO: 128) operably linked to the DNA encoding the *B. subtilis* aprE 5' UTR (SEQ ID NO: 139) operably linked to the DNA encoding the *B. licheniformis* AmyL signal sequence (SEQ ID NO: 130) operably linked to the DNA encoding amylase 5 (SEQ ID NO: 153) operably linked to the *B. licheniformis* amyL transcriptional terminator (SEQ ID NO: 102). The second cassette of amylase 5 (SEQ ID NO: 154), integrated in the lysA locus (SEQ ID NO: 133), contains the DNA encoding LysA (SEQ ID NO: 134 and the synthetic p2 promoter (SEQ ID NO: 135) operably linked to the DNA encoding the *B. subtilis* aprE 5' UTR (SEQ ID NO: 139) operably linked to the DNA encoding the *B. licheniformis* AmyL signal sequence (SEQ ID NO: 130) operably linked to the DNA encoding amylase 5 (SEQ ID NO: 153) operably linked to the *B. licheniformis* amyL transcriptional terminator (SEQ ID NO: 102).

All amylase expression cassettes were transformed into the modified host strains using the methods described PCT Publication No. WO2019/040412 (incorporated herein by referenced in its entirety).

Example 5

Effect of Modified Host Backgrounds on Amylase Production

In the present example the modified host strains (i.e., TABLE 19; BF140, BF561, BF598, BF602 and BF613)

containing two copies of expression cassettes for amylases 1-5 (Example 4) were assayed for production of α-amylase using standard small scale or lab-scale fermentation conditions (as described in PCT Publication No. WO2018/156705 and WO2019/055261, each incorporated herein by reference). Alpha-amylase production was quantified using the method of Bradford or the Ceralpha assay. The relative improvement in production of amylase is compared to the unmodified host comprising the same α-amylase expression cassettes presented below in TABLE 19.

TABLE 19

RELATIVE PERFORMANCE OF DIFFERENT MODIFIED HOST STRAINS ON AMYLASE PRODUCTION

| Amylase SEQ ID NO | Amylase SEQ ID NO | BF140 | BF561 | BF598 | BF602 | BF613 |
|---|---|---|---|---|---|---|
| Amylase 1 | | 1.00 | ND | 1.17 | 1.21 | 1.33 |
| Amylase 2 | | 1.00 | 1.72 | 1.83 | 1.87 | 1.87 |
| Amylase 3 | | 1.00 | 1.00 | 0.99 | 1.09 | 1.10 |
| Amylase 4 | | 1.00 | 1.48 | 1.45 | 1.56 | 1.62 |
| Amylase 5 | | 1.00 | 1.42 | 1.38 | ND | 1.41 |

Thus, all five (5) of the amylases tested from a diverse group of α-amylases demonstrate an improvement in α-amylase production in the BF613 modified background comprising the deleted dltA-2 (ΔdltA-2) allele (SEQ ID NO: 125), the deleted rghR2 (ΔrghR2) allele (SEQ ID NO: 80) and the insertion of a second copy of the native prsA gene controlled by the native prsA promoter (SEQ ID NO: 124), compared to the unmodified host BF140.

For amylase 2 and amylase 3, the improvement in α-amylase production in the BF602 modified background comprising the deleted rghR2 (ΔrghR2) allele (SEQ ID NO: 80) and the second copy of the native prsA gene controlled by the native prsA promoter (SEQ ID NO: 124), is nearly as good as the improvement seen in the BF613 modified host, suggesting that for some amylases the improvement only requires the presence of these two alleles, but also that the presence of the ΔdltA-2 allele is not harmful to this improvement.

REFERENCES

PCT Publication No. WO1989/06279
PCT Publication No. WO1990/11352
PCT Publication No. WO1994/18314
PCT Publication No. WO1999/19467
PCT Publication No. WO1999/20726
PCT Publication No. WO1999/20769
PCT Publication No. WO1999/20770
PCT Publication No. WO1999/43794
PCT Publication No. WO2000/29560
PCT Publication No. WO2000/60059
PCT Publication No. WO2001/51643
PCT Publication No. WO2002/14490
PCT Publication No. WO2003/083125
PCT Publication No. WO2003/089604
PCT Publication No. WO2006/037483
PCT Publication No. WO2006/037484
PCT Publication No. WO2006/089107
PCT Publication No. WO2008/112459
PCT Publication No. WO2014/164777
PCT Publication No. WO2019/040412
PCT Publication No. WO2018/156705
PCT Publication No. WO2019/055261
U.S. Publication No. US2014/0329309
U.S. Pat. No. 4,914,031
U.S. Pat. No. 4,980,288
U.S. Pat. No. 5,208,158
U.S. Pat. No. 5,310,675
U.S. Pat. No. 5,336,611
U.S. Pat. No. 5,399,283
U.S. Pat. No. 5,441,882
U.S. Pat. No. 5,482,849
U.S. Pat. No. 5,665,587
U.S. Pat. No. 5,700,676
U.S. Pat. No. 5,741,694
U.S. Pat. No. 5,858,757
U.S. Pat. No. 5,880,080
U.S. Pat. No. 6,197,567
U.S. Pat. No. 6,218,165.
U.S. RE34,606
Albertini and Galizzi, Bacteriol., 162:1203-1211, 1985.
Bergmeyer et al., "Methods of Enzymatic Analysis" vol. 5, Peptidases. Proteinases and their Inhibitors, Verlag Chemie, Weinheim, 1984.
Botstein and Shortle. Science 229: 4719, 1985.
Brode et al., "Subtilisin BPN' variants: increased hydrolytic activity on surface-bound substrates via decreased surface activity", Biochemistry, 35(10):3162-3169, 1996.
Caspers et al., "Improvement of Sec-dependent secretion of a heterologous model protein in *Bacillus subtilis* by saturation mutagenesis of the N-domain of the AmyE signal peptide". Appl. Microbiol. Biotechnol., 86(6): 1877-1885, 2010.
Chang et al., Mol. Gen. Genet., 168:11-115, 1979.
Christianson et al., Anal. Biochem., 223:119-129, 1994.
Devereux et a/., Nucl. Acid Res., 12: 387-395, 1984.
Earl et al., "Ecology and genomics of *Bacillus subtilis*". Trends in Microbiology., 16(6):269-275, 2008.
Ferrari et al., "Genetics," in Harwood et al. (ed.), *Bacillus*, Plenum Publishing Corp., 1989.
Fisher et. al., Arch. Microbiol., 139:213-217, 1981.
Guerot-Fleury, Gene, 167:335-337, 1995.
Hamoen et al., "Controlling competence in *Bacillus subtilis*: shared used of regulators", Microbiology, 149:9-17, 2003.
Hamoen et al., Genes Dev. 12:1539-1550, 1998.
Higuchi et al., Nucleic Acids Research 16: 7351, 1988.
Ho et al., Gene 77: 61, 1989.
Hoch et al., J. Bacteriol., 93:1925-1937, 1967.
Holubova, Folia Microbiol., 30:97, 1985.
Hopwood. The Isolation of Mutants in Methods in Microbiology (J. R. Norris and D. W. Ribbons, eds.) pp 363-433, Academic Press, New York, 1970.
Horton et al., Gene 77: 61, 1989.
Hsia et al., Anal Biochem., 242:221-227, 1999.
Iglesias and Trautner, Molecular General Genetics 189: 73-76, 1983.
Jensen et al., "Cell-associated degradation affects the yield of secreted engineered and heterologous proteins in the *Bacillus subtilis* expression system" Microbiology, 146 (Pt 10:2583-2594, 2000.
Kontinen and Sarvas, "The PrsA lipoprotein is essential for protein secretion in *Bacillus subtilis* and sets a limit for high-level secretion", Mol. Microbiol. May; 8(4):727-737, 1993.
Liu and Zuber, 1998,
Lo et al., Proceedings of the National Academy of Sciences USA 81: 2285, 1985.
May et al. "Inhibition of the D-alanine:D-alanyl carrier protein ligase in *Bacillus subtilis* increases the bacterium's susceptibility to antibiotics that target the cell wall", FEBS Journal, 272: 2993-3003, 2005.

McDonald, J. Gen. Microbiol., 130:203, 1984.

Needleman and Wunsch. J. Mol. Biol., 48: 443, 1970.

Ogura & Fujita, FEMS Microbiol Lett., 268(1): 73-80, 2007.

Olempska-Beer et al., "Food-processing enzymes from recombinant microorganisms—a review" Regul. Toxicol. Pharmacol., 45(2):144-158, 2006.

Palmeros et al., Gene 247:255-264, 2000.

Raul et al., "Production and partial purification of alpha amylase from *Bacillus subtilis* (MTCC 121) using solid state fermentation", Biochemistry Research International, 2014.

Sarkar and Sommer, BioTechniques 8: 404, 1990.

Saunders et al., J. Bacteriol., 157:718-726, 1984.

Shimada, Meth. Mol. Biol. 57: 157, 1996

Smith and Waterman, Adv. Appl. Math., 2: 482, 1981.

Smith et al., Appl. Env. Microbiol., 51:634 1986.

Stahl and Ferrari. J. Bacteriol., 158:411-418, 1984.

Stahl et al, J. Bacteriol., 158:411418, 1984.

Trieu-Cuot et al., Gene, 23:331-341, 1983.

Van Dijl and Hecker, "*Bacillus subtilis*: from soil bacterium to super-secreting cell factory". Microbial Cell Factories, 12(3). 2013.

Vorobjeva et al., FEMS Microbiol. Let., 7:261-263, 1980.

Ward, "Proteinases," in Fogarty (ed.)., Microbial Enzymes and Biotechnology. Applied Science, London, pp 251-317, 1983.

Wells et al., Nucleic Acids Res. 11:7911-7925, 1983.

Westers et al., "*Bacillus subtilis* as cell factory for pharmaceutical proteins: a biotechnological approach to optimize the host organism", Biochimica et Biophysica Acta., 1694:299-310, 2004.

The invention claimed is:

1. A method for producing an increased amount of a protein of interest (POI) in a modified *Bacillus licheniformis* cell comprising:

(a) modifying a parental *B. licheniformis* cell expressing a POI by introducing therein a polynucleotide comprising a native *B. licheniformis* prsA promoter operably linked to a native *B. licheniformis* prsA open reading frame (ORF), and (b) fermenting the modified cell under suitable conditions for the production of the POI, wherein the modified cell produces an increased amount of the POI relative to the parental cell when fermented under the same conditions, wherein the POI is a secreted protein.

2. The method of claim 1, wherein the introduced polynucleotide comprises a native *B. licheniformis* prsA promoter sequence comprising at least 95% sequence identity to SEQ ID NO: 100.

3. The method of claim 1, wherein the introduced polynucleotide comprises a native *B. licheniformis* prsA ORF sequence comprising at least 90% sequence identity to SEQ ID NO: 101.

4. The method of claim 1, wherein the parental cell comprises an endogenous *B. lichenformis* prsA gene encoding a native *B. licheniformis* prsA protein.

5. The method of claim 1, wherein the introduced polynucleotide is integrated into the genome of the modified cell.

6. The method of claim 1, wherein the modified cell does not comprise a functional dltA gene comprising at least 90% sequence identity to SEQ ID NO: 122 and/or a functional rghR2 gene comprising at least 90% sequence identity to SEQ ID NO: 121 or SEQ ID NO: 158.

7. The method of claim 1, wherein the POI is a secreted enzyme.

8. A modified *Bacillus licheniformis* cell derived from a parental *B. licheniformis* cell comprising an endogenous *B. licheniformis* prsA gene encoding a native *B. licheniformis* prsA protein, wherein the modified cell further comprises an introduced polynucleotide comprising a native *B. licheniformis* prsA promoter operably linked to a native *B. licheniformis* prsA open reading frame (ORF), wherein the modified cell produces an increased amount of a secreted protein of interest relative to the parental cell when fermented under the same conditions.

9. The modified cell of claim 8, wherein the introduced polynucleotide comprises a native *B. licheniformis* prsA promoter comprising at least 95% sequence identity to SEQ ID NO: 100.

10. The modified cell of claim 8, wherein the introduced polynucleotide comprises a native *B. licheniformis* prsA ORF comprises at least 90% sequence identity to SEQ ID NO: 101.

11. The modified cell of claim 8, wherein the introduced polynucleotide encodes a native *B. licheniformis* prsA protein comprising at least 90% sequence identity to SEQ ID NO: 155.

12. The modified cell of claim 8, which does not comprise a functional dltA gene comprising at least 90% sequence identity to SEQ ID NO: 122 and/or a functional rghR2 gene comprising at least 90% sequence identity to SEQ ID NO: 121 or SEQ ID NO: 158.

13. The modified cell of claim 8, comprising an introduced expression construct encoding a heterologous protein of interest (POI), wherein the POI is a secreted protein.

14. The modified cell of claim 13, wherein the POI is a secreted enzyme.

* * * * *